US010787682B2

(12) United States Patent
Brough et al.

(10) Patent No.: US 10,787,682 B2
(45) **Date of Patent: *Sep. 29, 2020**

(54) SIMIAN (GORILLA) ADENOVIRUS OR ADENOVIRAL VECTORS AND METHODS OF USE

(71) Applicant: GenVec, Inc., Gaithersburg, MD (US)

(72) Inventors: Douglas E. Brough, Gaithersburg, MD (US); Jason G. D. Gall, Germantown, MD (US); Duncan McVey, Derwood, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,501

(22) Filed: Jul. 24, 2018

(65) Prior Publication Data

US 2019/0055579 A1 Feb. 21, 2019

Related U.S. Application Data

(60) Continuation of application No. 15/482,991, filed on Apr. 10, 2017, now Pat. No. 10,059,962, which is a division of application No. 14/349,470, filed as application No. PCT/US2012/059006 on Oct. 5, 2012, now Pat. No. 9,617,560.

(60) Provisional application No. 61/543,661, filed on Oct. 5, 2011.

(51) Int. Cl.

| | |
|---|---|
| ***C12N 15/86*** | (2006.01) |
| ***C07K 14/005*** | (2006.01) |
| ***C12N 7/00*** | (2006.01) |
| *A61K 48/00* | (2006.01) |

(52) U.S. Cl.

CPC ............ *C12N 15/86* (2013.01); *C07K 14/005* (2013.01); *C12N 7/00* (2013.01); *A61K 48/00* (2013.01); *C12N 2710/10322* (2013.01); *C12N 2710/10333* (2013.01); *C12N 2710/10343* (2013.01); *C12N 2760/18034* (2013.01); *C12N 2760/18522* (2013.01); *C12N 2840/60* (2013.01)

(58) Field of Classification Search

None

See application file for complete search history.

(56) References Cited

U.S. PATENT DOCUMENTS

| | | | | |
|---|---|---|---|---|
| 5,837,511 | A | 11/1998 | Falck-Pedersen et al. | |
| 5,851,806 | A | 12/1998 | Kovesdi et al. | |
| 5,994,106 | A | 11/1999 | Kovesdi et al. | |
| 5,994,128 | A | 11/1999 | Fallaux et al. | |
| 5,998,205 | A | 12/1999 | Hallenbeck et al. | |
| 6,033,908 | A | 3/2000 | Bout et al. | |
| 6,127,175 | A | 10/2000 | Vigne et al. | |
| 6,225,289 | B1 | 5/2001 | Kovesdi et al. | |
| 6,482,616 | B1 | 11/2002 | Kovesdi et al. | |
| 6,514,943 | B2 | 2/2003 | Kovesdi et al. | |
| 6,551,586 | B1 | 4/2003 | Davidson et al. | |
| 6,677,156 | B2 | 1/2004 | Brough et al. | |
| 6,682,929 | B2 | 1/2004 | Brough et al. | |
| 7,195,896 | B2 | 3/2007 | Kovesdi et al. | |
| 8,940,290 | B2 | 1/2015 | Roy et al. | |
| 9,617,560 | B2 * | 4/2017 | Brough | C07K 14/005 |
| 9,676,824 | B2 * | 6/2017 | Wei | A61K 39/245 |
| 10,059,962 | B2 * | 8/2018 | Brough | C07K 14/005 |
| 2003/0165820 | A1 | 9/2003 | Day et al. | |
| 2004/0136963 | A1 | 7/2004 | Wilson et al. | |
| 2008/0233650 | A1 | 9/2008 | Gall et al. | |
| 2011/0123564 | A1 | 5/2011 | Mayall et al. | |
| 2011/0223135 | A1 | 9/2011 | Roy et al. | |
| 2011/0274654 | A1 | 11/2011 | Bahadoor et al. | |
| 2014/0248307 | A1 | 9/2014 | Gall et al. | |
| 2014/0248308 | A1 | 9/2014 | McVey et al. | |
| 2014/0271711 | A1 | 9/2014 | Brough et al. | |
| 2014/0314717 | A1 | 10/2014 | Brough et al. | |
| 2015/0140025 | A1 | 5/2015 | Wei et al. | |
| 2015/0152434 | A1 | 6/2015 | Roy et al. | |
| 2015/0157700 | A1 | 6/2015 | Bruder et al. | |

FOREIGN PATENT DOCUMENTS

| | | | |
|---|---|---|---|
| WO | WO 1994/028152 | A1 | 12/1994 |
| WO | WO 1995/002697 | A2 | 1/1995 |
| WO | WO 1995/016772 | A1 | 6/1995 |
| WO | WO 1995/034671 | A1 | 12/1995 |
| WO | WO 1996/022378 | A1 | 7/1996 |
| WO | WO 1997/000326 | A1 | 1/1997 |
| WO | WO 1997/012986 | A2 | 4/1997 |
| WO | WO 1997/021826 | A2 | 6/1997 |
| WO | WO 2000/000628 | A1 | 1/2000 |
| WO | WO 2000/034444 | A2 | 6/2000 |

(Continued)

OTHER PUBLICATIONS

Ahi et al., "Adenoviral Vector Immunity: Its Implications and Circumvention Strategies," *Curr. Gene Therapy*, 11(4): 307-320, Author Manuscript (Aug. 2011).

Alonso-Padilla et al., "Development of Novel Adenoviral Vectors to Overcome Challenges Observed With HAdV-5-based Constructs," *Molecular Therapy*, 24(1): 6-16 (Nov. 2015).

Altschul et al., "Basic Local Alignment Search Tool," *J. Molecular Biol.*, 215(3): 403-410 (1990).

Altschul et al., "Gapped BLAST and PSI-BLAST: a new generation of protein database search programs," *Nucleic Acids Res.*, 25(17): 3389-3402 (1997)

(Continued)

*Primary Examiner* — Benjamin P Blumel

(74) *Attorney, Agent, or Firm* — Leydig Voit and Mayer Ltd

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexon protein, and/or fiber protein.

21 Claims, No Drawings

Specification includes a Sequence Listing.

(56) References Cited

FOREIGN PATENT DOCUMENTS

| | | | |
|---|---|---|---|
| WO | WO 01/58940 | A2 | 8/2001 |
| WO | WO 2003/020879 | A2 | 3/2003 |
| WO | WO 2003/022311 | A1 | 3/2003 |
| WO | WO 2005/075506 | A1 | 8/2005 |
| WO | WO 2006/065827 | A2 | 6/2006 |
| WO | WO 2007/027860 | A2 | 3/2007 |
| WO | WO 2008/011609 | A2 | 1/2008 |
| WO | WO 2010/051367 | A1 | 5/2010 |
| WO | WO 2010/086189 | A2 | 8/2010 |
| WO | WO 2011/057248 | A2 | 5/2011 |
| WO | WO 2012/021730 | A2 | 2/2012 |

OTHER PUBLICATIONS

Aubert et al., "Accumulation of Herpes Simplex Virus Type 1 Early and Leaky-Late Proteins Correlates with Apoptosis Prevention in infected Human Hep-2 Cells," *J. Virol.*, 75(2): 1013-1030 (2001).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).
Brough et al., "Activation of transgene expression by early region 4 is responsible for a high level of persistent transgene expression from adenovirus vectors in vivo," *J. Virol.*, 71(12): 9206-9213 (1997).
Cartier et al., "Hematopoietic stem cell gene therapy with a lentiviral vector in X-linked adrenoleukodystrophy," *Science*, 326(5954): 818-823 (2009).
Cavazzana-Calvo et al., "Gene therapy of human severe combined immunodeficiency (SCID)-X1 disease," *Science*, 288(5466): 669-672 (2000).
Chen et al., "Persistence in muscle of an adenoviral vector that lacks all viral genes," *Proc. Natl. Acad. Sci. USA*, 94(5): 1645-1650 (1997).
Chroboczek et al., "The sequence of the genome of adenovirus type 5 and its comparison with the genome of adenovirus type 2," *Virology*, 186(1): 280-285 (1992).
Crawford-Miksza et al., "Analysis of 15 adenovirus hexon proteins reveals the location and structure of seven hypervariable regions containing serotype-specific residues," *J. Virol.*, 70(3): 1836-1844 (1996).
Curiel et al., "High-efficiency gene transfer mediated by adenovirus coupled to DNA-polylysine complexes," *Hum. Gene Ther.*, 3(2): 147-154 (1992).
Devaux et al., "Structure of adenovirus fibre. I. Analysis of crystals of fibre from adenovirus serotypes 2 and 5 by electron microscopy and X-ray crystallography," *J. Molec. Biol.*, 215(4): 567-588 (1990).
Dey et al., "Molecular epidemiology of adenovirus infection among infants and children with acute gastroenteritis in Dhaka City, Bangladesh," *Infect. Genet. Evol.*, 9(4) 518-522 (2009).
Dolan et al., "The genome sequence of herpes simplex virus type 2," *J. Virol.*72(3): 2010-2021 (1998).
European Patent Office, International Search Report in International Patent Application No. PCT/US/2013/041358 (dated Dec. 11, 2014).
Field et al., "Properties of the adenovirus DNA polymerase," *J. Biol. Chem.*, 259(15): 9487-9495 (1984).
Fu et al., "A prime-boost vaccination strategy using attenuated *Salmonella typhimurium* and a replication-deficient recombinant adenovirus vector elicits protective immunity against human respiratory syncytial virus," *Biochem. and Biophys. Res. Comm.*, 395: 87-92 (2010).
Gall et al., "Construction and characterization of hexon-chimeric adenoviruses: specification of adenovirus serotype," *J. Virol.*, 72(12): 10260-10264 (1998).
Genbank Accession No. ABU95388.1, "hexon, partial [Human adenovirus 9]," (Jun. 2009).
Genbank Accession No. ABX79578, "UL47 [Human herpesvirus 2]" (Apr. 14, 2009).
Genbank Accession No. CAB06743.1, "major capsid protein [Human herpesvirus 2]" (Nov. 14, 2006).
Genbank Accession No. EDA88859.1 , "hypothetical protein GOS_1918841, partial [marine metagenome]," (Apr. 2007).
Genbank Accession No. EDL20708.1, "mCG1048340," (Jun. 2007).
Genbank Accession No. FJ025900, "Simian adenovirus 43, complete genome," (Jul. 2009).
Genbank Accession No. FJ025900.1, "Simian adenovirus 43, complete genome," (Mar. 2012).
Genbank Accession No. FJ025901, "Simian adenovirus 45, complete genome," (Jul. 2009).
Genbank Accession No. FJ025901.1, "Simian adenovirus 45, complete genome," (Mar. 2012).
Genbank Accession No. JN163990.1, "Gorilla gorilla beringei adenovirus 6 hexon gene, partial cds," (Dec. 2011).
Genbank Accession No. KC702813.1," Gorilla beringei beringei adenovirus 7 isolate GC44 hexon gene, complete cds" (Sep. 2013).
Genbank Accession No. KC702815.1, "Gorilla beringei graueri adenovirus 9 isolate GC46 hexon gene, complete cds," (Sep. 2013).
Genbank Accession No. KC702816, "Gorilla beringei beringei adenovirus 7 isolate GC44 DNA polymerase gene, complete cds," (Sep. 2013).
Genbank Accession No. P89442.1, "Major capsid protein" (Nov. 2005).
Genbank Accession No. P89467, "Tegument protien and transactivator of immediate early genes," (Oct. 2006).
Ghosh-Choudhury et al., "Protein IX, a minor component of the human adenovirus capsid, is essential for the packaging of full length genomes," *EMBO J.*, 6(6): 1733-1739 (1987).
Ginsberg et al., "A proposed terminology for the adenovirus antigens and virion morphological subunits," *Virology*, 28(4): 782-783 (1966).
Goins et al.. "Herpes simplex virus vector-mediated gene delivery for the treatment of lower urinary tract pain," *Gene Ther.*, 16(4): 558-569 (2009).
Graham et al., "Characteristics of a human cell line transformed by DNA from human adenovirus type 5," *J. Gen. Virol.*, 36(1): 59-72 (1977).
Green et al., "Evidence for a repeating cross-beta sheet structure in the adenovirus fibre," *EMBO J.*, 2(8): 1357-1365 (1983).
Hacein-Bey-Abina et al., "A serious adverse event after successful gene therapy for X-linked severe combined immunodeficiency," *N. Engl. J. Med.*, 348(3): 255-256 (2003).
Henry et al., "Characterization of the knob domain of the adenovirus type 5 fiber protein expressed in *Escherichia coli*," *J. Virol.*, 68(8): 5239-5246 (1994).
Horvath et al., "Nonperrnissivity of human peripheral blood lymphocytes to adenovirus type 2 infection," *J. Virology*, 62(1): 341-345 (1988).
Jornvall et al., "The adenovirus hexon protein. The primary structure of the polypeptide and its correlation with the hexon gene," *J. Biol. Chem.*, 256(12): 6181-6186 (1981).
Kannan et al., "Structural and functional diversity of the microbial kinome," *PLoS Biol.*, 5(3) E17 (2007).
Kay et al., "Viral vectors for gene therapy: the art of turning infectious agents into vehicles of therapeutics," *Nature Medicine*, 7(1): 33-40 (2001).
Kochanek et al., "High-capacity adenoviral vectors for gene transfer and somatic gene therapy," *Hum. Gene Ther.*, 10(15): 2451-2459 (1999).
Koelle et al., "CD4 T-cell responses to herpes simplex virus type 2 major capsid protein VP5: Comparison with responses to tegument and envelope glycoproteins", *J. Virol.*, 74(23):11422-11425 (2000).
Kohlmann et al., "Protective efficacy and immunogenictiy of an adenoviral vector vaccine encoding the codon-optimized F protein of respiratory syncytial virus," *J Virol.* 83(23): 12601-12610 (2009).
Lasaro et al., "New insights on adenovirus as vaccine vectors," *Molecular Therapy*, 17(8): 1333-1339 (2009).

(56) References Cited

OTHER PUBLICATIONS

Lutz et al., "The product of the adenovirus intermediate gene IX is a transcriptional activator," *J. Virol.*, 71(7): 5102-5109 (1997).
Mayrhofer et al., "Nonreplicating vaccinia virus vectors expressing the H5 influenza virus hemagglutinin produced in modified Vero cells induce robust protection," *J. Virol.*, 83(10): 5192-5203 (2009).
McVey et al., "Adenoviruses isolated from wild gorillas are closely related to human species C viruses," *Virology*, 444: 119-123 (2013).
Mease et al., "Safety, tolerability, and clinical outcomes after intraarticular injection of a recombinant adeno-associated vector containing a tumor necrosis factor antagonist gene: results of a phase 1/2 Study," *Journal of Rheumatology*, 37(4): 692-703 (2010).
Morsy et al., An adenoviral vector deleted for all viral coding sequences results in enhanced safety and extended expression of a leptin transgene, *Proc. Natl. Acad. Sci. USA*, 95: 7866-7871 (1998).
Muller et al., "Herpes simplex virus type 2 tegument proteins contain subdominant T-cell epitopes detectable in BALB/c mice after DNA immunization and infection", *J. Virol.*, 90 (5): 1153-1163 (2009).
Narum et al., "Codon Optimization of Gene Fragments Encoding Plasmodium falciparum Merzoite Proteins Enhances DNA Vaccine Protein Expression and Immunogenicity in Mice," *Infect Immun*, 69(12): 7250-7253 (2001).
NCBI reference sequence AP_000218, "E3 12.5K [Human adenovirus 5]," (Dec. 2008).
NCBI reference sequence AP_000224.1, "*Homo sapiens* genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," *Gene*, 69(1) 153-157 (1988).
Novelli et al., "Deletion analysis of functional domains in baculovirus-expressed adenovirus type 2 fiber," *Virology*, 185(1): 365-376 (1991).
Roberts et al., "Three-dimensional structure of the adenovirus major coat protein hexon," *Science*, 232(4754): 1148-1151 (1986).
Roy et al., "Generation of an adenoviral vaccine vector based on simian adenovirus 21," *Journal of General Virology* 87: 2477-2485 (2006).
Roy et al., "Isolation and Characterization of Adenoviruses Persistently Shed from the Gastrointestinal Tract of Non-Human Primates," *PLOS Pathogens*, 5(7): E1000503, 1-9, (2009).
Rusch et al., "The Sorcerer II Global Ocean Sampling expedition: northwest Atlantic through eastern tropical Pacific," *PLoS Biol.*, 5(3) E77 (2007).
Rux et al., "Structural and phylogenetic analysis of adenovirus hexons by use of high-resolution x-ray crystallographic, molecular modeling, and sequence-based methods," *J. Virol.*, 77(17): 9553-9566 (2003).
Seregin et al., "Overcoming pre-existing adenovirus immunity by genetic engineering of adenovirus-based vectors," *Expert Opinion on Biological Therapy*, 9(12): 1521-1531 (2009).
Signas et al., Adenovirus 3 Fiber Polypeptide Gene: Implications for the Structure of the Fiber Protein, *J. Virol.*, 53(2): 672-678 (1985).
Silver et al., "Interaction of human adenovirus serotype 2 with human lymphoid cells," *Virology*, 165(2): 377-387 (1988).
Soding, "Protein homology detection by HMM-HMM comparison," *Bioinformatics*, 21(7): 951-960 (2005).
Stewart et al., "Difference imaging of adenovirus: bridging the resolution gap between X-ray crystallography and electron microscopy," *EMBO J.*, 12(7): 2589-99 (1993).
Stewart et al., "Image reconstruction reveals the complex molecular organization of adenovirus," *Cell*, 67(1): 145-154 (1991).
Subak-Sharpe et al., "HSV Molecular Biology: General Aspects of Herpes Simplex Virus Molecular Biology", *Virus Genes*, 16(3): 239-251 (1998).
Thomas et al., "Progress and problems with the use of viral vectors for gene therapy," *Nature Review Genetics*, 4(5): 346-358 (2003).
Van Oostrum et al, "Molecular composition of the adenovirus type 2 virion," *J. Virol.*, 56(2): 439-448 (1985).
Wevers et al., "A novel adenovirus of Western lowland gorillas (*Gorilla gorilla gorilla*)," *J. Virology*, 7(1): 1-8 (2010).
Wevers et al., "Novel Adenoviruses in Wild Primates: a High Level of Genetic Diversity and Evidence of Zoonotic Transmissions," *J. Virology*, 85(20): 10774-10784, (2011).
Yeh et al., "Human adenovirus type 41 contains two fibers," *Virus Res.*, 33(2): 179-198 (1994).
Yooseph et al., "The Sorcerer II Global Ocean Sampling expedition: expanding the universe of protein families," *PLoS Biol.*, 5(3) E16, (2007).
U.S. Appl. No. 14/349,470, filed Apr. 3, 2014.
U.S. Appl. No. 14/403,397, filed May 16, 2013.
U.S. Appl. No. 14/349,735, filed Sep. 18, 2014.
U.S. Appl. No. 14/373,574, filed Jun. 11, 2015.
U.S. Appl. No. 14/349,421, filed Apr. 3, 2014.
U.S. Appl. No. 14/992,152, filed Jan. 11, 2016.
U.S. Appl. No. 14/349,426, filed Apr. 3, 2014.
U.S. Appl. No. 15/492,016, filed Apr. 20, 2017.
U.S. Appl. No. 15/482,991, filed Apr. 10, 2017.
U.S. Appl. No. 15/618,740, filed Jun. 9, 2017.
U.S. Appl. No. 15/650,289, filed Jul. 14, 2017.
U.S. Appl. No. 16/156,520, filed Oct. 10, 2018.
U.S. Appl. No. 16/282,924, filed Feb. 22, 2019.
U.S. Appl. No. 16/352,459, filed Mar. 13, 2019.
Bernstein et al., "N-methanocarbathymidine is more effective than acyclovir for treating neonatal herpes simplex virus infection in guinea pigs," *Antiviral Res.*, 92(2): 386-388 (2011).
Braitman et al., "Evaluation of SQ 34,514: Pharrnacokinetics and Efficacy in Experimental Herpesvirus Infections in Mice," *Antimicrob. Agents Chemother.*, 35(7): 1464-1468 (1991).
Brough, Nov. 3, 2015, "Gorilla Adenovirus Vectors for Molecular Therapeutics and Vaccines," on p. 10 of the program from the International Conference on Vaccines Research & Development: A New Era in Vaccine Discovery, Baltimore, MD, USA (Nov. 2-4, 2015).

* cited by examiner

SEQUENCE LISTING

```
<160> NUMBER OF SEQ ID NOS: 28

<210> SEQ ID NO 1
<211> LENGTH: 83
<212> TYPE: DNA
<213> ORGANISM: Gorilla beringei graueri

<400> SEQUENCE: 1

ggcgcggcct ctcgcgcgtc tgctcgggat gagaaactga ccgctctgct gcttaaactg     60

gaagacttga cccgggagct ggc                                             83


<210> SEQ ID NO 2
<211> LENGTH: 100
<212> TYPE: DNA
<213> ORGANISM: Gorilla beringei graueri

<400> SEQUENCE: 2

gcttcgtcag ggactcggtg ggcttgcaag aagcaagctt caacgtcttc cagcggccca     60

ccatctcctc caactcccat gccatcttca ggcagatcgc                          100


<210> SEQ ID NO 3
<211> LENGTH: 45
<212> TYPE: DNA
<213> ORGANISM: Gorilla beringei graueri

<400> SEQUENCE: 3

gaggagggcg cacaggaggg cgcgcagaag gacatgaacg atggg                     45


<210> SEQ ID NO 4
<211> LENGTH: 111
<212> TYPE: DNA
<213> ORGANISM: Gorilla beringei graueri

<400> SEQUENCE: 4

tccctggccc ccaagggcgc tcccaattct tgcgagtggg aacaagagga aaatcaggtg     60

gtcgctgcag atgatgaact tgaagatgaa gaagcgcaag ctcaagagga c             111


<210> SEQ ID NO 5
<211> LENGTH: 38
<212> TYPE: DNA
<213> ORGANISM: Gorilla beringei graueri

<400> SEQUENCE: 5
```

```
tcgagggtat caatgctttg gcagtagcca caggtaag                          38


<210> SEQ ID NO 6
<211> LENGTH: 399
<212> TYPE: DNA
<213> ORGANISM: Gorilla beringei graueri

<400> SEQUENCE: 6

atgagcgaca ccggcaacag ctttgatgga agcatcttta gcccctatct gacagtgcgc    60

atgcctcact gggctggagt gcgtcagaat gtgatgggtt ccaacgtgga tggacgcccc   120

gttctgcctt caaattcgtc tacaatggcc tacgcgaccg tgggaggaac tccgctggac   180

gccgcgacct ccgccgccgc ctccgccgcc gccgcgaccg cgcgcagcat ggctacggac   240

ctttacagct ctttggtggc gagcggcgcg gcctctcgcg cgtctgctcg ggatgagaaa   300

ctgaccgctc tgctgcttaa actggaagac ttgacccggg agctggctca actgacccag   360

caggtctcca gcttgcgtga gagcagcctt gcctccccc                         399


<210> SEQ ID NO 7
<211> LENGTH: 3168
<212> TYPE: DNA
<213> ORGANISM: Gorilla beringei graueri

<400> SEQUENCE: 7

atggacagct ccaatgtgcg cgatgtcgtc atcaaactcc gcccgccgag cgccgagatc    60

tggacctgcg gctctcgcgg cgtggtggtc tgctccacca tcgccctcca ggagacagat   120

gctggcggcc agacaaccaa agtagaagac caccagccac acgggacccc aggcggggga   180

cttagattcc cgctgcgctt cctcgtcaga ggtcgccagg ttcacctcgt gcaagatata   240

caacccgtgc agcgctgcca gtactgcggt cgcttttaca aagccagca cgagtgctcg    300

gcccgcagac gggacttcta ctttcaccac atcaacagcc aatcctccaa ctggtggcgg   360

gagatccagt tcttcccgat cggctctcat cctcgcacgg agcgcctctt tgtcacctac   420

gatgtagaga cctacacttg gatgggagcc tttggcaagc agctcgtgcc cttcatgctg   480

gtcatgaaac tgggggggcaa cgaggctctg gtcgccgccg cgcgcgacct cgcccgagag   540

ctcagatggg acccctggga gaaagacccc ctcaccttct actgcatcac ccccgaaaag   600

atggccgtgg ggcgacagtt cagaaccttc cgcgaccgcc tgcagaccct catggcccgc   660

gacctctggc gatccttcct ggcggccaac cctcacttgc aagactgggc cctggaggag   720

cacggcctgg aatcgcccga ggagctcacc tacgaggaac tcaaaaagct cccctccatc   780

aagggccagc cccgcttttt ggagctctac atcgtgggcc acaacataaa cggctttgac   840

gagatcgtcc tggccgccca ggtcatcaac aaccgctcct cggtcccagg gccctttcgc   900

atcaccagaa acttcatgcc tcgagcgggg aagatcctct tcaatgacct caccttctcc   960

ctgcccaacc cgcgctccaa aaagcgcacg gactacaccc tgtgggaaca gggcggctgc  1020

gatgacacag acttcaaaca tcaatacctc aaagtcatgg tcagggacac tttcgccctc  1080

acccacacct ccctccgcaa ggcggcgcag gcctacgcgc tgcccgtgga gaagggctgt  1140

tgcccctacc aggccgtcaa ccagttctac atgctaggct cttaccgttc ggacacggac  1200

gggtttcccc tccaagagta ctggaaagac cgcgaagagt tcgtcctcaa ccgcgagctg  1260

tggaaaaaga agggggagga taagtatgac atcatccgcg agaccctcga ctactgcgcg  1320

ctcgacgtcc aggtcaccgc cgagctggtg cacaagctgc gcgagtccta cgcctgcttc  1380
```

gtcagggact cggtgggctt gcaagaagca agcttcaacg tcttccagcg gcccaccatc 1440
tcctccaact cccatgccat cttcaggcag atcgccttcc gcgccgagcg cccccagcgc 1500
accaacctcg ggcccaacat gctggccccc tcccacgagc tctatgacta cgtgcgcgcc 1560
agcatccgcg gggggcgctg ctaccccacc tacctcggca tcctcaggga accccctgtac 1620 gtgtatgaca tctgcggcat gtacgcctcc gcgctcaccc accccatgcc ctggggcccg 1680
cccctcaacc cctacgagcg cgcgctcgcc gcccgcgaat ggcagcgggc tctggacatg 1740
caagcttgca agatcgacta ctttgacccg cgcttgctcc ccggggtctt caccatcgac 1800
gcggaccccc caaacgagga ccagctggac cccctacccc ccttctgctc gcgcaagggc 1860
ggccgcctct gctggaccaa cgagcgcctg cgcggcgagg tcgccaccag cgtcgacatg 1920
gtcaccctgc acaaccgagg ctggagggtg cgcctgatcc cagacgagcg caccaccgtc 1980
ttccccgagt ggaagtgcgt ggcccgcgag tacgtgcaac tcaacatcgc ggccaaggag 2040
cgagccgacc gcgacaaaaa ccagaccctg cgctccatcg ccaagctgct ctccaacgcc 2100
ctctacgggt cgttcgccac caagcttgac aacaaaaaaa tagtgttttc tgaccagatg 2160
gacccaggta ccctcaaagg tatcacctcc ggacaggtga acatcaaatc ctcctcattt 2220
ttagaaactg acaacctgag cgctgaggtc atgcccgcct tcgagaggga atacttaccc 2280
cagcagctgg ctctcgcaga cagcgatgcg gaagagagtg aagatgaaag ggtgcccacc 2340 ccctttttata cccccccgtc gggaaccccc ggtcacgtgt cctacaccta caagccaatc 2400
acttttctgg acgcggagga gggggacatg tgcctgcaca ccctggagaa ggtggacccg 2460
ctagtggaca acgaccgcta cccctcccac gtggcctcct tcgtcctggc ctggacgcgg 2520
gccttcgtct cagagtggtc agagtttctc tacgaggagg acagaggcac tccgctggaa 2580
gacaggcccc tgaagtcggt ctacggagac acggacagcc tcttcgtcac cgagaaggga 2640
caccgcctca tggagagccg aggtaagaaa cgcatcaaaa agcatggggg caacctggtt 2700
tttgaccctg accgcccgga gctcacttgg ctggtggaat gcgagacggt ctgcgcttcc 2760
tgcggcgcgg acgcctactc cccagagtcc gtgtttctcg ctcccaagct ctacgccctg 2820
aagagcctgc agtgcccctc gtgcggcgcc acctccaagg gaaagctccg cgccaagggg 2880
cacgccgccg agggtctcga ctacgagacc atggtcaaat gctacctggc cgacgcgcag 2940
ggcgaagagc ggcagcgatt cagcaccagc agaaccagcc tcaagcgcac cctggccagc 3000
gcccaacccg gagcgcaccc cttcaccgtg acccagacca ccctgacgag gaccctgcgc 3060
ccatggaagg acatgactct ggccccgctg gacgcccatc ggctggtgcc ctacagcgaa 3120
agccgcccca acccgcgaaa cgaggagatc tgctggatcg agatgccg 3168

<210> SEQ ID NO 8
<211> LENGTH: 1974
<212> TYPE: DNA
<213> ORGANISM: Gorilla beringei graueri

<400> SEQUENCE: 8
atgcggcgcg cggcgatgtt cgaggagggg cctccccccct cttacgagag cgcgatgggg 60
atttctcctg cggcgcccct gcagcctccc tacgtgcctc ctcggtacct gcaacctaca 120
ggggggagaa atagcatctg ttactctgag ctgcagcccc tgtacgatac caccagactg 180
tacctggtgg acaacaagtc cgcggacgtg gcctccctga actaccagaa cgaccacagc 240
gattttttga ccacggtgat ccaaaacaac gacttcaccc caaccgaggc cagcactcag 300
accataaacc tggataacag gtcgaactgg ggcggcgacc tgaagaccat cttgcacacc 360

```
aacatgccca acgtgaacga gttcatgttc accaactctt ttaaggcgcg ggtgatggtg    420
gcgcgcgagc agggggaggc gaagtacgag tgggtggact tcacgctgcc cgagggcaac    480
tactcagaga ccatgactct cgacctgatg aacaatgcga tcgtggaaca ctatctgaaa    540
gtgggcaggc agaacggggt gaaggaaagc gatatcgggg tcaagtttga caccagaaac    600
ttccgtctgg gctgggaccc cgtgaccggg ctggtcatgc cgggggtcta caccaacgag    660
gcctttcatc ccgacatagt gcttctgccc ggctgtgggg tggacttcac ccagagccgg    720
ctgagcaacc tgctgggcat tcgcaagcgg cagcctttcc aggagggttt caagatcacc    780
tatgaggatc tgaagggggg caacattccc gcgctccttg atctggacgc ctacgaggag    840
agcttgaaac ccgaggagag cgctggcgac agcggcgaga gtggcgagga gcaagccggc    900
ggcggtggcg gcgcgtcggt agaaaacgaa agtacgcccg cagtggcggc ggacgctgcg    960
gaggtcgagc cggaggccat gcagcaggac gcagaggagg gcgcacagga gggcgcgcag   1020
aaggacatga acgatgggga gatcagggga gacacattcg ccacccgggg cgaagaaaaa   1080
gaggcagagg cggcggcggc ggcgacggcg gaggccgaaa ccgaggttga ggcagaggca   1140
gagcccgaga ccgaagttat ggaagacatg aatgatggag aacgtagggg cgacacgttc   1200
gccacccggg gcgaagagaa ggcggcggag gcagaagccg cggctgagga ggcggctgcg   1260
gctgcggcca agactgaggc tgcggctaag gctgaggtcg aagccaatgt tgcggttgag   1320
gctcaggctg aggaggaggc ggcggctgaa gcagttaagg aaaaggccca ggcagagcag   1380
gaagagaaaa aacctgtcat tcaacctcta aaagaagata gcaaaaagcg cagttacaac   1440
gtcatcgagg gcagcacctt tacccagtac cgcagctggt acctggcgta caactacggc   1500
gacccggtca agggggtgcg ctcgtggacc ctgctctgca cgccggacgt cacctgcggc   1560
tccgagcaga tgtactggtc gctgccgaac atgatgcaag acccggtgac cttccgctcc   1620
acgcggcagg ttagcaactt cccggtggtg ggcgccgaac tgctgcccgt gcactccaag   1680
agtttttaca acgagcaggc cgtctactcc cagctgatcc gccaggccac ctctctgacc   1740
cacgtgttca atcgctttcc cgagaaccag attttggcgc gcccgccggc ccccaccatc   1800
accaccgtga gtgaaaacgt tcctgccctc acagatcacg ggacgctacc gctgcgcaac   1860
agcatctcag gagtccagcg agtgaccatt actgacgcca gacgccggac ctgcccctac   1920
gtttacaagg ccttgggcat agtctcgccg cgcgtcctct ccagtcgcac tttt         1974
```

<210> SEQ ID NO 9
<211> LENGTH: 2865
<212> TYPE: DNA
<213> ORGANISM: Gorilla beringei graueri

<400> SEQUENCE: 9

```
atggcgaccc catcgatgat gcctcagtgg tcgtacatgc acatctcggg ccaggacgct     60
tcggagtacc tgagccccgg gctggtgcag ttcgcccgcg ccacagacac ctacttcaac    120
atgagtaaca agttcaggaa ccccactgtg gcgcccaccc acgatgtgac cacggaccgg    180
tcgcagcgcc tgacgctgcg gttcatcccc gtggatcggg aggacaccgc ctactcttac    240
aaggcgcggt tcacgctggc cgtgggcgac aaccgcgtgc tggacatggc ctccacttac    300
tttgacatca ggggggtgct ggacaggggc cccaccttca agccctactc gggtactgcc    360
tacaactccc tggcccccaa gggcgctccc aattcttgcg agtgggaaca agaggaaaat    420
caggtggtcg ctgcagatga tgaacttgaa gatgaagaag cgcaagctca agaggacgcc    480
```

-continued

```
ccagctaaaa aaattcatgt atatgcccag gcgcctcttg ctggcgaaaa gattaccaag    540
gatggtttgc aaataggtac tgaagttgta ggagatacat ctaaggacac ttttgcagac    600
aaaacattcc aacccgaacc tcagataggc gagtctcagt ggaacgaggc tgatgccaca    660
gtagcaggag gcagagtctt gaaaaaaacc accccctatga gaccttgcta tggatcctat    720
gccaggccta caaatgccaa cgggggtcaa ggaattatgg ttgccaatga acaaggagtg    780
ttggagtcta aagtggagat gcaatttttt tctaacacta caacccttaa tgcgcgggat    840
ggagctggca atcccgaacc aaaggtggtg ttgtacagtg aagatgtcca cttggaatct    900
cctgacactc atttgtctta caagcccaaa aaggatgatg ttaatgctaa aattatgttg    960
ggtcagcaag ctatggctaa caggcccaac ctcattgctt ttagagataa tttcattgga   1020
ctcatgtact acaacagcac tggtaacatg ggagtgctgg cgggtcaggc ctctcagttg   1080
aatgccgtgg tggacctgca ggatagaaac acagaactgt catatcagct tatgcttgat   1140
tccattgggg atagatccag atacttctcc atgtggaacc aggcagtgga tagctatgac   1200
ccagatgtca gaatcattga aaaccatggt gtcgaggacg agctacccaa ctactgcttc   1260
cctctgggcg gcataggaat tactgatact tatcaaggga tcaaaaatac caatggcaat   1320
ggtcagtgga ccaaagatga tcagttcgcg gaccgtaatg aaataggggt gggaaacaac   1380
ttcgccatgg agatcaacat ccaggccaac ctctggagga acttcctcta tgcgaacgtg   1440
gggctctacc tgccagacaa gctcaagtac aaccccacca acgtggacat ctctgacaac   1500
cccaacacct atgactacat gaacaagcgt gtggtggctc ccggcctggt ggactgcttt   1560
gtcaatgtgg gagccaggtg gtccctggac tacatggaca acgtcaaccc cttcaaccac   1620
caccgcaatg cgggtctgcg ctaccgctcc atgatcctgg gcaacgggcg ctacgtgccc   1680
ttccacattc aggtgcccca gaagttcttt gccatcaaga acctcctcct cctgccgggc   1740
tcctacactt acgagtggaa cttcaggaag gatgtcaaca tggtcctgca gagctctctg   1800
ggcaatgacc ttagggtgga cggggccagc atcaagtttg acagcgtcac cctctatgct   1860
accttcttcc ccatggctca caacaccgcc tccacgctcg aggccatgct gaggaacgac   1920
accaacgacc agtccttcaa tgactacctc tctggggcca acatgctcta ccccatcccc   1980
gccaaggcca ccaacgtgcc catctccatt ccctctcgca actgggccgc cttcagaggc   2040
tgggccttta cccgccttaa gaccaaggaa acccccctccc tgggctcggg ttttgacccc   2100
tactttgtct actcgggatc catcccctac ctggatggca ccttctacct caaccacact   2160
tttaagaaga tatccatcat gtatgactcc tccgtcagct ggccgggcaa tgaccgcctg   2220
ctcacccccca atgagttcga ggtcaagcgc gccgtggacg gcgagggcta caacgtggcc   2280
cagtgcaaca tgaccaagga ctggttcctg gtgcagatgc tggccaacta caacataggc   2340
taccagggct tctacatccc agagagctac aaggacagga tgtactcctt cttcagaaat   2400
ttccaaccca tgagcaggca ggtggtggac gagaccaaat acaaggacta tcaggccatt   2460
ggcatcactc accagcacaa caactcggga ttcgtgggct acctggctcc caccatgcgc   2520
gaggggcagg cctaccccgc caacttcccc tacccgttga taggcaagac cgcggtcgac   2580
agcgtcaccc agaaaaagtt cctctgcgac cgcaccctct ggcgcatccc cttctctagc   2640
aacttcatgt ccatgggtgc gctcacggac ctgggccaga acctgctcta tgccaactcc   2700
gcccatgcgc tggacatgac ttttgaggtg gaccccatgg acgagcccac ccttctctat   2760
attgtgtttg aagtgttcga cgtggtcaga gtgcaccagc cgcaccgcgg tgtcatcgag   2820
accgtgtacc tgcgcacgcc cttctcggcc ggcaacgcca ccacc                   2865
```

<210> SEQ ID NO 10
<211> LENGTH: 1740
<212> TYPE: DNA
<213> ORGANISM: Gorilla beringei graueri

<400> SEQUENCE: 10

```
atgaaacgcg cgagatcgtc tgacgagacc ttcaaccccg tgtaccccta cgataccgag     60
atcgctccga cttctgtccc tttccttacc cctccctttg tgtcatccgc aggaatgcaa    120
gaaaatccag ctggggtgct gtccctgcac ttgtcagagc cccttaccac ccacaatggg    180
gccctgactc taaaaatggg gggcggcctg accctggaca aggaagggaa tctcacttcc    240
caaaacatca ccagtgtcga tcccccctctc aaaaaaagca agaacaacat cagccttcag    300
accgccgcac ccctcgccgt cagctccggg gccctaacac tttttgccac tcccccccta    360
gcggtcagtg gtgacaacct tactgtgcag tctcaggccc ctctcacttt ggaagactca    420
aaactaactc tggccaccaa aggaccccta actgtgtccg aaggcaaact tgtcctagaa    480
acagaggctc ccctgcatgc aagtgacagc agcagcctgg gccttagcgt tacggcccca    540
cttagcatta acaatgacag cctaggacta gacatgcaag cgcccattag ctctcgagat    600
ggaaaactgg ctctaacagt ggcggccccc ctaactgtgg tcgagggtat caatgctttg    660
gcagtagcca caggtaaggg tattgggcta aatgaaacca acacacacct gcaggcaaaa    720
ctggtcgcac ccctaggctt tgataccaac ggcaacatta agctaagcgt tgcaggaggc    780
atgaggctaa acaataacac actgatacta gatgtaaact acccatttga ggctcaaggc    840
caactgagcc taagagtggg ctcgggccca ctatatgtag attctagtag tcataaccta    900
accattagat gccttagggg attgtatata acatcttcta acaaccaaaa cggtctagaa    960
gccaacatta aactaacaag aggccttgtg tatgacggaa atgccatagc agttaatgtt   1020
ggcaaagggc tggaatacag ccctactgac acaacagaaa aacctataca gactaaaata   1080
ggtctaggca tggagtatga taccgaggga gccatgatga caaaactagg ctctggacta   1140
agctttgaca attcaggagc cattgtagtg ggaaacaaaa atgatgacag gcttactttg   1200
tggaccacac cggacccatc gcccaactgt cagatctact ctgaaaaaga tgctaaacta   1260
accttggtac tgactaaatg tggcagtcag gttgtaggca cagtatctat tgccgctctt   1320
aaaggtagcc tcgtgccaat cactagtgca atcagtgtgg ttcaggtata cctaaggttt   1380
gatgaaaatg ggtactaat gagtaactct tcacttaatg gcgaatactg gaattttaga    1440
aacggagact caactaatgg cacaccatat acaaacgcag tgggtttcat gcctaatcta   1500
ctggcctatc ctaaaggtca aactacaact gcaaaaagta acattgtcag ccaggtctac   1560
atgaatgggg acgatactaa acccatgaca tttacaatca acttcaatgg ccttagtgaa   1620
acaggggata cccctgttag taaatattcc atgacattct catggaggtg gccaaatgga   1680
agctacatag ggcacaattt tgtaacaaac tcctttacct tctcctacat cgcccaagaa   1740
```

<210> SEQ ID NO 11
<211> LENGTH: 28
<212> TYPE: PRT
<213> ORGANISM: Gorilla beringei graueri

<400> SEQUENCE: 11

```
Gly Ala Ala Ser Arg Ala Ser Ala Arg Asp Glu Lys Leu Thr Ala Leu
1               5                   10                  15

Leu Leu Lys Leu Glu Asp Leu Thr Arg Glu Leu Ala
```

20 25

<210> SEQ ID NO 12
<211> LENGTH: 34
<212> TYPE: PRT
<213> ORGANISM: Gorilla beringei graueri

<400> SEQUENCE: 12

Cys Phe Val Arg Asp Ser Val Gly Leu Gln Glu Ala Ser Phe Asn Val
1 5 10 15

Phe Gln Arg Pro Thr Ile Ser Ser Asn Ser His Ala Ile Phe Arg Gln
20 25 30

Ile Ala

<210> SEQ ID NO 13
<211> LENGTH: 15
<212> TYPE: PRT
<213> ORGANISM: Gorilla beringei graueri

<400> SEQUENCE: 13

Glu Glu Gly Ala Gln Glu Gly Ala Gln Lys Asp Met Asn Asp Gly
1 5 10 15

<210> SEQ ID NO 14
<211> LENGTH: 37
<212> TYPE: PRT
<213> ORGANISM: Gorilla beringei graueri

<400> SEQUENCE: 14

Ser Leu Ala Pro Lys Gly Ala Pro Asn Ser Cys Glu Trp Glu Gln Glu
1 5 10 15

Glu Asn Gln Val Val Ala Ala Asp Asp Glu Leu Glu Asp Glu Glu Ala
20 25 30

Gln Ala Gln Glu Asp
35

<210> SEQ ID NO 15
<211> LENGTH: 15
<212> TYPE: PRT
<213> ORGANISM: Gorilla beringei graueri

<400> SEQUENCE: 15

Val Glu Gly Ile Asn Ala Leu Ala Val Ala Thr Gly Lys Gly Ile
1 5 10 15

<210> SEQ ID NO 16
<211> LENGTH: 133
<212> TYPE: PRT
<213> ORGANISM: Gorilla beringei graueri

<400> SEQUENCE: 16

Met Ser Asp Thr Gly Asn Ser Phe Asp Gly Ser Ile Phe Ser Pro Tyr
1 5 10 15

Leu Thr Val Arg Met Pro His Trp Ala Gly Val Arg Gln Asn Val Met
20 25 30

Gly Ser Asn Val Asp Gly Arg Pro Val Leu Pro Ser Asn Ser Ser Thr
35 40 45

Met Ala Tyr Ala Thr Val Gly Gly Thr Pro Leu Asp Ala Ala Thr Ser
50 55 60

Ala Ala Ala Ser Ala Ala Ala Ala Thr Ala Arg Ser Met Ala Thr Asp
65 70 75 80

```
Leu Tyr Ser Ser Leu Val Ala Ser Gly Ala Ala Ser Arg Ala Ser Ala
                85                  90                  95

Arg Asp Glu Lys Leu Thr Ala Leu Leu Leu Lys Leu Glu Asp Leu Thr
            100                 105                 110

Arg Glu Leu Ala Gln Leu Thr Gln Gln Val Ser Ser Leu Arg Glu Ser
        115                 120                 125

Ser Leu Ala Ser Pro
    130


<210> SEQ ID NO 17
<211> LENGTH: 1056
<212> TYPE: PRT
<213> ORGANISM: Gorilla beringei graueri

<400> SEQUENCE: 17

Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Val Cys Ser
            20                  25                  30

Thr Ile Ala Leu Gln Glu Thr Asp Ala Gly Gly Gln Thr Thr Lys Val
        35                  40                  45

Glu Asp His Gln Pro His Gly Thr Pro Gly Gly Gly Leu Arg Phe Pro
    50                  55                  60

Leu Arg Phe Leu Val Arg Gly Arg Gln Val His Leu Val Gln Asp Ile
65                  70                  75                  80

Gln Pro Val Gln Arg Cys Gln Tyr Cys Gly Arg Phe Tyr Lys Ser Gln
                85                  90                  95

His Glu Cys Ser Ala Arg Arg Arg Asp Phe Tyr Phe His His Ile Asn
            100                 105                 110

Ser Gln Ser Ser Asn Trp Trp Arg Glu Ile Gln Phe Phe Pro Ile Gly
        115                 120                 125

Ser His Pro Arg Thr Glu Arg Leu Phe Val Thr Tyr Asp Val Glu Thr
    130                 135                 140

Tyr Thr Trp Met Gly Ala Phe Gly Lys Gln Leu Val Pro Phe Met Leu
145                 150                 155                 160

Val Met Lys Leu Gly Gly Asn Glu Ala Leu Val Ala Ala Ala Arg Asp
                165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
        195                 200                 205

Thr Phe Arg Asp Arg Leu Gln Thr Leu Met Ala Arg Asp Leu Trp Arg
    210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Ala Gln Val
        275                 280                 285

Ile Asn Asn Arg Ser Ser Val Pro Gly Pro Phe Arg Ile Thr Arg Asn
    290                 295                 300

Phe Met Pro Arg Ala Gly Lys Ile Leu Phe Asn Asp Leu Thr Phe Ser
```

```
305                 310                 315                 320

Leu Pro Asn Pro Arg Ser Lys Lys Arg Thr Asp Tyr Thr Leu Trp Glu
                325                 330                 335

Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
        355                 360                 365

Ala Gln Ala Tyr Ala Leu Pro Val Glu Lys Gly Cys Cys Pro Tyr Gln
    370                 375                 380

Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
                405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
        435                 440                 445

Leu Val His Lys Leu Arg Glu Ser Tyr Ala Cys Phe Val Arg Asp Ser
    450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
            500                 505                 510

Glu Leu Tyr Asp Tyr Val Arg Ala Ser Ile Arg Gly Gly Arg Cys Tyr
        515                 520                 525

Pro Thr Tyr Leu Gly Ile Leu Arg Glu Pro Leu Tyr Val Tyr Asp Ile
    530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
    610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
                645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
        675                 680                 685

Thr Leu Arg Ser Ile Ala Lys Leu Leu Ser Asn Ala Leu Tyr Gly Ser
    690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735
```

```
Ser Ser Ser Phe Leu Glu Thr Asp Asn Leu Ser Ala Glu Val Met Pro
            740                 745                 750

Ala Phe Glu Arg Glu Tyr Leu Pro Gln Gln Leu Ala Leu Ala Asp Ser
        755                 760                 765

Asp Ala Glu Glu Ser Glu Asp Glu Arg Val Pro Thr Pro Phe Tyr Thr
    770                 775                 780

Pro Pro Ser Gly Thr Pro Gly His Val Ser Tyr Thr Tyr Lys Pro Ile
785                 790                 795                 800

Thr Phe Leu Asp Ala Glu Glu Gly Asp Met Cys Leu His Thr Leu Glu
                805                 810                 815

Lys Val Asp Pro Leu Val Asp Asn Asp Arg Tyr Pro Ser His Val Ala
            820                 825                 830

Ser Phe Val Leu Ala Trp Thr Arg Ala Phe Val Ser Glu Trp Ser Glu
        835                 840                 845

Phe Leu Tyr Glu Glu Asp Arg Gly Thr Pro Leu Glu Asp Arg Pro Leu
    850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
            900                 905                 910

Glu Cys Glu Thr Val Cys Ala Ser Cys Gly Ala Asp Ala Tyr Ser Pro
        915                 920                 925

Glu Ser Val Phe Leu Ala Pro Lys Leu Tyr Ala Leu Lys Ser Leu Gln
    930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
            980                 985                 990

Ser Leu Lys Arg Thr Leu Ala Ser  Ala Gln Pro Gly Ala  His Pro Phe
        995                 1000                1005

Thr Val  Thr Gln Thr Thr Leu  Thr Arg Thr Leu Arg  Pro Trp Lys
    1010                 1015                 1020

Asp Met  Thr Leu Ala Pro Leu  Asp Ala His Arg Leu  Val Pro Tyr
    1025                 1030                 1035

Ser Glu  Ser Arg Pro Asn Pro  Arg Asn Glu Glu Ile  Cys Trp Ile
    1040                 1045                 1050

Glu Met  Pro
    1055


<210> SEQ ID NO 18
<211> LENGTH: 658
<212> TYPE: PRT
<213> ORGANISM: Gorilla beringei graueri

<400> SEQUENCE: 18

Met Arg Arg Ala Ala Met Phe Glu Glu Gly Pro Pro Pro Ser Tyr Glu
1               5                   10                  15

Ser Ala Met Gly Ile Ser Pro Ala Ala Pro Leu Gln Pro Pro Tyr Val
            20                  25                  30

Pro Pro Arg Tyr Leu Gln Pro Thr Gly Gly Arg Asn Ser Ile Cys Tyr
```

```
        35                  40                  45

Ser Glu Leu Gln Pro Leu Tyr Asp Thr Thr Arg Leu Tyr Leu Val Asp
    50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
            100                 105                 110

Asp Leu Lys Thr Ile Leu His Thr Asn Met Pro Asn Val Asn Glu Phe
        115                 120                 125

Met Phe Thr Asn Ser Phe Lys Ala Arg Val Met Val Ala Arg Glu Gln
    130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
        195                 200                 205

Thr Gly Leu Val Met Pro Gly Val Tyr Thr Asn Glu Ala Phe His Pro
    210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
        275                 280                 285

Gly Asp Ser Gly Glu Ser Gly Glu Glu Gln Ala Gly Gly Gly Gly Gly
    290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
        355                 360                 365

Thr Ala Glu Ala Glu Thr Glu Val Glu Ala Glu Ala Glu Pro Glu Thr
    370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Ala Lys Thr Glu Ala Ala Ala Lys Ala Glu
            420                 425                 430

Val Glu Ala Asn Val Ala Val Glu Ala Gln Ala Glu Glu Glu Ala Ala
        435                 440                 445

Ala Glu Ala Val Lys Glu Lys Ala Gln Ala Glu Gln Glu Glu Lys Lys
    450                 455                 460
```

```
Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
        515                 520                 525

Pro Asn Met Met Gln Asp Pro Val Thr Phe Arg Ser Thr Arg Gln Val
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe


<210> SEQ ID NO 19
<211> LENGTH: 955
<212> TYPE: PRT
<213> ORGANISM: Gorilla beringei graueri

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Glu Asn Gln Val Val Ala
    130                 135                 140

Ala Asp Asp Glu Leu Glu Asp Glu Glu Ala Gln Ala Gln Glu Asp Ala
145                 150                 155                 160

Pro Ala Lys Lys Ile His Val Tyr Ala Gln Ala Pro Leu Ala Gly Glu
                165                 170                 175
```

```
Lys Ile Thr Lys Asp Gly Leu Gln Ile Gly Thr Glu Val Val Gly Asp
            180                 185                 190

Thr Ser Lys Asp Thr Phe Ala Asp Lys Thr Phe Gln Pro Glu Pro Gln
        195                 200                 205

Ile Gly Glu Ser Gln Trp Asn Glu Ala Asp Ala Thr Val Ala Gly Gly
    210                 215                 220

Arg Val Leu Lys Lys Thr Thr Pro Met Arg Pro Cys Tyr Gly Ser Tyr
225                 230                 235                 240

Ala Arg Pro Thr Asn Ala Asn Gly Gly Gln Gly Ile Met Val Ala Asn
                245                 250                 255

Glu Gln Gly Val Leu Glu Ser Lys Val Glu Met Gln Phe Phe Ser Asn
            260                 265                 270

Thr Thr Thr Leu Asn Ala Arg Asp Gly Ala Gly Asn Pro Glu Pro Lys
        275                 280                 285

Val Val Leu Tyr Ser Glu Asp Val His Leu Glu Ser Pro Asp Thr His
    290                 295                 300

Leu Ser Tyr Lys Pro Lys Lys Asp Asp Val Asn Ala Lys Ile Met Leu
305                 310                 315                 320

Gly Gln Gln Ala Met Ala Asn Arg Pro Asn Leu Ile Ala Phe Arg Asp
                325                 330                 335

Asn Phe Ile Gly Leu Met Tyr Tyr Asn Ser Thr Gly Asn Met Gly Val
            340                 345                 350

Leu Ala Gly Gln Ala Ser Gln Leu Asn Ala Val Val Asp Leu Gln Asp
        355                 360                 365

Arg Asn Thr Glu Leu Ser Tyr Gln Leu Met Leu Asp Ser Ile Gly Asp
    370                 375                 380

Arg Ser Arg Tyr Phe Ser Met Trp Asn Gln Ala Val Asp Ser Tyr Asp
385                 390                 395                 400

Pro Asp Val Arg Ile Ile Glu Asn His Gly Val Glu Asp Glu Leu Pro
                405                 410                 415

Asn Tyr Cys Phe Pro Leu Gly Gly Ile Gly Ile Thr Asp Thr Tyr Gln
            420                 425                 430

Gly Ile Lys Asn Thr Asn Gly Asn Gly Gln Trp Thr Lys Asp Asp Gln
        435                 440                 445

Phe Ala Asp Arg Asn Glu Ile Gly Val Gly Asn Asn Phe Ala Met Glu
    450                 455                 460

Ile Asn Ile Gln Ala Asn Leu Trp Arg Asn Phe Leu Tyr Ala Asn Val
465                 470                 475                 480

Gly Leu Tyr Leu Pro Asp Lys Leu Lys Tyr Asn Pro Thr Asn Val Asp
                485                 490                 495

Ile Ser Asp Asn Pro Asn Thr Tyr Asp Tyr Met Asn Lys Arg Val Val
            500                 505                 510

Ala Pro Gly Leu Val Asp Cys Phe Val Asn Val Gly Ala Arg Trp Ser
        515                 520                 525

Leu Asp Tyr Met Asp Asn Val Asn Pro Phe Asn His His Arg Asn Ala
    530                 535                 540

Gly Leu Arg Tyr Arg Ser Met Ile Leu Gly Asn Gly Arg Tyr Val Pro
545                 550                 555                 560

Phe His Ile Gln Val Pro Gln Lys Phe Phe Ala Ile Lys Asn Leu Leu
                565                 570                 575

Leu Leu Pro Gly Ser Tyr Thr Tyr Glu Trp Asn Phe Arg Lys Asp Val
            580                 585                 590
```

```
Asn Met Val Leu Gln Ser Ser Leu Gly Asn Asp Leu Arg Val Asp Gly
        595                 600                 605

Ala Ser Ile Lys Phe Asp Ser Val Thr Leu Tyr Ala Thr Phe Phe Pro
    610                 615                 620

Met Ala His Asn Thr Ala Ser Thr Leu Glu Ala Met Leu Arg Asn Asp
625                 630                 635                 640

Thr Asn Asp Gln Ser Phe Asn Asp Tyr Leu Ser Gly Ala Asn Met Leu
                645                 650                 655

Tyr Pro Ile Pro Ala Lys Ala Thr Asn Val Pro Ile Ser Ile Pro Ser
            660                 665                 670

Arg Asn Trp Ala Ala Phe Arg Gly Trp Ala Phe Thr Arg Leu Lys Thr
        675                 680                 685

Lys Glu Thr Pro Ser Leu Gly Ser Gly Phe Asp Pro Tyr Phe Val Tyr
    690                 695                 700

Ser Gly Ser Ile Pro Tyr Leu Asp Gly Thr Phe Tyr Leu Asn His Thr
705                 710                 715                 720

Phe Lys Lys Ile Ser Ile Met Tyr Asp Ser Ser Val Ser Trp Pro Gly
                725                 730                 735

Asn Asp Arg Leu Leu Thr Pro Asn Glu Phe Glu Val Lys Arg Ala Val
            740                 745                 750

Asp Gly Glu Gly Tyr Asn Val Ala Gln Cys Asn Met Thr Lys Asp Trp
        755                 760                 765

Phe Leu Val Gln Met Leu Ala Asn Tyr Asn Ile Gly Tyr Gln Gly Phe
    770                 775                 780

Tyr Ile Pro Glu Ser Tyr Lys Asp Arg Met Tyr Ser Phe Phe Arg Asn
785                 790                 795                 800

Phe Gln Pro Met Ser Arg Gln Val Val Asp Glu Thr Lys Tyr Lys Asp
                805                 810                 815

Tyr Gln Ala Ile Gly Ile Thr His Gln His Asn Asn Ser Gly Phe Val
            820                 825                 830

Gly Tyr Leu Ala Pro Thr Met Arg Glu Gly Gln Ala Tyr Pro Ala Asn
        835                 840                 845

Phe Pro Tyr Pro Leu Ile Gly Lys Thr Ala Val Asp Ser Val Thr Gln
    850                 855                 860

Lys Lys Phe Leu Cys Asp Arg Thr Leu Trp Arg Ile Pro Phe Ser Ser
865                 870                 875                 880

Asn Phe Met Ser Met Gly Ala Leu Thr Asp Leu Gly Gln Asn Leu Leu
                885                 890                 895

Tyr Ala Asn Ser Ala His Ala Leu Asp Met Thr Phe Glu Val Asp Pro
            900                 905                 910

Met Asp Glu Pro Thr Leu Leu Tyr Ile Val Phe Glu Val Phe Asp Val
        915                 920                 925

Val Arg Val His Gln Pro His Arg Gly Val Ile Glu Thr Val Tyr Leu
    930                 935                 940

Arg Thr Pro Phe Ser Ala Gly Asn Ala Thr Thr
945                 950                 955


<210> SEQ ID NO 20
<211> LENGTH: 580
<212> TYPE: PRT
<213> ORGANISM: Gorilla beringei graueri

<400> SEQUENCE: 20

Met Lys Arg Ala Arg Ser Ser Asp Glu Thr Phe Asn Pro Val Tyr Pro
1               5                   10                  15
```

-continued

```
Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
        35                  40                  45

Leu His Leu Ser Glu Pro Leu Thr Thr His Asn Gly Ala Leu Thr Leu
    50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Lys Ser Lys Asn Asn
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Ser Leu Gly Leu Ser
                165                 170                 175

Val Thr Ala Pro Leu Ser Ile Asn Asn Asp Ser Leu Gly Leu Asp Met
            180                 185                 190

Gln Ala Pro Ile Ser Ser Arg Asp Gly Lys Leu Ala Leu Thr Val Ala
        195                 200                 205

Ala Pro Leu Thr Val Val Glu Gly Ile Asn Ala Leu Ala Val Ala Thr
    210                 215                 220

Gly Lys Gly Ile Gly Leu Asn Glu Thr Asn Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asn Thr Leu Ile Leu Asp Val
            260                 265                 270

Asn Tyr Pro Phe Glu Ala Gln Gly Gln Leu Ser Leu Arg Val Gly Ser
        275                 280                 285

Gly Pro Leu Tyr Val Asp Ser Ser Ser His Asn Leu Thr Ile Arg Cys
    290                 295                 300

Leu Arg Gly Leu Tyr Ile Thr Ser Ser Asn Asn Gln Asn Gly Leu Glu
305                 310                 315                 320

Ala Asn Ile Lys Leu Thr Arg Gly Leu Val Tyr Asp Gly Asn Ala Ile
                325                 330                 335

Ala Val Asn Val Gly Lys Gly Leu Glu Tyr Ser Pro Thr Asp Thr Thr
            340                 345                 350

Glu Lys Pro Ile Gln Thr Lys Ile Gly Leu Gly Met Glu Tyr Asp Thr
        355                 360                 365

Glu Gly Ala Met Met Thr Lys Leu Gly Ser Gly Leu Ser Phe Asp Asn
    370                 375                 380

Ser Gly Ala Ile Val Val Gly Asn Lys Asn Asp Asp Arg Leu Thr Leu
385                 390                 395                 400

Trp Thr Thr Pro Asp Pro Ser Pro Asn Cys Gln Ile Tyr Ser Glu Lys
                405                 410                 415

Asp Ala Lys Leu Thr Leu Val Leu Thr Lys Cys Gly Ser Gln Val Val
            420                 425                 430
```

```
Gly Thr Val Ser Ile Ala Ala Leu Lys Gly Ser Leu Val Pro Ile Thr
        435                 440                 445

Ser Ala Ile Ser Val Val Gln Val Tyr Leu Arg Phe Asp Glu Asn Gly
    450                 455                 460

Val Leu Met Ser Asn Ser Ser Leu Asn Gly Glu Tyr Trp Asn Phe Arg
465                 470                 475                 480

Asn Gly Asp Ser Thr Asn Gly Thr Pro Tyr Thr Asn Ala Val Gly Phe
                485                 490                 495

Met Pro Asn Leu Leu Ala Tyr Pro Lys Gly Gln Thr Thr Thr Ala Lys
            500                 505                 510

Ser Asn Ile Val Ser Gln Val Tyr Met Asn Gly Asp Asp Thr Lys Pro
        515                 520                 525

Met Thr Phe Thr Ile Asn Phe Asn Gly Leu Ser Glu Thr Gly Asp Thr
    530                 535                 540

Pro Val Ser Lys Tyr Ser Met Thr Phe Ser Trp Arg Trp Pro Asn Gly
545                 550                 555                 560

Ser Tyr Ile Gly His Asn Phe Val Thr Asn Ser Phe Thr Phe Ser Tyr
                565                 570                 575

Ile Ala Gln Glu
            580


<210> SEQ ID NO 21
<211> LENGTH: 37211
<212> TYPE: DNA
<213> ORGANISM: Gorilla beringei graueri

<400> SEQUENCE: 21

catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagtgcgtaa tatttaccga gggccgaggg    360

actttgaccg attacgtgga ggactcgccc aggtgttttt tacgtgaatt tccgcgttcc    420

gggtcaaagt ctccgtttta ttgtcaccgt catttgacgc ggagggtatt taaacccgct    480

gcgctcctca agaggccact cttgagtgcc agcgagaaga gttttctcct ctgctccgct    540

tcggtgatcg aaaaatgaga cacatagcct gcactccggg tcttttgtcc ggtcgggcgg    600

cggccgagct tttggacgct ttgatcaatg atgtcctgag cgatgatttt ccgtctacta    660

cccactttag cccacctact cttcacgaac tgtacgatct ggatgtactg gtggatgtga    720

acgatcccaa cgaggaggcg gtttctgcgt tttttcccga gtctgcgctg ttggccgctc    780

aggagggatt tgacctacac actccgccgc ctattttaga gtctccgctg ccggagccca    840

gtggtatacc ttatatgcct gaactgcttc ccgaagtggt agacctgacc tgccacgagc    900

ctggctttcc gcccagcgac gatgatggtg agccttttgt tttagacttt gctgagatac    960

ctgggcacgg ttgcaggtct tgtgcatatc atcagagggt taccggagac cccgaggtta   1020

agtgttcgct gtgctatatg aggatgacct cttcctttat ctacagtaag tttttgtcta   1080

ggtgggcttt tgggtaggtg ggttttgtgt cagaacaggt gtaaacgttg cttgtgtttt   1140

ttgtacctgt aggtccggtg tccgagccag acccggagcc cgaccgcgat cccgagccgg   1200

atcccgagcc tcctcgtagg gcaagaaaat taccttctat tctgtgcaag tctaagacac   1260
```

```
ctgtgaggac cagcgaggcg gacagcaccg actctggcac ttctacctct cctcctgaaa   1320
ttcacccagt ggttcctctg ggtatacata gacctgttgc tgttagagtt tgcgggcgac   1380
gctctgcagt agagtgcatt gaggacttgc ttcacgaacc cgaggaacct ttggacttga   1440
gcgttaaacg ccctaggcaa taaaccccac ctaagtaata aaccccacct aagtaataaa   1500
ccctgccgcc cttggttatt gagatgacgc ccaatgtttg cttttgaatg acttcatgtg   1560
tgtaataaaa gtgagtgtga tcataggtct cttgtttgtc tgggcggggc ttaagggtat   1620
ataagtctct tggggctaaa cttggttaca cttgacccca atggaggcgt gggggtgctt   1680
ggaggagttt gcggacgtgc gccgtttgct ggacgagagc tctagcaata cctatactat   1740
ttggaggtat ctgtggggct ctactcaggc caagttggtc tccagaatta agcaggatta   1800
caagtgcgat tttgaagagc tttttagttc ctgcggtgag cttttgcaat ccttgaatct   1860
gggccatcag gctattttcc aggaaaaggt tctctcgact ttggattttt ccactcccgg   1920
gcgcaccgcc gcttgtgtgg cttttgtgtc ttttgtgcaa gataaatgga gcgaggagac   1980
ccacctgagt cacggctacg tactggattt catggcgatg gctctttgga gggcttacaa   2040
caaatggaag attcagaagg aactgtacgg ttccgcccta cgtcgtccac ttctgtcgcg   2100
acaggggctg aggtttcccg accatcggca gcatcagaat ctggaagacg agtcggagga   2160
gcgagcggag gagaagatca gcttgagagc cggcctggac cctcctcagg aggaatgaat   2220
ctcccgcagg tggttgacct gtttccagaa ctgagacggg tcctgactat cagggaggat   2280
ggtcagtttg tgaagaagtt taagagggat cggggtgagg gagatgatga ggcggctagc   2340
aatttagctt ttagtctgat gactcgccac cgaccggaat gtattaccta tcagcagatt   2400
aaggagagtt gtgccaacga gctggatctt ttgggtcaga agtatagcat agaacagctt   2460
accacttact ggcttcagcc tggggatgat tgggaagagg cgatcagggt gtatgcaaag   2520
gtggccctgc ggcccgattg caagtataag attactaagt tggttaatat tagaaactgc   2580
tgctatattt ctgggaacgg ggccgaagtg gagatagata ctcaggacag ggtggctttt   2640
aggtgttgca tgataaacat gtggcccggg atactgggga tggatggggt ggtattcatg   2700
aatgtgaggt ttacgggccc caactttaat ggcacggtgt tcatgggcaa caccaacttg   2760
ctcctgcatg gtgcgagttt ctatgggttt aataacacct gtatagaggc ctggaccgat   2820
gtaaaggttc gaggttgttc cttttatagc tgttggaagg cggtggtgtg tcgccctaaa   2880
agcaggggtt ctgtgaaaaa atgcttgttt gaaaggtgca ccttaggcat cctctctgag   2940
ggcaactcca gggtgcgcca taatgtggct tcgaactgcg gttgcttcat gcaagtgaag   3000
ggggtgagcg ttatcaagca taactcggtg tgtggaaact gcgaggatcg cgcctcccag   3060
atgctgacct gctttgatgg caactgtcac ctgttgaaga ccattcatat aagcagccac   3120
cccagaaagg cctggcccgt gtttgagcat aacatcttga cccgctgctc cttgcatctg   3180
ggggtcagga ggggtatgtt cctgccttac cagtgtaact ttagccacac taaaatcctg   3240
ctggaacccg agtgcatgac caaggtcagc ctgaatggtg tgtttgatgt gactctgaaa   3300
atctggaagg tgctgaggta tgatgagacc aggaccaggt gccgaccctg cgagtgcggc   3360
ggcaagcaca tgagaaatca gcctgtgatg ttggatgtga ccgaggagct taggcctgac   3420
catctggtgc tggcctgcac cagggccgag tttgggtcta gcgatgagga taccgattga   3480
ggtgggtaag gtgggcgtgg ctagaagggt ggggcgtgta taaattgggg gtctaagggt   3540
ctctctgttt tgtcttgcaa cagccgccgc catgagcgac accggcaaca gctttgatgg   3600
```

```
aagcatcttt agcccctatc tgacagtgcg catgcctcac tgggctggag tgcgtcagaa   3660
tgtgatgggt tccaacgtgg atggacgccc cgttctgcct tcaaattcgt ctacaatggc   3720
ctacgcgacc gtgggaggaa ctccgctgga cgccgcgacc tccgccgccg cctccgccgc   3780
cgccgcgacc gcgcgcagca tggctacgga cctttacagc tctttggtgg cgagcggcgc   3840
ggcctctcgc gcgtctgctc gggatgagaa actgaccgct ctgctgctta aactggaaga   3900
cttgacccgg gagctggctc aactgaccca gcaggtctcc agcttgcgtg agagcagcct   3960
tgcctccccc taatggccca taatataaat aaaagccagt ctgtttggat taagcaagtg   4020
tatgttcttt atttaactct ccgcgcgcgg taagcccggg accagcggtc tcggtcgttt   4080
agggtgcggt ggattctttc caacacgtgg tacaggtggc tctggatgtt tagatacatg   4140
ggcatgagtc catccctggg gtggaggtag caccactgca gagcttcgtg ctcgggggtg   4200
gtgttgtata tgatccagtc gtagcaggag cgctgggcgt ggtgctgaaa aatgtcctta   4260
agcaagaggc ttatagctag gggaggccc ttggtgtaag tgtttacaaa tctgctcagt   4320
tgggaggggt gcatccgggg ggatataatg tgcatcttgg actggatttt taggttggct   4380
atgttcccac ccagatccct tctgggattc atgttgtgca ggaccaccag cacggtatat   4440
ccagtacact tgggaaattt atcgtggagc ttagacggga atgcatggaa gaacttggag   4500
acgcccttgt ggcctcccag attttccata cattcgtcca tgatgatggc aatgggcccg   4560
tgggaagctg cctgagcaaa aatgtttctg ggatcgctca catcgtagtt atgttccagg   4620
gtgaggtcat cataggacat ctttacaaat cgggggcgga gggtcccgga ctgggggatg   4680
atggtgccct cgggccccgg ggcgtagttc ccctcacaga tctgcatctc ccaggctttc   4740
atttcagagg gagggatcat atccacctgc ggagcgatga aaaacacagt ttctggcgca   4800
ggggagatta actgggatga gagcaggttt ctgagcagct gtgactttcc acagccggtg   4860
ggcccatata tcacgcctat caccggctgc agctggtagt taagagagct gcagctgccg   4920
tcctcccgga gcaggggggc cacctcgttc agcatatccc tgacgtggat gttctccctg   4980
accaattccg ccagaaggcg ctcgccgccc agcgaaagca gctcttgcaa ggaagcaaaa   5040
tttttcagcg gttttaggcc gtcggccgtg ggcatgtttt tcagcgtctg ggtcagcagt   5100
tccagtctgt cccacagctc ggtgatgtgc tctacggcat ctcgatccag cagatctcct   5160
cgtttcgcgg gttggggcgg ctttcgctgt agggcaccag ccgatgggcg tccagcgggg   5220
ccagagtcat gtccttccat gggcgcaggg tcctcgtcag ggtggtctgg gtcacggtga   5280
aggggtgcgc tccgggttgg gcgctggcca gggtgcgctt gaggctggtt ctgctggtgc   5340
tgaatcgctg ccgctcttcg ccctgcgcgt cggccaggta gcatttgacc atggtctcgt   5400
agtcgagacc ctcggcggcg tgccccttgg cgcggagctt tcccttggag gtggcgccgc   5460
acgaggggca ctgcaggctc ttcagggcgt agagcttggg agcgagaaac acggactctg   5520
gggagtaggc gtccgcgccg caggaagcgc agaccgtctc gcattccacc agccaagtga   5580
gctccgggcg gtcagggtca aaaaccaggt tgccccccatg ctttttgatg cgtttcttac   5640
ctcggctctc catgaggcgg tgtcccttct cggtgacgaa gaggctgtcc gtgtctccgt   5700
agaccgactt caggggcctg tcttccagcg gagtgcctct gtcctcctcg tagagaaact   5760
ctgaccactc tgagacgaag gcccgcgtcc aggccaggac gaaggaggcc acgtgggagg   5820
ggtagcggtc gttgtccact agcgggtcca ccttctccag ggtgtgcagg cacatgtccc   5880
cctcctccgc gtccagaaaa gtgattggct tgtaggtgta ggacacgtga ccgggggttc   5940
ccgacggggg ggtataaaag gggtgggca cccttcatc ttcactctct tccgcatcgc   6000
```

```
tgtctgcgag agccagctgc tggggtaagt attccctctc gaaggcgggc atgacctcag   6060
cgctcaggtt gtcagtttct aaaaatgagg aggatttgat gttcacctgt ccggaggtga   6120
tacctttgag ggtacctggg tccatctggt cagaaaacac tatttttttg ttgtcaagct   6180
tggtggcgaa cgacccgtag agggcgttgg agagcagctt ggcgatggag cgcagggtct   6240
ggtttttgtc gcggtcggct cgctccttgg ccgcgatgtt gagttgcacg tactcgcggg   6300
ccacgcactt ccactcgggg aagacggtgg tgcgctcgtc tgggatcagg cgcaccctcc   6360
agcctcggtt gtgcagggtg accatgtcga cgctggtggc gacctcgccg cgcaggcgct   6420
cgttggtcca gcagaggcgg ccgcccttgc gcgagcagaa ggggggtagg gggtccagct   6480
ggtcctcgtt tgggggggtcc gcgtcgatgg tgaagacccc ggggagcaag cgcgggtcaa   6540
agtagtcgat cttgcaagct tgcatgtcca gagcccgctg ccattcgcgg gcggcgagcg   6600
cgcgctcgta ggggttgagg ggcgggcccc agggcatggg gtgggtgagc gcggaggcgt   6660
acatgccgca gatgtcatac acgtacaggg gttccctgag gatgccgagg taggtggggt   6720
agcagcgccc cccgcggatg ctggcgcgca cgtagtcata gagctcgtgg gaggggggcca   6780
gcatgttggg cccgaggttg gtgcgctggg ggcgctcggc gcggaaggcg atctgcctga   6840
agatggcatg ggagttggag gagatggtgg gccgctggaa gacgttgaag cttgcttctt   6900
gcaagcccac cgagtccctg acgaagcagg cgtaggactc gcgcagcttg tgcaccagct   6960
cggcggtgac ctggacgtcg agcgcgcagt agtcgagggt ctcgcggatg atgtcatact   7020
tatcctcccc cttctttttc cacagctcgc ggttgaggac gaactcttcg cggtctttcc   7080
agtactcttg gaggggaaac ccgtccgtgt ccgaacggta agagcctagc atgtagaact   7140
ggttgacggc ctggtagggg caacagccct tctccacggg cagcgcgtag gcctgcgccg   7200
ccttgcggag ggaggtgtgg gtgagggcga aagtgtccct gaccatgact ttgaggtatt   7260
gatgtttgaa gtctgtgtca tcgcagccgc cctgttccca cagggtgtag tccgtgcgct   7320
ttttggagcg cgggttgggc agggagaagg tgaggtcatt gaagaggatc ttccccgctc   7380
gaggcatgaa gtttctggtg atgcgaaagg gccctgggac cgaggagcgg ttgttgatga   7440
cctgggcggc caggacgatc tcgtcaaagc cgtttatgtt gtggcccacg atgtagagct   7500
ccaaaaagcg gggctggccc ttgatggagg ggagcttttt gagttcctcg taggtgagct   7560
cctcgggcga ttccaggccg tgctcctcca gggcccagtc ttgcaagtga gggttggccg   7620
ccaggaagga tcgccagagg tcgcgggcca tgagggtctg caggcggtcg cggaaggttc   7680
tgaactgtcg ccccacggcc atcttttcgg gggtgatgca gtagaaggtg agggggtctt   7740
tctcccaggg gtcccatctg agctctcggg cgaggtcgcg cgcggcggcg accagagcct   7800
cgttgccccc cagtttcatg accagcatga agggcacgag ctgcttgcca aaggctccca   7860
tccaagtgta ggtctctaca tcgtaggtga caaagaggcg ctccgtgcga ggatgagagc   7920
cgatcgggaa gaactggatc tcccgccacc agttggagga ttggctgttg atgtggtgaa   7980
agtagaagtc ccgtctgcgg gccgagcact cgtgctggct tttgtaaaag cgaccgcagt   8040
actggcagcg ctgcacgggt tgtatatctt gcacgaggtg aacctggcga cctctgacga   8100
ggaagcgcag cgggaatcta agtcccccgc ctggggtccc gtgtggctgg tggtcttcta   8160
ctttggttgt ctggccgcca gcatctgtct cctggagggc gatggtggag cagaccacca   8220
cgccgcgaga gccgcaggtc cagatctcgg cgctcggcgg gcggagtttg atgacgacat   8280
cgcgcacatt ggagctgtcc atggtctcca gctcccgcgg cggcaggtca gctgggagtt   8340
```

-continued

```
cctggaggtt cacctcgcag agacgggtca aggcgcgggc agtgttgaga tggtatctga   8400
tttcaagggg cgtgttggcg gcggagtcga tggcttgcag gaggccgcag ccccgggggg   8460
ccacgatggt tccccgcggg gcgcgagggg aggcggaagc tgggggtgtg ttcagaagcg   8520
gtgacgcggg cgggcccccg gaggtagggg gggttccggc cccacaggca tgggcggcag   8580
gggcacgtct tcgccgcgcg cgggcagggg ctggtgctgg ctccgaagag cgcttgcgtg   8640
cgcgacgacg cgacggttgg tgtcctgtat ctgacgcctc tgagtgaaga ccacgggtcc   8700
cgtgaccttg aacctgaaag agagttcgac agaatcaatc tcggcatcgt tgacagcggc   8760
ctggcgcagg atctcctgca cgtcgcccga gttgtcctgg taggcgatct ctgccatgaa   8820
ctgctcgatc tcttcttcct ggagatctcc tcgtccggcg cgctccacgg tggccgccag   8880
gtcgttggag atgcgaccca tgagctgcga gaaggcgttg agcccgccct cgttccagac   8940
ccggctgtag accacgcccc cctcggcgtt gcgggcgcgc atgaccacct gggccaggtt   9000
gagctccacg tgtcgcgtga agacggcgta gttgcgcagg cgctggaaaa ggtagttcag   9060
ggtggtggcg gtgtgctcgg cgacgaagaa gtacatgacc cagcgccgca acgtggattc   9120
attgatgtcc cccaaggcct ccaggcgctc catggcctcg tagaagtcca cggcgaagtt   9180
gaaaaactgg gagttgcgag cggacacggt caactcctcc tccagaagac ggatgagctc   9240
ggcgacagtg tcgcgcacct cgcgctcgaa ggccacgggg ggcgcttctt cctcttccac   9300
ctcttcttcc atgatcgctt cttcttcttc ctcagccggg acgggagggg gcggcggcgg   9360
cgggggaggg gcgcggcggc ggcggcggcg caccgggagg cggtcgatga agcgctcgat   9420
catctccccc cgcatgcggc gcatggtctc ggtgacggcg cggccgttct cccgggggcg   9480
cagctcgaag acgccgcctc tcatctcgcc gcggggcggg cggccgtgag gtagcgagac   9540
ggcgctgact atgcatctta acaattgctg tgtaggtaca ccgccgaggg acctgattga   9600
gtccagatcc accggatccg aaaacctttg gaggaaagcg tctatccagt cgcagtcgca   9660
aggtaggctg agcaccgtgg cgggcggggg cgggtctgga gagttcctgg cggagatgct   9720
gctgatgatg taattaaagt aggcggtctt gagaaggcgg atggtggaca ggagcaccat   9780
gtctttgggt ccggcctgtt ggatgcggag gcggtcggcc atgccccagg cctcgttctg   9840
acaccggcgc aggtctttgt agtagtcttg catgagtctt tccaccggca cctcttctcc   9900
ttcctcttct ccatctcgcc ggtggtttct cgcgccgccc atgcgcgtga ccccaaagcc   9960
cctgagcggc tgcagcaggg ccaggtcggc gaccacgcgc tcggccaaga tggcctgctg  10020
cacctgagtg agggtcctct cgaagtcatc catgtccacg aagcggtggt aggcgcccgt  10080
gttgatggtg taggtgcagt tggccatgac ggaccagttg acggtctggt gtcccggctg  10140
cgagagctcc gtgtaccgca ggcgcgagaa ggcgcgggaa tcgaacacgt agtcgttgca  10200
agtccgcacc agatactggt agcccaccag gaagtgcggc ggaggttggc gatagagggg  10260
ccagcgctgg gtggcggggg cgccgggcgc caggttttcc agcatgaggc ggtggtatcc  10320
gtagatgtac ctggacatcc aggtgatgcc ggcggcggtg gtggtggcgc gcgcgtagtc  10380
gcggacccgg ttccagatgt ttcgcagggg cgagaagtgt tccatggtcg gcacgctctg  10440
gccggtgagg cgcgcgcagt cgttgacgct ctatacacac acaaaaacga aagcgtttac  10500
agggctttcg ttctgtagcc tggaggaaag taaatgggtt gggttgcggt gtgccccggt  10560
tcgagaccaa gctgagctcg gccggctgaa gccgcagcta acgtggtatt ggcagtcccg  10620
tctcgaccca ggccctgtat cctccaggat acggtcgaga gcccttttgc tttcttggcc  10680
aagcgcccgt ggcgcgatct gggatagatg gtcgcgatga gaggacaaaa gcggctcgct  10740
```

```
tccgtagtct ggagaaacaa tcgccagggt tgcgttgcgg cgtaccccgg ttcgagcccc  10800
tatggcggct tgaatcggcc ggaaccgcgg ctaacgaggg ccgtggcagc cccgtcctca  10860
ggaccccgcc agccgacttc tccagttacg ggagcgagcc ccttttgttt tttatttttt  10920
agatgcatcc cgtgctgcgg cagatgcgcc cctcgccccg gcccgatcag cagcagcaac  10980
agcaggcatg cagacccccc tctccccttt ccgccccggt caccacggcc gcggcggccg  11040
tgtcgggcgc ggggggcgcg ctggagtcag atgagccacc gcggcggcga cctaggcagt  11100
atctggactt ggaagagggc gagggactgg cgcggctggg ggcgaactct ccagagcgcc  11160
acccgcgggt gcagttgaaa agggacgcgc gcgaggcgta cctgccgcgg cagaacctgt  11220
ttcgcgaccg cgggggcgag gagcccgagg agatgcgaga ctgcaggttc caagcggggc  11280
gcgagctgcg gcgcgggctg gacagacagc gcctgctgcg cgaggaggac tttgagcccg  11340
acacgcagac gggcatcagc cccgcgcgcg cgcacgtagc cgcggccgac ctggtgaccg  11400
cctacgagca gacggtgaac caggagcgca acttccaaaa gagcttcaac aaccacgtgc  11460
gcacgctggt ggcgcgcgag gaggtgaccc tgggtctcat gcatctgtgg gacctggtgg  11520
aggcgatcgt gcagaacccc agcagcaagc ccctgaccgc gcagctgttc ctggtggtgc  11580
agcacagcag ggacaacgag gccttcaggg aggcgctgct gaacatcacc gagccggagg  11640
ggcgctggct cctggacctg ataaacatcc tgcagagcat agtggtgcag gagcgcagcc  11700
tgagcctggc cgagaaggtg gcggccatca actactctat gctgagcctg ggcaagttct  11760
acgcccgcaa gatctacaag acccccctacg tgcccataga caaggaggtg aagatagaca  11820
gcttctacat gcgcatggcg ctgaaggtgc tgaccctgag cgacgacctg ggagtgtacc  11880
gcaacgagcg catccacaag gccgtgagcg ccagccggcg gcgcgagctg agcgaccgcg  11940
agctgatgca cagtctgcag cgcgcgctga ccggcgcggg cgagggcgac agggaggtcg  12000
agtcctactt cgacatgggg gccgacctgc actggcagcc gagccgccgc gccctggagg  12060
cggcgggggc gtacggcggc cccctggcgg ccgatgacca ggaagaggag gactatgagc  12120
tagaggaggg cgagtacctg gaggactgac ctggctggtg gtgttttggt atagatgcaa  12180
gatccgaacg tggcggaccc ggcggtccgg gcggcgctgc aaagccagcc gtccggcatt  12240
aactcctctg acgactgggc cgcggccatg ggtcgcatca tggccctgac cgcgcgcaac  12300
cccgaggctt tcaggcagca gcctcaggcc aaccggctgg cggccatctt ggaagcggta  12360
gtgcccgcgc gctccaaccc cacccacgag aaggtgctgg ccatagtcaa cgcgctggcg  12420
gagagcaggg ccatccgcgc ggacgaggcc ggactggtgt acgatgcgct gctgcagcgg  12480
gtggcgcggt acaacagcgg caacgtgcag accaacctgg accgcctggt gacggacgtg  12540
cgcgaggccg tggcgcagcg cgagcgcttg catcaggacg gtaacctggg ctcgctggtg  12600
gcgctaaacg ccttcctcag cacccagccg gccaacgtac cgcgggggca ggaggactac  12660
accaactttt tgagcgcgct gcggctgatg gtgaccgagg tccctcagag cgaggtgtac  12720
cagtcggggc ccgactactt cttccagacc agcagacagg gcttgcaaac cgtgaacctg  12780
agccaggctt tcaagaacct gcgggggctg tggggagtga aggcgcccac cggcgaccgg  12840
gctacggtgt ccagcctgct aacccccaac tcgcgcctgc tgctgctgct gatcgcgccc  12900
ttcacggaca gcgggagcgt ctcgcgggag acctatctgg gccacctgct gacgctgtac  12960
cgcgaggcca tcgggcaggc gcaggtggac gagcacacct tccaagagat caccagcgtg  13020
agccacgcgc tggggcagga ggacacgggc agcctgcagg cgaccctgaa ctacctgctg  13080
```

```
accaacaggc ggcagaagat tcccacgctg cacagcctga cccaggagga ggagcgcatc  13140
ttgcgctacg tgcagcagag cgtgagcctg aacctgatgc gcgacggcgt gacgcccagc  13200
gtggcgctgg acatgaccgc gcgcaacatg gaaccgggca tgtacgcctc ccaccggccg  13260
ttcatcaacc gcctgatgga ctacttgcat cgggcggcgg ccgtgaaccc cgagtacttc  13320
actaatgcca ttctgaatcc ccactggatg ccccctccgg gtttctacaa cggggacttt  13380
gaggtgcccg aggtcaacga cgggttcctc tgggatgaca tggatgacag tgtgttctca  13440
cccaacccgc tgcgcgccgc gtctctgcga ttgaaggagg gctctgacag ggaaggaccg  13500
agaagtctgg cctcctccct ggctctggga gcggtgggcg ccacgggcgc ggcggcgcgg  13560
ggcagtagcc ccttccccag cctggcagac tctctgaaca gcgggcgggt gagcaggccc  13620
cgcttgctag gcgaggagga gtatctgaac aactccctgc tgcagcccgc gagggacaag  13680
aacgctcagc ggcagcagtt tcccaacaat gggatagaga gcctggtgga caagatgtcc  13740
agatggaaga cgtatgcgca ggagtacaag gagtgggagg accgccagcc gcggcccttg  13800
ccgcccccta ggcagcgctg gcagcggcgc gcgtccaacc gccgctggag gcaggggccc  13860
gaggacgatg atgactctgc agatgacagc agcgtgttgg acctgggcgg gagcgggaac  13920
cccttttcgc acctgcgccc acgcctgggc aagatgtttt aaaagaaaaa aaaaaaataa  13980
aactcaccaa ggccatggcg acgagcgttg gttttttgtt cccttcctta gtatgcggcg  14040
cgcggcgatg ttcgaggagg ggcctccccc ctcttacgag agcgcgatgg ggatttctcc  14100
tgcggcgccc ctgcagcctc cctacgtgcc tcctcggtac ctgcaaccta caggggggag  14160
aaatagcatc tgttactctg agctgcagcc cctgtacgat accaccagac tgtacctggt  14220
ggacaacaag tccgcggacg tggcctccct gaactaccag aacgaccaca gcgatttttt  14280
gaccacggtg atccaaaaca acgacttcac ccccaaccgag gccagcactc agaccataaa  14340
cctggataac aggtcgaact ggggcggcga cctgaagacc atcttgcaca ccaacatgcc  14400
caacgtgaac gagttcatgt tcaccaactc ttttaaggcg cgggtgatgg tggcgcgcga  14460
gcagggggag gcgaagtacg agtgggtgga cttcacgctg cccgagggca actactcaga  14520
gaccatgact ctcgacctga tgaacaatgc gatcgtggaa cactatctga aagtgggcag  14580
gcagaacggg gtgaaggaaa gcgatatcgg ggtcaagttt gacaccagaa acttccgtct  14640
gggctgggac cccgtgaccg ggctggtcat gccgggggtc tacaccaacg aggcctttca  14700
tcccgacata gtgcttctgc ccggctgtgg ggtggacttc acccagagcc ggctgagcaa  14760
cctgctgggc attcgcaagc ggcagccttt ccaggagggt ttcaagatca cctatgagga  14820
tctgaagggg ggcaacattc ccgcgctcct tgatctggac gcctacgagg agagcttgaa  14880
acccgaggag agcgctggcg acagcggcga gagtggcgag gagcaagccg gcggcggtgg  14940
cggcgcgtcg gtagaaaacg aaagtacgcc cgcagtggcg gcggacgctg cggaggtcga  15000
gccggaggcc atgcagcagg acgcagagga gggcgcacag gagggcgcgc agaaggacat  15060
gaacgatggg gagatcaggg gagacacatt cgccacccgg ggcgaagaaa aagaggcaga  15120
ggcggcggcg gcggcgacgg cggaggccga aaccgaggtt gaggcagagg cagagcccga  15180
gaccgaagtt atggaagaca tgaatgatgg agaacgtagg ggcgacacgt tcgccacccg  15240
gggcgaagag aaggcggcgg aggcagaagc cgcggctgag gaggcggctg cggctgcggc  15300
caagactgag gctgcggcta aggctgaggt cgaagccaat gttgcggttg aggctcaggc  15360
tgaggaggag gcggcggctg aagcagttaa ggaaaaggcc caggcagagc aggaagagaa  15420
aaaacctgtc attcaacctc taaaagaaga tagcaaaaag cgcagttaca acgtcatcga  15480
```

gggcagcacc tttacccagt accgcagctg gtacctggcg tacaactacg gcgacccggt 15540
caagggggtg cgctcgtgga ccctgctctg cacgccggac gtcacctgcg gctccgagca 15600
gatgtactgg tcgctgccga acatgatgca agacccggtg accttccgct ccacgcggca 15660
ggttagcaac ttcccggtgg tgggcgccga actgctgccc gtgcactcca agagttttta 15720
caacgagcag gccgtctact cccagctgat ccgccaggcc acctctctga cccacgtgtt 15780
caatcgcttt cccgagaacc agattttggc gcgcccgccg gcccccacca tcaccaccgt 15840
gagtgaaaac gttcctgccc tcacagatca cgggacgcta ccgctgcgca acagcatctc 15900
aggagtccag cgagtgacca ttactgacgc cagacgccgg acctgcccct acgtttacaa 15960
ggccttgggc atagtctcgc cgcgcgtcct ctccagtcgc actttttaaa acacatctac 16020
ccacacgttc caaaatcatg tccgtactca tctcacccag caacaacacc ggctgggggc 16080
tgcgcgcgcc cagcaagatg tttggagggg cgaggaagcg ctccgaccag caccctgtgc 16140
gcgtgcgcgg ccactaccgc gcgccctggg gagcgcacaa gcgcgggcgc acagggcgca 16200
ccactgtgga cgacgtcatt gactccgtag tggagcaagc gcgccactac acacccggcg 16260
cgccgaccgc ccccgccgtg tccaccgtgg accaggcgat cgaaagcgtg gtacagggcg 16320
cgcggcacta tgccaacctt aaaagtcgcc gccgccgcgt ggcccgccgc catcgccgga 16380
gaccccgggc caccgccgcc gcgcgcctta ctaaggctct gctcaggcgc gccaggcgaa 16440
ctggccaccg ggccgccatg agggccgcac ggcgggctgc cgctgccgca agcgccgtgg 16500
ccccgcgggc acgaaggcgc gcggccgccg ccgccgccgc cgccatttcc agcttggcct 16560
cgacgcggcg cggtaacata tactgggtgc gcgactcggt aaccggcacg cgggtacccg 16620
tgcgctttcg ccccccgcgg aattagcaca agacaacata cacactgagt ctcctgctgt 16680
tgtgtatccc agcggcgacc gtcagcagcg gcgacatgtc caagcgcaaa attaaagaag 16740
agatgctcca ggtcatcgcg ccggagatct atgggccccc gaagaaggag gaggatgatt 16800
acaagccccg caagctaaag cgggtcaaaa agaaaaagaa agatgatgat gatgacgagg 16860
cggtggagtt tgtccgccgc atggcaccca ggcgccccgt gcagtggaag ggccggcgcg 16920
tgcagcgcgt tttgcgcccc ggcaccgcgg tggtcttcac gcccggcgag cgctccacgc 16980
gcactttcaa gcgggtgtac gatgaggtgt acggcgacga ggacctgttg gagcaggcca 17040
accagcgctt tggggagttt gcatatggga aacggccccg cgagagtcta aaagaggacc 17100
tgctggcgct accgctggac gagggcaatc ccaccccgag tctgaagccg gtaaccctgc 17160
aacaggtgct gcctttgagc gcgcccagcg agcataagcg agggttgaag cgcgaaggcg 17220
gggacctggc gcccaccgtg cagttgatgg tgcccaagcg gcagaagctg gaggacgtgc 17280
tggagaaaat gaaagtagag cccgggatcc agcccgagat caaggtccgc cccatcaagc 17340
aggtggcgcc cggcgtggga gtccagaccg tggacgttag gattcccacg gaggagatgg 17400
aaacccaaac cgccactccc tcttcggcgg ccagcgccac caccggcacc gcttcggtag 17460
aggtgcagac ggacccctgg ctacccgcca ccgctgttgc cgccgccgcc ccccgttcgc 17520
gcgggcgcaa gagaaattat ccagcggcca gcgcgctcat gccccagtac gcactgcatc 17580
catccatcgc gcccaccccc ggctaccgcg ggtactcgta ccgcccgcgc agatcagccg 17640
gcactcgcgg ccgccgccgc cgtgcgacca caaccagccg ccgccgtcgc cgccgccgcc 17700
agccagtgct gacccccgtg tctgtaagga aggtggctcg ctcggggagc acgctggtgg 17760
tgcccagagc gcgctaccac cccagcatcg tttaaagccg gtctctgtat ggttcttgca 17820

```
gatatggccc tcacttgtcg cctccgcttc ccggtgccgg gataccgagg aagaactcac  17880
cgccgcagag gcatggcggg cagcggtctc cgcggcggcc gtcgccatcg ccggcgcgca  17940
aaaagcaggc gcatgcgcgg cggtgtgctg cctctgctaa tcccgctaat cgccgcggcg  18000
atcggtgccg tacccgggat cgcctccgtg gccctgcagg cgtcccagaa acgttgactc  18060
ttgcaacctt gcaagcttgc atttttgga ggaaaaataa aaaaagtcta gactctcacg  18120
ctcgcttggt cctgtgacta ttttgtagaa aaaagatgga agacatcaac tttgcgtcgc  18180
tggccccgcg tcacggctcg cgcccgttca tgggagactg gacagatatc ggcaccagca  18240
atatgagcgg tggcgccttc agctggggca gtctgtggag cggccttaaa aattttggtt  18300
ccaccattaa gaactatggc aacaaagcgt ggaacagcag cacgggccag atgctgagag  18360
acaagttgaa agagcagaac ttccaggaga aggtggcgca gggcctggcc tctggcatca  18420
gcggggtggt ggacatagct aaccaggccg tgcagaaaaa gataaacagt catctggacc  18480
cccgtcctca ggtggaggaa atgcctccag cgatggagac ggtgtctccc gagggcaaag  18540
gcgaaaagcg cccgcggccc gacagagaag agaccctggt gtcacacacc gaggagccgc  18600
cctcttacga ggaggcagtc aaggccggcc tgcccaccac tcgccccata gcccccatgg  18660
ccaccggtgt ggtgggccac aggcaacaca ctcccgcaac actagatctg cccccgccgt  18720
ccgagccgcc gcgccagcca aaggcggcga cggtgcccgc tccctccact tccgccgcca  18780
acagagtgcc cctgcgccgc gccgcgagcg gcccccgggc ctcgcgagtt agcggcaact  18840
ggcagagcac actgaacagc atcgtgggcc tgggagtgag gagtgtgaag cgccgccgtt  18900
gctactgaat gagcaagcta gctaacgtgt tgtatgtgtg tatgcgtcct atgtcgccgc  18960
cagaggagct gttgagccgc cggcgccgtc tgcactccag cgaatttcaa gatggcgacc  19020
ccatcgatga tgcctcagtg gtcgtacatg cacatctcgg gccaggacgc ttcggagtac  19080
ctgagccccg ggctggtgca gttcgcccgc gccacagaca cctacttcaa catgagtaac  19140
aagttcagga accccactgt ggcgcccacc cacgatgtga ccacggaccg gtcgcagcgc  19200
ctgacgctgc ggttcatccc cgtggatcgg gaggacaccg cctactctta caaggcgcgg  19260
ttcacgctgg ccgtgggcga caaccgcgtg ctggacatgg cctccactta ctttgacatc  19320
aggggggtgc tggacagggg ccccaccttc aagccctact cgggtactgc ctacaactcc  19380
ctggccccca agggcgctcc caattcttgc gagtgggaac aagaggaaaa tcaggtggtc  19440
gctgcagatg atgaacttga agatgaagaa gcgcaagctc aagaggacgc cccagctaaa  19500
aaaattcatg tatatgccca ggcgcctctt gctggcgaaa agattaccaa ggatggtttg  19560
caaataggta ctgaagttgt aggagataca tctaaggaca cttttgcaga caaaaacattc  19620
caacccgaac ctcagatagg cgagtctcag tggaacgagg ctgatgccac agtagcagga  19680
ggcagagtct tgaaaaaaac cacccctatg agaccttgct atggatccta tgccaggcct  19740
acaaatgcca acgggggtca aggaattatg gttgccaatg aacaaggagt gttggagtct  19800
aaagtggaga tgcaattttt ttctaacact acaaccctta atgcgcggga tggagctggc  19860
aatcccgaac caaaggtggt gttgtacagt gaagatgtcc acttggaatc tcctgacact  19920
catttgtctt acaagcccaa aaaggatgat gttaatgcta aaattatgtt gggtcagcaa  19980
gctatggcta acaggcccaa cctcattgct tttagagata atttcattgg actcatgtac  20040
tacaacagca ctggtaacat gggagtgctg gcgggtcagg cctctcagtt gaatgccgtg  20100
gtggacctgc aggatagaaa cacagaactg tcatatcagc ttatgcttga ttccattggg  20160
gatagatcca gatacttctc catgtggaac caggcagtgg atagctatga cccagatgtc  20220
```

```
agaatcattg aaaaccatgg tgtcgaggac gagctaccca actactgctt ccctctgggc  20280
ggcataggaa ttactgatac ttatcaaggg atcaaaaata ccaatggcaa tggtcagtgg  20340
accaaagatg atcagttcgc ggaccgtaat gaaatagggg tgggaaacaa cttcgccatg  20400
gagatcaaca tccaggccaa cctctggagg aacttcctct atgcgaacgt ggggctctac  20460
ctgccagaca agctcaagta caaccccacc aacgtggaca tctctgacaa ccccaacacc  20520
tatgactaca tgaacaagcg tgtggtggct cccggcctgg tggactgctt tgtcaatgtg  20580
ggagccaggt ggtccctgga ctacatggac aacgtcaacc ccttcaacca ccaccgcaat  20640
gcgggtctgc gctaccgctc catgatcctg ggcaacgggc gctacgtgcc cttccacatt  20700
caggtgcccc agaagttctt tgccatcaag aacctcctcc tcctgccggg ctcctacact  20760
tacgagtgga acttcaggaa ggatgtcaac atggtcctgc agagctctct gggcaatgac  20820
cttagggtgg acggggccag catcaagttt gacagcgtca ccctctatgc taccttcttc  20880
cccatggctc acaacaccgc ctccacgctc gaggccatgc tgaggaacga caccaacgac  20940
cagtccttca atgactacct ctctggggcc aacatgctct accccatccc cgccaaggcc  21000
accaacgtgc ccatctccat tccctctcgc aactgggccg ccttcagagg ctgggccttt  21060
acccgcctta agaccaagga aacccctcc ctgggctcgg gttttgaccc ctactttgtc  21120
tactcgggat ccatccccta cctggatggc accttctacc tcaaccacac ttttaagaag  21180
atatccatca tgtatgactc ctccgtcagc tggccgggca atgaccgcct gctcaccccc  21240
aatgagttcg aggtcaagcg cgccgtggac ggcgagggct acaacgtggc ccagtgcaac  21300
atgaccaagg actggttcct ggtgcagatg ctggccaact acaacatagg ctaccagggc  21360
ttctacatcc cagagagcta caaggacagg atgtactcct tcttcagaaa tttccaaccc  21420
atgagcaggc aggtggtgga cgagaccaaa tacaaggact atcaggccat tggcatcact  21480
caccagcaca acaactcggg attcgtgggc tacctggctc ccaccatgcg cgaggggcag  21540
gcctaccccg ccaacttccc ctacccgttg ataggcaaga ccgcggtcga cagcgtcacc  21600
cagaaaaagt tcctctgcga ccgcaccctc tggcgcatcc ccttctctag caacttcatg  21660
tccatgggtg cgctcacgga cctgggccag aacctgctct atgccaactc cgcccatgcg  21720
ctggacatga cttttgaggt ggaccccatg gacgagccca cccttctcta tattgtgttt  21780
gaagtgttcg acgtggtcag agtgcaccag ccgcaccgcg gtgtcatcga gaccgtgtac  21840
ctgcgcacgc ccttctcggc cggcaacgcc accacctaag gagacagcgc cgccgcctgc  21900
atgacgggtt ccaccgagca agagctcagg gccatcgcca gagacctggg atgcggaccc  21960
tatttttggg gcacctatga caaacgcttc ccgggcttca tctcccgaga caagctcgcc  22020
tgcgccatcg tcaacacggc cgcgcgcgag accgggggcg tgcactggct ggcctttggc  22080
tgggacccgc gctccaaaac ctgctacctc ttcgacccct ttggcttctc cgatcagcgc  22140
ctcagacaga tctatgagtt tgagtacgag ggctgctgc gccgcagcgc gcttgcctcc  22200
tcgcccgacc gctgcatcac ccttgagaag tccaccgaga ccgtgcaggg gccccactcg  22260
gccgcctgcg gtctcttctg ctgcatgttt ttgcacgcct ttgtgcgctg gccccagagt  22320
cccatggatc gcaaccccac catgaacttg ctcaagggag tgcccaacgc catgctccag  22380
agcccccagg tccagcccac cctgcgccac aaccaggaac agctctaccg cttcctggag  22440
cgccactccc cctacttccg cagtcacagc gcgcacatcc ggggggccac ctctttctgc  22500
cacttgcaac aaaacatgca agacggaaaa tgatgtacag ctcgcttttt aataaatgta  22560
```

```
aagactgtgc actttattta tacacgggct ctttctggtt atttattcaa caccgccgtc  22620
gccatctaga aatcgaaagg gttctgccgc gcgtcgccgt gcgccacggg cagagacacg  22680
ttgcgatact ggaagcggct cgcccacttg aactcgggca ccaccatgcg gggcagtggc  22740
tcctcgggga agttctcgcc ccacagggtg cgggtcagct gcagcgcgct caggaggtcg  22800
ggagccgaga tcttgaagtc gcagttgggg ccggaaccct gcgcgcgcga gttgcggtac  22860
acggggttgc agcactggaa caccagcagg gccggattac gcacgctggc cagcaggctc  22920
tcgtcgctga tcatgtcgct gtccagatcc tccgcgttgc tcagggcgaa tggggtcatc  22980
ttgcagacct gcctgcccag gaaaggcggc agcccgggct tgccgttgca gtcgcagcgc  23040
aggggcatca gcaggtgccc gtggcccgtc tgcgcctgcg ggtacagcgc gcgcatgaag  23100
gcttcgatct gcctgaaagc cacctgcgtc ttggctccct ccgaaaagaa catcccacag  23160
gacttgctgg agaactggtt cgcgggacag ctggcatcgt gcaggcagca gcgcgcgtcg  23220
gtgttggcga tctgcaccac gttgcgaccc caccggttct tcactatctt ggccttggaa  23280
gcctgctcct tcagcgcgcg ctggccgttc tcgctggtca catccatctc tatcacctgc  23340
tccttgttga tcatgtttgt cccgtgcaga cacttcaggt cgccctccgt ctgggtgcag  23400
cggtgctccc acagcgcgca accggtgggc tcccaatttt tgtgggtcac ccccgcgtag  23460
gcctgcaggt aggcctgcaa gaagcgcccc atcatggcca caaaggtctt ctggctcgta  23520
aaggtcagct gcaggccgcg atgctcttcg ttcagccagg tcttgcagat ggcggccagc  23580
gcctcggtct gctcgggcag catcctaaaa tttgtcttca ggtcgttatc cacgtggtac  23640
ttgtccatca tggcgcgcgc cgcctccatg cccttctccc aggcggacac catgggcagg  23700
cttagggggt ttatcacttc caccggcgag gacaccgtac tttcgatttc ttcttcctcc  23760
ccctcttccc ggcgcgcgcc cacgctgctg cgcgctctca ccgcctgcac caaggggtcg  23820
tcttcaggca agcgccgcac cgagcgcttg ccgcccttga cctgcttaat cagcaccggc  23880
gggttgctga agcccaccat ggtcagctcc gcctgctctt cttcgtcttc gctgtctacc  23940
actatctctg gggaagggct tctccgctct gcggcggtgc gcttcttttt tttcttggga  24000
gcagccgtga cggagtccgc cacggcgacg gaggtcgagg gcgtggggct gggggtgcgc  24060
ggtaccaggg cctcgtcgcc ctcggactct tcctctgact ccaggcggcg gcggagacgc  24120
ttctttgggg gcgcgcgcgt cagcggcggc ggagacgggg acggggacgg ggacgggacg  24180
ccctccacag gggtggtctt cgcgcagacc ccgcggccgc gctcgggggt cttttcgagc  24240
tggtcttggt cccgactggc cattgtatcc tcctcctcct aggcagagag acataaggag  24300
tctatcatgc aagtcgagaa ggaggagagc ttaaccaccc cctctgagac cgccgatgcg  24360
cccgccgtcg ccgtcgcccc cgctgccgcc gacgcgcccg ccacaccgag cgacaccccc  24420
gcggaccccc cagccgacgc acccctgttc gaggaagcgg ccgtggagca ggacccgggc  24480
tttgtctcgg cagaggagga tttgcgagag gaggaggata aggagaagaa gccctcagtg  24540
ccaaaagatg ataaagagca agacgagcac gacgcagatg cacaccaggg tgaagtcggg  24600
cggggggacg gagggcatga cggcgccgac tacctagacg aagggaacga cgtgctcttg  24660
aagcacctgc atcgtcagtg cgccatcgtt tgcgacgctc tgcaggagcg cagcgaagtg  24720
cccctcagcg tggcggaggt cagccacgcc tacgagctca gcctcttctc ccccccgggtg  24780
cccccccgcc gccgcgaaaa cggcacatgc gagcccaacc cgcgcctcaa cttctacccc  24840
gcctttgtgg tgcccgaggt cctggccacc tatcacatct tctttcaaaa ttgcaagatc  24900
cccctctcgt gccgcgccaa ccgtagccgc gccgataaga tgctggccct gcgccagggc  24960
```

```
gaccacatac ctgatatcgc cgctttggaa gatgtgccaa agatcttcga gggtctgggt  25020
cgcaacgaga agcgggcagc aaactctctg caacaggaaa acagcgaaaa tgagagtcac  25080
accggggtac tggtggagct cgagggcgac aacgcccgcc tggcggtggt caagcgcagc  25140
atcgaggtca cccactttgc ctaccccgcg ctcaacctgc cccccaaagt catgaacgcg  25200
gccatggacg ggctgatcat gcgccgcggc cggcccctcg ctccagatgc aaacttgcat  25260
gaggagaccg aggacggcca gcccgtggtc agcgacgagc agctggcgcg ctggctggag  25320
accgcggacc ccgccgaact ggaggagcgg cgcaagatga tgatggccgc ggtgctggtc  25380
accgtagagc tggagtgtct gcagcgcttc ttcggcgacc ccgagatgca gagaaaggtc  25440
gaggagaccc tgcactacac cttccgccag ggctacgtgc gccaggcttg caagatctcc  25500
aacgtggagc tcagcaacct ggtgtcctac ctgggcatct tgcatgagaa ccgcctcggg  25560
cagagcgtgc tgcactccac cctgcgcggg gaggcgcgcc gcgactacgt gcgcgactgc  25620
gtttacctct tcctctgcta cacctggcag acggccatgg gggtctggca gcagtgcctg  25680
gaggagcgca acctcaagga gctggagaag ctcctgcagc gcgcgctcaa agacctctgg  25740
acgggctaca acgagcgctc ggtggccgcc gcgctggccg acctcatctt ccccgagcgc  25800
ctgctcaaaa ccctccagca ggggctgccc gacttcacca gccaaagcat gttgcaaaac  25860
ttcaggaact ttatcctgga gcgttctggc atcctacccg ccacctgctg cgccctgccc  25920
agcgactttg tcccccctcgt gtaccgcgag tgcccccgc cgctgtgggg tcactgctac  25980
ctgttccaac tggccaacta cctgtcctac cacgcggacc tcatggagga ctccagcggc  26040
gaggggctca tggagtgcca ctgccgctgc aacctctgca cgccccaccg ctccctggtc  26100
tgcaacaccc aactgctcag cgagagtcag attatcggta ccttcgagct acagggtccg  26160
tcctcctcag acgagaagtc cgcggctccg gggctaaaac tcactccggg gctgtggact  26220
tccgcctacc tgcgcaaatt tgtacctgaa gactaccacg cccacgagat caggttttac  26280
gaagaccaat cccgcccgcc caaggcggag ctgaccgcct gcgtcatcac ccagggcgag  26340
atcctaggcc aattgcaagc catccaaaaa gcccgccaag attttttgct gagaaagggt  26400
cggggggtgt atctggaccc ccagtcgggt gaggagctca acccggttcc cccgctgccg  26460
ccgccgcggg accttgcttc ccaggataag catcgccatg gctcccagaa agaagcagca  26520
gcggccgcca ctgccgccac ccccacatgct ggaggaagag gaggaatact gggacagtca  26580
ggcagaggag gtttcggacg aggaggagcc ggagacggag atggaagagt gggaggagga  26640
cagcttagac gaggaggctt ccgaagccga agaggcagac gcaacaccgt caccctcggc  26700
cgcagccccc tcgcaggcgc ccccgaagtc cgctcccagc atcagcagca acagcagcgc  26760
tataacctcc gctcctccac cgccgcgacc cacggccgac cgcagaccca accgtagatg  26820
ggacaccacc ggaaccgggg ccggtaagtc ctccgggaga ggcaagcaag cgcagcgcca  26880
aggctaccgc tcgtggcgcg ctcacaagaa cgccatagtc gcttgcttgc aagactgcgg  26940
ggggaacatc tccttcgccc gccgcttcct gctcttccac cacggtgtgg ccttcccccg  27000
taacgtcctg cattactacc gtcatctcta cagcccctac tgcggcggca gtgagccaga  27060
gacggtcggc ggcggcggcg gcgcccgttt cggcgcctag gaagacccag ggcaagactt  27120
cagccaagaa actcgcggcg gccgcggcga acgcggtcgc gggggccctg cgcctgacgg  27180
tgaacgaacc cctgtcgacc cgcgaactga gaaaccgaat cttccccact ctctatgcca  27240
tcttccagca gagcagaggg caggatcagg aactgaaagt aaaaaacagg tctctgcgct  27300
```

```
ccctcacccg cagctgtctg tatcacaaga gcgaagacca gcttcggcgc acgctggagg  27360
acgctgaggc actcttcagc aaatactgcg cgctcactct taaggactag ctccgcgccc  27420
ttctcgaatt taggcgggaa cgcctacgtc atcgcagcgc cgccgtcatg agcaaggaca  27480
ttcccacgcc atacatgtgg agctatcagc cgcagatggg actcgcggcg ggcgcctccc  27540
aagactactc cacccgcatg aactggctca gtgccggccc acacatgatc tcacaggtta  27600
atgatatccg cacccatcga aaccaaatat tggtggagca ggcggcaatt accaccacgc  27660
cccgcaataa tcccaacccc agggagtggc ccgcgtccct ggtgtatcag gaaattcccg  27720
gccccaccac cgtactactt ccgcgtgatt cccaggccga agtccaaatg actaactcag  27780
gggcgcagct cgcgggcggc tgtcgtcaca gggtgcggcc tcctcgccag ggtataactc  27840
acctggagat ccgaggcaga ggtattcagc tcaacgacga gtcggtgagc tcctcgctcg  27900
gtctaagacc tgacgggacc ttccagatag ccggagccgg ccgatcttcc ttcacgcccc  27960
gccaggcgta cctgactctg cagagctcgt cctcggcgcc gcgctcgggc ggcatcggga  28020
ctctccagtt cgtgcaggag tttgtgccct cggtctactt caaccccttc tcgggctctc  28080
ccggtcgcta cccggaccag ttcatctcga actttgacgc cgcgagggac tcggtggacg  28140
gctacgactg aatgtcgggt ggacccggtg cagagcaact tcgcctgaag cacctcgacc  28200
actgccgccg ccctcagtgc tttgcccgct gtcagaccgg tgagttccag tacttttccc  28260
tgcccgactc gcacccggac ggcccggcgc acggggtgcg ctttttcatc ccgagtcagg  28320
tgcgctctac cctaatcagg gagtttaccg cccgtcccct actggcggag ttggaaaagg  28380
ggccttctat cctaaccatt gcctgcatct gctctaaccc tggattgcac caagatcttt  28440
gctgtcattt gtgtgctgag tataataaag gctgagatca gaatctactc gggctcctgt  28500
cgccatcctg tcaacgccac cgtccaagcc cggcccgatc agcccgaggt gaacctcacc  28560
tgcggtctgc accggcgcct gaggaaatac ctagcttggt actacaacag cactcccttt  28620
gtggtttaca acagctttga ccaggacggg gtctcactga gggataacct ctcgaacctg  28680
agctactcca tcaggaagaa cagcaccctc gagctacttc ctccttacct gcccgggact  28740
taccagtgtg tcaccggtcc ctgcacccac acccacctgt tgatcgtaaa cgactctctt  28800
ccgagaacag acctcaataa ctcctcttcg cagttcccca gaacaggagg tgagctcagg  28860
aaaccccggg taaagaaggg tggacaagag ttaacacttg tggggtttct ggtgtatgtg  28920
acgctggtgg tggctctttt gattaaggct tttccttcca tgtctgaact ctccctcttt  28980
tatgaacaac tcgactagtg ctaacgggac cctacccaac gaatcgggat tgaatatcgg  29040
taaccaggtt gcagtttcac ttttgattac cttcatagtc ctcttcctgc tagtgctgtc  29100
gcttctgtgc ctgcggatcg gggctgctg catccacgtt tatatctggt gctggctgtt  29160
tagaaggttc ggagaccatc gcaggtagaa taaacatgct gctgcttacc ctctttgtcc  29220
tggcgctggc cgccagctgc caagcctttt ccgaggctga ctttatagag ccccagtgta  29280
acgtgacttt taaagcccat gcacagcgtt gtcatactat aatcaaatgt gccaccgaac  29340
acgatgaata ccttatccag tataaagata aatcacacaa agtggcactt gttgacatct  29400
ggaaacccga agaccctttg gaatacaatg tgaccgtttt ccagggtgac ctcttcaaaa  29460
tttacaatta cactttccca tttgaccaga tgtgtgactt tgtcatgtac atggaaaagc  29520
agcacaagct gtggcctccg actccccagg gctgtgtgga aaatccaggc tctttctgca  29580
tgatctctct ctgtgtaact gtgctggcac taatactcac gcttttgtat atcagattta  29640
aatcaaggca aagcttcatc gatgaaaaga aaatgcctta aacgctttca cgcttgattg  29700
```

```
ctaacaccgg gtttttatcc gcagaatgat tggaatcacc ctactaatca cctccctcct  29760
tgcgattgcc catgggttgg aacgaatcga agcccctgtg ggggccaatg ttaccctggt  29820
ggggcctgtc ggcaatgcta cattaatgtg ggaaaaatat actaaaaatc aatgggtctc  29880
ttactgcact aacaaaaaca gccacaagcc cagagccatc tgcgatgggc aaaatctaac  29940
cttgattgat gttcaaatgc tggatgcggg ctactattat gggcagctgg gtacaatgat  30000
taattactgg agaccccaca aagattacat gctccacgta gtaaagggtc cccttagcag  30060
cccacccact accacctcta ctacccccac taccaccact actcccacca ccagcactgc  30120
cgcccagcct cctcatagca gaacaaccac ttttatcaat tccaagtccc actcccccca  30180
cattgccggc gggccctccg cctcagactc cgagaccacc gagatctgct tctgcaaatg  30240
ctctgacgcc tttgctgagg atttggaaga ccacgaggaa gatgagcatg acttcgcaga  30300
tgcatgccag gcatcagagg cagaagcgct gccggtggcc ctcaaacagt atgcagaccc  30360
ccacaccacc cccaaccttc ctccaccttc ccagaagcca agtttcctgg gggaaaatga  30420
aactctgcct ctctccatac tcgctctgac atctgttgct atgttgaccg ctctgctggt  30480
gcttctatgc tctatatgct acctgatctg ctgcagaaag aaaaaatctc acggccatgc  30540
tcaccagccc ctcatgcact tcccttaccc tccagagctg ggcgaccaca aactttaagt  30600
ctgcagtaac tatctgccca tcccttgtca gtcgacagcg atgagcccca ctaatctaac  30660
ggcctctgga cttacaacat cgtctcttaa tgagaccacc gctcctcaag acctgtacga  30720
tggtgtctcc gcgctggtta accagtggga tcacctgggc atatggtggc tcctcatagg  30780
agcagtgacc ctgtgcctaa tcctggtctg gatcatctgc tgcatcaaaa gcagaagacc  30840
caggcggcgg cccatctaca ggccctttgt catcacacct gaagatgatg atgacaccac  30900
ttccaggctg cagaggctaa agcagctact cttctctttt acagcatggt aaattgaatc  30960
atgcctcgca ttttcatcta cttgtctctc cttccacttt ttctgggctc ttctacattg  31020
gccgctgtgt cccacatcga ggtagactgc ctcacgccct tcacagtcta cctgcttttc  31080
ggctttgtca tctgcacctt tgtctgcagc gttatcactg tagtgatctg cttcatacag  31140
tgcatcgact acgtctgcgt gcgggtggct tactttagac accaccccca gtatcgcaac  31200
agggacatag cggctctcct aagacttgtt taaaatcatg gccaaattaa ctgtgattgg  31260
tcttctgatc atctgctgcg tcctagccgc gattgggact caagctccta ccaccaccag  31320
cgctcccaga aagagacatg tatcctgcag cttcaagcgt ccctggaata taccccaatg  31380
ctttactgat gaacctgaaa tctctttggc ttggtacttc agcgtcaccg cccttcttat  31440
cttctgcagt acggttattg cccttgccat ctacccttcc cttgacctgg gctggaatgc  31500
tgtcaactct atggaatatc ccaccttccc agaaccagac ctgccagacc tggttgttct  31560
aaacgcgttt cctcctcctg ctcccgttca aaatcagttt cgccctccgt cccccacgcc  31620
cactgaggtc agctacttta atctaacagg cggagatgac tgaaaaccta gacctagaaa  31680
tggacggtct ctgcagcgag caacgcacac tagagaggcg ccggcaaaaa gagctcgagc  31740
gtcttaaaca agagctccaa gacgcggtgg ccatacacca gtgcaaaaaa ggtgtcttct  31800
gtctggtaaa acaggccacg ctcacctatg aaaaaacagg tgacacccac cgcctaggat  31860
acaagctgcc cacacagcgc cagaagttcg ccctcatgat aggcgaacaa cccatcaccg  31920
tgacccagca ctccgtggag acagaaggct gcatacacgc tccctgtagg ggcgctgact  31980
gcctctacac cttgatcaaa accctctgcg gtctcagaga cctcatccct tttaattaat  32040
```

```
cataactgta atcaataaaa aatcacttac ttgaaatctg atagcaagcc tctgtccaat  32100
tttttcagca acacttcctt cccctcctcc caactctggt actctaggcg cctcctagct  32160
gcaaacttcc tccacagtct gaagggaatg tcagattcct cctcctgtcc ctccgcaccc  32220
acgatcttca tgttgttgca gatgaaacgc gcgagatcgt ctgacgagac cttcaacccc  32280
gtgtacccct acgataccga gatcgctccg acttctgtcc ctttccttac ccctcccttt  32340
gtgtcatccg caggaatgca agaaaatcca gctggggtgc tgtccctgca cttgtcagag  32400
ccccttacca cccacaatgg ggccctgact ctaaaaatgg ggggcggcct gaccctggac  32460
aaggaaggga atctcacttc ccaaaacatc accagtgtcg atcccccctct caaaaaaagc  32520
aagaacaaca tcagccttca gaccgccgca cccctcgccg tcagctccgg ggccctaaca  32580
ctttttgcca ctcccccccct agcggtcagt ggtgacaacc ttactgtgca gtctcaggcc  32640
cctctcactt tggaagactc aaaactaact ctggccacca aaggacccct aactgtgtcc  32700
gaaggcaaac ttgtcctaga aacagaggct cccctgcatg caagtgacag cagcagcctg  32760
ggccttagcg ttacggcccc acttagcatt aacaatgaca gcctaggact agacatgcaa  32820
gcgcccatta gctctcgaga tggaaaactg gctctaacag tggcggcccc cctaactgtg  32880
gtcgagggta tcaatgcttt ggcagtagcc acaggtaagg gtattgggct aaatgaaacc  32940
aacacacacc tgcaggcaaa actggtcgca cccctaggct ttgataccaa cggcaacatt  33000
aagctaagcg ttgcaggagg catgaggcta aacaataaca cactgatact agatgtaaac  33060
tacccatttg aggctcaagg ccaactgagc ctaagagtgg gctcgggccc actatatgta  33120
gattctagta gtcataacct aaccattaga tgccttaggg gattgtatat aacatcttct  33180
aacaaccaaa acggtctaga agccaacatt aaactaacaa gaggccttgt gtatgacgga  33240
aatgccatag cagttaatgt tggcaaaggg ctggaataca gccctactga cacaacagaa  33300
aaacctatac agactaaaat aggtctaggc atggagtatg ataccgaggg agccatgatg  33360
acaaaactag gctctggact aagctttgac aattcaggag ccattgtagt gggaaacaaa  33420
aatgatgaca ggcttacttt gtggaccaca ccggacccat cgcccaactg tcagatctac  33480
tctgaaaaag atgctaaact aaccttggta ctgactaaat gtggcagtca ggttgtaggc  33540
acagtatcta ttgccgctct taaaggtagc ctcgtgccaa tcactagtgc aatcagtgtg  33600
gttcaggtat acctaaggtt tgatgaaaat ggggtactaa tgagtaactc ttcacttaat  33660
ggcgaatact ggaattttag aaacggagac tcaactaatg gcacaccata tacaaacgca  33720
gtgggtttca tgcctaatct actggcctat cctaaaggtc aaactacaac tgcaaaaagt  33780
aacattgtca gccaggtcta catgaatggg gacgatacta aacccatgac atttacaatc  33840
aacttcaatg gccttagtga aacaggggat acccctgtta gtaaatattc catgacattc  33900
tcatggaggt ggccaaatgg aagctacata gggcacaatt ttgtaacaaa ctcctttacc  33960
ttctcctaca tcgcccaaga ataaagaaag cacagagatg cttgtttttg atttcaaaat  34020
tgtgtgcttt tatttatttt cagcttacag tatttccagt agtcattcaa ataaagctta  34080
atcaaactgc atgagaaccc ttccacatag cttaaattag caccagtgca aatggagaaa  34140
aatcaacata cctttttttta tccagatatc agagaactct agtggtcagt tttcccccac  34200
cctcccagct cacagaatac acagtccttt cccccccggct ggctttaaac aacactatct  34260
cattggtaac agacatattc ttaggtgtaa taatccacac ggtctcttgg cgggccaaac  34320
gctggtcggt gatgttaata aactccccag gcagctcttt caagttcacg tcgctgtcca  34380
actgctgaag cgctcgcggc tccgactgcg cctctagcgg aggcaacggc aacacccgat  34440
```

```
ccttgatcta taaaggagta gagtcataat cccccataag aatagggcgg tgatgcagca  34500
acaaggcgcg cagcaactcc tgccgccgcc tctccgtacg gcaggaatgc aacggcgtgg  34560
tggtctcctc cgtgataatc cgcaccgctc gcagcatcag catcctcgtc ctccgggcac  34620
agcagcgcat cctgatctca ctgagatcgg cgcagtaagt gcagcacaaa accaagatgt  34680
tatttaagat cccacagtgc aaagcactgt acccaaagct catggcggga aggacagccc  34740
ccacgtgacc atcataccag atcctcaggt aaatcaaatg acgacctctc ataaacacgc  34800
tggacatgta catcacctcc ttgggcatgt gctgattcac cacctctcga taccacaagc  34860
atcgctgatt aattaaagac ccctcgagca ccatcctaaa ccaggaagcc agcacctgac  34920
cccccgccag gcactgcagg gaccccggtg aatcgcagtg gcagtgaaga ctccagcgct  34980
cgtagccgtg aaccatagag ctggtcatta tatccacatt ggcacaacac agacacactt  35040
tcatacactt tttcatgatt agcagctcct ctctagtcag gaccatatcc caaggaatca  35100
cccactcttg aatcaaggta aatcccacac agcagggcag gcctctcaca taactcacgt  35160
tatgcatagt gagcgtgtcg caatctggaa ataccggatg atcttccatc accgaagccc  35220
gggtctccgt ctcaaaggga ggtaaacggt ccctcgtgta gggacagtgg cgggataatc  35280
gagatcgtgt tgaacgtaga gtcatgccaa agggaacagc ggacgtactc atatttcctc  35340
cagcagaacc aagtgcgcgc gtggcagcta tccctgcgtc ttctgtctcg ccgcctgccc  35400
cgttcggtgt agtagttgta atacagccac tccctgagac cgtcaaggcg ctccctggcg  35460
tccggatcta tgacaacacc gtcctgcagc gccgccctga tgacatccac caccgtagag  35520
tatgccaagc ccagccagga aatgcattca ctttgacagc gagagatagg aggagcgggg  35580
agagatggaa gaaccatgat agtaaagaga acttttattc caatcgatct tctaagatat  35640
caaagtggag atctataaga tgacactggt ctcctccgct gagtcgatca aaaataacag  35700
ctaaaccaca aacaacacga ttggtcaaat gctccacaag ggcctgcagc ataaaattgc  35760
ctcggaactc caccgcaagc ataacatcaa agccaccgcc tctatcgtga tcaagaataa  35820
aaaccccaca gctatccacc agacccatat agttttcatc tctccatcgt gaaaaaagat  35880
ttacaagctc ctcctttaaa tcacctccaa ccaattgaaa aagttgaacc agaccgccct  35940
ccaccttcat tttcagcaag cgtatcatga ttgcaaaaat tcaggctcct cagacacctg  36000
tataagattg agaagcggaa cgttaacatc gatgtttcgc tcgcgtaaat cacgcctcag  36060
tgcaagcata atataatccc acaggtcgga gcggatcagc gaggacacct ccccgccagg  36120
aaccaactca acggagccta tgctgattat aatacgcata ttcggagcta tgctaaccag  36180
cacggccccc aaataggcgt actgcatagg cggcgacaaa aagtgaacag tttgggttaa  36240
aaaatcaggc aaacactcgc gcaaaaaagc aagaacatca taaccatgct catgcaaata  36300
gatgcaagta agctcaggaa caaccacaga aaaatgcaca atttttctct caaacatgac  36360
tgcgagccct gcaaaaaata aaaaagaaac attacacaag agtagcctgt cttacgatgg  36420
gatagactac tctaaccaac ataagacggg ccacaacatc gcccgcgtgg ccataaaaaa  36480
aattgtccgt gtgattaaaa agaagcacag atagctggcc agtcatatcc ggagtcatca  36540
cgtgtgaacc cgtgtagacc cccgggttgg acacatcggc caaagaaaga aagcggccaa  36600
tgtacccagg aggaattata acactaagac gaagatacaa cagaataacc ccatgagggg  36660
gaataacaaa gttagtaggt gaataaaaac gataaacacc cgaaactccc tcctgcgtag  36720
gcaaaatagc accctcccct tccaaaacaa catatagcgc ttccacagca gccatgacaa  36780
```

aagactcaaa acactcaaaa gactcagtct taccaggaaa ataaaagcac tctcacagca 36840
ccagcactaa tcagagtgtg aagagggcca agtgccgaac gagtatatat aggaataaaa 36900
aatgacgtaa atgtgtaaag gtcagaaaac gcccagaaaa atacacagac caacgcccga 36960
aacgaaaacc cgcgaaaaaa tacccagaac ttcctcaaca accgccactt ccgctttctc 37020
acggtacgtc acttccgcaa gaaaagcaaa actacatttc ccacatgtgt aaaaacgaaa 37080
ccccgcccct tgtaaccgcc cacaacttac atcatcaaaa cgtaaactcc tacgtcaccc 37140
gccccgcctc tccccgccca cctcattatc atattggcca caatccaaaa taaggtatat 37200
tattgatgat g 37211

<210> SEQ ID NO 22
<211> LENGTH: 37213
<212> TYPE: DNA
<213> ORGANISM: Gorilla beringei graueri

<400> SEQUENCE: 22
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagtgcgtaa tatttaccga gggccgaggg 360
actttgaccg attacgtgga ggactcgccc aggtgttttt tacgtgaatt tccgcgttcc 420
gggtcaaagt ctccgtttta ttgtcaccgt catttgacgc ggagggtatt taaacccgct 480
gcgctcctca agaggccact cttgagtgcc agcgagaaga gttttctcct ctgctccgct 540
tcggtgatcg aaaaatgaga cacatagcct gcactccggg tcttttgtcc ggtcgggcgg 600
cggccgagct tttggacgct ttgatcaatg atgtcctgag cgatgatttt ccgtctacta 660
cccactttag cccacctact cttcacgaac tgtacgatct ggatgtactg gtggatgtga 720
acgatcccaa cgaggaggcg gtttctgcgt tttttcccga gtctgcgctg ttggccgctc 780
aggagggatt tgacctacac actccgccgc ctattttaga gtctccgctg ccggagccca 840
gtggtatacc ttatatgcct gaactgcttc ccgaagtggt agacctgacc tgccacgagc 900
ctggctttcc gcccagcgac gatgatggtg agccttttgt tttagacttt gctgagatac 960
ctgggcacgg ttgcaggtct tgtgcatatc atcagagggt taccggagac cccgaggtta 1020
agtgttcgct gtgctatatg aggatgacct cttcctttat ctacagtaag tttttgtcta 1080
ggtgggcttt tgggtaggtg ggttttgtgt cagaacaggt gtaaacgttg cttgtgtttt 1140
ttgtacctgt aggtccggtg tccgagccag acccggagcc cgaccgcgat cccgagccgg 1200
atcccgagcc tcctcgtagg gcaagaaaat taccttctat tctgtgcaag tctaagacac 1260
ctgtgaggac cagcgaggcg gacagcaccg actctggcac ttctacctct cctcctgaaa 1320
ttcacccagt ggttcctctg ggtatacata gacctgttgc tgttagagtt tgcgggcgac 1380
gctctgcagt agagtgcatt gaggacttgc ttcacgaacc cgaggaacct ttggacttga 1440
gcgttaaacg ccctaggcaa taaaccccac ctaagtaata aaccccacct aagtaataaa 1500
ccctgccgcc cttggttatt gagatgacgc ccaatgtttg cttttgaatg acttcatgtg 1560
tgtaataaaa gtgagtgtga tcataggtct cttgtttgtc tgggcggggc ttaagggtat 1620
ataagtctct tggggctaaa cttggttaca cttgacccca atggaggcgt gggggtgctt 1680

```
ggaggagttt gcggacgtgc gccgtttgct ggacgagagc tctagcaata cctatactat   1740
ttggaggtat ctgtggggct ctactcaggc caagttggtc tccagaatta agcaggatta   1800
caagtgcgat tttgaagagc tttttagttc ctgcggtgag cttttgcaat ccttgaatct   1860
gggccatcag gctattttcc aggaaaaggt tctctcgact ttggattttt ccactcccgg   1920
gcgcaccgcc gcttgtgtgg cttttgtgtc ttttgtgcaa gataaatgga gcgaggagac   1980
ccacctgagt cacggctacg tactggattt catggcgatg gctctttgga gggcttacaa   2040
caaatggaag attcagaagg aactgtacgg ttccgcccta cgtcgtccac ttctgtcgcg   2100
acaggggctg aggtttcccg accatcggca gcatcagaat ctggaagacg agtcggagga   2160
gcgagcggag gagaagatca gcttgagagc cggcctggac cctcctcagg aggaatgaat   2220
ctcccgcagg tggttgacct gtttccagaa ctgagacggg tcctgactat cagggaggat   2280
ggtcagtttg tgaagaagtt taagagggat cggggtgagg gagatgatga ggcggctagc   2340
aatttagctt ttagtctgat gactcgccac cgaccggaat gtattaccta tcagcagatt   2400
aaggagagtt gtgccaacga gctggatctt ttgggtcaga agtatagcat agaacagctt   2460
accacttact ggcttcagcc tggggatgat tgggaagagg cgatcagggt gtatgcaaag   2520
gtggccctgc ggcccgattg caagtataag attactaagt tggttaatat tagaaactgc   2580
tgctatattt ctgggaacgg ggccgaagtg gagatagata ctcaggacag ggtggctttt   2640
aggtgttgca tgataaacat gtggcccggg atactgggga tggatggggt ggtattcatg   2700
aatgtgaggt ttacgggccc caactttaat ggcacggtgt tcatgggcaa caccaacttg   2760
ctcctgcatg gtgcgagttt ctatgggttt aataacacct gtatagaggc ctggaccgat   2820
gtaaaggttc gaggttgttc cttttatagc tgttggaagg cggtggtgtg tcgccctaaa   2880
agcaggggtt ctgtgaaaaa atgcttgttt gaaaggtgca ccttaggcat cctctctgag   2940
ggcaactcca gggtgcgcca taatgtggct tcgaactgcg gttgcttcat gcaagtgaag   3000
ggggtgagcg ttatcaagca taactcggtg tgtggaaact gcgaggatcg cgcctcccag   3060
atgctgacct gctttgatgg caactgtcac ctgttgaaga ccattcatat aagcagccac   3120
cccagaaagg cctggcccgt gtttgagcat aacatcttga cccgctgctc cttgcatctg   3180
ggggtcagga ggggtatgtt cctgccttac cagtgtaact ttagccacac taaaatcctg   3240
ctggaacccg agtgcatgac caaggtcagc ctgaatggtg tgtttgatgt gactctgaaa   3300
atctggaagg tgctgaggta tgatgagacc aggaccaggt gccgaccctg cgagtgcggc   3360
ggcaagcaca tgagaaatca gcctgtgatg ttggatgtga ccgaggagct taggcctgac   3420
catctggtgc tggcctgcac cagggccgag tttgggtcta gcgatgagga taccgattga   3480
ggtgggtaag gtgggcgtgg ctagaagggt ggggcgtgta taaattgggg gtctaagggt   3540
ctctctgttt tgtcttgcaa cagccgccgc catgagcgac accggcaaca gctttgatgg   3600
aagcatcttt agcccctatc tgacagtgcg catgcctcac tgggctggag tgcgtcagaa   3660
tgtgatgggt tccaacgtgg atggacgccc cgttctgcct tcaaattcgt ctacaatggc   3720
ctacgcgacc gtgggaggaa ctccgctgga cgccgcgacc tccgccgccg cctccgccgc   3780
cgccgcgacc gcgcgcagca tggctacgga cctttacagc tctttggtgg cgagcggcgc   3840
ggcctctcgc gcgtctgctc gggatgagaa actgaccgct ctgctgctta aactggaaga   3900
cttgacccgg gagctggctc aactgaccca gcaggtctcc agcttgcgtg agagcagcct   3960
tgcctccccc taatggccca taatataaat aaaagccagt ctgtttggat taagcaagtg   4020
```

```
tatgttcttt atttaactct ccgcgcgcgg taagcccggg accagcggtc tcggtcgttt   4080
agggtgcggt ggattctttc caacacgtgg tacaggtggc tctggatgtt tagatacatg   4140
ggcatgagtc catccctggg gtggaggtag caccactgca gagcttcgtg ctcgggggtg   4200
gtgttgtata tgatccagtc gtagcaggag cgctgggcgt ggtgctgaaa aatgtcctta   4260
agcaagaggc ttatagctag gggaggccc ttggtgtaag tgtttacaaa tctgctcagt    4320
tgggaggggt gcatccgggg ggatataatg tgcatcttgg actggatttt taggttggct   4380
atgttcccac ccagatccct tctgggattc atgttgtgca ggaccaccag cacggtatat   4440
ccagtacact tgggaaattt atcgtggagc ttagacggga atgcatggaa gaacttggag   4500
acgcccttgt ggcctcccag attttccata cattcgtcca tgatgatggc aatgggcccg   4560
tgggaagctg cctgagcaaa aatgtttctg ggatcgctca catcgtagtt atgttccagg   4620
gtgaggtcat cataggacat ctttacaaat cgggggcgga gggtcccgga ctgggggatg   4680
atggtgccct cgggccccgg ggcgtagttc ccctcacaga tctgcatctc ccaggctttc   4740
atttcagagg gagggatcat atccacctgc ggagcgatga aaaacacagt ttctggcgca   4800
ggggagatta actgggatga gagcaggttt ctgagcagct gtgactttcc acagccggtg   4860
ggcccatata tcacgcctat caccggctgc agctggtagt taagagagct gcagctgccg   4920
tcctcccgga gcaggggggc cacctcgttc agcatatccc tgacgtggat gttctccctg   4980
accaattccg ccagaaggcg ctcgccgccc agcgaaagca gctcttgcaa ggaagcaaaa   5040
tttttcagcg gttttaggcc gtcggccgtg ggcatgtttt tcagcgtctg ggtcagcagt   5100
tccagtctgt cccacagctc ggtgatgtgc tctacggcat ctcgatccag cagatctcct   5160
cgtttcgcgg gttggggcgg ctttcgctgt agggcaccag ccgatgggcg tccagcgggg   5220
ccagagtcat gtccttccat gggcgcaggg tcctcgtcag ggtggtctgg gtcacggtga   5280
aggggtgcgc tccgggttgg gcgctggcca gggtgcgctt gaggctggtt ctgctggtgc   5340
tgaatcgctg ccgctcttcg ccctgcgcgt cggccaggta gcatttgacc atggtctcgt   5400
agtcgagacc ctcggcggcg tgccccttgg cgcggagctt tcccttggag gtggcgccgc   5460
acgaggggca ctgcaggctc ttcagggcgt agagcttggg agcgagaaac acggactctg   5520
gggagtaggc gtccgcgccg caggaagcgc agaccgtctc gcattccacc agccaagtga   5580
gctccgggcg gtcagggtca aaaaccaggt tgcccccatg ctttttgatg cgtttcttac   5640
ctcggctctc catgaggcgg tgtcccttct cggtgacgaa gaggctgtcc gtgtctccgt   5700
agaccgactt caggggcctg tcttccagcg gagtgcctct gtcctcctcg tagagaaact   5760
ctgaccactc tgagacgaag gcccgcgtcc aggccaggac gaaggaggcc acgtgggagg   5820
ggtagcggtc gttgtccact agcgggtcca ccttctccag ggtgtgcagg cacatgtccc   5880
cctcctccgc gtccagaaaa gtgattggct tgtaggtgta ggacacgtga ccgggggttc   5940
ccgacggggg ggtataaaag gggtgggca cccctttcatc ttcactctct tccgcatcgc  6000
tgtctgcgag agccagctgc tggggtaagt attccctctc gaaggcgggc atgacctcag   6060
cgctcaggtt gtcagtttct aaaaatgagg aggatttgat gttcacctgt ccggaggtga   6120
tacctttgag ggtacctggg tccatctggt cagaaaacac tatttttttg ttgtcaagct   6180
tggtggcgaa cgacccgtag agggcgttgg agagcagctt ggcgatggag cgcagggtct   6240
ggtttttgtc gcggtcggct cgctccttgg ccgcgatgtt gagttgcacg tactcgcggg   6300
ccacgcactt ccactcgggg aagacggtgg tgcgctcgtc tgggatcagg cgcaccctcc   6360
agcctcggtt gtgcagggtg accatgtcga cgctggtggc gacctcgccg cgcaggcgct   6420
```

```
cgttggtcca gcagaggcgg ccgcccttgc gcgagcagaa ggggggtagg gggtccagct   6480
ggtcctcgtt tggggggtcc gcgtcgatgg tgaagacccc ggggagcaag cgcgggtcaa   6540
agtagtcgat cttgcaagct tgcatgtcca gagcccgctg ccattcgcgg gcggcgagcg   6600
cgcgctcgta ggggttgagg ggcgggcccc agggcatggg gtgggtgagc gcggaggcgt   6660
acatgccgca gatgtcatac acgtacaggg gttccctgag gatgccgagg taggtggggt   6720
agcagcgccc cccgcggatg ctggcgcgca cgtagtcata gagctcgtgg gagggggcca   6780
gcatgttggg cccgaggttg gtgcgctggg ggcgctcggc gcggaaggcg atctgcctga   6840
agatggcatg ggagttggag gagatggtgg gccgctggaa gacgttgaag cttgcttctt   6900
gcaagcccac cgagtccctg acgaagcagg cgtaggactc gcgcagcttg tgcaccagct   6960
cggcggtgac ctggacgtcg agcgcgcagt agtcgagggt ctcgcggatg atgtcatact   7020
tatcctcccc cttctttttc cacagctcgc ggttgaggac gaactcttcg cggtctttcc   7080
agtactcttg gaggggaaac ccgtccgtgt ccgaacggta agagcctagc atgtagaact   7140
ggttgacggc ctggtagggg caacagccct tctccacggg cagcgcgtag gcctgcgccg   7200
ccttgcggag ggaggtgtgg gtgagggcga aagtgtccct gaccatgact ttgaggtatt   7260
gatgtttgaa gtctgtgtca tcgcagccgc cctgttccca cagggtgtag tccgtgcgct   7320
ttttggagcg cgggttgggc agggagaagg tgaggtcatt gaagaggatc ttccccgctc   7380
gaggcatgaa gtttctggtg atgcgaaagg gccctgggac cgaggagcgg ttgttgatga   7440
cctgggcggc caggacgatc tcgtcaaagc cgtttatgtt gtggcccacg atgtagagct   7500
ccaaaaagcg gggctggccc ttgatggagg ggagcttttt gagttcctcg taggtgagct   7560
cctcgggcga ttccaggccg tgctcctcca gggcccagtc ttgcaagtga gggttggccg   7620
ccaggaagga tcgccagagg tcgcgggcca tgagggtctg caggcggtcg cggaaggttc   7680
tgaactgtcg ccccacggcc atcttttcgg gggtgatgca gtagaaggtg agggggtctt   7740
tctcccaggg gtcccatctg agctctcggg cgaggtcgcg cgcggcggcg accagagcct   7800
cgttgccccc cagtttcatg accagcatga agggcacgag ctgcttgcca aaggctccca   7860
tccaagtgta ggtctctaca tcgtaggtga caaagaggcg ctccgtgcga ggatgagagc   7920
cgatcgggaa gaactggatc tcccgccacc agttggagga ttggctgttg atgtggtgaa   7980
agtagaagtc ccgtctgcgg gccgagcact cgtgctggct tttgtaaaag cgaccgcagt   8040
actggcagcg ctgcacgggt tgtatatctt gcacgaggtg aacctggcga cctctgacga   8100
ggaagcgcag cgggaatcta agtcccccgc ctggggtccc gtgtggctgg tggtcttcta   8160
ctttggttgt ctggccgcca gcatctgtct cctggagggc gatggtggag cagaccacca   8220
cgccgcgaga gccgcaggtc cagatctcgg cgctcggcgg gcggagtttg atgacgacat   8280
cgcgcacatt ggagctgtcc atggtctcca gctcccgcgg cggcaggtca gctgggagtt   8340
cctggaggtt cacctcgcag agacgggtca aggcgcgggc agtgttgaga tggtatctga   8400
tttcaagggg cgtgttggcg gcggagtcga tggcttgcag gaggccgcag ccccgggggg   8460
ccacgatggt tccccgcggg gcgcgagggg aggcggaagc tgggggtgtg ttcagaagcg   8520
gtgacgcggg cgggcccccg gaggtagggg gggttccggc cccacaggca tgggcggcag   8580
gggcacgtct tcgccgcgcg cgggcagggg ctggtgctgg ctccgaagag cgcttgcgtg   8640
cgcgacgacg cgacggttgg tgtcctgtat ctgacgcctc tgagtgaaga ccacgggtcc   8700
cgtgaccttg aacctgaaag agagttcgac agaatcaatc tcggcatcgt tgacagcggc   8760
```

-continued

```
ctggcgcagg atctcctgca cgtcgcccga gttgtcctgg taggcgatct ctgccatgaa   8820
ctgctcgatc tcttcttcct ggagatctcc tcgtccggcg cgctccacgg tggccgccag   8880
gtcgttggag atgcgaccca tgagctgcga gaaggcgttg agcccgccct cgttccagac   8940
ccggctgtag accacgcccc cctcggcgtt gcgggcgcgc atgaccacct gggccaggtt   9000
gagctccacg tgtcgcgtga agacggcgta gttgcgcagg cgctggaaaa ggtagttcag   9060
ggtggtggcg gtgtgctcgg cgacgaagaa gtacatgacc cagcgccgca acgtggattc   9120
attgatgtcc cccaaggcct ccaggcgctc catggcctcg tagaagtcca cggcgaagtt   9180
gaaaaactgg gagttgcgag cggacacggt caactcctcc tccagaagac ggatgagctc   9240
ggcgacagtg tcgcgcacct cgcgctcgaa ggccacgggg ggcgcttctt cctcttccac   9300
ctcttcttcc atgatcgctt cttcttcttc ctcagccggg acgggagggg gcggcggcgg   9360
cgggggaggg gcgcggcggc ggcggcggcg caccgggagg cggtcgatga agcgctcgat   9420
catctccccc cgcatgcggc gcatggtctc ggtgacggcg cggccgttct cccgggggcg   9480
cagctcgaag acgccgcctc tcatctcgcc gcggggcggg cggccgtgag gtagcgagac   9540
ggcgctgact atgcatctta acaattgctg tgtaggtaca ccgccgaggg acctgattga   9600
gtccagatcc accggatccg aaaacctttg gaggaaagcg tctatccagt cgcagtcgca   9660
aggtaggctg agcaccgtgg cgggcggggg cgggtctgga gagttcctgg cggagatgct   9720
gctgatgatg taattaaagt aggcggtctt gagaaggcgg atggtggaca ggagcaccat   9780
gtctttgggt ccggcctgtt ggatgcggag gcggtcggcc atgccccagg cctcgttctg   9840
acaccggcgc aggtctttgt agtagtcttg catgagtctt tccaccggca cctcttctcc   9900
ttcctcttct ccatctcgcc ggtggtttct cgcgccgccc atgcgcgtga ccccaaagcc   9960
cctgagcggc tgcagcaggg ccaggtcggc gaccacgcgc tcggccaaga tggcctgctg  10020
cacctgagtg agggtcctct cgaagtcatc catgtccacg aagcggtggt aggcgcccgt  10080
gttgatggtg taggtgcagt tggccatgac ggaccagttg acggtctggt gtcccggctg  10140
cgagagctcc gtgtaccgca ggcgcgagaa ggcgcgggaa tcgaacacgt agtcgttgca  10200
agtccgcacc agatactggt agcccaccag gaagtgcggc ggaggttggc gatagagggg  10260
ccagcgctgg gtggcggggg cgccgggcgc caggttttcc agcatgaggc ggtggtatcc  10320
gtagatgtac ctggacatcc aggtgatgcc ggcggcggtg gtggtggcgc gcgcgtagtc  10380
gcggacccgg ttccagatgt ttcgcagggg cgagaagtgt tccatggtcg gcacgctctg  10440
gccggtgagg cgcgcgcagt cgttgacgct ctatacacac acaaaaacga aagcgtttac  10500
agggctttcg ttctgtagcc tggaggaaag taaatgggtt gggttgcggt gtgccccggt  10560
tcgagaccaa gctgagctcg gccggctgaa gccgcagcta acgtggtatt ggcagtcccg  10620
tctcgaccca ggccctgtat cctccaggat acggtcgaga gcccttttgc tttcttggcc  10680
aagcgcccgt ggcgcgatct gggatagatg gtcgcgatga gaggacaaaa gcggctcgct  10740
tccgtagtct ggagaaacaa tcgccagggt tgcgttgcgg cgtaccccgg ttcgagcccc  10800
tatggcggct tgaatcggcc ggaaccgcgg ctaacgaggg ccgtggcagc cccgtcctca  10860
ggaccccgcc agccgacttc tccagttacg ggagcgagcc ccttttgttt tttatttttt  10920
agatgcatcc cgtgctgcgg cagatgcgcc cctcgccccg gcccgatcag cagcagcaac  10980
agcaggcatg cagaccccccc tctccccttt ccgccccggt caccacggcc gcggcggccg  11040
tgtcgggcgc ggggggcgcg ctggagtcag atgagccacc gcggcggcga cctaggcagt  11100
atctggactt ggaagagggc gagggactgg cgcggctggg ggcgaactct ccagagcgcc  11160
```

```
acccgcgggt gcagttgaaa agggacgcgc gcgaggcgta cctgccgcgg cagaacctgt  11220
ttcgcgaccg cgggggcgag gagcccgagg agatgcgaga ctgcaggttc caagcggggc  11280
gcgagctgcg gcgcgggctg gacagacagc gcctgctgcg cgaggaggac tttgagcccg  11340
acacgcagac gggcatcagc cccgcgcgcg cgcacgtagc cgcggccgac ctggtgaccg  11400
cctacgagca gacggtgaac caggagcgca acttccaaaa gagcttcaac aaccacgtgc  11460
gcacgctggt ggcgcgcgag gaggtgaccc tgggtctcat gcatctgtgg gacctggtgg  11520
aggcgatcgt gcagaacccc agcagcaagc ccctgaccgc gcagctgttc ctggtggtgc  11580
agcacagcag ggacaacgag gccttcaggg aggcgctgct gaacatcacc gagccggagg  11640
ggcgctggct cctggacctg ataaacatcc tgcagagcat agtggtgcag gagcgcagcc  11700
tgagcctggc cgagaaggtg gcggccatca actactctat gctgagcctg ggcaagttct  11760
acgcccgcaa gatctacaag acccccctacg tgcccataga caaggaggtg aagatagaca  11820
gcttctacat gcgcatggcg ctgaaggtgc tgaccctgag cgacgacctg ggagtgtacc  11880
gcaacgagcg catccacaag gccgtgagcg ccagccggcg gcgcgagctg agcgaccgcg  11940
agctgatgca cagtctgcag cgcgcgctga ccggcgcggg cgagggcgac agggaggtcg  12000
agtcctactt cgacatgggg gccgacctgc actggcagcc gagccgccgc gccctggagg  12060
cggcgggggc gtacggcggc cccctggcgg ccgatgacca ggaagaggag gactatgagc  12120
tagaggaggg cgagtacctg gaggactgac ctggctggtg gtgttttggt atagatgcaa  12180
gatccgaacg tggcggaccc ggcggtccgg gcggcgctgc aaagccagcc gtccggcatt  12240
aactcctctg acgactgggc cgcggccatg ggtcgcatca tggccctgac cgcgcgcaac  12300
cccgaggctt tcaggcagca gcctcaggcc aaccggctgg cggccatctt ggaagcggta  12360
gtgcccgcgc gctccaaccc cacccacgag aaggtgctgg ccatagtcaa cgcgctggcg  12420
gagagcaggg ccatccgcgc ggacgaggcc ggactggtgt acgatgcgct gctgcagcgg  12480
gtggcgcggt acaacagcgg caacgtgcag accaacctgg accgcctggt gacggacgtg  12540
cgcgaggccg tggcgcagcg cgagcgcttg catcaggacg gtaacctggg ctcgctggtg  12600
gcgctaaacg ccttcctcag cacccagccg gccaacgtac cgcgggggca ggaggactac  12660
accaactttt tgagcgcgct gcggctgatg gtgaccgagg tccctcagag cgaggtgtac  12720
cagtcggggc ccgactactt cttccagacc agcagacagg gcttgcaaac cgtgaacctg  12780
agccaggctt tcaagaacct gcgggggctg tggggagtga aggcgcccac cggcgaccgg  12840
gctacggtgt ccagcctgct aacccccaac tcgcgcctgc tgctgctgct gatcgcgccc  12900
ttcacggaca gcgggagcgt ctcgcgggag acctatctgg gccacctgct gacgctgtac  12960
cgcgaggcca tcgggcaggc gcaggtggac gagcacacct tccaagagat caccagcgtg  13020
agccacgcgc tggggcagga ggacacgggc agcctgcagg cgaccctgaa ctacctgctg  13080
accaacaggc ggcagaagat tcccacgctg cacagcctga cccaggagga ggagcgcatc  13140
ttgcgctacg tgcagcagag cgtgagcctg aacctgatgc gcgacggcgt gacgcccagc  13200
gtggcgctgg acatgaccgc gcgcaacatg gaaccgggca tgtacgcctc ccaccggccg  13260
ttcatcaacc gcctgatgga ctacttgcat cgggcggcgg ccgtgaaccc cgagtacttc  13320
actaatgcca ttctgaatcc ccactggatg ccccctccgg gtttctacaa cggggacttt  13380
gaggtgcccg aggtcaacga cgggttcctc tgggatgaca tggatgacag tgtgttctca  13440
cccaacccgc tgcgcgccgc gtctctgcga ttgaaggagg gctctgacag ggaaggaccg  13500
```

agaagtctgg cctcctccct ggctctggga gcggtgggcg ccacgggcgc ggcggcgcgg 13560
ggcagtagcc ccttccccag cctggcagac tctctgaaca gcgggcgggt gagcaggccc 13620
cgcttgctag gcgaggagga gtatctgaac aactccctgc tgcagcccgc gagggacaag 13680
aacgctcagc ggcagcagtt tcccaacaat gggatagaga gcctggtgga caagatgtcc 13740
agatggaaga cgtatgcgca ggagtacaag gagtgggagg accgccagcc gcggcccttg 13800
ccgcccccta ggcagcgctg gcagcggcgc gcgtccaacc gccgctggag gcaggggccc 13860
gaggacgatg atgactctgc agatgacagc agcgtgttgg acctgggcgg gagcgggaac 13920
cccttttcgc acctgcgccc acgcctgggc aagatgtttt aaaagaaaaa aaaaaaaata 13980
aaactcacca aggccatggc gacgagcgtt ggtttttgt tcccttcctt agtatgcggc 14040
gcgcggcgat gttcgaggag gggcctcccc cctcttacga gagcgcgatg gggatttctc 14100
ctgcggcgcc cctgcagcct ccctacgtgc ctcctcggta cctgcaacct acaggggga 14160
gaaatagcat ctgttactct gagctgcagc ccctgtacga taccaccaga ctgtacctgg 14220
tggacaacaa gtccgcggac gtggcctccc tgaactacca gaacgaccac agcgattttt 14280
tgaccacggt gatccaaaac aacgacttca ccccaaccga ggccagcact cagaccataa 14340
acctggataa caggtcgaac tggggcggcg acctgaagac catcttgcac accaacatgc 14400
ccaacgtgaa cgagttcatg ttcaccaact cttttaaggc gcgggtgatg gtggcgcgcg 14460
agcaggggga ggcgaagtac gagtgggtgg acttcacgct gcccgagggc aactactcag 14520
agaccatgac tctcgacctg atgaacaatg cgatcgtgga acactatctg aaagtgggca 14580
ggcagaacgg ggtgaaggaa agcgatatcg gggtcaagtt tgacaccaga aacttccgtc 14640
tgggctggga ccccgtgacc gggctggtca tgccgggggt ctacaccaac gaggcctttc 14700
atcccgacat agtgcttctg cccggctgtg ggtggactt cacccagagc cggctgagca 14760
acctgctggg cattcgcaag cggcagcctt tccaggaggg tttcaagatc acctatgagg 14820
atctgaaggg gggcaacatt cccgcgctcc ttgatctgga cgcctacgag gagagcttga 14880
aacccgagga gagcgctggc gacagcggcg agagtggcga ggagcaagcc ggcggcggtg 14940
gcggcgcgtc ggtagaaaac gaaagtacgc ccgcagtggc ggcggacgct gcggaggtcg 15000
agccggaggc catgcagcag gacgcagagg agggcgcaca ggagggcgcg cagaaggaca 15060
tgaacgatgg ggagatcagg ggagacacat tcgccacccg gggcgaagaa aaagaggcag 15120
aggcggcggc ggcggcgacg gcggaggccg aaaccgaggt tgaggcagag gcagagcccg 15180
agaccgaagt tatggaagac atgaatgatg gagaacgtag ggcgacacg ttcgccaccc 15240
ggggcgaaga gaaggcggcg gaggcagaag ccgcggctga ggaggcggct gcggctgcgg 15300
ccaagactga ggctgcggct aaggctgagg tcgaagccaa tgttgcggtt gaggctcagg 15360
ctgaggagga ggcggcggct gaagcagtta aggaaaaggc ccaggcagag caggaagaga 15420
aaaaacctgt cattcaacct ctaaaagaag atagcaaaaa gcgcagttac aacgtcatcg 15480
agggcagcac ctttacccag taccgcagct ggtacctggc gtacaactac ggcgacccgg 15540
tcaagggggt gcgctcgtgg accctgctct gcacgccgga cgtcacctgc ggctccgagc 15600
agatgtactg gtcgctgccg aacatgatgc aagacccggt gaccttccgc tccacgcggc 15660
aggttagcaa cttcccggtg gtgggcgccg aactgctgcc cgtgcactcc aagagttttt 15720
acaacgagca ggccgtctac tcccagctga tccgccaggc cacctctctg acccacgtgt 15780
tcaatcgctt tcccgagaac cagattttgg cgcgcccgcc ggcccccacc atcaccaccg 15840
tgagtgaaaa cgttcctgcc ctcacagatc acgggacgct accgctgcgc aacagcatct 15900

```
caggagtcca gcgagtgacc attactgacg ccagacgccg gacctgcccc tacgtttaca  15960
aggccttggg catagtctcg ccgcgcgtcc tctccagtcg cactttttaa aacacatcta  16020
cccacacgtt ccaaaatcat gtccgtactc atctcaccca gcaacaacac cggctggggg  16080
ctgcgcgcgc ccagcaagat gtttggaggg gcgaggaagc gctccgacca gcaccctgtg  16140
cgcgtgcgcg gccactaccg cgcgccctgg ggagcgcaca agcgcgggcg cacagggcgc  16200
accactgtgg acgacgtcat tgactccgta gtggagcaag cgcgccacta cacacccggc  16260
gcgccgaccg cccccgccgt gtccaccgtg gaccaggcga tcgaaagcgt ggtacagggc  16320
gcgcggcact atgccaacct taaaagtcgc cgccgccgcg tggcccgccg ccatcgccgg  16380
agaccccggg ccaccgccgc cgcgcgcctt actaaggctc tgctcaggcg cgccaggcga  16440
actggccacc gggccgccat gagggccgca cggcgggctg ccgctgccgc aagcgccgtg  16500
gccccgcggg cacgaaggcg cgcggccgcc gccgccgccg ccgccatttc cagcttggcc  16560
tcgacgcggc gcggtaacat atactgggtg cgcgactcgg taaccggcac gcgggtaccc  16620
gtgcgctttc gcccccgcg gaattagcac aagacaacat acacactgag tctcctgctg  16680
ttgtgtatcc cagcggcgac cgtcagcagc ggcgacatgt ccaagcgcaa aattaaagaa  16740
gagatgctcc aggtcatcgc gccggagatc tatgggcccc cgaagaagga ggaggatgat  16800
tacaagcccc gcaagctaaa gcgggtcaaa aagaaaaaga aagatgatga tgatgacgag  16860
gcggtggagt ttgtccgccg catggcaccc aggcgccccg tgcagtggaa gggccggcgc  16920
gtgcagcgcg ttttgcgccc cggcaccgcg gtggtcttca cgcccggcga gcgctccacg  16980
cgcactttca agcgggtgta cgatgaggtg tacggcgacg aggacctgtt ggagcaggcc  17040
aaccagcgct ttggggagtt tgcatatggg aaacggcccc gcgagagtct aaaagaggac  17100
ctgctggcgc taccgctgga cgagggcaat cccacccga gtctgaagcc ggtaaccctg  17160
caacaggtgc tgcctttgag cgcgcccagc gagcataagc gagggttgaa gcgcgaaggc  17220
ggggacctgg cgcccaccgt gcagttgatg gtgcccaagc ggcagaagct ggaggacgtg  17280
ctggagaaaa tgaaagtaga gcccgggatc cagcccgaga tcaaggtccg ccccatcaag  17340
caggtggcgc ccggcgtggg agtccagacc gtggacgtta ggattcccac ggaggagatg  17400
gaaacccaaa ccgccactcc ctcttcggcg gccagcgcca ccaccggcac cgcttcggta  17460
gaggtgcaga cggacccctg gctacccgcc accgctgttg ccgccgccgc cccccgttcg  17520
cgcgggcgca agagaaatta tccagcggcc agcgcgctca tgccccagta cgcactgcat  17580
ccatccatcg cgcccacccc cggctaccgc gggtactcgt accgcccgcg cagatcagcc  17640
ggcactcgcg gccgccgccg ccgtgcgacc acaaccagcc gccgccgtcg ccgccgccgc  17700
cagccagtgc tgacccccgt gtctgtaagg aaggtggctc gctcggggag cacgctggtg  17760
gtgcccagag cgcgctacca ccccagcatc gtttaaagcc ggtctctgta tggttcttgc  17820
agatatggcc ctcacttgtc gcctccgctt cccggtgccg ggataccgag gaagaactca  17880
ccgccgcaga ggcatggcgg gcagcggtct ccgcggcggc cgtcgccatc gccggcgcgc  17940
aaaaagcagg cgcatgcgcg gcggtgtgct gcctctgcta atcccgctaa tcgccgcggc  18000
gatcggtgcc gtacccggga tcgcctccgt ggccctgcag gcgtcccaga aacgttgact  18060
cttgcaacct tgcaagcttg catttttgg aggaaaaaat aaaaaaagtc tagactctca  18120
cgctcgcttg gtcctgtgac tattttgtag aaaaaagatg gaagacatca actttgcgtc  18180
gctggccccg cgtcacggct cgcgcccgtt catgggagac tggacagata tcggcaccag  18240
```

caatatgagc ggtggcgcct tcagctgggg cagtctgtgg agcggcctta aaaattttgg 18300
ttccaccatt aagaactatg gcaacaaagc gtggaacagc agcacgggcc agatgctgag 18360
agacaagttg aaagagcaga acttccagga gaaggtggcg cagggcctgg cctctggcat 18420
cagcggggtg gtggacatag ctaaccaggc cgtgcagaaa aagataaaca gtcatctgga 18480
cccccgtcct caggtggagg aaatgcctcc agcgatggag acggtgtctc ccgagggcaa 18540
aggcgaaaag cgcccgcggc ccgacagaga agagaccctg gtgtcacaca ccgaggagcc 18600
gccctcttac gaggaggcag tcaaggccgg cctgcccacc actcgcccca tagcccccat 18660
ggccaccggt gtggtgggcc acaggcaaca cactcccgca acactagatc tgcccccgcc 18720
gtccgagccg ccgcgccagc caaaggcggc gacggtgccc gctccctcca cttccgccgc 18780
caacagagtg cccctgcgcc gcgccgcgag cggcccccgg gcctcgcgag ttagcggcaa 18840
ctggcagagc acactgaaca gcatcgtggg cctgggagtg aggagtgtga agcgccgccg 18900
ttgctactga atgagcaagc tagctaacgt gttgtatgtg tgtatgcgtc ctatgtcgcc 18960
gccagaggag ctgttgagcc gccggcgccg tctgcactcc agcgaatttc aagatggcga 19020
ccccatcgat gatgcctcag tggtcgtaca tgcacatctc gggccaggac gcttcggagt 19080
acctgagccc cgggctggtg cagttcgccc gcgccacaga cacctacttc aacatgagta 19140
acaagttcag gaaccccact gtggcgccca cccacgatgt gaccacggac cggtcgcagc 19200
gcctgacgct gcggttcatc cccgtggatc gggaggacac cgcctactct tacaaggcgc 19260
ggttcacgct ggccgtgggc gacaaccgcg tgctggacat ggcctccact tactttgaca 19320
tcaggggggt gctggacagg ggccccacct tcaagcccta ctcgggtact gcctacaact 19380
ccctggcccc caagggcgct cccaattctt gcgagtggga acaagaggaa aatcaggtgg 19440
tcgctgcaga tgatgaactt gaagatgaag aagcgcaagc tcaagaggac gccccagcta 19500
aaaaaattca tgtatatgcc caggcgcctc ttgctggcga aaagattacc aaggatggtt 19560
tgcaaatagg tactgaagtt gtaggagata catctaagga cacttttgca gacaaaacat 19620
tccaacccga acctcagata ggcgagtctc agtggaacga ggctgatgcc acagtagcag 19680
gaggcagagt cttgaaaaaa accaccccta tgagaccttg ctatggatcc tatgccaggc 19740
ctacaaatgc caacgggggt caaggaatta tggttgccaa tgaacaagga gtgttggagt 19800
ctaaagtgga gatgcaattt ttttctaaca ctacaaccct taatgcgcgg gatggagctg 19860
gcaatcccga accaaaggtg gtgttgtaca gtgaagatgt ccacttggaa tctcctgaca 19920
ctcatttgtc ttacaagccc aaaaaggatg atgttaatgc taaaattatg ttgggtcagc 19980
aagctatggc taacaggccc aacctcattg cttttagaga taatttcatt ggactcatgt 20040
actacaacag cactggtaac atgggagtgc tggcgggtca ggcctctcag ttgaatgccg 20100
tggtggacct gcaggataga aacacagaac tgtcatatca gcttatgctt gattccattg 20160 ggatagatc cagatacttc tccatgtgga accaggcagt ggatagctat gacccagatg 20220
tcagaatcat tgaaaaccat ggtgtcgagg acgagctacc caactactgc ttccctctgg 20280
gcggcatagg aattactgat acttatcaag ggatcaaaaa taccaatggc aatggtcagt 20340
ggaccaaaga tgatcagttc gcggaccgta atgaaatagg ggtgggaaac aacttcgcca 20400
tggagatcaa catccaggcc aacctctgga ggaacttcct ctatgcgaac gtggggctct 20460
acctgccaga caagctcaag tacaacccca ccaacgtgga catctctgac aaccccaaca 20520
cctatgacta catgaacaag cgtgtggtgg ctcccggcct ggtggactgc tttgtcaatg 20580
tgggagccag gtggtccctg gactacatgg acaacgtcaa ccccttcaac caccaccgca 20640

```
atgcgggtct gcgctaccgc tccatgatcc tgggcaacgg gcgctacgtg cccttccaca  20700
ttcaggtgcc ccagaagttc tttgccatca agaacctcct cctcctgccg ggctcctaca  20760
cttacgagtg gaacttcagg aaggatgtca acatggtcct gcagagctct ctgggcaatg  20820
accttagggt ggacggggcc agcatcaagt ttgacagcgt caccctctat gctaccttct  20880
tccccatggc tcacaacacc gcctccacgc tcgaggccat gctgaggaac gacaccaacg  20940
accagtcctt caatgactac ctctctgggg ccaacatgct ctaccccatc cccgccaagg  21000
ccaccaacgt gcccatctcc attccctctc gcaactgggc cgccttcaga ggctgggcct  21060
ttacccgcct taagaccaag gaaacccccct ccctgggctc gggttttgac ccctactttg  21120
tctactcggg atccatcccc tacctggatg gcaccttcta cctcaaccac acttttaaga  21180
agatatccat catgtatgac tcctccgtca gctggccggg caatgaccgc ctgctcaccc  21240
ccaatgagtt cgaggtcaag cgcgccgtgg acggcgaggg ctacaacgtg gcccagtgca  21300
acatgaccaa ggactggttc ctggtgcaga tgctggccaa ctacaacata ggctaccagg  21360
gcttctacat cccagagagc tacaaggaca ggatgtactc cttcttcaga aatttccaac  21420
ccatgagcag gcaggtggtg gacgagacca aatacaagga ctatcaggcc attggcatca  21480
ctcaccagca caacaactcg ggattcgtgg gctacctggc tcccaccatg cgcgaggggc  21540
aggcctaccc cgccaacttc ccctacccgt tgataggcaa gaccgcggtc gacagcgtca  21600
cccagaaaaa gttcctctgc gaccgcaccc tctggcgcat ccccttctct agcaacttca  21660
tgtccatggg tgcgctcacg gacctgggcc agaacctgct ctatgccaac tccgcccatg  21720
cgctggacat gacttttgag gtggacccca tggacgagcc cacccttctc tatattgtgt  21780
ttgaagtgtt cgacgtggtc agagtgcacc agccgcaccg cggtgtcatc gagaccgtgt  21840
acctgcgcac gcccttctcg gccggcaacg ccaccaccta aggagacagc gccgccgcct  21900
gcatgacggg ttccaccgag caagagctca gggccatcgc cagagacctg ggatgcggac  21960
cctatttttt gggcacctat gacaaacgct tcccgggctt catctcccga gacaagctcg  22020
cctgcgccat cgtcaacacg gccgcgcgcg agaccggggg cgtgcactgg ctggcctttg  22080
gctgggaccc gcgctccaaa acctgctacc tcttcgaccc ctttggcttc tccgatcagc  22140
gcctcagaca gatctatgag tttgagtacg aggggctgct gcgccgcagc gcgcttgcct  22200
cctcgcccga ccgctgcatc acccttgaga agtccaccga gaccgtgcag gggccccact  22260
cggccgcctg cggtctcttc tgctgcatgt ttttgcacgc ctttgtgcgc tggccccaga  22320
gtcccatgga tcgcaacccc accatgaact tgctcaaggg agtgcccaac gccatgctcc  22380
agagccccca ggtccagccc accctgcgcc acaaccagga acagctctac cgcttcctgg  22440
agcgccactc cccctacttc cgcagtcaca gcgcgcacat ccgggggggcc acctctttct  22500
gccacttgca acaaaaacatg caagacggaa aatgatgtac agctcgcttt ttaataaatg  22560
taaagactgt gcactttatt tatacacggg ctctttctgg ttatttattc aacaccgccg  22620
tcgccatcta gaaatcgaaa gggttctgcc gcgcgtcgcc gtgcgccacg ggcagagaca  22680
cgttgcgata ctggaagcgg ctcgcccact tgaactcggg caccaccatg cggggcagtg  22740
gctcctcggg gaagttctcg ccccacaggg tgcgggtcag ctgcagcgcg ctcaggaggt  22800
cgggagccga gatcttgaag tcgcagttgg ggccggaacc ctgcgcgcgc gagttgcggt  22860
acacggggtt gcagcactgg aacaccagca gggccggatt acgcacgctg gccagcaggc  22920
tctcgtcgct gatcatgtcg ctgtccagat cctccgcgtt gctcagggcg aatggggtca  22980
```

```
tcttgcagac ctgcctgccc aggaaaggcg gcagcccggg cttgccgttg cagtcgcagc  23040

gcaggggcat cagcaggtgc ccgtggcccg tctgcgcctg cgggtacagc gcgcgcatga  23100

aggcttcgat ctgcctgaaa gccacctgcg tcttggctcc ctccgaaaag aacatcccac  23160

aggacttgct ggagaactgg ttcgcgggac agctggcatc gtgcaggcag cagcgcgcgt  23220

cggtgttggc gatctgcacc acgttgcgac cccaccggtt cttcactatc ttggccttgg  23280

aagcctgctc cttcagcgcg cgctggccgt tctcgctggt cacatccatc tctatcacct  23340

gctccttgtt gatcatgttt gtcccgtgca gacacttcag gtcgccctcc gtctgggtgc  23400

agcggtgctc ccacagcgcg caaccggtgg gctcccaatt tttgtgggtc acccccgcgt  23460

aggcctgcag gtaggcctgc aagaagcgcc ccatcatggc cacaaaggtc ttctggctcg  23520

taaaggtcag ctgcaggccg cgatgctctt cgttcagcca ggtcttgcag atggcggcca  23580

gcgcctcggt ctgctcgggc agcatcctaa aatttgtctt caggtcgtta tccacgtggt  23640

acttgtccat catggcgcgc gccgcctcca tgcccttctc ccaggcggac accatgggca  23700

ggcttagggg gtttatcact tccaccggcg aggacaccgt actttcgatt tcttcttcct  23760

ccccctcttc ccggcgcgcg cccacgctgc tgcgcgctct caccgcctgc accaaggggt  23820

cgtcttcagg caagcgccgc accgagcgct tgccgccctt gacctgctta atcagcaccg  23880

gcgggttgct gaagcccacc atggtcagct ccgcctgctc ttcttcgtct tcgctgtcta  23940

ccactatctc tggggaaggg cttctccgct ctgcggcggt gcgcttcttt tttttcttgg  24000

gagcagccgt gacggagtcc gccacggcga cggaggtcga gggcgtgggg ctgggggtgc  24060

gcggtaccag ggcctcgtcg ccctcggact cttcctctga ctccaggcgg cggcggagac  24120

gcttctttgg gggcgcgcgc gtcagcggcg gcggagacgg ggacggggac ggggacggga  24180

cgccctccac agggggtggt cttcgcgcag acccgcggcc gcgctcgggg gtcttttcga  24240

gctggtcttg gtcccgactg gccattgtat cctcctcctc ctaggcagag agacataagg  24300

agtctatcat gcaagtcgag aaggaggaga gcttaaccac cccctctgag accgccgatg  24360

cgcccgccgt cgccgtcgcc cccgctgccg ccgacgcgcc cgccacaccg agcgacaccc  24420

ccgcggaccc cccagccgac gcacccctgt tcgaggaagc ggccgtggag caggacccgg  24480

gctttgtctc ggcagaggag gatttgcgag aggaggagga taaggagaag aagccctcag  24540

tgccaaaaga tgataaagag caagacgagc acgacgcaga tgcacaccag ggtgaagtcg  24600

ggcgggggga cggagggcat gacggcgccg actacctaga cgaagggaac gacgtgctct  24660

tgaagcacct gcatcgtcag tgcgccatcg tttgcgacgc tctgcaggag cgcagcgaag  24720

tgcccctcag cgtggcggag gtcagccacg cctacgagct cagcctcttc tccccccggg  24780

tgcccccccg ccgccgcgaa aacggcacat gcgagcccaa cccgcgcctc aacttctacc  24840

ccgcctttgt ggtgcccgag gtcctggcca cctatcacat cttctttcaa aattgcaaga  24900

tcccccctctc gtgccgcgcc aaccgtagcc gcgccgataa gatgctggcc ctgcgccagg  24960

gcgaccacat acctgatatc gccgctttgg aagatgtgcc aaagatcttc gagggtctgg  25020

gtcgcaacga gaagcgggca gcaaactctc tgcaacagga aaacagcgaa aatgagagtc  25080

acaccggggt actggtggag ctcgagggcg acaacgcccg cctggcggtg gtcaagcgca  25140

gcatcgaggt cacccacttt gcctaccccg cgctcaacct gccccccaaa gtcatgaacg  25200

cggccatgga cgggctgatc atgcgccgcg gccggcccct cgctccagat gcaaacttgc  25260

atgaggagac cgaggacggc cagcccgtgg tcagcgacga gcagctggcg cgctggctgg  25320

agaccgcgga ccccgccgaa ctggaggagc ggcgcaagat gatgatggcc gcggtgctgg  25380
```

```
tcaccgtaga gctggagtgt ctgcagcgct tcttcggcga ccccgagatg cagagaaagg  25440
tcgaggagac cctgcactac accttccgcc agggctacgt gcgccaggct tgcaagatct  25500
ccaacgtgga gctcagcaac ctggtgtcct acctgggcat cttgcatgag aaccgcctcg  25560
ggcagagcgt gctgcactcc accctgcgcg gggaggcgcg ccgcgactac gtgcgcgact  25620
gcgtttacct cttcctctgc tacacctggc agacggccat gggggtctgg cagcagtgcc  25680
tggaggagcg caacctcaag gagctggaga agctcctgca gcgcgcgctc aaagacctct  25740
ggacgggcta caacgagcgc tcggtggccg ccgcgctggc cgacctcatc ttccccgagc  25800
gcctgctcaa aaccctccag caggggctgc ccgacttcac cagccaaagc atgttgcaaa  25860
acttcaggaa ctttatcctg gagcgttctg gcatcctacc cgccacctgc tgcgccctgc  25920
ccagcgactt tgtcccccctc gtgtaccgcg agtgcccccc gccgctgtgg ggtcactgct  25980
acctgttcca actggccaac tacctgtcct accacgcgga cctcatggag gactccagcg  26040
gcgaggggct catggagtgc cactgccgct gcaacctctg cacgccccac cgctccctgg  26100
tctgcaacac ccaactgctc agcgagagtc agattatcgg taccttcgag ctacagggtc  26160
cgtcctcctc agacgagaag tccgcggctc cggggctaaa actcactccg ggctgtgga  26220
cttccgccta cctgcgcaaa tttgtacctg aagactacca cgcccacgag atcaggtttt  26280
acgaagacca atcccgcccg cccaaggcgg agctgaccgc ctgcgtcatc acccagggcg  26340
agatcctagg ccaattgcaa gccatccaaa aagcccgcca agatttttttg ctgagaaagg  26400
gtcggggggt gtatctggac ccccagtcgg gtgaggagct caacccggtt cccccgctgc  26460
cgccgccgcg ggaccttgct tcccaggata agcatcgcca tggctcccag aaagaagcag  26520
cagcggccgc cactgccgcc accccacatg ctggaggaag aggaggaata ctgggacagt  26580
caggcagagg aggtttcgga cgaggaggag ccggagacgg agatggaaga gtgggaggag  26640
gacagcttag acgaggaggc ttccgaagcc gaagaggcag acgcaacacc gtcaccctcg  26700
gccgcagccc cctcgcaggc gcccccgaag tccgctccca gcatcagcag caacagcagc  26760
gctataacct ccgctcctcc accgccgcga cccacggccg accgcagacc caaccgtaga  26820
tgggacacca ccggaaccgg ggccggtaag tcctccggga gaggcaagca agcgcagcgc  26880
caaggctacc gctcgtggcg cgctcacaag aacgccatag tcgcttgctt gcaagactgc  26940
ggggggaaca tctccttcgc ccgccgcttc ctgctcttcc accacggtgt ggccttcccc  27000
cgtaacgtcc tgcattacta ccgtcatctc tacagcccct actgcggcgg cagtgagcca  27060
gagacggtcg gcggcggcgg cggcgcccgt ttcggcgcct aggaagaccc agggcaagac  27120
ttcagccaag aaactcgcgg cggccgcggc gaacgcggtc gcgggggccc tgcgcctgac  27180
ggtgaacgaa cccctgtcga cccgcgaact gagaaaccga atcttcccca ctctctatgc  27240
catcttccag cagagcagag ggcaggatca ggaactgaaa gtaaaaaaca ggtctctgcg  27300
ctccctcacc cgcagctgtc tgtatcacaa gagcgaagac cagcttcggc gcacgctgga  27360
ggacgctgag gcactcttca gcaaatactg cgcgctcact cttaaggact agctccgcgc  27420
ccttctcgaa tttaggcggg aacgcctacg tcatcgcagc gccgccgtca tgagcaagga  27480
cattcccacg ccatacatgt ggagctatca gccgcagatg ggactcgcgg cgggcgcctc  27540
ccaagactac tccacccgca tgaactggct cagtgccggc ccacacatga tctcacaggt  27600
taatgatatc cgcacccatc gaaaccaaat attggtggag caggcggcaa ttaccaccac  27660
gccccgcaat aatcccaacc ccagggagtg gcccgcgtcc ctggtgtatc aggaaattcc  27720
```

-continued

```
cggccccacc accgtactac ttccgcgtga ttcccaggcc gaagtccaaa tgactaactc  27780
aggggcgcag ctcgcgggcg gctgtcgtca cagggtgcgg cctcctcgcc agggtataac  27840
tcacctggag atccgaggca gaggtattca gctcaacgac gagtcggtga gctcctcgct  27900
cggtctaaga cctgacggga ccttccagat agccggagcc ggccgatctt ccttcacgcc  27960
ccgccaggcg tacctgactc tgcagagctc gtcctcggcg ccgcgctcgg gcggcatcgg  28020
gactctccag ttcgtgcagg agtttgtgcc ctcggtctac ttcaacccct tctcgggctc  28080
tcccggtcgc tacccggacc agttcatctc gaactttgac gccgcgaggg actcggtgga  28140
cggctacgac tgaatgtcgg gtggacccgg tgcagagcaa cttcgcctga agcacctcga  28200
ccactgccgc cgccctcagt gctttgcccg ctgtcagacc ggtgagttcc agtacttttc  28260
cctgcccgac tcgcacccgg acggcccggc gcacggggtg cgctttttca tcccgagtca  28320
ggtgcgctct accctaatca gggagtttac cgcccgtccc ctactggcgg agttggaaaa  28380
ggggccttct atcctaacca ttgcctgcat ctgctctaac cctggattgc accaagatct  28440
ttgctgtcat ttgtgtgctg agtataataa aggctgagat cagaatctac tcgggctcct  28500
gtcgccatcc tgtcaacgcc accgtccaag cccggcccga tcagcccgag gtgaacctca  28560
cctgcggtct gcaccggcgc ctgaggaaat acctagcttg gtactacaac agcactccct  28620
ttgtggttta caacagcttt gaccaggacg gggtctcact gagggataac ctctcgaacc  28680
tgagctactc catcaggaag aacagcaccc tcgagctact tcctccttac ctgcccggga  28740
cttaccagtg tgtcaccggt ccctgcaccc acacccacct gttgatcgta aacgactctc  28800
ttccgagaac agacctcaat aactcctctt cgcagttccc cagaacagga ggtgagctca  28860
ggaaaccccg ggtaaagaag ggtggacaag agttaacact tgtggggttt ctggtgtatg  28920
tgacgctggt ggtggctctt ttgattaagg cttttccttc catgtctgaa ctctccctct  28980
tttatgaaca actcgactag tgctaacggg accctaccca acgaatcggg attgaatatc  29040
ggtaaccagg ttgcagtttc acttttgatt accttcatag tcctcttcct gctagtgctg  29100
tcgcttctgt gcctgcggat cgggggctgc tgcatccacg tttatatctg gtgctggctg  29160
tttagaaggt tcggagacca tcgcaggtag aataaacatg ctgctgctta ccctctttgt  29220
cctggcgctg gccgccagct gccaagcctt ttccgaggct gactttatag agccccagtg  29280
taacgtgact tttaaagccc atgcacagcg ttgtcatact ataatcaaat gtgccaccga  29340
acacgatgaa taccttatcc agtataaaga taaatcacac aaagtggcac ttgttgacat  29400
ctggaaaccc gaagaccctt tggaatacaa tgtgaccgtt ttccagggtg acctcttcaa  29460
aatttacaat tacactttcc catttgacca gatgtgtgac tttgtcatgt acatggaaaa  29520
gcagcacaag ctgtggcctc cgactcccca gggctgtgtg gaaaatccag gctctttctg  29580
catgatctct ctctgtgtaa ctgtgctggc actaatactc acgcttttgt atatcagatt  29640
taaatcaagg caaagcttca tcgatgaaaa gaaaatgcct taaacgcttt cacgcttgat  29700
tgctaacacc gggtttttat ccgcagaatg attggaatca ccctactaat cacctccctc  29760
cttgcgattg cccatgggtt ggaacgaatc gaagcccctg tgggggccaa tgttaccctg  29820
gtggggcctg tcggcaatgc tacattaatg tgggaaaaat atactaaaaa tcaatgggtc  29880
tcttactgca ctaacaaaaa cagccacaag cccagagcca tctgcgatgg gcaaaatcta  29940
accttgattg atgttcaaat gctggatgcg ggctactatt atgggcagct gggtacaatg  30000
attaattact ggagacccca caaagattac atgctccacg tagtaaaggg tcccccttagc  30060
agcccaccca ctaccacctc tactaccccc actaccacca ctactcccac caccagcact  30120
```

```
gccgcccagc ctcctcatag cagaacaacc acttttatca attccaagtc ccactccccc  30180
cacattgccg gcgggccctc cgcctcagac tccgagacca ccgagatctg cttctgcaaa  30240
tgctctgacg cctttgctga ggatttggaa gaccacgagg aagatgagca tgacttcgca  30300
gatgcatgcc aggcatcaga ggcagaagcg ctgccggtgg ccctcaaaca gtatgcagac  30360
ccccacacca cccccaacct tcctccacct tcccagaagc caagtttcct gggggaaaat  30420
gaaactctgc ctctctccat actcgctctg acatctgttg ctatgttgac cgctctgctg  30480
gtgcttctat gctctatatg ctacctgatc tgctgcagaa agaaaaaatc tcacggccat  30540
gctcaccagc ccctcatgca cttcccttac cctccagagc tgggcgacca caaactttaa  30600
gtctgcagta actatctgcc catcccttgt cagtcgacag cgatgagccc cactaatcta  30660
acggcctctg gacttacaac atcgtctctt aatgagacca ccgctcctca agacctgtac  30720
gatggtgtct ccgcgctggt taaccagtgg gatcacctgg gcatatggtg gctcctcata  30780
ggagcagtga ccctgtgcct aatcctggtc tggatcatct gctgcatcaa aagcagaaga  30840
cccaggcggc ggcccatcta caggcccttt gtcatcacac ctgaagatga tgatgacacc  30900
acttccaggc tgcagaggct aaagcagcta ctcttctctt ttacagcatg gtaaattgaa  30960
tcatgcctcg cattttcatc tacttgtctc tccttccact tttctgggc tcttctacat  31020
tggccgctgt gtcccacatc gaggtagact gcctcacgcc cttcacagtc tacctgcttt  31080
tcggctttgt catctgcacc tttgtctgca gcgttatcac tgtagtgatc tgcttcatac  31140
agtgcatcga ctacgtctgc gtgcgggtgg cttactttag acaccacccc cagtatcgca  31200
acagggacat agcggctctc ctaagacttg tttaaaatca tggccaaatt aactgtgatt  31260
ggtcttctga tcatctgctg cgtcctagcc gcgattggga ctcaagctcc taccaccacc  31320
agcgctccca gaaagagaca tgtatcctgc agcttcaagc gtccctggaa tataccccaa  31380
tgctttactg atgaacctga aatctctttg gcttggtact tcagcgtcac cgcccttctt  31440
atcttctgca gtacggttat tgcccttgcc atctaccctt cccttgacct gggctggaat  31500
gctgtcaact ctatggaata tcccaccttc ccagaaccag acctgccaga cctggttgtt  31560
ctaaacgcgt ttcctcctcc tgctcccgtt caaaatcagt ttcgccctcc gtcccccacg  31620
cccactgagg tcagctactt taatctaaca ggcggagatg actgaaaacc tagacctaga  31680
aatggacggt ctctgcagcg agcaacgcac actagagagg cgccggcaaa aagagctcga  31740
gcgtcttaaa caagagctcc aagacgcggt ggccatacac cagtgcaaaa aaggtgtctt  31800
ctgtctggta aaacaggcca cgctcaccta tgaaaaaaca ggtgacaccc accgcctagg  31860
atacaagctg cccacacagc gccagaagtt cgccctcatg ataggcgaac aacccatcac  31920
cgtgacccag cactccgtgg agacagaagg ctgcatacac gctccctgta ggggcgctga  31980
ctgcctctac accttgatca aaaccctctg cggtctcaga gacctcatcc cttttaatta  32040
atcataactg taatcaataa aaaatcactt acttgaaatc tgatagcaag cctctgtcca  32100
attttttcag caacacttcc ttcccctcct cccaactctg gtactctagg cgcctcctag  32160
ctgcaaactt cctccacagt ctgaagggaa tgtcagattc ctcctcctgt ccctccgcac  32220
ccacgatctt catgttgttg cagatgaaac gcgcgagatc gtctgacgag accttcaacc  32280
ccgtgtaccc ctacgatacc gagatcgctc cgacttctgt ccctttcctt acccctccct  32340
ttgtgtcatc cgcaggaatg caagaaaatc cagctggggt gctgtccctg cacttgtcag  32400
agccccttac cacccacaat ggggccctga ctctaaaaat ggggggcggc ctgaccctgg  32460
```

```
acaaggaagg gaatctcact tcccaaaaca tcaccagtgt cgatccccct ctcaaaaaaa  32520
gcaagaacaa catcagcctt cagaccgccg cacccctcgc cgtcagctcc ggggccctaa  32580
cactttttgc cactcccccc ctagcggtca gtggtgacaa ccttactgtg cagtctcagg  32640
cccctctcac tttggaagac tcaaaactaa ctctggccac caaaggaccc ctaactgtgt  32700
ccgaaggcaa acttgtccta gaaacagagg ctcccctgca tgcaagtgac agcagcagcc  32760
tgggccttag cgttacggcc ccacttagca ttaacaatga cagcctagga ctagacatgc  32820
aagcgcccat tagctctcga gatggaaaac tggctctaac agtggcggcc cccctaactg  32880
tggtcgaggg tatcaatgct ttggcagtag ccacaggtaa gggtattggg ctaaatgaaa  32940
ccaacacaca cctgcaggca aaactggtcg cacccctagg ctttgatacc aacggcaaca  33000
ttaagctaag cgttgcagga ggcatgaggc taaacaataa cacactgata ctagatgtaa  33060
actacccatt tgaggctcaa ggccaactga gcctaagagt gggctcgggc ccactatatg  33120
tagattctag tagtcataac ctaaccatta gatgccttag ggattgtat ataacatctt  33180
ctaacaacca aaacggtcta gaagccaaca ttaaactaac aagaggcctt gtgtatgacg  33240
gaaatgccat agcagttaat gttggcaaag ggctggaata cagccctact gacacaacag  33300
aaaaacctat acagactaaa ataggtctag gcatggagta tgataccgag ggagccatga  33360
tgacaaaact aggctctgga ctaagctttg acaattcagg agccattgta gtgggaaaca  33420
aaaatgatga caggcttact ttgtggacca caccggaccc atcgcccaac tgtcagatct  33480
actctgaaaa agatgctaaa ctaaccttgg tactgactaa atgtggcagt caggttgtag  33540
gcacagtatc tattgccgct cttaaaggta gcctcgtgcc aatcactagt gcaatcagtg  33600
tggttcaggt atacctaagg tttgatgaaa atggggtact aatgagtaac tcttcactta  33660
atggcgaata ctggaatttt agaaacggag actcaactaa tggcacacca tatacaaacg  33720
cagtgggttt catgcctaat ctactggcct atcctaaagg tcaaactaca actgcaaaaa  33780
gtaacattgt cagccaggtc tacatgaatg gggacgatac taaacccatg acatttacaa  33840
tcaacttcaa tggccttagt gaaacagggg atacccctgt tagtaaatat tccatgacat  33900
tctcatggag gtggccaaat ggaagctaca tagggcacaa ttttgtaaca aactccttta  33960
ccttctccta catcgcccaa gaataaagaa agcacagaga tgcttgtttt tgatttcaaa  34020
attgtgtgct tttatttatt ttcagcttac agtatttcca gtagtcattc aaataaagct  34080
taatcaaact gcatgagaac ccttccacat agcttaaatt agcaccagtg caaatggaga  34140
aaaatcaaca tacctttttt tatccagata tcagagaact ctagtggtca gttttccccc  34200
accctcccag ctcacagaat acacagtcct ttcccccgg ctggctttaa acaacactat  34260
ctcattggta acagacatat tcttaggtgt aataatccac acggtctctt ggcgggccaa  34320
acgctggtcg gtgatgttaa taaactcccc aggcagctct ttcaagttca cgtcgctgtc  34380
caactgctga agcgctcgcg gctccgactg cgcctctagc ggaggcaacg gcaacacccg  34440
atccttgatc tataaaggag tagagtcata atcccccata agaatagggc ggtgatgcag  34500
caacaaggcg cgcagcaact cctgccgccg cctctccgta cggcaggaat gcaacggcgt  34560
ggtggtctcc tccgtgataa tccgcaccgc tcgcagcatc agcatcctcg tcctccgggc  34620
acagcagcgc atcctgatct cactgagatc ggcgcagtaa gtgcagcaca aaaccaagat  34680
gttatttaag atcccacagt gcaaagcact gtacccaaag ctcatggcgg gaaggacagc  34740
ccccacgtga ccatcatacc agatcctcag gtaaatcaaa tgacgacctc tcataaacac  34800
gctggacatg tacatcacct ccttgggcat gtgctgattc accacctctc gataccacaa  34860
```

```
gcatcgctga ttaattaaag acccctcgag caccatccta aaccaggaag ccagcacctg  34920
acccccgcc aggcactgca gggaccccgg tgaatcgcag tggcagtgaa gactccagcg  34980
ctcgtagccg tgaaccatag agctggtcat tatatccaca ttggcacaac acagacacac  35040
tttcatacac tttttcatga ttagcagctc ctctctagtc aggaccatat cccaaggaat  35100
cacccactct tgaatcaagg taaatcccac acagcagggc aggcctctca cataactcac  35160
gttatgcata gtgagcgtgt cgcaatctgg aaataccgga tgatcttcca tcaccgaagc  35220
ccgggtctcc gtctcaaagg gaggtaaacg gtccctcgtg tagggacagt ggcgggataa  35280
tcgagatcgt gttgaacgta gagtcatgcc aaagggaaca gcggacgtac tcatatttcc  35340
tccagcagaa ccaagtgcgc gcgtggcagc tatccctgcg tcttctgtct cgccgcctgc  35400
cccgttcggt gtagtagttg taatacagcc actccctgag accgtcaagg cgctccctgg  35460
cgtccggatc tatgacaaca ccgtcctgca gcgccgccct gatgacatcc accaccgtag  35520
agtatgccaa gcccagccag gaaatgcatt cactttgaca gcgagagata ggaggagcgg  35580
ggagagatgg aagaaccatg atagtaaaga gaacttttat tccaatcgat cttctaagat  35640
atcaaagtgg agatctataa gatgacactg gtctcctccg ctgagtcgat caaaaataac  35700
agctaaacca caaacaacac gattggtcaa atgctccaca agggcctgca gcataaaatt  35760
gcctcggaac tccaccgcaa gcataacatc aaagccaccg cctctatcgt gatcaagaat  35820
aaaaacccca cagctatcca ccagacccat atagttttca tctctccatc gtgaaaaaag  35880
atttacaagc tcctccttta aatcacctcc aaccaattga aaaagttgaa ccagaccgcc  35940
ctccaccttc attttcagca agcgtatcat gattgcaaaa attcaggctc ctcagacacc  36000
tgtataagat tgagaagcgg aacgttaaca tcgatgtttc gctcgcgtaa atcacgcctc  36060
agtgcaagca taatataatc ccacaggtcg gagcggatca gcgaggacac ctccccgcca  36120
ggaaccaact caacggagcc tatgctgatt ataatacgca tattcggagc tatgctaacc  36180
agcacggccc ccaaataggc gtactgcata ggcggcgaca aaaagtgaac agtttgggtt  36240
aaaaaatcag gcaaacactc gcgcaaaaaa gcaagaacat cataaccatg ctcatgcaaa  36300
tagatgcaag taagctcagg aacaaccaca gaaaaatgca caatttttct ctcaaacatg  36360
actgcgagcc ctgcaaaaaa taaaaaagaa acattacaca agagtagcct gtcttacgat  36420
gggatagact actctaacca acataagacg ggccacaaca tcgcccgcgt ggccataaaa  36480
aaaattgtcc gtgtgattaa aaagaagcac agatagctgg ccagtcatat ccggagtcat  36540
cacgtgtgaa cccgtgtaga cccccgggtt ggacacatcg gccaaagaaa gaaagcggcc  36600
aatgtaccca ggaggaatta taacactaag acgaagatac aacagaataa ccccatgagg  36660
gggaataaca aagttagtag gtgaataaaa acgataaaca cccgaaactc cctcctgcgt  36720
aggcaaaata gcaccctccc cttccaaaac aacatatagc gcttccacag cagccatgac  36780
aaaagactca aaacactcaa aagactcagt cttaccagga aaataaaagc actctcacag  36840
caccagcact aatcagagtg tgaagagggc caagtgccga acgagtatat ataggaataa  36900
aaaatgacgt aaatgtgtaa aggtcagaaa acgcccagaa aaatacacag accaacgccc  36960
gaaacgaaaa cccgcgaaaa aatacccaga acttcctcaa caaccgccac ttccgctttc  37020
tcacggtacg tcacttccgc aagaaaagca aaactacatt tcccacatgt gtaaaaacga  37080
aaccccgccc cttgtaaccg cccacaactt acatcatcaa aacgtaaact cctacgtcac  37140
ccgccccgcc tctccccgcc cacctcatta tcatattggc cacaatccaa aataaggtat  37200
```

```
attattgatg atg                                                    37213

<210> SEQ ID NO 23
<211> LENGTH: 37195
<212> TYPE: DNA
<213> ORGANISM: Gorilla beringei graueri

<400> SEQUENCE: 23

ataatatacc ttattttgga ttgtggccaa tatgataatg aggtgggcgg ggagaggcgg      60

ggcgggtgac gtaggacgcg cgagtagggt tgggaggtgt ggcggaagtg tggcatttgc     120

aagtgggagg agctcacatg caagcttccg tcgcggaaaa tgtgacgttt ttgatgagcg     180

ccgcctacct ccggaagtgc caattttcgc gcgcttttca ccggatatcg tagtaatttt     240

gggcgggacc atgtaagatt tggccatttt cgcgcgaaaa gtgaaacggg gaagtgaaaa     300

ctgaataata gggcgttagt catagtgcgt aatatttacc gagggccgag ggactttgac     360

cgattacgtg gaggactcgc ccaggtgttt tttacgtgaa tttccgcgtt ccgggtcaaa     420

gtctccgttt tattgtcacc gtcatttgac gcggagggta tttaaacccg ctgcgctcct     480

caagaggcca ctcttgagtg ccagcgagaa gagttttctc ctctgctccg cttcggtgat     540

cgaaaaatga gacacatagc ctgcactccg ggtcttttgt ccggtcgggc ggcggccgag     600

cttttggacg ctttgatcaa tgatgtcctg agcgatgatt ttccgtctac tacccacttt     660

agcccaccta ctcttcacga actgtacgat ctggatgtac tggtggatgt gaacgatccc     720

aacgaggagg cggtttctgc gttttttccc gagtctgcgc tgttggccgc tcaggaggga     780

tttgacctac acactccgcc gcctatttta gagtctccgc tgccggagcc cagtggtata     840

ccttatatgc ctgaactgct tcccgaagtg gtagacctga cctgccacga gcctggcttt     900

ccgcccagcg acgatgatgg tgagcctttt gttttagact ttgctgagat acctgggcac     960

ggttgcaggt cttgtgcata tcatcagagg gttaccggag accccgaggt taagtgttcg    1020

ctgtgctata tgaggatgac ctcttccttt atctacagta agtttttgtc taggtgggct    1080

tttgggtagg tgggttttgt gtcagaacag gtgtaaacgt tgcttgtgtt ttttgtacct    1140

gtaggtccgg tgtccgagcc agacccggag cccgaccgcg atcccgagcc ggatcccgag    1200

cctcctcgta gggcaagaaa attaccttct attctgtgca agtctaagac acctgtgagg    1260

accagcgagg cggacagcac cgactctggc acttctacct ctcctcctga aattcaccca    1320

gtggttcctc tgggtataca tagacctgtt gctgttagag tttgcgggcg acgctctgca    1380

gtagagtgca ttgaggactt gcttcacgaa cccgaggaac ctttggactt gagcgttaaa    1440

cgccctaggc aataaacccc acctaagtaa taaaccccac ctaagtaata aaccctgccg    1500

cccttggtta ttgagatgac gcccaatgtt tgcttttgaa tgacttcatg tgtgtaataa    1560

aagtgagtgt gatcataggt ctcttgtttg tctgggcggg gcttaagggt atataagtct    1620

cttggggcta aacttggtta cacttgaccc caatggaggc gtgggggtgc ttggaggagt    1680

ttgcggacgt gcgccgtttg ctggacgaga gctctagcaa tacctatact atttggaggt    1740

atctgtgggg ctctactcag gccaagttgg tctccagaat taagcaggat tacaagtgcg    1800

attttgaaga gctttttagt tcctgcggtg agcttttgca atccttgaat ctgggccatc    1860

aggctatttt ccaggaaaag gttctctcga ctttggattt ttccactccc gggcgcaccg    1920

ccgcttgtgt ggcttttgtg tcttttgtgc aagataaatg gagcgaggag acccacctga    1980

gtcacggcta cgtactggat ttcatggcga tggctctttg gagggcttac aacaaatgga    2040

agattcagaa ggaactgtac ggttccgccc tacgtcgtcc acttctgtcg cgacaggggc    2100
```

```
tgaggtttcc cgaccatcgg cagcatcaga atctggaaga cgagtcggag gagcgagcgg   2160
aggagaagat cagcttgaga gccggcctgg accctcctca ggaggaatga atctcccgca   2220
ggtggttgac ctgtttccag aactgagacg ggtcctgact atcagggagg atggtcagtt   2280
tgtgaagaag tttaagaggg atcggggtga gggagatgat gaggcggcta gcaatttagc   2340
ttttagtctg atgactcgcc accgaccgga atgtattacc tatcagcaga ttaaggagag   2400
ttgtgccaac gagctggatc ttttgggtca gaagtatagc atagaacagc ttaccactta   2460
ctggcttcag cctggggatg attgggaaga ggcgatcagg gtgtatgcaa aggtggccct   2520
gcggcccgat tgcaagtata agattactaa gttggttaat attagaaact gctgctatat   2580
ttctgggaac ggggccgaag tggagataga tactcaggac agggtggctt ttaggtgttg   2640
catgataaac atgtggcccg ggatactggg gatggatggg gtggtattca tgaatgtgag   2700
gtttacgggc cccaacttta atggcacggt gttcatgggc aacaccaact tgctcctgca   2760
tggtgcgagt ttctatgggt ttaataacac ctgtatagag gcctggaccg atgtaaaggt   2820
tcgaggttgt tccttttata gctgttggaa ggcggtggtg tgtcgcccta aaagcagggg   2880
ttctgtgaaa aaatgcttgt ttgaaaggtg caccttaggc atcctctctg agggcaactc   2940
cagggtgcgc cataatgtgg cttcgaactg cggttgcttc atgcaagtga agggggtgag   3000
cgttatcaag cataactcgg tgtgtggaaa ctgcgaggat cgcgcctccc agatgctgac   3060
ctgctttgat ggcaactgtc acctgttgaa gaccattcat ataagcagcc accccagaaa   3120
ggcctggccc gtgtttgagc ataacatctt gacccgctgc tccttgcatc tgggggtcag   3180
gaggggtatg ttcctgcctt accagtgtaa ctttagccac actaaaatcc tgctggaacc   3240
cgagtgcatg accaaggtca gcctgaatgg tgtgtttgat gtgactctga aaatctggaa   3300
ggtgctgagg tatgatgaga ccaggaccag gtgccgaccc tgcgagtgcg gcggcaagca   3360
catgagaaat cagcctgtga tgttggatgt gaccgaggag cttaggcctg accatctggt   3420
gctggcctgc accagggccg agtttgggtc tagcgatgag gataccgatt gaggtgggta   3480
aggtgggcgt ggctagaagg gtggggcgtg tataaattgg gggtctaagg gtctctctgt   3540
tttgtcttgc aacagccgcc gccatgagcg acaccggcaa cagctttgat ggaagcatct   3600
ttagccccta tctgacagtg cgcatgcctc actgggctgg agtgcgtcag aatgtgatgg   3660
gttccaacgt ggatggacgc cccgttctgc cttcaaattc gtctacaatg gcctacgcga   3720
ccgtgggagg aactccgctg gacgccgcga cctccgccgc cgcctccgcc gccgccgcga   3780
ccgcgcgcag catggctacg gacctttaca gctctttggt ggcgagcggc gcggcctctc   3840
gcgcgtctgc tcgggatgag aaactgaccg ctctgctgct taaactggaa gacttgaccc   3900
gggagctggc tcaactgacc cagcaggtct ccagcttgcg tgagagcagc cttgcctccc   3960
cctaatggcc cataatataa ataaaagcca gtctgtttgg attaagcaag tgtatgttct   4020
ttatttaact ctccgcgcgc ggtaagcccg ggaccagcgg tctcggtcgt ttagggtgcg   4080
gtggattctt tccaacacgt ggtacaggtg gctctggatg tttagataca tgggcatgag   4140
tccatccctg gggtggaggt agcaccactg cagagcttcg tgctcggggg tggtgttgta   4200
tatgatccag tcgtagcagg agcgctgggc gtggtgctga aaaatgtcct taagcaagag   4260
gcttatagct agggggaggc ccttggtgta agtgtttaca aatctgctca gttgggaggg   4320
gtgcatccgg ggggatataa tgtgcatctt ggactggatt tttaggttgg ctatgttccc   4380
acccagatcc cttctgggat tcatgttgtg caggaccacc agcacggtat atccagtaca   4440
```

```
cttgggaaat ttatcgtgga gcttagacgg gaatgcatgg aagaacttgg agacgccctt   4500
gtggcctccc agattttcca tacattcgtc catgatgatg gcaatgggcc cgtgggaagc   4560
tgcctgagca aaaatgtttc tgggatcgct cacatcgtag ttatgttcca gggtgaggtc   4620
atcataggac atctttacaa atcgggggcg gagggtcccg gactggggga tgatggtgcc   4680
ctcgggcccc ggggcgtagt tcccctcaca gatctgcatc tcccaggctt tcatttcaga   4740
gggagggatc atatccacct gcggagcgat gaaaaacaca gtttctggcg caggggagat   4800
taactgggat gagagcaggt ttctgagcag ctgtgacttt ccacagccgg tgggcccata   4860
tatcacgcct atcaccggct gcagctggta gttaagagag ctgcagctgc cgtcctcccg   4920
gagcaggggg gccacctcgt tcagcatatc cctgacgtgg atgttctccc tgaccaattc   4980
cgccagaagg cgctcgccgc ccagcgaaag cagctcttgc aaggaagcaa aatttttcag   5040
cggttttagg ccgtcggccg tgggcatgtt tttcagcgtc tgggtcagca gttccagtct   5100
gtcccacagc tcggtgatgt gctctacggc atctcgatcc agcagatctc ctcgtttcgc   5160
gggttggggc ggctttcgct gtagggcacc agccgatggg cgtccagcgg ggccagagtc   5220
atgtccttcc atgggcgcag ggtcctcgtc agggtggtct gggtcacggt gaaggggtgc   5280
gctccgggtt gggcgctggc cagggtgcgc ttgaggctgg ttctgctggt gctgaatcgc   5340
tgccgctctt cgccctgcgc gtcggccagg tagcatttga ccatggtctc gtagtcgaga   5400
ccctcggcgg cgtgcccctt ggcgcggagc tttcccttgg aggtggcgcc gcacgagggg   5460
cactgcaggc tcttcagggc gtagagcttg ggagcgagaa acacggactc tggggagtag   5520
gcgtccgcgc cgcaggaagc gcagaccgtc tcgcattcca ccagccaagt gagctccggg   5580
cggtcagggt caaaaaccag gttgccccca tgctttttga tgcgtttctt acctcggctc   5640
tccatgaggc ggtgtccctt ctcggtgacg aagaggctgt ccgtgtctcc gtagaccgac   5700
ttcaggggcc tgtcttccag cggagtgcct ctgtcctcct cgtagagaaa ctctgaccac   5760
tctgagacga aggcccgcgt ccaggccagg acgaaggagg ccacgtggga ggggtagcgg   5820
tcgttgtcca ctagcgggtc caccttctcc agggtgtgca ggcacatgtc cccctcctcc   5880
gcgtccagaa aagtgattgg cttgtaggtg taggacacgt gaccgggggt tcccgacggg   5940
ggggtataaa agggggtggg caccctttca tcttcactct cttccgcatc gctgtctgcg   6000
agagccagct gctggggtaa gtattccctc tcgaaggcgg gcatgacctc agcgctcagg   6060
ttgtcagttt ctaaaaatga ggaggatttg atgttcacct gtccggaggt gatacctttg   6120
agggtacctg ggtccatctg gtcagaaaac actatttttt tgttgtcaag cttggtggcg   6180
aacgacccgt agagggcgtt ggagagcagc ttggcgatgg agcgcagggt ctggtttttg   6240
tcgcggtcgg ctcgctcctt ggccgcgatg ttgagttgca cgtactcgcg ggccacgcac   6300
ttccactcgg ggaagacggt ggtgcgctcg tctgggatca ggcgcaccct ccagcctcgg   6360
ttgtgcaggg tgaccatgtc gacgctggtg gcgacctcgc cgcgcaggcg ctcgttggtc   6420
cagcagaggc ggccgccctt gcgcgagcag aagggggggta gggggtccag ctggtcctcg   6480
tttggggggt ccgcgtcgat ggtgaagacc ccggggagca agcgcgggtc aaagtagtcg   6540
atcttgcaag cttgcatgtc cagagcccgc tgccattcgc gggcggcgag cgcgcgctcg   6600
taggggttga ggggcgggcc ccagggcatg gggtgggtga gcgcggaggc gtacatgccg   6660
cagatgtcat acacgtacag gggttccctg aggatgccga ggtaggtggg gtagcagcgc   6720
cccccgcgga tgctggcgcg cacgtagtca tagagctcgt gggagggggc cagcatgttg   6780
ggcccgaggt tggtgcgctg gggcgctcg gcgcggaagg cgatctgcct gaagatggca   6840
```

```
tgggagttgg aggagatggt gggccgctgg aagacgttga agcttgcttc ttgcaagccc   6900
accgagtccc tgacgaagca ggcgtaggac tcgcgcagct tgtgcaccag ctcggcggtg   6960
acctggacgt cgagcgcgca gtagtcgagg gtctcgcgga tgatgtcata cttatcctcc   7020
cccttctttt tccacagctc gcggttgagg acgaactctt cgcggtcttt ccagtactct   7080
tggaggggaa acccgtccgt gtccgaacgg taagagccta gcatgtagaa ctggttgacg   7140
gcctggtagg ggcaacagcc cttctccacg ggcagcgcgt aggcctgcgc cgccttgcgg   7200
agggaggtgt gggtgagggc gaaagtgtcc ctgaccatga ctttgaggta ttgatgtttg   7260
aagtctgtgt catcgcagcc gccctgttcc cacagggtgt agtccgtgcg ctttttggag   7320
cgcgggttgg gcagggagaa ggtgaggtca ttgaagagga tcttccccgc tcgaggcatg   7380
aagtttctgg tgatgcgaaa gggccctggg accgaggagc ggttgttgat gacctgggcg   7440
gccaggacga tctcgtcaaa gccgtttatg ttgtggccca cgatgtagag ctccaaaaag   7500
cggggctggc ccttgatgga ggggagcttt ttgagttcct cgtaggtgag ctcctcgggc   7560
gattccaggc cgtgctcctc cagggcccag tcttgcaagt gagggttggc cgccaggaag   7620
gatcgccaga ggtcgcgggc catgagggtc tgcaggcggt cgcggaaggt tctgaactgt   7680
cgccccacgg ccatcttttc gggggtgatg cagtagaagg tgagggggtc tttctcccag   7740
gggtcccatc tgagctctcg ggcgaggtcg cgcgcggcgg cgaccagagc ctcgttgccc   7800
cccagtttca tgaccagcat gaagggcacg agctgcttgc caaaggctcc catccaagtg   7860
taggtctcta catcgtaggt gacaaagagg cgctccgtgc gaggatgaga gccgatcggg   7920
aagaactgga tctcccgcca ccagttggag gattggctgt tgatgtggtg aaagtagaag   7980
tcccgtctgc gggccgagca ctcgtgctgg cttttgtaaa agcgaccgca gtactggcag   8040
cgctgcacgg gttgtatatc ttgcacgagg tgaacctggc gacctctgac gaggaagcgc   8100
agcgggaatc taagtccccc gcctggggtc ccgtgtggct ggtggtcttc tactttggtt   8160
gtctggccgc cagcatctgt ctcctggagg gcgatggtgg agcagaccac cacgccgcga   8220
gagccgcagg tccagatctc ggcgctcggc gggcggagtt tgatgacgac atcgcgcaca   8280
ttggagctgt ccatggtctc cagctcccgc ggcggcaggt cagctgggag ttcctggagg   8340
ttcacctcgc agagacgggt caaggcgcgg gcagtgttga gatggtatct gatttcaagg   8400
ggcgtgttgg cggcggagtc gatggcttgc aggaggccgc agccccgggg ggccacgatg   8460
gttccccgcg gggcgcgagg ggaggcggaa gctgggggtg tgttcagaag cggtgacgcg   8520
ggcgggcccc cggaggtagg gggggttccg gccccacagg catgggcggc aggggcacgt   8580
cttcgccgcg cgcgggcagg ggctggtgct ggctccgaag agcgcttgcg tgcgcgacga   8640
cgcgacggtt ggtgtcctgt atctgacgcc tctgagtgaa gaccacgggt cccgtgacct   8700
tgaacctgaa agagagttcg acagaatcaa tctcggcatc gttgacagcg gcctggcgca   8760
ggatctcctg cacgtcgccc gagttgtcct ggtaggcgat ctctgccatg aactgctcga   8820
tctcttcttc ctggagatct cctcgtccgg cgcgctccac ggtggccgcc aggtcgttgg   8880
agatgcgacc catgagctgc gagaaggcgt tgagcccgcc ctcgttccag acccggctgt   8940
agaccacgcc cccctcggcg ttgcgggcgc gcatgaccac ctgggccagg ttgagctcca   9000
cgtgtcgcgt gaagacggcg tagttgcgca ggcgctggaa aaggtagttc agggtggtgg   9060
cggtgtgctc ggcgacgaag aagtacatga cccagcgccg caacgtggat tcattgatgt   9120
cccccaaggc ctccaggcgc tccatggcct cgtagaagtc cacggcgaag ttgaaaaact   9180
```

```
gggagttgcg agcggacacg gtcaactcct cctccagaag acggatgagc tcggcgacag   9240
tgtcgcgcac ctcgcgctcg aaggccacgg ggggcgcttc ttcctcttcc acctcttctt   9300
ccatgatcgc ttcttcttct tcctcagccg ggacgggagg gggcggcggc ggcgggggag   9360
gggcgcggcg gcggcggcgg cgcaccggga ggcggtcgat gaagcgctcg atcatctccc   9420
cccgcatgcg gcgcatggtc tcggtgacgg cgcggccgtt ctcccggggg cgcagctcga   9480
agacgccgcc tctcatctcg ccgcggggcg ggcggccgtg aggtagcgag acggcgctga   9540
ctatgcatct taacaattgc tgtgtaggta caccgccgag ggacctgatt gagtccagat   9600
ccaccggatc cgaaaacctt tggaggaaag cgtctatcca gtcgcagtcg caaggtaggc   9660
tgagcaccgt ggcgggcggg ggcgggtctg gagagttcct ggcggagatg ctgctgatga   9720
tgtaattaaa gtaggcggtc ttgagaaggc ggatggtgga caggagcacc atgtctttgg   9780
gtccggcctg ttggatgcgg aggcggtcgg ccatgcccca ggcctcgttc tgacaccggc   9840
gcaggtcttt gtagtagtct tgcatgagtc tttccaccgg cacctcttct ccttcctctt   9900
ctccatctcg ccggtggttt ctcgcgccgc ccatgcgcgt gaccccaaag cccctgagcg   9960
gctgcagcag ggccaggtcg gcgaccacgc gctcggccaa gatggcctgc tgcacctgag  10020
tgagggtcct ctcgaagtca tccatgtcca cgaagcggtg gtaggcgccc gtgttgatgg  10080
tgtaggtgca gttggccatg acggaccagt tgacggtctg gtgtcccggc tgcgagagct  10140
ccgtgtaccg caggcgcgag aaggcgcggg aatcgaacac gtagtcgttg caagtccgca  10200
ccagatactg gtagcccacc aggaagtgcg gcggaggttg gcgatagagg ggccagcgct  10260
gggtggcggg ggcgccgggc gccaggtttt ccagcatgag gcggtggtat ccgtagatgt  10320
acctggacat ccaggtgatg ccggcggcgg tggtggtggc gcgcgcgtag tcgcggaccc  10380
ggttccagat gtttcgcagg ggcgagaagt gttccatggt cggcacgctc tggccggtga  10440
ggcgcgcgca gtcgttgacg ctctatacac acacaaaaac gaaagcgttt acagggcttt  10500
cgttctgtag cctggaggaa agtaaatggg ttgggttgcg gtgtgccccg gttcgagacc  10560
aagctgagct cggccggctg aagccgcagc taacgtggta ttggcagtcc cgtctcgacc  10620
caggccctgt atcctccagg atacggtcga gagccctttt gctttcttgg ccaagcgccc  10680
gtggcgcgat ctgggataga tggtcgcgat gagaggacaa aagcggctcg cttccgtagt  10740
ctggagaaac aatcgccagg gttgcgttgc ggcgtacccc ggttcgagcc cctatggcgg  10800
cttgaatcgg ccggaaccgc ggctaacgag ggccgtggca gccccgtcct caggaccccg  10860
ccagccgact tctccagtta cgggagcgag ccccttttgt tttttatttt ttagatgcat  10920
cccgtgctgc ggcagatgcg cccctcgccc cggcccgatc agcagcagca acagcaggca  10980
tgcagacccc cctctcccct ttccgccccg gtcaccacgg ccgcggcggc cgtgtcgggc  11040
gcgggggcgg cgctggagtc agatgagcca ccgcggcggc gacctaggca gtatctggac  11100
ttggaagagg gcgagggact ggcgcggctg gggcgaact ctccagagcg ccacccgcgg  11160
gtgcagttga aaagggacgc gcgcgaggcg tacctgccgc ggcagaacct gtttcgcgac  11220
cgcgggggcg aggagcccga ggagatgcga gactgcaggt tccaagcggg gcgcgagctg  11280
cggcgcgggc tggacagaca gcgcctgctg cgcgaggagg actttgagcc cgacacgcag  11340
acgggcatca gccccgcgcg cgcgcacgta gccgcggccg acctggtgac cgcctacgag  11400
cagacggtga accaggagcg caacttccaa aagagcttca acaaccacgt gcgcacgctg  11460
gtggcgcgcg aggaggtgac cctgggtctc atgcatctgt gggacctggt ggaggcgatc  11520
gtgcagaacc ccagcagcaa gcccctgacc gcgcagctgt tcctggtggt gcagcacagc  11580
```

```
agggacaacg aggccttcag ggaggcgctg ctgaacatca ccgagccgga ggggcgctgg  11640
ctcctggacc tgataaacat cctgcagagc atagtggtgc aggagcgcag cctgagcctg  11700
gccgagaagg tggcggccat caactactct atgctgagcc tgggcaagtt ctacgcccgc  11760
aagatctaca agacccccta cgtgcccata gacaaggagg tgaagataga cagcttctac  11820
atgcgcatgg cgctgaaggt gctgaccctg agcgacgacc tgggagtgta ccgcaacgag  11880
cgcatccaca aggccgtgag cgccagccgg cggcgcgagc tgagcgaccg cgagctgatg  11940
cacagtctgc agcgcgcgct gaccggcgcg ggcgagggcg acagggaggt cgagtcctac  12000
ttcgacatgg gggccgacct gcactggcag ccgagccgcc gcgccctgga ggcggcgggg  12060
gcgtacggcg gccccctggc ggccgatgac caggaagagg aggactatga gctagaggag  12120
ggcgagtacc tggaggactg acctggctgg tggtgttttg gtatagatgc aagatccgaa  12180
cgtggcggac ccggcggtcc gggcggcgct gcaaagccag ccgtccggca ttaactcctc  12240
tgacgactgg gccgcggcca tgggtcgcat catggccctg accgcgcgca accccgaggc  12300
tttcaggcag cagcctcagg ccaaccggct ggcggccatc ttggaagcgg tagtgcccgc  12360
gcgctccaac cccacccacg agaaggtgct ggccatagtc aacgcgctgg cggagagcag  12420
ggccatccgc gcggacgagg ccggactggt gtacgatgcg ctgctgcagc gggtggcgcg  12480
gtacaacagc ggcaacgtgc agaccaacct ggaccgcctg gtgacggacg tgcgcgaggc  12540
cgtggcgcag cgcgagcgct tgcatcagga cggtaacctg ggctcgctgg tggcgctaaa  12600
cgccttcctc agcacccagc cggccaacgt accgcggggg caggaggact acaccaactt  12660
tttgagcgcg ctgcggctga tggtgaccga ggtccctcag agcgaggtgt accagtcggg  12720
gcccgactac ttcttccaga ccagcagaca gggcttgcaa accgtgaacc tgagccaggc  12780
tttcaagaac ctgcgggggc tgtggggagt gaaggcgccc accggcgacc gggctacggt  12840
gtccagcctg ctaaccccca actcgcgcct gctgctgctg ctgatcgcgc ccttcacgga  12900
cagcgggagc gtctcgcggg agacctatct gggccacctg ctgacgctgt accgcgaggc  12960
catcgggcag gcgcaggtgg acgagcacac cttccaagag atcaccagcg tgagccacgc  13020
gctggggcag gaggacacgg gcagcctgca ggcgaccctg aactacctgc tgaccaacag  13080
gcggcagaag attcccacgc tgcacagcct gacccaggag gaggagcgca tcttgcgcta  13140
cgtgcagcag agcgtgagcc tgaacctgat gcgcgacggc gtgacgccca gcgtggcgct  13200
ggacatgacc gcgcgcaaca tggaaccggg catgtacgcc tcccaccggc cgttcatcaa  13260
ccgcctgatg gactacttgc atcgggcggc ggccgtgaac cccgagtact tcactaatgc  13320
cattctgaat ccccactgga tgccccctcc gggtttctac aacggggact ttgaggtgcc  13380
cgaggtcaac gacgggttcc tctgggatga catggatgac agtgtgttct cacccaaccc  13440
gctgcgcgcc gcgtctctgc gattgaagga gggctctgac agggaaggac cgagaagtct  13500
ggcctcctcc ctggctctgg gagcggtggg cgccacgggc gcggcggcgc ggggcagtag  13560
ccccttcccc agcctggcag actctctgaa cagcgggcgg gtgagcaggc cccgcttgct  13620
aggcgaggag gagtatctga acaactccct gctgcagccc gcgagggaca agaacgctca  13680
gcggcagcag tttcccaaca atgggataga gagcctggtg gacaagatgt ccagatggaa  13740
gacgtatgcg caggagtaca aggagtggga ggaccgccag ccgcggccct tgccgccccc  13800
taggcagcgc tggcagcggc gcgcgtccaa ccgccgctgg aggcaggggc ccgaggacga  13860
tgatgactct gcagatgaca gcagcgtgtt ggacctgggc gggagcggga accccttttc  13920
```

gcacctgcgc ccacgcctgg gcaagatgtt ttaaaagaaa aaaaaaaaat aaaactcacc 13980
aaggccatgg cgacgagcgt tggttttttg ttcccttcct tagtatgcgg cgcgcggcga 14040
tgttcgagga ggggcctccc ccctcttacg agagcgcgat ggggatttct cctgcggcgc 14100
ccctgcagcc tccctacgtg cctcctcggt acctgcaacc tacagggggg agaaatagca 14160
tctgttactc tgagctgcag cccctgtacg ataccaccag actgtacctg gtggacaaca 14220
agtccgcgga cgtggcctcc ctgaactacc agaacgacca cagcgatttt ttgaccacgg 14280
tgatccaaaa caacgacttc accccaaccg aggccagcac tcagaccata aacctggata 14340
acaggtcgaa ctggggcggc gacctgaaga ccatcttgca caccaacatg cccaacgtga 14400
acgagttcat gttcaccaac tcttttaagg cgcgggtgat ggtggcgcgc gagcaggggg 14460
aggcgaagta cgagtgggtg gacttcacgc tgcccgaggg caactactca gagaccatga 14520
ctctcgacct gatgaacaat gcgatcgtgg aacactatct gaaagtgggc aggcagaacg 14580
gggtgaagga aagcgatatc ggggtcaagt ttgacaccag aaacttccgt ctgggctggg 14640
accccgtgac cgggctggtc atgccggggg tctacaccaa cgaggccttt catcccgaca 14700
tagtgcttct gcccggctgt ggggtggact tcacccagag ccggctgagc aacctgctgg 14760
gcattcgcaa gcggcagcct ttccaggagg gtttcaagat cacctatgag gatctgaagg 14820
ggggcaacat tcccgcgctc cttgatctgg acgcctacga ggagagcttg aaacccgagg 14880
agagcgctgg cgacagcggc gagagtggcg aggagcaagc cggcggcggt ggcggcgcgt 14940
cggtagaaaa cgaaagtacg cccgcagtgg cggcggacgc tgcggaggtc gagccggagg 15000
ccatgcagca ggacgcagag gagggcgcac aggagggcgc gcagaaggac atgaacgatg 15060
gggagatcag gggagacaca ttcgccaccc ggggcgaaga aaaagaggca gaggcggcgg 15120
cggcggcgac ggcggaggcc gaaaccgagg ttgaggcaga ggcagagccc gagaccgaag 15180
ttatggaaga catgaatgat ggagaacgta ggggcgacac gttcgccacc cggggcgaag 15240
agaaggcggc ggaggcagaa gccgcggctg aggaggcggc tgcggctgcg gccaagactg 15300
aggctgcggc taaggctgag gtcgaagcca atgttgcggt tgaggctcag gctgaggagg 15360
aggcggcggc tgaagcagtt aaggaaaagg cccaggcaga gcaggaagag aaaaaacctg 15420
tcattcaacc tctaaaagaa gatagcaaaa agcgcagtta caacgtcatc gagggcagca 15480
cctttaccca gtaccgcagc tggtacctgg cgtacaacta cggcgacccg gtcaaggggg 15540
tgcgctcgtg gaccctgctc tgcacgccgg acgtcacctg cggctccgag cagatgtact 15600
ggtcgctgcc gaacatgatg caagacccgg tgaccttccg ctccacgcgg caggttagca 15660
acttcccggt ggtgggcgcc gaactgctgc ccgtgcactc caagagtttt tacaacgagc 15720
aggccgtcta ctcccagctg atccgccagg ccacctctct gacccacgtg ttcaatcgct 15780
ttcccgagaa ccagattttg gcgcgcccgc cggcccccac catcaccacc gtgagtgaaa 15840
acgttcctgc cctcacagat cacgggacgc taccgctgcg caacagcatc tcaggagtcc 15900
agcgagtgac cattactgac gccagacgcc ggacctgccc ctacgtttac aaggccttgg 15960
gcatagtctc gccgcgcgtc ctctccagtc gcactttttta aaacacatct acccacacgt 16020
tccaaaatca tgtccgtact catctcaccc agcaacaaca ccggctgggg gctgcgcgcg 16080
cccagcaaga tgtttggagg ggcgaggaag cgctccgacc agcaccctgt gcgcgtgcgc 16140
ggccactacc gcgcgccctg gggagcgcac aagcgcgggc gcacagggcg caccactgtg 16200
gacgacgtca ttgactccgt agtggagcaa gcgcgccact acacacccgg cgcgccgacc 16260
gcccccgccg tgtccaccgt ggaccaggcg atcgaaagcg tggtacaggg cgcgcggcac 16320

```
tatgccaacc ttaaaagtcg ccgccgccgc gtggcccgcc gccatcgccg gagaccccgg  16380
gccaccgccg ccgcgcgcct tactaaggct ctgctcaggc gcgccaggcg aactggccac  16440
cgggccgcca tgagggccgc acggcgggct gccgctgccg caagcgccgt ggccccgcgg  16500
gcacgaaggc gcgcggccgc cgccgccgcc gccgccattt ccagcttggc ctcgacgcgg  16560
cgcggtaaca tatactgggt gcgcgactcg gtaaccggca cgcgggtacc cgtgcgcttt  16620
cgccccccgc ggaattagca caagacaaca tacacactga gtctcctgct gttgtgtatc  16680
ccagcggcga ccgtcagcag cggcgacatg tccaagcgca aaattaaaga agagatgctc  16740
caggtcatcg cgccggagat ctatgggccc ccgaagaagg aggaggatga ttacaagccc  16800
cgcaagctaa agcgggtcaa aaagaaaaag aaagatgatg atgatgacga ggcggtggag  16860
tttgtccgcc gcatggcacc caggcgcccc gtgcagtgga agggccggcg cgtgcagcgc  16920
gttttgcgcc ccggcaccgc ggtggtcttc acgcccggcg agcgctccac gcgcactttc  16980
aagcgggtgt acgatgaggt gtacggcgac gaggacctgt tggagcaggc caaccagcgc  17040
tttggggagt ttgcatatgg gaaacggccc cgcgagagtc taaaagagga cctgctggcg  17100
ctaccgctgg acgagggcaa tcccaccccg agtctgaagc cggtaaccct gcaacaggtg  17160
ctgcctttga gcgcgcccag cgagcataag cgagggttga agcgcgaagg cggggacctg  17220
gcgcccaccg tgcagttgat ggtgcccaag cggcagaagc tggaggacgt gctggagaaa  17280
atgaaagtag agcccgggat ccagcccgag atcaaggtcc gccccatcaa gcaggtggcg  17340
cccggcgtgg gagtccagac cgtggacgtt aggattccca cggaggagat ggaaacccaa  17400
accgccactc cctcttcggc ggccagcgcc accaccggca ccgcttcggt agaggtgcag  17460
acggacccct ggctacccgc caccgctgtt gccgccgccg ccccccgttc gcgcgggcgc  17520
aagagaaatt atccagcggc cagcgcgctc atgccccagt acgcactgca tccatccatc  17580
gcgcccaccc ccggctaccg cgggtactcg taccgcccgc gcagatcagc cggcactcgc  17640
ggccgccgcc gccgtgcgac cacaaccagc cgccgccgtc gccgccgccg ccagccagtg  17700
ctgacccccg tgtctgtaag gaaggtggct cgctcgggga gcacgctggt ggtgcccaga  17760
gcgcgctacc accccagcat cgtttaaagc cggtctctgt atggttcttg cagatatggc  17820
cctcacttgt cgcctccgct tcccggtgcc gggataccga ggaagaactc accgccgcag  17880
aggcatggcg ggcagcggtc tccgcggcgg ccgtcgccat cgccggcgcg caaaaagcag  17940
gcgcatgcgc ggcggtgtgc tgcctctgct aatcccgcta atcgccgcgg cgatcggtgc  18000
cgtacccggg atcgcctccg tggccctgca ggcgtcccag aaacgttgac tcttgcaacc  18060
ttgcaagctt gcatttttg gaggaaaaat aaaaaaagtc tagactctca cgctcgcttg  18120
gtcctgtgac tattttgtag aaaaaagatg gaagacatca actttgcgtc gctggccccg  18180
cgtcacggct cgcgcccgtt catgggagac tggacagata tcggcaccag caatatgagc  18240
ggtggcgcct tcagctgggg cagtctgtgg agcggcctta aaaattttgg ttccaccatt  18300
aagaactatg gcaacaaagc gtggaacagc agcacgggcc agatgctgag agacaagttg  18360
aaagagcaga acttccagga gaaggtggcg cagggcctgg cctctggcat cagcggggtg  18420
gtggacatag ctaaccaggc cgtgcagaaa aagataaaca gtcatctgga cccccgtcct  18480
caggtggagg aaatgcctcc agcgatggag acggtgtctc ccgagggcaa aggcgaaaag  18540
cgcccgcggc ccgacagaga agagaccctg gtgtcacaca ccgaggagcc gccctcttac  18600
gaggaggcag tcaaggccgg cctgcccacc actcgcccca tagcccccat ggccaccggt  18660
```

```
gtggtgggcc acaggcaaca cactcccgca acactagatc tgccccccgcc gtccgagccg  18720
ccgcgccagc caaaggcggc gacggtgccc gctccctcca cttccgccgc caacagagtg  18780
cccctgcgcc gcgccgcgag cggcccccgg gcctcgcgag ttagcggcaa ctggcagagc  18840
acactgaaca gcatcgtggg cctgggagtg aggagtgtga agcgccgccg ttgctactga  18900
atgagcaagc tagctaacgt gttgtatgtg tgtatgcgtc ctatgtcgcc gccagaggag  18960
ctgttgagcc gccggcgccg tctgcactcc agcgaatttc aagatggcga ccccatcgat  19020
gatgcctcag tggtcgtaca tgcacatctc gggccaggac gcttcggagt acctgagccc  19080
cgggctggtg cagttcgccc gcgccacaga cacctacttc aacatgagta acaagttcag  19140
gaaccccact gtggcgccca cccacgatgt gaccacggac cggtcgcagc gcctgacgct  19200
gcggttcatc cccgtggatc gggaggacac cgcctactct tacaaggcgc ggttcacgct  19260
ggccgtgggc gacaaccgcg tgctggacat ggcctccact tactttgaca tcaggggggt  19320
gctggacagg ggccccacct tcaagcccta ctcgggtact gcctacaact ccctggcccc  19380
caagggcgct cccaattctt gcgagtggga acaagaggaa aatcaggtgg tcgctgcaga  19440
tgatgaactt gaagatgaag aagcgcaagc tcaagaggac gccccagcta aaaaaattca  19500
tgtatatgcc caggcgcctc ttgctggcga aaagattacc aaggatggtt tgcaaatagg  19560
tactgaagtt gtaggagata catctaagga cacttttgca gacaaaacat tccaacccga  19620
acctcagata ggcgagtctc agtggaacga ggctgatgcc acagtagcag gaggcagagt  19680
cttgaaaaaa accaccccta tgagaccttg ctatggatcc tatgccaggc ctacaaatgc  19740
caacgggggt caaggaatta tggttgccaa tgaacaagga gtgttggagt ctaaagtgga  19800
gatgcaattt ttttctaaca ctacaaccct taatgcgcgg gatggagctg gcaatcccga  19860
accaaaggtg gtgttgtaca gtgaagatgt ccacttggaa tctcctgaca ctcatttgtc  19920
ttacaagccc aaaaaggatg atgttaatgc taaaattatg ttgggtcagc aagctatggc  19980
taacaggccc aacctcattg cttttagaga taatttcatt ggactcatgt actacaacag  20040
cactggtaac atgggagtgc tggcgggtca ggcctctcag ttgaatgccg tggtggacct  20100
gcaggataga aacacagaac tgtcatatca gcttatgctt gattccattg gggatagatc  20160
cagatacttc tccatgtgga accaggcagt ggatagctat gacccagatg tcagaatcat  20220
tgaaaaccat ggtgtcgagg acgagctacc caactactgc ttccctctgg gcggcatagg  20280
aattactgat acttatcaag ggatcaaaaa taccaatggc aatggtcagt ggaccaaaga  20340
tgatcagttc gcggaccgta atgaaatagg ggtgggaaac aacttcgcca tggagatcaa  20400
catccaggcc aacctctgga ggaacttcct ctatgcgaac gtggggctct acctgccaga  20460
caagctcaag tacaacccca ccaacgtgga catctctgac aaccccaaca cctatgacta  20520
catgaacaag cgtgtggtgg ctcccggcct ggtggactgc tttgtcaatg tgggagccag  20580
gtggtccctg gactacatgg acaacgtcaa cccccttcaac caccaccgca atgcgggtct  20640
gcgctaccgc tccatgatcc tgggcaacgg gcgctacgtg cccttccaca ttcaggtgcc  20700
ccagaagttc tttgccatca agaacctcct cctcctgccg ggctcctaca cttacgagtg  20760
gaacttcagg aaggatgtca acatggtcct gcagagctct ctgggcaatg accttagggt  20820
ggacggggcc agcatcaagt ttgacagcgt caccctctat gctaccttct tccccatggc  20880
tcacaacacc gcctccacgc tcgaggccat gctgaggaac gacaccaacg accagtcctt  20940
caatgactac ctctctgggg ccaacatgct ctaccccatc cccgccaagg ccaccaacgt  21000
gcccatctcc attccctctc gcaactgggc cgccttcaga ggctgggcct ttacccgcct  21060
```

```
taagaccaag gaaaccccct ccctgggctc gggttttgac ccctactttg tctactcggg  21120
atccatcccc tacctggatg gcaccttcta cctcaaccac acttttaaga agatatccat  21180
catgtatgac tcctccgtca gctggccggg caatgaccgc ctgctcaccc ccaatgagtt  21240
cgaggtcaag cgcgccgtgg acggcgaggg ctacaacgtg gcccagtgca acatgaccaa  21300
ggactggttc ctggtgcaga tgctggccaa ctacaacata ggctaccagg gcttctacat  21360
cccagagagc tacaaggaca ggatgtactc cttcttcaga aatttccaac ccatgagcag  21420
gcaggtggtg gacgagacca aatacaagga ctatcaggcc attggcatca ctcaccagca  21480
caacaactcg ggattcgtgg gctacctggc tcccaccatg cgcgaggggc aggcctaccc  21540
cgccaacttc ccctacccgt tgataggcaa gaccgcggtc gacagcgtca cccagaaaaa  21600
gttcctctgc gaccgcaccc tctggcgcat cccccttctct agcaacttca tgtccatggg  21660
tgcgctcacg gacctgggcc agaacctgct ctatgccaac tccgcccatg cgctggacat  21720
gacttttgag gtggaccccca tggacgagcc caccccttctc tatattgtgt ttgaagtgtt  21780
cgacgtggtc agagtgcacc agccgcaccg cggtgtcatc gagaccgtgt acctgcgcac  21840
gcccttctcg gccggcaacg ccaccaccta aggagacagc gccgccgcct gcatgacggg  21900
ttccaccgag caagagctca gggccatcgc cagagacctg ggatgcggac cctatttttt  21960
gggcacctat gacaaacgct tcccgggctt catctcccga gacaagctcg cctgcgccat  22020
cgtcaacacg gccgcgcgcg agaccggggg cgtgcactgg ctggcctttg gctgggaccc  22080
gcgctccaaa acctgctacc tcttcgaccc ctttggcttc tccgatcagc gcctcagaca  22140
gatctatgag tttgagtacg aggggctgct gcgccgcagc gcgcttgcct cctcgcccga  22200
ccgctgcatc acccttgaga agtccaccga gaccgtgcag gggccccact cggccgcctg  22260
cggtctcttc tgctgcatgt tttgcacgc ctttgtgcgc tggccccaga gtcccatgga  22320
tcgcaacccc accatgaact tgctcaaggg agtgcccaac gccatgctcc agagccccca  22380
ggtccagccc accctgcgcc acaaccagga acagctctac cgcttcctgg agcgccactc  22440
cccctacttc cgcagtcaca gcgcgcacat ccggggggcc acctctttct gccacttgca  22500
acaaaacatg caagacggaa aatgatgtac agctcgcttt ttaataaatg taaagactgt  22560
gcactttatt tatacacggg ctctttctgg ttatttattc aacaccgccg tcgccatcta  22620
gaaatcgaaa gggttctgcc gcgcgtcgcc gtgcgccacg ggcagagaca cgttgcgata  22680
ctggaagcgg ctcgcccact tgaactcggg caccaccatg cggggcagtg gctcctcggg  22740
gaagttctcg ccccacaggg tgcgggtcag ctgcagcgcg ctcaggaggt cgggagccga  22800
gatcttgaag tcgcagttgg ggccggaacc ctgcgcgcgc gagttgcggt acacggggtt  22860
gcagcactgg aacaccagca gggccggatt acgcacgctg gccagcaggc tctcgtcgct  22920
gatcatgtcg ctgtccagat cctccgcgtt gctcagggcg aatggggtca tcttgcagac  22980
ctgcctgccc aggaaaggcg gcagcccggg cttgccgttg cagtcgcagc gcaggggcat  23040
cagcaggtgc ccgtggcccg tctgcgcctg cgggtacagc gcgcgcatga aggcttcgat  23100
ctgcctgaaa gccacctgcg tcttggctcc ctccgaaaag aacatcccac aggacttgct  23160
ggagaactgg ttcgcgggac agctggcatc gtgcaggcag cagcgcgcgt cggtgttggc  23220
gatctgcacc acgttgcgac cccaccggtt cttcactatc ttggccttgg aagcctgctc  23280
cttcagcgcg cgctggccgt tctcgctggt cacatccatc tctatcacct gctccttgtt  23340
gatcatgttt gtcccgtgca gacacttcag gtcgccctcc gtctgggtgc agcggtgctc  23400
```

```
ccacagcgcg caaccggtgg gctcccaatt tttgtgggtc acccccgcgt aggcctgcag  23460
gtaggcctgc aagaagcgcc ccatcatggc cacaaaggtc ttctggctcg taaaggtcag  23520
ctgcaggccg cgatgctctt cgttcagcca ggtcttgcag atggcggcca gcgcctcggt  23580
ctgctcgggc agcatcctaa aatttgtctt caggtcgtta tccacgtggt acttgtccat  23640
catggcgcgc gccgcctcca tgcccttctc ccaggcggac accatgggca ggcttagggg  23700
gtttatcact tccaccggcg aggacaccgt actttcgatt tcttcttcct ccccctcttc  23760
ccggcgcgcg cccacgctgc tgcgcgctct caccgcctgc accaaggggt cgtcttcagg  23820
caagcgccgc accgagcgct tgccgccctt gacctgctta atcagcaccg gcgggttgct  23880
gaagcccacc atggtcagct ccgcctgctc ttcttcgtct tcgctgtcta ccactatctc  23940
tggggaaggg cttctccgct ctgcggcggt gcgcttcttt tttttcttgg gagcagccgt  24000
gacggagtcc gccacggcga cggaggtcga gggcgtgggg ctgggggtgc gcggtaccag  24060
ggcctcgtcg ccctcggact cttcctctga ctccaggcgg cggcggagac gcttctttgg  24120
gggcgcgcgc gtcagcggcg gcggagacgg ggacggggac ggggacggga cgccctccac  24180
agggggtggt cttcgcgcag acccgcggcc gcgctcgggg gtcttttcga gctggtcttg  24240
gtcccgactg gccattgtat cctcctcctc ctaggcagag agacataagg agtctatcat  24300
gcaagtcgag aaggaggaga gcttaaccac cccctctgag accgccgatg cgcccgccgt  24360
cgccgtcgcc cccgctgccg ccgacgcgcc cgccacaccg agcgacaccc ccgcggaccc  24420
cccagccgac gcacccctgt tcgaggaagc ggccgtggag caggacccgg gctttgtctc  24480
ggcagaggag gatttgcgag aggaggagga taaggagaag aagccctcag tgccaaaaga  24540
tgataaagag caagacgagc acgacgcaga tgcacaccag ggtgaagtcg ggcgggggga  24600
cggagggcat gacggcgccg actacctaga cgaagggaac gacgtgctct tgaagcacct  24660
gcatcgtcag tgcgccatcg tttgcgacgc tctgcaggag cgcagcgaag tgcccctcag  24720
cgtggcggag gtcagccacg cctacgagct cagcctcttc tccccccggg tgcccccccg  24780
ccgccgcgaa aacggcacat gcgagcccaa cccgcgcctc aacttctacc ccgcctttgt  24840
ggtgcccgag gtcctggcca cctatcacat cttctttcaa aattgcaaga tccccctctc  24900
gtgccgcgcc aaccgtagcc gcgccgataa gatgctggcc ctgcgccagg gcgaccacat  24960
acctgatatc gccgctttgg aagatgtgcc aaagatcttc gagggtctgg gtcgcaacga  25020
gaagcgggca gcaaactctc tgcaacagga aaacagcgaa aatgagagtc acaccggggt  25080
actggtggag ctcgagggcg acaacgcccg cctggcggtg gtcaagcgca gcatcgaggt  25140
cacccacttt gcctaccccg cgctcaacct gccccccaaa gtcatgaacg cggccatgga  25200
cgggctgatc atgcgccgcg gccggcccct cgctccagat gcaaacttgc atgaggagac  25260
cgaggacggc cagcccgtgg tcagcgacga gcagctggcg cgctggctgg agaccgcgga  25320
ccccgccgaa ctggaggagc ggcgcaagat gatgatggcc gcggtgctgg tcaccgtaga  25380
gctggagtgt ctgcagcgct tcttcggcga ccccgagatg cagagaaagg tcgaggagac  25440
cctgcactac accttccgcc agggctacgt gcgccaggct tgcaagatct ccaacgtgga  25500
gctcagcaac ctggtgtcct acctgggcat cttgcatgag aaccgcctcg ggcagagcgt  25560
gctgcactcc accctgcgcg gggaggcgcg ccgcgactac gtgcgcgact gcgtttacct  25620
cttcctctgc tacacctggc agacggccat gggggtctgg cagcagtgcc tggaggagcg  25680
caacctcaag gagctggaga agctcctgca gcgcgcgctc aaagacctct ggacgggcta  25740
caacgagcgc tcggtggccg ccgcgctggc cgacctcatc ttccccgagc gcctgctcaa  25800
```

```
aaccctccag caggggctgc ccgacttcac cagccaaagc atgttgcaaa acttcaggaa  25860
ctttatcctg gagcgttctg gcatcctacc cgccacctgc tgcgccctgc ccagcgactt  25920
tgtcccccctc gtgtaccgcg agtgcccccc gccgctgtgg ggtcactgct acctgttcca  25980
actggccaac tacctgtcct accacgcgga cctcatggag gactccagcg gcgaggggct  26040
catggagtgc cactgccgct gcaacctctg cacgccccac cgctccctgg tctgcaacac  26100
ccaactgctc agcgagagtc agattatcgg taccttcgag ctacagggtc cgtcctcctc  26160
agacgagaag tccgcggctc cggggctaaa actcactccg gggctgtgga cttccgccta  26220
cctgcgcaaa tttgtacctg aagactacca cgcccacgag atcaggtttt acgaagacca  26280
atcccgcccg cccaaggcgg agctgaccgc ctgcgtcatc acccagggcg agatcctagg  26340
ccaattgcaa gccatccaaa aagcccgcca agattttttg ctgagaaagg gtcggggggt  26400
gtatctggac ccccagtcgg gtgaggagct caacccggtt cccccgctgc cgccgccgcg  26460
ggaccttgct tcccaggata agcatcgcca tggctcccag aaagaagcag cagcggccgc  26520
cactgccgcc accccacatg ctggaggaag aggaggaata ctgggacagt caggcagagg  26580
aggtttcgga cgaggaggag ccggagacgg agatggaaga gtgggaggag gacagcttag  26640
acgaggaggc ttccgaagcc gaagaggcag acgcaacacc gtcaccctcg gccgcagccc  26700
cctcgcaggc gcccccgaag tccgctccca gcatcagcag caacagcagc gctataacct  26760
ccgctcctcc accgccgcga cccacggccg accgcagacc caaccgtaga tgggacacca  26820
ccggaaccgg ggccggtaag tcctccggga gaggcaagca agcgcagcgc caaggctacc  26880
gctcgtggcg cgctcacaag aacgccatag tcgcttgctt gcaagactgc ggggggaaca  26940
tctccttcgc ccgccgcttc ctgctcttcc accacggtgt ggccttcccc cgtaacgtcc  27000
tgcattacta ccgtcatctc tacagcccct actgcggcgg cagtgagcca gagacggtcg  27060
gcggcggcgg cggcgcccgt ttcggcgcct aggaagaccc agggcaagac ttcagccaag  27120
aaactcgcgg cggccgcggc gaacgcggtc gcgggggccc tgcgcctgac ggtgaacgaa  27180
cccctgtcga cccgcgaact gagaaaccga atcttcccca ctctctatgc catcttccag  27240
cagagcagag ggcaggatca ggaactgaaa gtaaaaaaca ggtctctgcg ctccctcacc  27300
cgcagctgtc tgtatcacaa gagcgaagac cagcttcggc gcacgctgga ggacgctgag  27360
gcactcttca gcaaatactg cgcgctcact cttaaggact agctccgcgc ccttctcgaa  27420
tttaggcggg aacgcctacg tcatcgcagc gccgccgtca tgagcaagga cattcccacg  27480
ccatacatgt ggagctatca gccgcagatg ggactcgcgg cgggcgcctc ccaagactac  27540
tccacccgca tgaactggct cagtgccggc ccacacatga tctcacaggt taatgatatc  27600
cgcacccatc gaaaccaaat attggtggag caggcggcaa ttaccaccac gccccgcaat  27660
aatcccaacc ccagggagtg gcccgcgtcc ctggtgtatc aggaaattcc cggccccacc  27720
accgtactac ttccgcgtga ttcccaggcc gaagtccaaa tgactaactc aggggcgcag  27780
ctcgcgggcg gctgtcgtca cagggtgcgg cctcctcgcc agggtataac tcacctggag  27840
atccgaggca gaggtattca gctcaacgac gagtcggtga gctcctcgct cggtctaaga  27900
cctgacggga ccttccagat agccggagcc ggccgatctt ccttcacgcc ccgccaggcg  27960
tacctgactc tgcagagctc gtcctcggcg ccgcgctcgg gcggcatcgg gactctccag  28020
ttcgtgcagg agtttgtgcc ctcggtctac ttcaacccct tctcgggctc tcccggtcgc  28080
tacccggacc agttcatctc gaactttgac gccgcgaggg actcggtgga cggctacgac  28140
```

```
tgaatgtcgg gtggacccgg tgcagagcaa cttcgcctga agcacctcga ccactgccgc  28200
cgccctcagt gctttgcccg ctgtcagacc ggtgagttcc agtacttttc cctgcccgac  28260
tcgcacccgg acggcccggc gcacggggtg cgctttttca tcccgagtca ggtgcgctct  28320
accctaatca gggagtttac cgcccgtccc ctactggcgg agttggaaaa ggggccttct  28380
atcctaacca ttgcctgcat ctgctctaac cctggattgc accaagatct ttgctgtcat  28440
ttgtgtgctg agtataataa aggctgagat cagaatctac tcgggctcct gtcgccatcc  28500
tgtcaacgcc accgtccaag cccggcccga tcagcccgag gtgaacctca cctgcggtct  28560
gcaccggcgc ctgaggaaat acctagcttg gtactacaac agcactccct ttgtggttta  28620
caacagcttt gaccaggacg gggtctcact gagggataac ctctcgaacc tgagctactc  28680
catcaggaag aacagcaccc tcgagctact tcctccttac ctgcccggga cttaccagtg  28740
tgtcaccggt ccctgcaccc acacccacct gttgatcgta aacgactctc ttccgagaac  28800
agacctcaat aactcctctt cgcagttccc cagaacagga ggtgagctca ggaaaccccg  28860
ggtaaagaag ggtggacaag agttaacact tgtggggttt ctggtgtatg tgacgctggt  28920
ggtggctctt ttgattaagg cttttccttc catgtctgaa ctctccctct tttatgaaca  28980
actcgactag tgctaacggg accctaccca acgaatcggg attgaatatc ggtaaccagg  29040
ttgcagtttc acttttgatt accttcatag tcctcttcct gctagtgctg tcgcttctgt  29100
gcctgcggat cgggggctgc tgcatccacg tttatatctg gtgctggctg tttagaaggt  29160
tcggagacca tcgcaggtag aataaacatg ctgctgctta ccctctttgt cctggcgctg  29220
gccgccagct gccaagcctt ttccgaggct gactttatag agccccagtg taacgtgact  29280
tttaaagccc atgcacagcg ttgtcatact ataatcaaat gtgccaccga acacgatgaa  29340
taccttatcc agtataaaga taaatcacac aaagtggcac ttgttgacat ctggaaaccc  29400
gaagaccctt tggaatacaa tgtgaccgtt ttccagggtg acctcttcaa aatttacaat  29460
tacactttcc catttgacca gatgtgtgac tttgtcatgt acatggaaaa gcagcacaag  29520
ctgtggcctc cgactcccca gggctgtgtg gaaaatccag gctctttctg catgatctct  29580
ctctgtgtaa ctgtgctggc actaatactc acgcttttgt atatcagatt taaatcaagg  29640
caaagcttca tcgatgaaaa gaaaatgcct taaacgcttt cacgcttgat tgctaacacc  29700
gggtttttat ccgcagaatg attggaatca ccctactaat cacctccctc cttgcgattg  29760
cccatgggtt ggaacgaatc gaagcccctg tggggggccaa tgttaccctg gtggggcctg  29820
tcggcaatgc tacattaatg tgggaaaaat atactaaaaa tcaatgggtc tcttactgca  29880
ctaacaaaaa cagccacaag cccagagcca tctgcgatgg gcaaaatcta accttgattg  29940
atgttcaaat gctggatgcg ggctactatt atgggcagct gggtacaatg attaattact  30000
ggagacccca caaagattac atgctccacg tagtaaaggg tccccttagc agcccaccca  30060
ctaccacctc tactaccccc actaccacca ctactcccac caccagcact gccgcccagc  30120
ctcctcatag cagaacaacc acttttatca attccaagtc ccactccccc cacattgccg  30180
gcgggccctc cgcctcagac tccgagacca ccgagatctg cttctgcaaa tgctctgacg  30240
cctttgctga ggatttggaa gaccacgagg aagatgagca tgacttcgca gatgcatgcc  30300
aggcatcaga ggcagaagcg ctgccggtgg ccctcaaaca gtatgcagac ccccacacca  30360
cccccaacct tcctccacct tcccagaagc caagtttcct gggggaaaat gaaactctgc  30420
ctctctccat actcgctctg acatctgttg ctatgttgac cgctctgctg gtgcttctat  30480
gctctatatg ctacctgatc tgctgcagaa agaaaaaatc tcacggccat gctcaccagc  30540
```

```
ccctcatgca cttcccttac cctccagagc tgggcgacca caaactttaa gtctgcagta  30600
actatctgcc catcccttgt cagtcgacag cgatgagccc cactaatcta acggcctctg  30660
gacttacaac atcgtctctt aatgagacca ccgctcctca agacctgtac gatggtgtct  30720
ccgcgctggt taaccagtgg gatcacctgg gcatatggtg gctcctcata ggagcagtga  30780
ccctgtgcct aatcctggtc tggatcatct gctgcatcaa aagcagaaga cccaggcggc  30840
ggcccatcta caggcccttt gtcatcacac ctgaagatga tgatgacacc acttccaggc  30900
tgcagaggct aaagcagcta ctcttctctt ttacagcatg gtaaattgaa tcatgcctcg  30960
cattttcatc tacttgtctc tccttccact ttttctgggc tcttctacat tggccgctgt  31020
gtcccacatc gaggtagact gcctcacgcc cttcacagtc tacctgcttt tcggctttgt  31080
catctgcacc tttgtctgca gcgttatcac tgtagtgatc tgcttcatac agtgcatcga  31140
ctacgtctgc gtgcgggtgg cttactttag acaccacccc cagtatcgca acagggacat  31200
agcggctctc ctaagacttg tttaaaatca tggccaaatt aactgtgatt ggtcttctga  31260
tcatctgctg cgtcctagcc gcgattggga ctcaagctcc taccaccacc agcgctccca  31320
gaaagagaca tgtatcctgc agcttcaagc gtccctggaa tataccccaa tgctttactg  31380
atgaacctga aatctctttg gcttggtact tcagcgtcac cgcccttctt atcttctgca  31440
gtacggttat tgcccttgcc atctaccctt cccttgacct gggctggaat gctgtcaact  31500
ctatggaata tcccaccttc ccagaaccag acctgccaga cctggttgtt ctaaacgcgt  31560
ttcctcctcc tgctcccgtt caaaatcagt ttcgccctcc gtcccccacg cccactgagg  31620
tcagctactt taatctaaca ggcggagatg actgaaaacc tagacctaga aatggacggt  31680
ctctgcagcg agcaacgcac actagagagg cgccggcaaa aagagctcga gcgtcttaaa  31740
caagagctcc aagacgcggt ggccatacac cagtgcaaaa aaggtgtctt ctgtctggta  31800
aaacaggcca cgctcaccta tgaaaaaaca ggtgacaccc accgcctagg atacaagctg  31860
cccacacagc gccagaagtt cgccctcatg ataggcgaac aacccatcac cgtgacccag  31920
cactccgtgg agacagaagg ctgcatacac gctccctgta ggggcgctga ctgcctctac  31980
accttgatca aaaccctctg cggtctcaga gacctcatcc cttttaatta atcataactg  32040
taatcaataa aaaatcactt acttgaaatc tgatagcaag cctctgtcca attttttcag  32100
caacacttcc ttccctcct cccaactctg gtactctagg cgcctcctag ctgcaaactt  32160
cctccacagt ctgaagggaa tgtcagattc ctcctcctgt ccctccgcac ccacgatctt  32220
catgttgttg cagatgaaac gcgcgagatc gtctgacgag accttcaacc ccgtgtaccc  32280
ctacgatacc gagatcgctc cgacttctgt ccctttcctt acccctccct ttgtgtcatc  32340
cgcaggaatg caagaaaatc cagctggggt gctgtccctg cacttgtcag agccccttac  32400
cacccacaat ggggccctga ctctaaaaat ggggggcggc ctgaccctgg acaaggaagg  32460
gaatctcact tcccaaaaca tcaccagtgt cgatcccccct ctcaaaaaaa gcaagaacaa  32520
catcagcctt cagaccgccg cacccctcgc cgtcagctcc ggggccctaa cactttttgc  32580
cactcccccc ctagcggtca gtggtgacaa ccttactgtg cagtctcagg cccctctcac  32640
tttggaagac tcaaaactaa ctctggccac caaaggaccc ctaactgtgt ccgaaggcaa  32700
acttgtccta gaaacagagg ctcccctgca tgcaagtgac agcagcagcc tgggccttag  32760
cgttacggcc ccacttagca ttaacaatga cagcctagga ctagacatgc aagcgcccat  32820
tagctctcga gatggaaaac tggctctaac agtggcggcc cccctaactg tggtcgaggg  32880
```

```
tatcaatgct ttggcagtag ccacaggtaa gggtattggg ctaaatgaaa ccaacacaca  32940
cctgcaggca aaactggtcg cacccctagg ctttgatacc aacggcaaca ttaagctaag  33000
cgttgcagga ggcatgaggc taaacaataa cacactgata ctagatgtaa actacccatt  33060
tgaggctcaa ggccaactga gcctaagagt gggctcgggc ccactatatg tagattctag  33120
tagtcataac ctaaccatta gatgccttag gggattgtat ataacatctt ctaacaacca  33180
aaacggtcta gaagccaaca ttaaactaac aagaggcctt gtgtatgacg gaaatgccat  33240
agcagttaat gttggcaaag ggctggaata cagccctact gacacaacag aaaaacctat  33300
acagactaaa ataggtctag gcatggagta tgataccgag ggagccatga tgacaaaact  33360
aggctctgga ctaagctttg acaattcagg agccattgta gtgggaaaca aaaatgatga  33420
caggcttact ttgtggacca caccggaccc atcgcccaac tgtcagatct actctgaaaa  33480
agatgctaaa ctaaccttgg tactgactaa atgtggcagt caggttgtag gcacagtatc  33540
tattgccgct cttaaaggta gcctcgtgcc aatcactagt gcaatcagtg tggttcaggt  33600
atacctaagg tttgatgaaa atggggtact aatgagtaac tcttcactta atggcgaata  33660
ctggaatttt agaaacggag actcaactaa tggcacacca tatacaaacg cagtgggttt  33720
catgcctaat ctactggcct atcctaaagg tcaaactaca actgcaaaaa gtaacattgt  33780
cagccaggtc tacatgaatg ggacgatac taaacccatg acatttacaa tcaacttcaa  33840
tggccttagt gaaacagggg atacccctgt tagtaaatat tccatgacat tctcatggag  33900
gtggccaaat ggaagctaca tagggcacaa ttttgtaaca aactccttta ccttctccta  33960
catcgcccaa gaataaagaa agcacagaga tgcttgtttt tgatttcaaa attgtgtgct  34020
tttatttatt ttcagcttac agtatttcca gtagtcattc aaataaagct taatcaaact  34080
gcatgagaac ccttccacat agcttaaatt agcaccagtg caaatggaga aaaatcaaca  34140
taccttttt tatccagata tcagagaact ctagtggtca gttttccccc accctcccag  34200
ctcacagaat acacagtcct ttcccccgg ctggctttaa acaacactat ctcattggta  34260
acagacatat tcttaggtgt aataatccac acggtctctt ggcgggccaa acgctggtcg  34320
gtgatgttaa taaactcccc aggcagctct ttcaagttca cgtcgctgtc caactgctga  34380
agcgctcgcg gctccgactg cgcctctagc ggaggcaacg gcaacacccg atccttgatc  34440
tataaaggag tagagtcata atcccccata agaatagggc ggtgatgcag caacaaggcg  34500
cgcagcaact cctgccgccg cctctccgta cggcaggaat gcaacggcgt ggtggtctcc  34560
tccgtgataa tccgcaccgc tcgcagcatc agcatcctcg tcctccgggc acagcagcgc  34620
atcctgatct cactgagatc ggcgcagtaa gtgcagcaca aaaccaagat gttatttaag  34680
atcccacagt gcaaagcact gtacccaaag ctcatggcgg gaaggacagc ccccacgtga  34740
ccatcatacc agatcctcag gtaaatcaaa tgacgacctc tcataaacac gctggacatg  34800
tacatcacct ccttgggcat gtgctgattc accacctctc gataccacaa gcatcgctga  34860
ttaattaaag accccctcgag caccatccta aaccaggaag ccagcacctg accccccgcc  34920
aggcactgca gggaccccgg tgaatcgcag tggcagtgaa gactccagcg ctcgtagccg  34980
tgaaccatag agctggtcat tatatccaca ttggcacaac acagacacac tttcatacac  35040
tttttcatga ttagcagctc ctctctagtc aggaccatat cccaaggaat cacccactct  35100
tgaatcaagg taaatcccac acagcagggc aggcctctca cataactcac gttatgcata  35160
gtgagcgtgt cgcaatctgg aaataccgga tgatcttcca tcaccgaagc ccgggtctcc  35220
gtctcaaagg gaggtaaacg gtccctcgtg tagggacagt ggcgggataa tcgagatcgt  35280
```

```
gttgaacgta gagtcatgcc aaagggaaca gcggacgtac tcatatttcc tccagcagaa  35340
ccaagtgcgc gcgtggcagc tatccctgcg tcttctgtct cgccgcctgc cccgttcggt  35400
gtagtagttg taatacagcc actccctgag accgtcaagg cgctccctgg cgtccggatc  35460
tatgacaaca ccgtcctgca gcgccgccct gatgacatcc accaccgtag agtatgccaa  35520
gcccagccag gaaatgcatt cactttgaca gcgagagata ggaggagcgg ggagagatgg  35580
aagaaccatg atagtaaaga gaacttttat tccaatcgat cttctaagat atcaaagtgg  35640
agatctataa gatgacactg gtctcctccg ctgagtcgat caaaaataac agctaaacca  35700
caaacaacac gattggtcaa atgctccaca agggcctgca gcataaaatt gcctcggaac  35760
tccaccgcaa gcataacatc aaagccaccg cctctatcgt gatcaagaat aaaaacccca  35820
cagctatcca ccagacccat atagttttca tctctccatc gtgaaaaaag atttacaagc  35880
tcctccttta aatcacctcc aaccaattga aaaagttgaa ccagaccgcc ctccaccttc  35940
attttcagca agcgtatcat gattgcaaaa attcaggctc ctcagacacc tgtataagat  36000
tgagaagcgg aacgttaaca tcgatgtttc gctcgcgtaa atcacgcctc agtgcaagca  36060
taatataatc ccacaggtcg gagcggatca gcgaggacac ctccccgcca ggaaccaact  36120
caacggagcc tatgctgatt ataatacgca tattcggagc tatgctaacc agcacggccc  36180
ccaaataggc gtactgcata ggcggcgaca aaaagtgaac agtttgggtt aaaaaatcag  36240
gcaaacactc gcgcaaaaaa gcaagaacat cataaccatg ctcatgcaaa tagatgcaag  36300
taagctcagg aacaaccaca gaaaaatgca caatttttct ctcaaacatg actgcgagcc  36360
ctgcaaaaaa taaaaaagaa acattacaca agagtagcct gtcttacgat gggatagact  36420
actctaacca acataagacg ggccacaaca tcgcccgcgt ggccataaaa aaaattgtcc  36480
gtgtgattaa aaagaagcac agatagctgg ccagtcatat ccggagtcat cacgtgtgaa  36540
cccgtgtaga cccccgggtt ggacacatcg gccaaagaaa gaaagcggcc aatgtaccca  36600
ggaggaatta taacactaag acgaagatac aacagaataa ccccatgagg gggaataaca  36660
aagttagtag gtgaataaaa acgataaaca cccgaaactc cctcctgcgt aggcaaaata  36720
gcaccctccc cttccaaaac aacatatagc gcttccacag cagccatgac aaaagactca  36780
aaacactcaa aagactcagt cttaccagga aaataaaagc actctcacag caccagcact  36840
aatcagagtg tgaagagggc caagtgccga acgagtatat ataggaataa aaaatgacgt  36900
aaatgtgtaa aggtcagaaa acgcccagaa aaatacacag accaacgccc gaaacgaaaa  36960
cccgcgaaaa aatacccaga acttcctcaa caaccgccac ttccgctttc tcacggtacg  37020
tcacttccgc aagaaaagca aaactacatt tcccacatgt gtaaaaacga aaccccgccc  37080
cttgtaaccg cccacaactt acatcatcaa aacgtaaact cctacgtcac ccgccccgcc  37140
tctccccgcc cacctcatta tcatattggc cacaatccaa aataaggtat attat       37195
```

```
<210> SEQ ID NO 24
<211> LENGTH: 37197
<212> TYPE: DNA
<213> ORGANISM: Gorilla beringei graueri

<400> SEQUENCE: 24

ataatatacc ttattttgga ttgtggccaa tatgataatg aggtgggcgg ggagaggcgg     60
ggcgggtgac gtaggacgcg cgagtagggt tgggaggtgt ggcggaagtg tggcatttgc    120
aagtgggagg agctcacatg caagcttccg tcgcggaaaa tgtgacgttt ttgatgagcg    180
```

-continued

```
ccgcctacct ccggaagtgc caattttcgc gcgcttttca ccggatatcg tagtaatttt    240
gggcgggacc atgtaagatt tggccatttt cgcgcgaaaa gtgaaacggg gaagtgaaaa    300
ctgaataata gggcgttagt catagtgcgt aatatttacc gagggccgag ggactttgac    360
cgattacgtg gaggactcgc ccaggtgttt tttacgtgaa tttccgcgtt ccgggtcaaa    420
gtctccgttt tattgtcacc gtcatttgac gcggagggta tttaaacccg ctgcgctcct    480
caagaggcca ctcttgagtg ccagcgagaa gagttttctc ctctgctccg cttcggtgat    540
cgaaaaatga gacacatagc ctgcactccg ggtcttttgt ccggtcgggc ggcggccgag    600
cttttggacg ctttgatcaa tgatgtcctg agcgatgatt ttccgtctac tacccacttt    660
agcccaccta ctcttcacga actgtacgat ctggatgtac tggtggatgt gaacgatccc    720
aacgaggagg cggtttctgc gtttttttccc gagtctgcgc tgttggccgc tcaggaggga    780
tttgacctac acactccgcc gcctatttta gagtctccgc tgccggagcc cagtggtata    840
ccttatatgc ctgaactgct tcccgaagtg gtagacctga cctgccacga gcctggcttt    900
ccgcccagcg acgatgatgg tgagcctttt gttttagact ttgctgagat acctgggcac    960
ggttgcaggt cttgtgcata tcatcagagg gttaccggag accccgaggt taagtgttcg   1020
ctgtgctata tgaggatgac ctcttccttt atctacagta agtttttgtc taggtgggct   1080
tttgggtagg tgggttttgt gtcagaacag gtgtaaacgt tgcttgtgtt ttttgtacct   1140
gtaggtccgg tgtccgagcc agacccggag cccgaccgcg atcccgagcc ggatcccgag   1200
cctcctcgta gggcaagaaa attaccttct attctgtgca agtctaagac acctgtgagg   1260
accagcgagg cggacagcac cgactctggc acttctacct ctcctcctga aattcaccca   1320
gtggttcctc tgggtataca tagacctgtt gctgttagag tttgcgggcg acgctctgca   1380
gtagagtgca ttgaggactt gcttcacgaa cccgaggaac ctttggactt gagcgttaaa   1440
cgccctaggc aataaacccc acctaagtaa taaaccccac ctaagtaata aaccctgccg   1500
cccttggtta ttgagatgac gcccaatgtt tgcttttgaa tgacttcatg tgtgtaataa   1560
aagtgagtgt gatcataggt ctcttgtttg tctgggcggg gcttaagggt atataagtct   1620
cttggggcta aacttggtta cacttgaccc caatggaggc gtgggggtgc ttggaggagt   1680
ttgcggacgt gcgccgtttg ctggacgaga gctctagcaa tacctatact atttggaggt   1740
atctgtgggg ctctactcag gccaagttgg tctccagaat taagcaggat tacaagtgcg   1800
attttgaaga gctttttagt tcctgcggtg agcttttgca atccttgaat ctgggccatc   1860
aggctatttt ccaggaaaag gttctctcga ctttggattt ttccactccc gggcgcaccg   1920
ccgcttgtgt ggcttttgtg tcttttgtgc aagataaatg gagcgaggag acccacctga   1980
gtcacggcta cgtactggat ttcatggcga tggctctttg gagggcttac aacaaatgga   2040
agattcagaa ggaactgtac ggttccgccc tacgtcgtcc acttctgtcg cgacaggggc   2100
tgaggtttcc cgaccatcgg cagcatcaga atctggaaga cgagtcggag gagcgagcgg   2160
aggagaagat cagcttgaga gccggcctgg accctcctca ggaggaatga atctcccgca   2220
ggtggttgac ctgtttccag aactgagacg ggtcctgact atcagggagg atggtcagtt   2280
tgtgaagaag tttaagaggg atcggggtga gggagatgat gaggcggcta gcaatttagc   2340
ttttagtctg atgactcgcc accgaccgga atgtattacc tatcagcaga ttaaggagag   2400
ttgtgccaac gagctggatc ttttgggtca gaagtatagc atagaacagc ttaccactta   2460
ctggcttcag cctggggatg attgggaaga ggcgatcagg gtgtatgcaa aggtggccct   2520
gcggcccgat tgcaagtata agattactaa gttggttaat attagaaact gctgctatat   2580
```

```
ttctgggaac ggggccgaag tggagataga tactcaggac agggtggctt ttaggtgttg   2640
catgataaac atgtggcccg ggatactggg gatggatggg gtggtattca tgaatgtgag   2700
gtttacgggc cccaacttta atggcacggt gttcatgggc aacaccaact tgctcctgca   2760
tggtgcgagt ttctatgggt ttaataacac ctgtatagag gcctggaccg atgtaaaggt   2820
tcgaggttgt tccttttata gctgttggaa ggcggtggtg tgtcgcccta aaagcagggg   2880
ttctgtgaaa aaatgcttgt ttgaaaggtg caccttaggc atcctctctg agggcaactc   2940
cagggtgcgc cataatgtgg cttcgaactg cggttgcttc atgcaagtga agggggtgag   3000
cgttatcaag cataactcgg tgtgtggaaa ctgcgaggat cgcgcctccc agatgctgac   3060
ctgctttgat ggcaactgtc acctgttgaa gaccattcat ataagcagcc accccagaaa   3120
ggcctggccc gtgtttgagc ataacatctt gacccgctgc tccttgcatc tgggggtcag   3180
gaggggtatg ttcctgcctt accagtgtaa ctttagccac actaaaatcc tgctggaacc   3240
cgagtgcatg accaaggtca gcctgaatgg tgtgtttgat gtgactctga aaatctggaa   3300
ggtgctgagg tatgatgaga ccaggaccag gtgccgaccc tgcgagtgcg gcggcaagca   3360
catgagaaat cagcctgtga tgttggatgt gaccgaggag cttaggcctg accatctggt   3420
gctggcctgc accagggccg agtttgggtc tagcgatgag gataccgatt gaggtgggta   3480
aggtgggcgt ggctagaagg gtggggcgtg tataaattgg gggtctaagg gtctctctgt   3540
tttgtcttgc aacagccgcc gccatgagcg acaccggcaa cagctttgat ggaagcatct   3600
ttagccccta tctgacagtg cgcatgcctc actgggctgg agtgcgtcag aatgtgatgg   3660
gttccaacgt ggatggacgc ccgttctgc cttcaaattc gtctacaatg gcctacgcga    3720
ccgtgggagg aactccgctg gacgccgcga cctccgccgc cgcctccgcc gccgccgcga   3780
ccgcgcgcag catggctacg gacctttaca gctctttggt ggcgagcggc gcggcctctc   3840
gcgcgtctgc tcgggatgag aaactgaccg ctctgctgct taaactggaa gacttgaccc   3900
gggagctggc tcaactgacc cagcaggtct ccagcttgcg tgagagcagc cttgcctccc   3960
cctaatggcc cataatataa ataaaagcca gtctgtttgg attaagcaag tgtatgttct   4020
ttatttaact ctccgcgcgc ggtaagcccg ggaccagcgg tctcggtcgt ttagggtgcg   4080
gtggattctt tccaacacgt ggtacaggtg gctctggatg tttagataca tgggcatgag   4140
tccatccctg gggtggaggt agcaccactg cagagcttcg tgctcggggg tggtgttgta   4200
tatgatccag tcgtagcagg agcgctgggc gtggtgctga aaaatgtcct taagcaagag   4260
gcttatagct agggggaggc ccttggtgta agtgtttaca aatctgctca gttgggaggg   4320
gtgcatccgg ggggatataa tgtgcatctt ggactggatt tttaggttgg ctatgttccc   4380
acccagatcc cttctgggat tcatgttgtg caggaccacc agcacggtat atccagtaca   4440
cttgggaaat ttatcgtgga gcttagacgg gaatgcatgg aagaacttgg agacgccctt   4500
gtggcctccc agattttcca tacattcgtc catgatgatg gcaatgggcc cgtgggaagc   4560
tgcctgagca aaaatgtttc tgggatcgct cacatcgtag ttatgttcca gggtgaggtc   4620
atcataggac atctttacaa atcgggggcg gagggtcccg gactggggga tgatggtgcc   4680
ctcgggcccc ggggcgtagt tcccctcaca gatctgcatc tcccaggctt tcatttcaga   4740
gggagggatc atatccacct gcggagcgat gaaaaacaca gtttctggcg caggggagat   4800
taactgggat gagagcaggt ttctgagcag ctgtgacttt ccacagccgg tgggcccata   4860
tatcacgcct atcaccggct gcagctggta gttaagagag ctgcagctgc cgtcctcccg   4920
```

```
gagcaggggg gccacctcgt tcagcatatc cctgacgtgg atgttctccc tgaccaattc   4980
cgccagaagg cgctcgccgc ccagcgaaag cagctcttgc aaggaagcaa aatttttcag   5040
cggttttagg ccgtcggccg tgggcatgtt tttcagcgtc tgggtcagca gttccagtct   5100
gtcccacagc tcggtgatgt gctctacggc atctcgatcc agcagatctc ctcgtttcgc   5160
gggttggggc ggctttcgct gtagggcacc agccgatggg cgtccagcgg ggccagagtc   5220
atgtccttcc atgggcgcag ggtcctcgtc agggtggtct gggtcacggt gaaggggtgc   5280
gctccgggtt gggcgctggc cagggtgcgc ttgaggctgg ttctgctggt gctgaatcgc   5340
tgccgctctt cgccctgcgc gtcggccagg tagcatttga ccatggtctc gtagtcgaga   5400
ccctcggcgg cgtgcccctt ggcgcggagc tttcccttgg aggtggcgcc gcacgagggg   5460
cactgcaggc tcttcagggc gtagagcttg ggagcgagaa acacggactc tggggagtag   5520
gcgtccgcgc cgcaggaagc gcagaccgtc tcgcattcca ccagccaagt gagctccggg   5580
cggtcagggt caaaaaccag gttgccccca tgctttttga tgcgtttctt acctcggctc   5640
tccatgaggc ggtgtccctt ctcggtgacg aagaggctgt ccgtgtctcc gtagaccgac   5700
ttcaggggcc tgtcttccag cggagtgcct ctgtcctcct cgtagagaaa ctctgaccac   5760
tctgagacga aggcccgcgt ccaggccagg acgaaggagg ccacgtggga ggggtagcgg   5820
tcgttgtcca ctagcgggtc caccttctcc agggtgtgca ggcacatgtc cccctcctcc   5880
gcgtccagaa aagtgattgg cttgtaggtg taggacacgt gaccgggggt tcccgacggg   5940
ggggtataaa agggggtggg caccctttca tcttcactct cttccgcatc gctgtctgcg   6000
agagccagct gctggggtaa gtattccctc tcgaaggcgg gcatgacctc agcgctcagg   6060
ttgtcagttt ctaaaaatga ggaggatttg atgttcacct gtccggaggt gatacctttg   6120
agggtacctg ggtccatctg gtcagaaaac actatttttt tgttgtcaag cttggtggcg   6180
aacgacccgt agagggcgtt ggagagcagc ttggcgatgg agcgcagggt ctggtttttg   6240
tcgcggtcgg ctcgctcctt ggccgcgatg ttgagttgca cgtactcgcg ggccacgcac   6300
ttccactcgg ggaagacggt ggtgcgctcg tctgggatca ggcgcaccct ccagcctcgg   6360
ttgtgcaggg tgaccatgtc gacgctggtg gcgacctcgc cgcgcaggcg ctcgttggtc   6420
cagcagaggc ggccgccctt gcgcgagcag aagggggggta gggggtccag ctggtcctcg   6480
tttgggggggt ccgcgtcgat ggtgaagacc ccggggagca agcgcgggtc aaagtagtcg   6540
atcttgcaag cttgcatgtc cagagcccgc tgccattcgc gggcggcgag cgcgcgctcg   6600
taggggttga ggggcgggcc ccagggcatg ggtgggtga gcgcggaggc gtacatgccg   6660
cagatgtcat acacgtacag gggttccctg aggatgccga ggtaggtggg gtagcagcgc   6720
cccccgcgga tgctggcgcg cacgtagtca tagagctcgt gggagggggc cagcatgttg   6780
ggcccgaggt tggtgcgctg ggggcgctcg gcgcggaagg cgatctgcct gaagatggca   6840
tgggagttgg aggagatggt gggccgctgg aagacgttga agcttgcttc ttgcaagccc   6900
accgagtccc tgacgaagca ggcgtaggac tcgcgcagct tgtgcaccag ctcggcggtg   6960
acctggacgt cgagcgcgca gtagtcgagg gtctcgcgga tgatgtcata cttatcctcc   7020
cccttctttt tccacagctc gcggttgagg acgaactctt cgcggtcttt ccagtactct   7080
tggaggggaa acccgtccgt gtccgaacgg taagagccta gcatgtagaa ctggttgacg   7140
gcctggtagg ggcaacagcc cttctccacg ggcagcgcgt aggcctgcgc cgccttgcgg   7200
agggaggtgt gggtgagggc gaaagtgtcc ctgaccatga ctttgaggta ttgatgtttg   7260
aagtctgtgt catcgcagcc gccctgttcc cacagggtgt agtccgtgcg ctttttggag   7320
```

```
cgcgggttgg gcagggagaa ggtgaggtca ttgaagagga tcttccccgc tcgaggcatg   7380
aagtttctgg tgatgcgaaa gggccctggg accgaggagc ggttgttgat gacctgggcg   7440
gccaggacga tctcgtcaaa gccgtttatg ttgtggccca cgatgtagag ctccaaaaag   7500
cggggctggc ccttgatgga ggggagcttt ttgagttcct cgtaggtgag ctcctcgggc   7560
gattccaggc cgtgctcctc cagggcccag tcttgcaagt gagggttggc cgccaggaag   7620
gatcgccaga ggtcgcgggc catgagggtc tgcaggcggt cgcggaaggt tctgaactgt   7680
cgccccacgg ccatcttttc gggggtgatg cagtagaagg tgagggggtc tttctcccag   7740
gggtcccatc tgagctctcg ggcgaggtcg cgcgcggcgg cgaccagagc ctcgttgccc   7800
cccagtttca tgaccagcat gaagggcacg agctgcttgc caaaggctcc catccaagtg   7860
taggtctcta catcgtaggt gacaaagagg cgctccgtgc gaggatgaga gccgatcggg   7920
aagaactgga tctcccgcca ccagttggag gattggctgt tgatgtggtg aaagtagaag   7980
tcccgtctgc gggccgagca ctcgtgctgg cttttgtaaa agcgaccgca gtactggcag   8040
cgctgcacgg gttgtatatc ttgcacgagg tgaacctggc gacctctgac gaggaagcgc   8100
agcgggaatc taagtccccc gcctggggtc ccgtgtggct ggtggtcttc tactttggtt   8160
gtctggccgc cagcatctgt ctcctggagg gcgatggtgg agcagaccac cacgccgcga   8220
gagccgcagg tccagatctc ggcgctcggc gggcggagtt tgatgacgac atcgcgcaca   8280
ttggagctgt ccatggtctc cagctcccgc ggcggcaggt cagctgggag ttcctggagg   8340
ttcacctcgc agagacgggt caaggcgcgg gcagtgttga gatggtatct gatttcaagg   8400
ggcgtgttgg cggcggagtc gatggcttgc aggaggccgc agccccgggg ggccacgatg   8460
gttccccgcg gggcgcgagg ggaggcggaa gctgggggtg tgttcagaag cggtgacgcg   8520
ggcgggcccc cggaggtagg gggggttccg gccccacagg catgggcggc aggggcacgt   8580
cttcgccgcg cgcgggcagg ggctggtgct ggctccgaag agcgcttgcg tgcgcgacga   8640
cgcgacggtt ggtgtcctgt atctgacgcc tctgagtgaa gaccacgggt cccgtgacct   8700
tgaacctgaa agagagttcg acagaatcaa tctcggcatc gttgacagcg gcctggcgca   8760
ggatctcctg cacgtcgccc gagttgtcct ggtaggcgat ctctgccatg aactgctcga   8820
tctcttcttc ctggagatct cctcgtccgg cgcgctccac ggtggccgcc aggtcgttgg   8880
agatgcgacc catgagctgc gagaaggcgt tgagcccgcc ctcgttccag acccggctgt   8940
agaccacgcc cccctcggcg ttgcgggcgc gcatgaccac ctgggccagg ttgagctcca   9000
cgtgtcgcgt gaagacggcg tagttgcgca ggcgctggaa aaggtagttc agggtggtgg   9060
cggtgtgctc ggcgacgaag aagtacatga cccagcgccg caacgtggat tcattgatgt   9120
cccccaaggc ctccaggcgc tccatggcct cgtagaagtc cacggcgaag ttgaaaaact   9180
gggagttgcg agcggacacg gtcaactcct cctccagaag acggatgagc tcggcgacag   9240
tgtcgcgcac ctcgcgctcg aaggccacgg ggggcgcttc ttcctcttcc acctcttctt   9300
ccatgatcgc ttcttcttct tcctcagccg ggacgggagg gggcggcggc ggcgggggag   9360
gggcgcggcg gcggcggcgg cgcaccggga ggcggtcgat gaagcgctcg atcatctccc   9420
cccgcatgcg gcgcatggtc tcggtgacgg cgcggccgtt ctcccggggg cgcagctcga   9480
agacgccgcc tctcatctcg ccgcggggcg ggcggccgtg aggtagcgag acggcgctga   9540
ctatgcatct taacaattgc tgtgtaggta caccgccgag ggacctgatt gagtccagat   9600
ccaccggatc cgaaaacctt tggaggaaag cgtctatcca gtcgcagtcg caaggtaggc   9660
```

```
tgagcaccgt ggcgggcggg ggcgggtctg gagagttcct ggcggagatg ctgctgatga   9720
tgtaattaaa gtaggcggtc ttgagaaggc ggatggtgga caggagcacc atgtctttgg   9780
gtccggcctg ttggatgcgg aggcggtcgg ccatgcccca ggcctcgttc tgacaccggc   9840
gcaggtcttt gtagtagtct tgcatgagtc tttccaccgg cacctcttct ccttcctctt   9900
ctccatctcg ccggtggttt ctcgcgccgc ccatgcgcgt gaccccaaag cccctgagcg   9960
gctgcagcag ggccaggtcg gcgaccacgc gctcggccaa gatggcctgc tgcacctgag  10020
tgagggtcct ctcgaagtca tccatgtcca cgaagcggtg gtaggcgccc gtgttgatgg  10080
tgtaggtgca gttggccatg acggaccagt tgacggtctg gtgtcccggc tgcgagagct  10140
ccgtgtaccg caggcgcgag aaggcgcggg aatcgaacac gtagtcgttg caagtccgca  10200
ccagatactg gtagcccacc aggaagtgcg gcggaggttg gcgatagagg ggccagcgct  10260
gggtggcggg ggcgccgggc gccaggtttt ccagcatgag gcggtggtat ccgtagatgt  10320
acctggacat ccaggtgatg ccggcggcgg tggtggtggc gcgcgcgtag tcgcggaccc  10380
ggttccagat gtttcgcagg ggcgagaagt gttccatggt cggcacgctc tggccggtga  10440
ggcgcgcgca gtcgttgacg ctctatacac acacaaaaac gaaagcgttt acagggcttt  10500
cgttctgtag cctggaggaa agtaaatggg ttgggttgcg gtgtgccccg gttcgagacc  10560
aagctgagct cggccggctg aagccgcagc taacgtggta ttggcagtcc cgtctcgacc  10620
caggccctgt atcctccagg atacggtcga gagccctttt gctttcttgg ccaagcgccc  10680
gtggcgcgat ctgggataga tggtcgcgat gagaggacaa aagcggctcg cttccgtagt  10740
ctggagaaac aatcgccagg gttgcgttgc ggcgtacccc ggttcgagcc cctatggcgg  10800
cttgaatcgg ccggaaccgc ggctaacgag ggccgtggca gccccgtcct caggaccccg  10860
ccagccgact tctccagtta cgggagcgag ccccttttgt tttttatttt ttagatgcat  10920
cccgtgctgc ggcagatgcg cccctcgccc cggcccgatc agcagcagca acagcaggca  10980
tgcagacccc cctctcccct ttccgccccg gtcaccacgg ccgcggcggc cgtgtcgggc  11040
gcgggggcgg cgctggagtc agatgagcca ccgcggcggc gacctaggca gtatctggac  11100
ttggaagagg gcgagggact ggcgcggctg gggggcgaact ctccagagcg ccacccgcgg  11160
gtgcagttga aaagggacgc gcgcgaggcg tacctgccgc ggcagaacct gtttcgcgac  11220
cgcgggggcg aggagcccga ggagatgcga gactgcaggt tccaagcggg gcgcgagctg  11280
cggcgcgggc tggacagaca gcgcctgctg cgcgaggagg actttgagcc cgacacgcag  11340
acgggcatca gccccgcgcg cgcgcacgta gccgcggccg acctggtgac cgcctacgag  11400
cagacggtga accaggagcg caacttccaa aagagcttca acaaccacgt gcgcacgctg  11460
gtggcgcgcg aggaggtgac cctgggtctc atgcatctgt gggacctggt ggaggcgatc  11520
gtgcagaacc ccagcagcaa gcccctgacc gcgcagctgt tcctggtggt gcagcacagc  11580
agggacaacg aggccttcag ggaggcgctg ctgaacatca ccgagccgga ggggcgctgg  11640
ctcctggacc tgataaacat cctgcagagc atagtggtgc aggagcgcag cctgagcctg  11700
gccgagaagg tggcggccat caactactct atgctgagcc tgggcaagtt ctacgcccgc  11760
aagatctaca agacccccta cgtgcccata gacaaggagg tgaagataga cagcttctac  11820
atgcgcatgg cgctgaaggt gctgaccctg agcgacgacc tgggagtgta ccgcaacgag  11880
cgcatccaca aggccgtgag cgccagccgg cggcgcgagc tgagcgaccg cgagctgatg  11940
cacagtctgc agcgcgcgct gaccggcgcg ggcgagggcg acagggaggt cgagtcctac  12000
ttcgacatgg gggccgacct gcactggcag ccgagccgcc gcgccctgga ggcggcgggg  12060
```

```
gcgtacggcg gccccctggc ggccgatgac caggaagagg aggactatga gctagaggag  12120
ggcgagtacc tggaggactg acctggctgg tggtgttttg gtatagatgc aagatccgaa  12180
cgtggcggac ccggcggtcc gggcggcgct gcaaagccag ccgtccggca ttaactcctc  12240
tgacgactgg gccgcggcca tgggtcgcat catggccctg accgcgcgca accccgaggc  12300
tttcaggcag cagcctcagg ccaaccggct ggcggccatc ttggaagcgg tagtgcccgc  12360
gcgctccaac cccacccacg agaaggtgct ggccatagtc aacgcgctgg cggagagcag  12420
ggccatccgc gcggacgagg ccggactggt gtacgatgcg ctgctgcagc gggtggcgcg  12480
gtacaacagc ggcaacgtgc agaccaacct ggaccgcctg gtgacggacg tgcgcgaggc  12540
cgtggcgcag cgcgagcgct tgcatcagga cggtaacctg ggctcgctgg tggcgctaaa  12600
cgccttcctc agcacccagc cggccaacgt accgcggggg caggaggact acaccaactt  12660
tttgagcgcg ctgcggctga tggtgaccga ggtccctcag agcgaggtgt accagtcggg  12720
gcccgactac ttcttccaga ccagcagaca gggcttgcaa accgtgaacc tgagccaggc  12780
tttcaagaac ctgcgggggc tgtggggagt gaaggcgccc accggcgacc gggctacggt  12840
gtccagcctg ctaaccccca actcgcgcct gctgctgctg ctgatcgcgc ccttcacgga  12900
cagcgggagc gtctcgcggg agacctatct gggccacctg ctgacgctgt accgcgaggc  12960
catcgggcag gcgcaggtgg acgagcacac cttccaagag atcaccagcg tgagccacgc  13020
gctggggcag gaggacacgg gcagcctgca ggcgaccctg aactacctgc tgaccaacag  13080
gcggcagaag attcccacgc tgcacagcct gacccaggag gaggagcgca tcttgcgcta  13140
cgtgcagcag agcgtgagcc tgaacctgat gcgcgacggc gtgacgccca gcgtggcgct  13200
ggacatgacc gcgcgcaaca tggaaccggg catgtacgcc tcccaccggc cgttcatcaa  13260
ccgcctgatg gactacttgc atcgggcggc ggccgtgaac cccgagtact tcactaatgc  13320
cattctgaat ccccactgga tgccccctcc gggtttctac aacggggact ttgaggtgcc  13380
cgaggtcaac gacgggttcc tctgggatga catggatgac agtgtgttct cacccaaccc  13440
gctgcgcgcc gcgtctctgc gattgaagga gggctctgac agggaaggac cgagaagtct  13500
ggcctcctcc ctggctctgg gagcggtggg cgccacgggc gcggcggcgc ggggcagtag  13560
ccccttcccc agcctggcag actctctgaa cagcgggcgg gtgagcaggc cccgcttgct  13620
aggcgaggag gagtatctga acaactccct gctgcagccc gcgagggaca agaacgctca  13680
gcggcagcag tttcccaaca atgggataga gagcctggtg gacaagatgt ccagatggaa  13740
gacgtatgcg caggagtaca aggagtggga ggaccgccag ccgcggccct tgccgccccc  13800
taggcagcgc tggcagcggc gcgcgtccaa ccgccgctgg aggcaggggc ccgaggacga  13860
tgatgactct gcagatgaca gcagcgtgtt ggacctgggc gggagcggga accccttttc  13920
gcacctgcgc ccacgcctgg gcaagatgtt ttaaaagaaa aaaaaaaaaa taaaactcac  13980
caaggccatg gcgacgagcg ttggtttttt gttcccttcc ttagtatgcg gcgcgcggcg  14040
atgttcgagg aggggcctcc cccctcttac gagagcgcga tggggatttc tcctgcggcg  14100
cccctgcagc ctccctacgt gcctcctcgg tacctgcaac ctacaggggg gagaaatagc  14160
atctgttact ctgagctgca gcccctgtac gataccacca gactgtacct ggtggacaac  14220
aagtccgcgg acgtggcctc cctgaactac cagaacgacc acagcgattt tttgaccacg  14280
gtgatccaaa acaacgactt caccccaacc gaggccagca ctcagaccat aaacctggat  14340
aacaggtcga actggggcgg cgacctgaag accatcttgc acaccaacat gcccaacgtg  14400
```

aacgagttca tgttcaccaa ctcttttaag gcgcgggtga tggtggcgcg cgagcagggg 14460
gaggcgaagt acgagtgggt ggacttcacg ctgcccgagg gcaactactc agagaccatg 14520
actctcgacc tgatgaacaa tgcgatcgtg gaacactatc tgaaagtggg caggcagaac 14580
ggggtgaagg aaagcgatat cggggtcaag tttgacacca gaaacttccg tctgggctgg 14640
gaccccgtga ccgggctggt catgccgggg gtctacacca acgaggcctt tcatcccgac 14700
atagtgcttc tgcccggctg tggggtggac ttcacccaga gccggctgag caacctgctg 14760
ggcattcgca agcggcagcc tttccaggag ggtttcaaga tcacctatga ggatctgaag 14820
gggggcaaca ttcccgcgct ccttgatctg gacgcctacg aggagagctt gaaacccgag 14880
gagagcgctg gcgacagcgg cgagagtggc gaggagcaag ccggcggcgg tggcggcgcg 14940
tcggtagaaa acgaaagtac gcccgcagtg gcggcggacg ctgcggaggt cgagccggag 15000
gccatgcagc aggacgcaga ggagggcgca caggagggcg cgcagaagga catgaacgat 15060
ggggagatca ggggagacac attcgccacc cggggcgaag aaaaagaggc agaggcggcg 15120
gcggcggcga cggcggaggc cgaaaccgag gttgaggcag aggcagagcc cgagaccgaa 15180
gttatggaag acatgaatga tggagaacgt aggggcgaca cgttcgccac ccggggcgaa 15240
gagaaggcgg cggaggcaga agccgcggct gaggaggcgg ctgcggctgc ggccaagact 15300
gaggctgcgg ctaaggctga ggtcgaagcc aatgttgcgg ttgaggctca ggctgaggag 15360
gaggcggcgg ctgaagcagt taaggaaaag gcccaggcag agcaggaaga gaaaaaacct 15420
gtcattcaac ctctaaaaga agatagcaaa aagcgcagtt acaacgtcat cgagggcagc 15480
acctttaccc agtaccgcag ctggtacctg gcgtacaact acggcgaccc ggtcaagggg 15540
gtgcgctcgt ggaccctgct ctgcacgccg gacgtcacct gcggctccga gcagatgtac 15600
tggtcgctgc cgaacatgat gcaagacccg gtgaccttcc gctccacgcg gcaggttagc 15660
aacttcccgg tggtgggcgc cgaactgctg cccgtgcact ccaagagttt ttacaacgag 15720
caggccgtct actcccagct gatccgccag gccacctctc tgacccacgt gttcaatcgc 15780
tttcccgaga accagatttt ggcgcgcccg ccggccccca ccatcaccac cgtgagtgaa 15840
aacgttcctg ccctcacaga tcacgggacg ctaccgctgc gcaacagcat ctcaggagtc 15900
cagcgagtga ccattactga cgccagacgc cggacctgcc cctacgttta caaggccttg 15960
ggcatagtct cgccgcgcgt cctctccagt cgcacttttt aaaacacatc tacccacacg 16020
ttccaaaatc atgtccgtac tcatctcacc cagcaacaac accggctggg ggctgcgcgc 16080
gcccagcaag atgtttggag ggcgaggaa gcgctccgac cagcaccctg tgcgcgtgcg 16140
cggccactac cgcgcgccct ggggagcgca caagcgcggg cgcacagggc gcaccactgt 16200
ggacgacgtc attgactccg tagtggagca agcgcgccac tacacacccg gcgcgccgac 16260
cgcccccgcc gtgtccaccg tggaccaggc gatcgaaagc gtggtacagg gcgcgcggca 16320
ctatgccaac cttaaaagtc gccgccgccg cgtggcccgc cgccatcgcc ggagaccccg 16380
ggccaccgcc gccgcgcgcc ttactaaggc tctgctcagg cgcgccaggc gaactggcca 16440
ccgggccgcc atgagggccg cacggcgggc tgccgctgcc gcaagcgccg tggccccgcg 16500
ggcacgaagg cgcgcggccg ccgccgccgc cgccgccatt tccagcttgg cctcgacgcg 16560
gcgcggtaac atatactggg tgcgcgactc ggtaaccggc acgcgggtac ccgtgcgctt 16620
tcgccccccg cggaattagc acaagacaac atacacactg agtctcctgc tgttgtgtat 16680
cccagcggcg accgtcagca gcggcgacat gtccaagcgc aaaattaaag aagagatgct 16740
ccaggtcatc gcgccggaga tctatgggcc cccgaagaag gaggaggatg attacaagcc 16800

```
ccgcaagcta aagcgggtca aaaagaaaaa gaaagatgat gatgatgacg aggcggtgga  16860
gtttgtccgc cgcatggcac ccaggcgccc cgtgcagtgg aagggccggc gcgtgcagcg  16920
cgttttgcgc cccggcaccg cggtggtctt cacgcccggc gagcgctcca cgcgcacttt  16980
caagcgggtg tacgatgagg tgtacggcga cgaggacctg ttggagcagg ccaaccagcg  17040
ctttggggag tttgcatatg ggaaacggcc ccgcgagagt ctaaaagagg acctgctggc  17100
gctaccgctg gacgagggca atcccacccc gagtctgaag ccggtaaccc tgcaacaggt  17160
gctgcctttg agcgcgccca gcgagcataa gcgagggttg aagcgcgaag gcggggacct  17220
ggcgcccacc gtgcagttga tggtgcccaa gcggcagaag ctggaggacg tgctggagaa  17280
aatgaaagta gagcccggga tccagcccga gatcaaggtc cgccccatca agcaggtggc  17340
gcccggcgtg ggagtccaga ccgtggacgt taggattccc acggaggaga tggaaaccca  17400
aaccgccact ccctcttcgg cggccagcgc caccaccggc accgcttcgg tagaggtgca  17460
gacggacccc tggctacccg ccaccgctgt tgccgccgcc gcccccgtt cgcgcgggcg  17520
caagagaaat tatccagcgg ccagcgcgct catgccccag tacgcactgc atccatccat  17580
cgcgcccacc cccggctacc gcgggtactc gtaccgcccg cgcagatcag ccggcactcg  17640
cggccgccgc cgccgtgcga ccacaaccag ccgccgccgt cgccgccgcc gccagccagt  17700
gctgaccccc gtgtctgtaa ggaaggtggc tcgctcgggg agcacgctgg tggtgcccag  17760
agcgcgctac caccccagca tcgtttaaag ccggtctctg tatggttctt gcagatatgg  17820
ccctcacttg tcgcctccgc ttcccggtgc cgggataccg aggaagaact caccgccgca  17880
gaggcatggc gggcagcggt ctccgcggcg gccgtcgcca tcgccggcgc gcaaaaagca  17940
ggcgcatgcg cggcggtgtg ctgcctctgc taatcccgct aatcgccgcg gcgatcggtg  18000
ccgtacccgg gatcgcctcc gtggccctgc aggcgtccca gaaacgttga ctcttgcaac  18060
cttgcaagct tgcatttttt ggaggaaaaa ataaaaaaag tctagactct cacgctcgct  18120
tggtcctgtg actattttgt agaaaaaaga tggaagacat caactttgcg tcgctggccc  18180
cgcgtcacgg ctcgcgcccg ttcatgggag actggacaga tatcggcacc agcaatatga  18240
gcggtggcgc cttcagctgg ggcagtctgt ggagcggcct taaaaatttt ggttccacca  18300
ttaagaacta tggcaacaaa gcgtggaaca gcagcacggg ccagatgctg agagacaagt  18360
tgaaagagca gaacttccag gagaaggtgg cgcagggcct ggcctctggc atcagcgggg  18420
tggtggacat agctaaccag gccgtgcaga aaaagataaa cagtcatctg gacccccgtc  18480
ctcaggtgga ggaaatgcct ccagcgatgg agacggtgtc tcccgagggc aaaggcgaaa  18540
agcgcccgcg gcccgacaga gaagagaccc tggtgtcaca caccgaggag ccgccctctt  18600
acgaggaggc agtcaaggcc ggcctgccca ccactcgccc catagccccc atggccaccg  18660
gtgtggtggg ccacaggcaa cacactcccg caacactaga tctgcccccg ccgtccgagc  18720
cgccgcgcca gccaaaggcg gcgacggtgc ccgctccctc cacttccgcc gccaacagag  18780
tgcccctgcg ccgcgccgcg agcggccccc gggcctcgcg agttagcggc aactggcaga  18840
gcacactgaa cagcatcgtg ggcctgggag tgaggagtgt gaagcgccgc cgttgctact  18900
gaatgagcaa gctagctaac gtgttgtatg tgtgtatgcg tcctatgtcg ccgccagagg  18960
agctgttgag ccgccggcgc cgtctgcact ccagcgaatt tcaagatggc gaccccatcg  19020
atgatgcctc agtggtcgta catgcacatc tcgggccagg acgcttcgga gtacctgagc  19080
cccgggctgg tgcagttcgc ccgcgccaca gacacctact tcaacatgag taacaagttc  19140
```

```
aggaacccca ctgtggcgcc cacccacgat gtgaccacgg accggtcgca gcgcctgacg  19200
ctgcggttca tccccgtgga tcgggaggac accgcctact cttacaaggc gcggttcacg  19260
ctggccgtgg gcgacaaccg cgtgctggac atggcctcca cttactttga catcaggggg  19320
gtgctggaca ggggccccac cttcaagccc tactcgggta ctgcctacaa ctccctggcc  19380
cccaagggcg ctcccaattc ttgcgagtgg gaacaagagg aaaatcaggt ggtcgctgca  19440
gatgatgaac ttgaagatga agaagcgcaa gctcaagagg acgccccagc taaaaaaatt  19500
catgtatatg cccaggcgcc tcttgctggc gaaaagatta ccaaggatgg tttgcaaata  19560
ggtactgaag ttgtaggaga tacatctaag gacacttttg cagacaaaac attccaaccc  19620
gaacctcaga taggcgagtc tcagtggaac gaggctgatg ccacagtagc aggaggcaga  19680
gtcttgaaaa aaaccacccc tatgagacct tgctatggat cctatgccag gcctacaaat  19740
gccaacgggg gtcaaggaat tatggttgcc aatgaacaag gagtgttgga gtctaaagtg  19800
gagatgcaat ttttttctaa cactacaacc cttaatgcgc gggatggagc tggcaatccc  19860
gaaccaaagg tggtgttgta cagtgaagat gtccacttgg aatctcctga cactcatttg  19920
tcttacaagc ccaaaaagga tgatgttaat gctaaaatta tgttgggtca gcaagctatg  19980
gctaacaggc ccaacctcat tgcttttaga gataatttca ttggactcat gtactacaac  20040
agcactggta acatgggagt gctggcgggt caggcctctc agttgaatgc cgtggtggac  20100
ctgcaggata gaaacacaga actgtcatat cagcttatgc ttgattccat tggggataga  20160
tccagatact tctccatgtg gaaccaggca gtggatagct atgacccaga tgtcagaatc  20220
attgaaaacc atggtgtcga ggacgagcta cccaactact gcttccctct gggcggcata  20280
ggaattactg atacttatca agggatcaaa aataccaatg gcaatggtca gtggaccaaa  20340
gatgatcagt tcgcggaccg taatgaaata ggggtgggaa acaacttcgc catggagatc  20400
aacatccagg ccaacctctg gaggaacttc ctctatgcga acgtggggct ctacctgcca  20460
gacaagctca agtacaaccc caccaacgtg gacatctctg acaaccccaa cacctatgac  20520
tacatgaaca agcgtgtggt ggctcccggc ctggtggact gctttgtcaa tgtgggagcc  20580
aggtggtccc tggactacat ggacaacgtc aacccctca accaccaccg caatgcgggt  20640
ctgcgctacc gctccatgat cctgggcaac gggcgctacg tgcccttcca cattcaggtg  20700
ccccagaagt tctttgccat caagaacctc ctcctcctgc cgggctccta cacttacgag  20760
tggaacttca ggaaggatgt caacatggtc ctgcagagct ctctgggcaa tgaccttagg  20820
gtggacgggg ccagcatcaa gtttgacagc gtcaccctct atgctacctt cttccccatg  20880
gctcacaaca ccgcctccac gctcgaggcc atgctgagga acgacaccaa cgaccagtcc  20940
ttcaatgact acctctctgg ggccaacatg ctctacccca tccccgccaa ggccaccaac  21000
gtgcccatct ccattccctc tcgcaactgg gccgccttca gaggctgggc ctttacccgc  21060
cttaagacca aggaaacccc ctccctgggc tcgggttttg acccctactt tgtctactcg  21120
ggatccatcc cctacctgga tggcaccttc tacctcaacc acacttttaa gaagatatcc  21180
atcatgtatg actcctccgt cagctggccg ggcaatgacc gcctgctcac ccccaatgag  21240
ttcgaggtca agcgcgccgt ggacggcgag ggctacaacg tggcccagtg caacatgacc  21300
aaggactggt tcctggtgca gatgctggcc aactacaaca taggctacca gggcttctac  21360
atcccagaga gctacaagga caggatgtac tccttcttca gaaatttcca acccatgagc  21420
aggcaggtgg tggacgagac caaatacaag gactatcagg ccattggcat cactcaccag  21480
cacaacaact cgggattcgt gggctacctg gctcccacca tgcgcgaggg gcaggcctac  21540
```

```
cccgccaact tcccctaccc gttgataggc aagaccgcgg tcgacagcgt cacccagaaa  21600
aagttcctct gcgaccgcac cctctggcgc atccccttct ctagcaactt catgtccatg  21660
ggtgcgctca cggacctggg ccagaacctg ctctatgcca actccgccca tgcgctggac  21720
atgactttg aggtggaccc catggacgag cccacccttc tctatattgt gtttgaagtg  21780
ttcgacgtgg tcagagtgca ccagccgcac cgcggtgtca tcgagaccgt gtacctgcgc  21840
acgcccttct cggccggcaa cgccaccacc taaggagaca gcgccgccgc ctgcatgacg  21900
ggttccaccg agcaagagct cagggccatc gccagagacc tgggatgcgg accctatttt  21960
ttgggcacct atgacaaacg cttcccgggc ttcatctccc gagacaagct cgcctgcgcc  22020
atcgtcaaca cggccgcgcg cgagaccggg ggcgtgcact ggctggcctt tggctgggac  22080
ccgcgctcca aaacctgcta cctcttcgac ccctttggct tctccgatca gcgcctcaga  22140
cagatctatg agtttgagta cgaggggctg ctgcgccgca gcgcgcttgc ctcctcgccc  22200
gaccgctgca tcacccttga gaagtccacc gagaccgtgc aggggcccca ctcggccgcc  22260
tgcggtctct tctgctgcat gtttttgcac gcctttgtgc gctggcccca gagtcccatg  22320
gatcgcaacc ccaccatgaa cttgctcaag ggagtgccca acgccatgct ccagagcccc  22380
caggtccagc ccaccctgcg ccacaaccag gaacagctct accgcttcct ggagcgccac  22440
tccccctact tccgcagtca cagcgcgcac atccgggggg ccacctcttt ctgccacttg  22500
caacaaaaca tgcaagacgg aaaatgatgt acagctcgct tttaataaa tgtaaagact  22560
gtgcacttta tttatacacg ggctctttct ggttatttat tcaacaccgc cgtcgccatc  22620
tagaaatcga aagggttctg ccgcgcgtcg ccgtgcgcca cgggcagaga cacgttgcga  22680
tactggaagc ggctcgccca cttgaactcg ggcaccacca tgcggggcag tggctcctcg  22740
gggaagttct cgccccacag ggtgcgggtc agctgcagcg cgctcaggag gtcgggagcc  22800
gagatcttga agtcgcagtt ggggccggaa ccctgcgcgc gcgagttgcg gtacacgggg  22860
ttgcagcact ggaacaccag cagggccgga ttacgcacgc tggccagcag gctctcgtcg  22920
ctgatcatgt cgctgtccag atcctccgcg ttgctcaggg cgaatggggt catcttgcag  22980
acctgcctgc ccaggaaagg cggcagcccg ggcttgccgt tgcagtcgca gcgcaggggc  23040
atcagcaggt gcccgtggcc cgtctgcgcc tgcgggtaca gcgcgcgcat gaaggcttcg  23100
atctgcctga aagccacctg cgtcttggct ccctccgaaa agaacatccc acaggacttg  23160
ctggagaact ggttcgcggg acagctggca tcgtgcaggc agcagcgcgc gtcggtgttg  23220
gcgatctgca ccacgttgcg accccaccgg ttcttcacta tcttggcctt ggaagcctgc  23280
tccttcagcg cgcgctggcc gttctcgctg gtcacatcca tctctatcac ctgctccttg  23340
ttgatcatgt ttgtcccgtg cagacacttc aggtcgccct ccgtctgggt gcagcggtgc  23400
tcccacagcg cgcaaccggt gggctcccaa tttttgtggg tcacccccgc gtaggcctgc  23460
aggtaggcct gcaagaagcg ccccatcatg gccacaaagg tcttctggct cgtaaaggtc  23520
agctgcaggc cgcgatgctc ttcgttcagc caggtcttgc agatggcggc cagcgcctcg  23580
gtctgctcgg gcagcatcct aaaatttgtc ttcaggtcgt tatccacgtg gtacttgtcc  23640
atcatggcgc gcgccgcctc catgcccttc tcccaggcgg acaccatggg caggcttagg  23700
gggtttatca cttccaccgg cgaggacacc gtactttcga tttcttcttc ctccccctct  23760
tcccggcgcg cgcccacgct gctgcgcgct ctcaccgcct gcaccaaggg gtcgtcttca  23820
ggcaagcgcc gcaccgagcg cttgccgccc ttgacctgct taatcagcac cggcgggttg  23880
```

ctgaagccca ccatggtcag ctccgcctgc tcttcttcgt cttcgctgtc taccactatc 23940
tctggggaag ggcttctccg ctctgcggcg gtgcgcttct tttttttctt gggagcagcc 24000
gtgacggagt ccgccacggc gacggaggtc gagggcgtgg ggctgggggt gcgcggtacc 24060
agggcctcgt cgccctcgga ctcttcctct gactccaggc ggcggcggag acgcttcttt 24120
gggggcgcgc gcgtcagcgg cggcggagac ggggacgggg acggggacgg gacgccctcc 24180
acagggggtg gtcttcgcgc agacccgcgg ccgcgctcgg gggtcttttc gagctggtct 24240
tggtcccgac tggccattgt atcctcctcc tcctaggcag agagacataa ggagtctatc 24300
atgcaagtcg agaaggagga gagcttaacc accccctctg agaccgccga tgcgcccgcc 24360
gtcgccgtcg cccccgctgc cgccgacgcg cccgccacac cgagcgacac ccccgcggac 24420
cccccagccg acgcacccct gttcgaggaa gcggccgtgg agcaggaccc gggctttgtc 24480
tcggcagagg aggatttgcg agaggaggag gataaggaga agaagccctc agtgccaaaa 24540
gatgataaag agcaagacga gcacgacgca gatgcacacc agggtgaagt cgggcggggg 24600
gacggagggc atgacggcgc cgactaccta gacgaaggga acgacgtgct cttgaagcac 24660
ctgcatcgtc agtgcgccat cgtttgcgac gctctgcagg agcgcagcga agtgcccctc 24720
agcgtggcgg aggtcagcca cgcctacgag ctcagcctct tctccccccg ggtgcccccc 24780
cgccgccgcg aaaacggcac atgcgagccc aacccgcgcc tcaacttcta ccccgccttt 24840
gtggtgcccg aggtcctggc cacctatcac atcttctttc aaaattgcaa gatccccctc 24900
tcgtgccgcg ccaaccgtag ccgcgccgat aagatgctgg ccctgcgcca gggcgaccac 24960
atacctgata tcgccgcttt ggaagatgtg ccaaagatct tcgagggtct gggtcgcaac 25020
gagaagcggg cagcaaactc tctgcaacag gaaaacagcg aaaatgagag tcacaccggg 25080
gtactggtgg agctcgaggg cgacaacgcc cgcctggcgg tggtcaagcg cagcatcgag 25140
gtcacccact ttgcctaccc cgcgctcaac ctgcccccca aagtcatgaa cgcggccatg 25200
gacgggctga tcatgcgccg cggccggccc ctcgctccag atgcaaactt gcatgaggag 25260
accgaggacg gccagcccgt ggtcagcgac gagcagctgg cgcgctggct ggagaccgcg 25320
gaccccgccg aactggagga gcggcgcaag atgatgatgg ccgcggtgct ggtcaccgta 25380
gagctggagt gtctgcagcg cttcttcggc gaccccgaga tgcagagaaa ggtcgaggag 25440
accctgcact acaccttccg ccagggctac gtgcgccagg cttgcaagat ctccaacgtg 25500
gagctcagca acctggtgtc ctacctgggc atcttgcatg agaaccgcct cgggcagagc 25560
gtgctgcact ccaccctgcg cggggaggcg cgccgcgact acgtgcgcga ctgcgtttac 25620
ctcttcctct gctacacctg gcagacggcc atgggggtct ggcagcagtg cctggaggag 25680
cgcaacctca aggagctgga gaagctcctg cagcgcgcgc tcaaagacct ctggacgggc 25740
tacaacgagc gctcggtggc cgccgcgctg gccgacctca tcttccccga gcgcctgctc 25800
aaaaccctcc agcaggggct gcccgacttc accagccaaa gcatgttgca aaacttcagg 25860
aactttatcc tggagcgttc tggcatccta cccgccacct gctgcgccct gcccagcgac 25920
tttgtccccc tcgtgtaccg cgagtgcccc ccgccgctgt ggggtcactg ctacctgttc 25980
caactggcca actacctgtc ctaccacgcg gacctcatgg aggactccag cggcgagggg 26040
ctcatggagt gccactgccg ctgcaacctc tgcacgcccc accgctccct ggtctgcaac 26100
acccaactgc tcagcgagag tcagattatc ggtaccttcg agctacaggg tccgtcctcc 26160
tcagacgaga agtccgcggc tccggggcta aaactcactc cggggctgtg gacttccgcc 26220
tacctgcgca aatttgtacc tgaagactac cacgcccacg agatcaggtt ttacgaagac 26280

```
caatcccgcc cgcccaaggc ggagctgacc gcctgcgtca tcacccaggg cgagatccta  26340
ggccaattgc aagccatcca aaaagcccgc caagattttt tgctgagaaa gggtcggggg  26400
gtgtatctgg acccccagtc gggtgaggag ctcaacccgg ttcccccgct gccgccgccg  26460
cgggaccttg cttcccagga taagcatcgc catggctccc agaaagaagc agcagcggcc  26520
gccactgccg ccaccccaca tgctggagga agaggaggaa tactgggaca gtcaggcaga  26580
ggaggtttcg gacgaggagg agccggagac ggagatggaa gagtgggagg aggacagctt  26640
agacgaggag gcttccgaag ccgaagaggc agacgcaaca ccgtcaccct cggccgcagc  26700
cccctcgcag gcgcccccga agtccgctcc cagcatcagc agcaacagca gcgctataac  26760
ctccgctcct ccaccgccgc gacccacggc cgaccgcaga cccaaccgta gatgggacac  26820
caccggaacc ggggccggta agtcctccgg gagaggcaag caagcgcagc gccaaggcta  26880
ccgctcgtgg cgcgctcaca agaacgccat agtcgcttgc ttgcaagact gcgggggaa  26940
catctccttc gcccgccgct tcctgctctt ccaccacggt gtggccttcc cccgtaacgt  27000
cctgcattac taccgtcatc tctacagccc ctactgcggc ggcagtgagc cagagacggt  27060
cggcggcggc ggcggcgccc gtttcggcgc ctaggaagac ccagggcaag acttcagcca  27120
agaaactcgc ggcggccgcg gcgaacgcgg tcgcgggggc cctgcgcctg acggtgaacg  27180
aacccctgtc gacccgcgaa ctgagaaacc gaatcttccc cactctctat gccatcttcc  27240
agcagagcag agggcaggat caggaactga aagtaaaaaa caggtctctg cgctccctca  27300
cccgcagctg tctgtatcac aagagcgaag accagcttcg gcgcacgctg gaggacgctg  27360
aggcactctt cagcaaatac tgcgcgctca ctcttaagga ctagctccgc gcccttctcg  27420
aatttaggcg ggaacgccta cgtcatcgca gcgccgccgt catgagcaag gacattccca  27480
cgccatacat gtggagctat cagccgcaga tgggactcgc ggcgggcgcc tcccaagact  27540
actccacccg catgaactgg ctcagtgccg gcccacacat gatctcacag gttaatgata  27600
tccgcaccca tcgaaaccaa atattggtgg agcaggcggc aattaccacc acgccccgca  27660
ataatcccaa ccccagggag tggcccgcgt ccctggtgta tcaggaaatt cccggcccca  27720
ccaccgtact acttccgcgt gattcccagg ccgaagtcca aatgactaac tcaggggcgc  27780
agctcgcggg cggctgtcgt cacagggtgc ggcctcctcg ccagggtata actcacctgg  27840
agatccgagg cagaggtatt cagctcaacg acgagtcggt gagctcctcg ctcggtctaa  27900
gacctgacgg gaccttccag atagccggag ccggccgatc ttccttcacg ccccgccagg  27960
cgtacctgac tctgcagagc tcgtcctcgg cgccgcgctc gggcggcatc gggactctcc  28020
agttcgtgca ggagtttgtg ccctcggtct acttcaaccc cttctcgggc tctcccggtc  28080
gctacccgga ccagttcatc tcgaactttg acgccgcgag ggactcggtg gacggctacg  28140
actgaatgtc gggtggaccc ggtgcagagc aacttcgcct gaagcacctc gaccactgcc  28200
gccgccctca gtgctttgcc cgctgtcaga ccggtgagtt ccagtacttt tccctgcccg  28260
actcgcaccc ggacggcccg gcgcacgggg tgcgcttttt catcccgagt caggtgcgct  28320
ctaccctaat cagggagttt accgcccgtc ccctactggc ggagttggaa aaggggcctt  28380
ctatcctaac cattgcctgc atctgctcta accctggatt gcaccaagat ctttgctgtc  28440
atttgtgtgc tgagtataat aaaggctgag atcagaatct actcgggctc ctgtcgccat  28500
cctgtcaacg ccaccgtcca agcccggccc gatcagcccg aggtgaacct cacctgcggt  28560
ctgcaccggc gcctgaggaa atacctagct tggtactaca acagcactcc ctttgtggtt  28620
```

```
tacaacagct ttgaccagga cggggtctca ctgagggata acctctcgaa cctgagctac  28680
tccatcagga agaacagcac cctcgagcta cttcctcctt acctgcccgg gacttaccag  28740
tgtgtcaccg gtccctgcac ccacacccac ctgttgatcg taaacgactc tcttccgaga  28800
acagacctca ataactcctc ttcgcagttc cccagaacag gaggtgagct caggaaaccc  28860
cgggtaaaga agggtggaca agagttaaca cttgtggggt ttctggtgta tgtgacgctg  28920
gtggtggctc ttttgattaa ggctttttcct tccatgtctg aactctccct cttttatgaa  28980
caactcgact agtgctaacg ggaccctacc caacgaatcg ggattgaata tcggtaacca  29040
ggttgcagtt tcacttttga ttaccttcat agtcctcttc ctgctagtgc tgtcgcttct  29100
gtgcctgcgg atcgggggct gctgcatcca cgtttatatc tggtgctggc tgtttagaag  29160
gttcggagac catcgcaggt agaataaaca tgctgctgct taccctcttt gtcctggcgc  29220
tggccgccag ctgccaagcc ttttccgagg ctgactttat agagccccag tgtaacgtga  29280
cttttaaagc ccatgcacag cgttgtcata ctataatcaa atgtgccacc gaacacgatg  29340
aataccttat ccagtataaa gataaatcac acaaagtggc acttgttgac atctggaaac  29400
ccgaagaccc tttggaatac aatgtgaccg ttttccaggg tgacctcttc aaaatttaca  29460
attacacttt cccatttgac cagatgtgtg actttgtcat gtacatggaa aagcagcaca  29520
agctgtggcc tccgactccc cagggctgtg tggaaaatcc aggctctttc tgcatgatct  29580
ctctctgtgt aactgtgctg gcactaatac tcacgctttt gtatatcaga tttaaatcaa  29640
ggcaaagctt catcgatgaa aagaaaatgc cttaaacgct ttcacgcttg attgctaaca  29700
ccgggttttt atccgcagaa tgattggaat caccctacta atcacctccc tccttgcgat  29760
tgcccatggg ttggaacgaa tcgaagcccc tgtgggggcc aatgttaccc tggtggggcc  29820
tgtcggcaat gctacattaa tgtgggaaaa atatactaaa aatcaatggg tctcttactg  29880
cactaacaaa aacagccaca agcccagagc catctgcgat gggcaaaatc taaccttgat  29940
tgatgttcaa atgctggatg cgggctacta ttatgggcag ctgggtacaa tgattaatta  30000
ctggagaccc cacaaagatt acatgctcca cgtagtaaag ggtcccctta gcagcccacc  30060
cactaccacc tctactaccc ccactaccac cactactccc accaccagca ctgccgccca  30120
gcctcctcat agcagaacaa ccacttttat caattccaag tcccactccc cccacattgc  30180
cggcgggccc tccgcctcag actccgagac caccgagatc tgcttctgca aatgctctga  30240
cgcctttgct gaggatttgg aagaccacga ggaagatgag catgacttcg cagatgcatg  30300
ccaggcatca gaggcagaag cgctgccggt ggccctcaaa cagtatgcag acccccacac  30360
cacccccaac cttcctccac cttcccagaa gccaagtttc ctgggggaaa atgaaactct  30420
gcctctctcc atactcgctc tgacatctgt tgctatgttg accgctctgc tggtgcttct  30480
atgctctata tgctacctga tctgctgcag aaagaaaaaa tctcacggcc atgctcacca  30540
gcccctcatg cacttccctt accctccaga gctgggcgac cacaaacttt aagtctgcag  30600
taactatctg cccatccctt gtcagtcgac agcgatgagc cccactaatc taacggcctc  30660
tggacttaca acatcgtctc ttaatgagac caccgctcct caagacctgt acgatggtgt  30720
ctccgcgctg gttaaccagt gggatcacct gggcatatgg tggctcctca taggagcagt  30780
gaccctgtgc ctaatcctgg tctggatcat ctgctgcatc aaaagcagaa gacccaggcg  30840
gcggcccatc tacaggccct ttgtcatcac acctgaagat gatgatgaca ccacttccag  30900
gctgcagagg ctaaagcagc tactcttctc ttttacagca tggtaaattg aatcatgcct  30960
cgcattttca tctacttgtc tctccttcca ctttttctgg gctcttctac attggccgct  31020
```

```
gtgtcccaca tcgaggtaga ctgcctcacg cccttcacag tctacctgct tttcggcttt  31080
gtcatctgca cctttgtctg cagcgttatc actgtagtga tctgcttcat acagtgcatc  31140
gactacgtct gcgtgcgggt ggcttacttt agacaccacc cccagtatcg caacagggac  31200
atagcggctc tcctaagact tgtttaaaat catggccaaa ttaactgtga ttggtcttct  31260
gatcatctgc tgcgtcctag ccgcgattgg gactcaagct cctaccacca ccagcgctcc  31320
cagaaagaga catgtatcct gcagcttcaa gcgtccctgg aatatacccc aatgctttac  31380
tgatgaacct gaaatctctt tggcttggta cttcagcgtc accgcccttc ttatcttctg  31440
cagtacggtt attgcccttg ccatctaccc ttcccttgac ctgggctgga atgctgtcaa  31500
ctctatggaa tatcccacct tcccagaacc agacctgcca gacctggttg ttctaaacgc  31560
gtttcctcct cctgctcccg ttcaaaatca gtttcgccct ccgtccccca cgcccactga  31620
ggtcagctac tttaatctaa caggcggaga tgactgaaaa cctagaccta gaaatggacg  31680
gtctctgcag cgagcaacgc acactagaga ggcgccggca aaaagagctc gagcgtctta  31740
aacaagagct ccaagacgcg gtggccatac accagtgcaa aaaaggtgtc ttctgtctgg  31800
taaaacaggc cacgctcacc tatgaaaaaa caggtgacac ccaccgccta ggatacaagc  31860
tgcccacaca gcgccagaag ttcgccctca tgataggcga acaacccatc accgtgaccc  31920
agcactccgt ggagacagaa ggctgcatac acgctccctg taggggcgct gactgcctct  31980
acaccttgat caaaaccctc tgcggtctca gagacctcat cccttttaat taatcataac  32040
tgtaatcaat aaaaaatcac ttacttgaaa tctgatagca agcctctgtc caatttttttc  32100
agcaacactt ccttcccctc ctcccaactc tggtactcta ggcgcctcct agctgcaaac  32160
ttcctccaca gtctgaaggg aatgtcagat tcctcctcct gtccctccgc acccacgatc  32220
ttcatgttgt tgcagatgaa acgcgcgaga tcgtctgacg agaccttcaa ccccgtgtac  32280
ccctacgata ccgagatcgc tccgacttct gtcccttcc ttacccctcc ctttgtgtca  32340
tccgcaggaa tgcaagaaaa tccagctggg gtgctgtccc tgcacttgtc agagcccctt  32400
accacccaca atggggccct gactctaaaa atggggggcg gcctgaccct ggacaaggaa  32460
gggaatctca cttcccaaaa catcaccagt gtcgatcccc ctctcaaaaa aagcaagaac  32520
aacatcagcc ttcagaccgc cgcacccctc gccgtcagct ccggggccct aacacttttt  32580
gccactcccc ccctagcggt cagtggtgac aaccttactg tgcagtctca ggcccctctc  32640
actttggaag actcaaaact aactctggcc accaaaggac ccctaactgt gtccgaaggc  32700
aaacttgtcc tagaaacaga ggctcccctg catgcaagtg acagcagcag cctgggcctt  32760
agcgttacgg ccccacttag cattaacaat gacagcctag gactagacat gcaagcgccc  32820
attagctctc gagatggaaa actggctcta acagtggcgg cccccctaac tgtggtcgag  32880
ggtatcaatg ctttggcagt agccacaggt aagggtattg ggctaaatga aaccaacaca  32940
cacctgcagg caaaactggt cgcaccccta ggctttgata ccaacggcaa cattaagcta  33000
agcgttgcag gaggcatgag gctaaacaat aacacactga tactagatgt aaactaccca  33060
tttgaggctc aaggccaact gagcctaaga gtgggctcgg gcccactata tgtagattct  33120
agtagtcata acctaaccat tagatgcctt aggggattgt atataacatc ttctaacaac  33180
caaaacggtc tagaagccaa cattaaacta acaagaggcc ttgtgtatga cggaaatgcc  33240
atagcagtta atgttggcaa agggctggaa tacagcccta ctgacacaac agaaaaacct  33300
atacagacta aaataggtct aggcatggag tatgataccg agggagccat gatgacaaaa  33360
```

```
ctaggctctg gactaagctt tgacaattca ggagccattg tagtgggaaa caaaaatgat  33420
gacaggctta ctttgtggac cacaccggac ccatcgccca actgtcagat ctactctgaa  33480
aaagatgcta aactaacctt ggtactgact aaatgtggca gtcaggttgt aggcacagta  33540
tctattgccg ctcttaaagg tagcctcgtg ccaatcacta gtgcaatcag tgtggttcag  33600
gtatacctaa ggtttgatga aaatggggta ctaatgagta actcttcact taatggcgaa  33660
tactggaatt ttagaaacgg agactcaact aatggcacac catatacaaa cgcagtgggt  33720
ttcatgccta atctactggc ctatcctaaa ggtcaaacta caactgcaaa aagtaacatt  33780
gtcagccagg tctacatgaa tggggacgat actaaaccca tgacatttac aatcaacttc  33840
aatggcctta gtgaaacagg ggatacccct gttagtaaat attccatgac attctcatgg  33900
aggtggccaa atggaagcta catagggcac aattttgtaa caaactcctt taccttctcc  33960
tacatcgccc aagaataaag aaagcacaga gatgcttgtt tttgatttca aaattgtgtg  34020
cttttattta ttttcagctt acagtatttc cagtagtcat tcaaataaag cttaatcaaa  34080
ctgcatgaga acccttccac atagcttaaa ttagcaccag tgcaaatgga gaaaaatcaa  34140
catacctttt tttatccaga tatcagagaa ctctagtggt cagttttccc ccaccctccc  34200
agctcacaga atacacagtc ctttcccccc ggctggcttt aaacaacact atctcattgg  34260
taacagacat attcttaggt gtaataatcc acacggtctc ttggcgggcc aaacgctggt  34320
cggtgatgtt aataaactcc ccaggcagct ctttcaagtt cacgtcgctg tccaactgct  34380
gaagcgctcg cggctccgac tgcgcctcta gcggaggcaa cggcaacacc cgatccttga  34440
tctataaagg agtagagtca taatccccca taagaatagg gcggtgatgc agcaacaagg  34500
cgcgcagcaa ctcctgccgc cgcctctccg tacggcagga atgcaacggc gtggtggtct  34560
cctccgtgat aatccgcacc gctcgcagca tcagcatcct cgtcctccgg gcacagcagc  34620
gcatcctgat ctcactgaga tcggcgcagt aagtgcagca caaaaccaag atgttattta  34680
agatcccaca gtgcaaagca ctgtacccaa agctcatggc gggaaggaca gcccccacgt  34740
gaccatcata ccagatcctc aggtaaatca aatgacgacc tctcataaac acgctggaca  34800
tgtacatcac ctccttgggc atgtgctgat tcaccacctc tcgataccac aagcatcgct  34860
gattaattaa agacccctcg agcaccatcc taaaccagga agccagcacc tgaccccccg  34920
ccaggcactg cagggacccc ggtgaatcgc agtggcagtg aagactccag cgctcgtagc  34980
cgtgaaccat agagctggtc attatatcca cattggcaca acacagacac actttcatac  35040
actttttcat gattagcagc tcctctctag tcaggaccat atcccaagga atcacccact  35100
cttgaatcaa ggtaaatccc acacagcagg gcaggcctct cacataactc acgttatgca  35160
tagtgagcgt gtcgcaatct ggaaataccg gatgatcttc catcaccgaa gcccgggtct  35220
ccgtctcaaa gggaggtaaa cggtccctcg tgtagggaca gtggcgggat aatcgagatc  35280
gtgttgaacg tagagtcatg ccaaagggaa cagcggacgt actcatattt cctccagcag  35340
aaccaagtgc gcgcgtggca gctatccctg cgtcttctgt ctcgccgcct gccccgttcg  35400
gtgtagtagt tgtaatacag ccactccctg agaccgtcaa ggcgctccct ggcgtccgga  35460
tctatgacaa caccgtcctg cagcgccgcc ctgatgacat ccaccaccgt agagtatgcc  35520
aagcccagcc aggaaatgca ttcactttga cagcgagaga taggaggagc ggggagagat  35580
ggaagaacca tgatagtaaa gagaactttt attccaatcg atcttctaag atatcaaagt  35640
ggagatctat aagatgacac tggtctcctc cgctgagtcg atcaaaaata acagctaaac  35700
cacaaacaac acgattggtc aaatgctcca caagggcctg cagcataaaa ttgcctcgga  35760
```

```
actccaccgc aagcataaca tcaaagccac cgcctctatc gtgatcaaga ataaaaaccc  35820

cacagctatc caccagaccc atatagtttt catctctcca tcgtgaaaaa agatttacaa  35880

gctcctcctt taaatcacct ccaaccaatt gaaaaagttg aaccagaccg ccctccacct  35940

tcattttcag caagcgtatc atgattgcaa aaattcaggc tcctcagaca cctgtataag  36000

attgagaagc ggaacgttaa catcgatgtt tcgctcgcgt aaatcacgcc tcagtgcaag  36060

cataatataa tcccacaggt cggagcggat cagcgaggac acctccccgc caggaaccaa  36120

ctcaacggag cctatgctga ttataatacg catattcgga gctatgctaa ccagcacggc  36180

ccccaaatag gcgtactgca taggcggcga caaaaagtga acagtttggg ttaaaaaatc  36240

aggcaaacac tcgcgcaaaa aagcaagaac atcataacca tgctcatgca aatagatgca  36300

agtaagctca ggaacaacca cagaaaaatg cacaattttt ctctcaaaca tgactgcgag  36360

ccctgcaaaa aataaaaaag aaacattaca caagagtagc ctgtcttacg atgggataga  36420

ctactctaac caacataaga cgggccacaa catcgcccgc gtggccataa aaaaaattgt  36480

ccgtgtgatt aaaaagaagc acagatagct ggccagtcat atccggagtc atcacgtgtg  36540

aacccgtgta gacccccggg ttggacacat cggccaaaga aagaaagcgg ccaatgtacc  36600

caggaggaat tataacacta agacgaagat acaacagaat aaccccatga gggggaataa  36660

caaagttagt aggtgaataa aaacgataaa cacccgaaac tccctcctgc gtaggcaaaa  36720

tagcaccctc cccttccaaa acaacatata gcgcttccac agcagccatg acaaaagact  36780

caaaacactc aaaagactca gtcttaccag gaaaataaaa gcactctcac agcaccagca  36840

ctaatcagag tgtgaagagg gccaagtgcc gaacgagtat atataggaat aaaaaatgac  36900

gtaaatgtgt aaaggtcaga aaacgcccag aaaaatacac agaccaacgc ccgaaacgaa  36960

aacccgcgaa aaaataccca gaacttcctc aacaaccgcc acttccgctt tctcacggta  37020

cgtcacttcc gcaagaaaag caaaactaca tttcccacat gtgtaaaaac gaaaccccgc  37080

cccttgtaac cgcccacaac ttacatcatc aaaacgtaaa ctcctacgtc acccgccccg  37140

cctctccccg cccacctcat tatcatattg gccacaatcc aaaataaggt atattat     37197
```

<210> SEQ ID NO 25
<211> LENGTH: 34075
<212> TYPE: DNA
<213> ORGANISM: Gorilla beringei graueri

<400> SEQUENCE: 25

```
catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagtgcgtaa tatttaccga gggccgaggg    360

actttgaccg attacgtgga ggactcgccc aggtgttttt tacgtgaatt tccgcgttcc    420

gggtcaaagt ctccgtttta ttgtcaccgt catttgacgc ttaggcctga ccatctggtg    480

ctggcctgca ccagggccga gtttgggtct agcgatgagg ataccgattg aggtgggtaa    540

ggtgggcgtg gctagaaggg tggggcgtgt ataaattggg ggtctaaggg tctctctgtt    600

ttgtcttgca acagccgccg ccatgagcga caccggcaac agctttgatg gaagcatctt    660
```

```
tagcccctat ctgacagtgc gcatgcctca ctgggctgga gtgcgtcaga atgtgatggg    720
ttccaacgtg gatggacgcc ccgttctgcc ttcaaattcg tctacaatgg cctacgcgac    780
cgtgggagga actccgctgg acgccgcgac ctccgccgcc gcctccgccg ccgccgcgac    840
cgcgcgcagc atggctacgg acctttacag ctctttggtg gcgagcggcg cggcctctcg    900
cgcgtctgct cgggatgaga aactgaccgc tctgctgctt aaactggaag acttgacccg    960
ggagctggct caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcgggggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtacac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aatgtttctg ggatcgctc acatcgtagt tatgttccag ggtgaggtca   1680
tcataggaca tctttacaaa tcgggggcgg agggtcccgg actgggggat gatggtgccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagtctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aaggggtgcg   2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtctccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc accctttcat cttcactctc ttccgcatcg ctgtctgcga   3060
```

```
gagccagctg ctggggtaag tattccctct cgaaggcggg catgacctca gcgctcaggt   3120
tgtcagtttc taaaaatgag gaggatttga tgttcacctg tccggaggtg atacctttga   3180
gggtacctgg gtccatctgg tcagaaaaca ctattttttt gttgtcaagc ttggtggcga   3240
acgacccgta gagggcgttg gagagcagct tggcgatgga gcgcagggtc tggtttttgt   3300
cgcggtcggc tcgctccttg gccgcgatgt tgagttgcac gtactcgcgg gccacgcact   3360
tccactcggg gaagacggtg gtgcgctcgt ctgggatcag gcgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga aggggggtag gggtccagc tggtcctcgt    3540
ttgggggtc cgcgtcgatg gtgaagaccc cggggagcaa gcgcgggtca aagtagtcga    3600
tcttgcaagc ttgcatgtcc agagcccgct gccattcgcg ggcggcgagc gcgcgctcgt   3660
aggggttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggaggggggcc agcatgttgg  3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaagcag gcgtaggact cgcgcagctt gtgcaccagc tcggcggtga   4020
cctggacgtc gagcgcgcag tagtcgaggg tctcgcggat gatgtcatac ttatcctccc   4080
ccttcttttt ccacagctcg cggttgagga cgaactcttc gcggtctttc cagtactctt   4140
ggaggggaaa cccgtccgtg tccgaacggt aagagcctag catgtagaac tggttgacgg   4200
cctggtaggg gcaacagccc ttctccacgg gcagcgcgta ggcctgcgcc gccttgcgga   4260
gggaggtgtg ggtgagggcg aaagtgtccc tgaccatgac tttgaggtat tgatgtttga   4320
agtctgtgtc atcgcagccg ccctgttccc acagggtgta gtccgtgcgc tttttggagc   4380
gcgggttggg cagggagaag gtgaggtcat tgaagaggat cttccccgct cgaggcatga   4440
agtttctggt gatgcgaaag ggccctggga ccgaggagcg gttgttgatg acctgggcgg   4500
ccaggacgat ctcgtcaaag ccgtttatgt tgtggcccac gatgtagagc tccaaaaagc   4560
ggggctggcc cttgatggag gggagctttt tgagttcctc gtaggtgagc tcctcgggcg   4620
attccaggcc gtgctcctcc agggcccagt cttgcaagtg agggttggcc gccaggaagg   4680
atcgccagag gtcgcgggcc atgagggtct gcaggcggtc gcggaaggtt ctgaactgtc   4740
gccccacggc catcttttcg gggtgatgc agtagaaggt gagggggtct ttctcccagg    4800
ggtcccatct gagctctcgg gcgaggtcgc gcgcggcggc gaccagagcc tcgttgcccc   4860
ccagtttcat gaccagcatg aagggcacga gctgcttgcc aaaggctccc atccaagtgt   4920
aggtctctac atcgtaggtg acaaagaggc gctccgtgcg aggatgagag ccgatcggga   4980
agaactggat ctcccgccac cagttggagg attggctgtt gatgtggtga aagtagaagt   5040
cccgtctgcg ggccgagcac tcgtgctggc ttttgtaaaa gcgaccgcag tactggcagc   5100
gctgcacggg ttgtatatct tgcacgaggt gaacctggcg acctctgacg aggaagcgca   5160
gcgggaatct aagtcccccg cctggggtcc cgtgtggctg gtggtcttct actttggttg   5220
tctggccgcc agcatctgtc tcctggaggg cgatggtgga gcagaccacc acgccgcgag   5280
agccgcaggt ccagatctcg gcgctcggcg ggcggagttt gatgacgaca tcgcgcacat   5340
tggagctgtc catggtctcc agctcccgcg gcggcaggtc agctgggagt tcctggaggt   5400
```

```
tcacctcgca gagacgggtc aaggcgcggg cagtgttgag atggtatctg atttcaaggg   5460
gcgtgttggc ggcggagtcg atggcttgca ggaggccgca gccccggggg gccacgatgg   5520
ttccccgcgg ggcgcgaggg gaggcggaag ctgggggtgt gttcagaagc ggtgacgcgg   5580
gcgggccccc ggaggtaggg ggggttccgg ccccacaggc atgggcggca ggggcacgtc   5640
ttcgccgcgc gcgggcaggg gctggtgctg gctccgaaga gcgcttgcgt gcgcgacgac   5700
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgcg agaaggcgtt gagcccgccc tcgttccaga cccggctgta   6000
gaccacgccc ccctcggcgt tgcgggcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
ggagttgcga gcggacacgg tcaactcctc ctccagaaga cggatgagct cggcgacagt   6300
gtcgcgcacc tcgcgctcga aggccacggg gggcgcttct tcctcttcca cctcttcttc   6360
catgatcgct tcttcttctt cctcagccgg gacgggaggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcgg gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggttttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacggtcgag agccctttttg ctttcttggc caagcgcccg   7740
tggcgcgatc tgggatagat ggtcgcgatg agaggacaaa agcggctcgc ttccgtagtc   7800
```

```
tggagaaaca atcgccaggg ttgcgttgcg gcgtaccccg gttcgagccc ctatggcggc   7860
ttgaatcggc cggaaccgcg gctaacgagg gccgtggcag ccccgtcctc aggaccccgc   7920
cagccgactt ctccagttac gggagcgagc cccttttgtt ttttattttt tagatgcatc   7980
ccgtgctgcg gcagatgcgc ccctcgcccc ggcccgatca gcagcagcaa cagcaggcat   8040
gcagaccccc ctctcccctt tccgccccgg tcaccacggc cgcggcggcc gtgtcgggcg   8100
cggggggcgc gctggagtca gatgagccac cgcggcggcg acctaggcag tatctggact   8160
tggaagaggg cgagggactg gcgcggctgg gggcgaactc tccagagcgc cacccgcggg   8220
tgcagttgaa aagggacgcg cgcgaggcgt acctgccgcg gcagaacctg tttcgcgacc   8280
gcgggggcga ggagcccgag gagatgcgag actgcaggtt ccaagcgggg cgcgagctgc   8340
ggcgcgggct ggacagacag cgcctgctgc gcgaggagga ctttgagccc gacacgcaga   8400
cgggcatcag ccccgcgcgc gcgcacgtag ccgcggccga cctggtgacc gcctacgagc   8460
agacggtgaa ccaggagcgc aacttccaaa agagcttcaa caaccacgtg cgcacgctgg   8520
tggcgcgcga ggaggtgacc ctgggtctca tgcatctgtg ggacctggtg gaggcgatcg   8580
tgcagaaccc cagcagcaag cccctgaccg cgcagctgtt cctggtggtg cagcacagca   8640
gggacaacga ggccttcagg gaggcgctgc tgaacatcac cgagccggag gggcgctggc   8700
tcctggacct gataaacatc ctgcagagca tagtggtgca ggagcgcagc ctgagcctgg   8760
ccgagaaggt ggcggccatc aactactcta tgctgagcct gggcaagttc tacgcccgca   8820
agatctacaa gacccoctac gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg cccccctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taacccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
```

```
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
gacatgaccg cgcgcaacat ggaaccgggc atgtacgcct cccaccggcc gttcatcaac  10320
cgcctgatgg actacttgca tcgggcggcg gccgtgaacc ccgagtactt cactaatgcc  10380
attctgaatc cccactggat gcccccctccg ggtttctaca acggggactt tgaggtgccc  10440
gaggtcaacg acgggttcct ctgggatgac atggatgaca gtgtgttctc acccaacccg  10500
ctgcgcgccg cgtctctgcg attgaaggag ggctctgaca gggaaggacc gagaagtctg  10560
gcctcctccc tggctctggg agcggtgggc gccacgggcg cggcggcgcg gggcagtagc  10620
cccttcccca gcctggcaga ctctctgaac agcgggcggg tgagcaggcc ccgcttgcta  10680
ggcgaggagg agtatctgaa caactccctg ctgcagcccg cgagggacaa gaacgctcag  10740
cggcagcagt ttcccaacaa tgggatagag agcctggtgg acaagatgtc cagatggaag  10800
acgtatgcgc aggagtacaa ggagtgggag gaccgccagc cgcggccctt gccgcccccct  10860
aggcagcgct ggcagcggcg cgcgtccaac cgccgctgga ggcaggggcc cgaggacgat  10920
gatgactctg cagatgacag cagcgtgttg gacctgggcg ggagcgggaa ccccttttcg  10980
cacctgcgcc cacgcctggg caagatgttt taaaagaaaa aaaaaaaata aaactcacca  11040
aggccatggc gacgagcgtt ggttttttgt tcccttcctt agtatgcggc gcgcggcgat  11100
gttcgaggag gggcctcccc cctcttacga gagcgcgatg ggatttctc ctgcggcgcc  11160
cctgcagcct ccctacgtgc ctcctcggta cctgcaacct acagggggga gaaatagcat  11220
ctgttactct gagctgcagc cctgtacgga taccaccaga ctgtacctgg tggacaacaa  11280
gtccgcggac gtggcctccc tgaactacca gaacgaccac agcgattttt tgaccacggt  11340
gatccaaaac aacgacttca ccccaaccga ggccagcact cagaccataa acctggataa  11400
caggtcgaac tggggcggcg acctgaagac catcttgcac accaacatgc ccaacgtgaa  11460
cgagttcatg ttcaccaact cttttaaggc gcgggtgatg gtggcgcgcg agcaggggga  11520
ggcgaagtac gagtgggtgg acttcacgct gcccgagggc aactactcag agaccatgac  11580
tctcgacctg atgaacaatg cgatcgtgga acactatctg aaagtgggca ggcagaacgg  11640
ggtgaaggaa agcgatatcg ggtcaagtt tgacaccaga aacttccgtc tgggctggga  11700
ccccgtgacc gggctggtca tgccgggggt ctacaccaac gaggcctttc atcccgacat  11760
agtgcttctg cccggctgtg ggtggactt cacccagagc cggctgagca acctgctggg  11820
cattcgcaag cggcagcctt tccaggaggg tttcaagatc acctatgagg atctgaaggg  11880
gggcaacatt cccgcgctcc ttgatctgga cgcctacgag gagagcttga aacccgagga  11940
gagcgctggc gacagcggcg agagtggcga ggagcaagcc ggcggcggtg gcggcgcgtc  12000
ggtagaaaac gaaagtacgc ccgcagtggc ggcggacgct gcggaggtcg agccggaggc  12060
catgcagcag gacgcagagg agggcgcaca ggagggcgcg cagaaggaca tgaacgatgg  12120
ggagatcagg ggagacacat tcgccacccg gggcgaagaa aaagaggcag aggcggcggc  12180
ggcggcgacg gcggaggccg aaaccgaggt tgaggcagag gcagagcccg agaccgaagt  12240
tatggaagac atgaatgatg gagaacgtag ggcgacacg ttcgccaccc ggggcgaaga  12300
gaaggcggcg gaggcagaag ccgcggctga ggaggcggct gcggctgcgg ccaagactga  12360
ggctgcggct aaggctgagg tcgaagccaa tgttgcggtt gaggctcagg ctgaggagga  12420
ggcggcggct gaagcagtta aggaaaaggc ccaggcagag caggaagaga aaaaacctgt  12480
cattcaacct ctaaaagaag atagcaaaaa gcgcagttac aacgtcatcg agggcagcac  12540
```

```
ctttacccag taccgcagct ggtacctggc gtacaactac ggcgacccgg tcaagggggt  12600
gcgctcgtgg accctgctct gcacgccgga cgtcacctgc ggctccgagc agatgtactg  12660
gtcgctgccg aacatgatgc aagacccggt gaccttccgc tccacgcggc aggttagcaa  12720
cttcccggtg gtgggcgccg aactgctgcc cgtgcactcc aagagttttt acaacgagca  12780
ggccgtctac tcccagctga tccgccaggc cacctctctg acccacgtgt tcaatcgctt  12840
tcccgagaac cagattttgg cgcgcccgcc ggcccccacc atcaccaccg tgagtgaaaa  12900
cgttcctgcc ctcacagatc acgggacgct accgctgcgc aacagcatct caggagtcca  12960
gcgagtgacc attactgacg ccagacgccg gacctgcccc tacgtttaca aggccttggg  13020
catagtctcg ccgcgcgtcc tctccagtcg cactttttaa aacacatcta cccacacgtt  13080
ccaaaatcat gtccgtactc atctcaccca gcaacaacac cggctggggg ctgcgcgcgc  13140
ccagcaagat gtttggaggg gcgaggaagc gctccgacca gcaccctgtg cgcgtgcgcg  13200
gccactaccg cgcgccctgg ggagcgcaca agcgcgggcg cacagggcgc accactgtgg  13260
acgacgtcat tgactccgta gtggagcaag cgcgccacta cacacccggc gcgccgaccg  13320
cccccgccgt gtccaccgtg gaccaggcga tcgaaagcgt ggtacagggc gcgcggcact  13380
atgccaacct taaaagtcgc cgccgccgcg tggcccgccg ccatcgccgg agaccccggg  13440
ccaccgccgc cgcgcgcctt actaaggctc tgctcaggcg cgccaggcga actggccacc  13500
gggccgccat gagggccgca cggcgggctg ccgctgccgc aagcgccgtg gccccgcggg  13560
cacgaaggcg cgcggccgcc gccgccgccg ccgccatttc cagcttggcc tcgacgcggc  13620
gcggtaacat atactgggtg cgcgactcgg taaccggcac gcgggtaccc gtgcgctttc  13680
gcccccgcg gaattagcac aagacaacat acacactgag tctcctgctg ttgtgtatcc  13740
cagcggcgac cgtcagcagc ggcgacatgt ccaagcgcaa aattaaagaa gagatgctcc  13800
aggtcatcgc gccggagatc tatgggcccc cgaagaagga ggaggatgat tacaagcccc  13860
gcaagctaaa gcgggtcaaa aagaaaaaga aagatgatga tgatgacgag gcggtggagt  13920
ttgtccgccg catggcaccc aggcgccccg tgcagtggaa gggccggcgc gtgcagcgcg  13980
ttttgcgccc cggcaccgcg gtggtcttca cgcccggcga gcgctccacg cgcactttca  14040
agcgggtgta cgatgaggtg tacggcgacg aggacctgtt ggagcaggcc aaccagcgct  14100
ttggggagtt tgcatatggg aaacggcccc gcgagagtct aaaagaggac ctgctggcgc  14160
taccgctgga cgagggcaat cccaccccga gtctgaagcc ggtaaccctg caacaggtgc  14220
tgcctttgag cgcgcccagc gagcataagc gagggttgaa gcgcgaaggc ggggacctgg  14280
cgcccaccgt gcagttgatg gtgcccaagc ggcagaagct ggaggacgtg ctggagaaaa  14340
tgaaagtaga gcccgggatc cagcccgaga tcaaggtccg ccccatcaag caggtggcgc  14400
ccggcgtggg agtccagacc gtggacgtta ggattcccac ggaggagatg gaaacccaaa  14460
ccgccactcc ctcttcggcg gccagcgcca ccaccggcac cgcttcggta gaggtgcaga  14520
cggacccctg gctacccgcc accgctgttg ccgccgccgc cccccgttcg cgcgggcgca  14580
agagaaatta tccagcggcc agcgcgctca tgccccagta cgcactgcat ccatccatcg  14640
cgcccacccc cggctaccgc gggtactcgt accgcccgcg cagatcagcc ggcactcgcg  14700
gccgccgccg ccgtgcgacc acaaccagcc gccgccgtcg ccgccgccgc cagccagtgc  14760
tgacccccgt gtctgtaagg aaggtggctc gctcggggag cacgctggtg gtgcccagag  14820
cgcgctacca ccccagcatc gtttaaagcc ggtctctgta tggttcttgc agatatggcc  14880
```

```
ctcacttgtc gcctccgctt cccggtgccg ggataccgag gaagaactca ccgccgcaga  14940
ggcatggcgg gcagcggtct ccgcggcggc cgtcgccatc gccggcgcgc aaaaagcagg  15000
cgcatgcgcg gcggtgtgct gcctctgcta atcccgctaa tcgccgcggc gatcggtgcc  15060
gtacccggga tcgcctccgt ggccctgcag gcgtcccaga aacgttgact cttgcaacct  15120
tgcaagcttg catttttgg aggaaaaata aaaaaagtct agactctcac gctcgcttgg  15180
tcctgtgact attttgtaga aaaaagatgg aagacatcaa ctttgcgtcg ctggccccgc  15240
gtcacggctc gcgcccgttc atgggagact ggacagatat cggcaccagc aatatgagcg  15300
gtggcgcctt cagctggggc agtctgtgga gcggccttaa aaattttggt tccaccatta  15360
agaactatgg caacaaagcg tggaacagca gcacgggcca gatgctgaga gacaagttga  15420
aagagcagaa cttccaggag aaggtggcgc agggcctggc ctctggcatc agcggggtgg  15480
tggacatagc taaccaggcc gtgcagaaaa agataaacag tcatctggac ccccgtcctc  15540
aggtggagga aatgcctcca gcgatggaga cggtgtctcc cgagggcaaa ggcgaaaagc  15600
gcccgcggcc cgacagagaa gagaccctgg tgtcacacac cgaggagccg ccctcttacg  15660
aggaggcagt caaggccggc ctgcccacca ctcgccccat agcccccatg gccaccggtg  15720
tggtgggcca caggcaacac actcccgcaa cactagatct gcccccgccg tccgagccgc  15780
cgcgccagcc aaaggcggcg acggtgcccg ctccctccac ttccgccgcc aacagagtgc  15840
ccctgcgccg cgccgcgagc ggcccccggg cctcgcgagt tagcggcaac tggcagagca  15900
cactgaacag catcgtgggc ctgggagtga ggagtgtgaa gcgccgccgt tgctactgaa  15960
tgagcaagct agctaacgtg ttgtatgtgt gtatgcgtcc tatgtcgccg ccagaggagc  16020
tgttgagccg ccggcgccgt ctgcactcca gcgaatttca agatggcgac cccatcgatg  16080
atgcctcagt ggtcgtacat gcacatctcg ggccaggacg cttcggagta cctgagcccc  16140
gggctggtgc agttcgcccg cgccacagac acctacttca acatgagtaa caagttcagg  16200
aaccccactg tggcgcccac ccacgatgtg accacggacc ggtcgcagcg cctgacgctg  16260
cggttcatcc ccgtggatcg ggaggacacc gcctactctt acaaggcgcg gttcacgctg  16320
gccgtgggcg acaaccgcgt gctggacatg gcctccactt actttgacat caggggggtg  16380
ctggacaggg gccccacctt caagccctac tcgggtactg cctacaactc cctggccccc  16440
aagggcgctc ccaattcttg cgagtgggaa caagaggaaa atcaggtggt cgctgcagat  16500
gatgaacttg aagatgaaga agcgcaagct caagaggacg ccccagctaa aaaaattcat  16560
gtatatgccc aggcgcctct tgctggcgaa aagattacca aggatggttt gcaaataggt  16620
actgaagttg taggagatac atctaaggac acttttgcag acaaaacatt ccaacccgaa  16680
cctcagatag gcgagtctca gtggaacgag gctgatgcca cagtagcagg aggcagagtc  16740
ttgaaaaaaa ccacccctat gagaccttgc tatggatcct atgccaggcc tacaaatgcc  16800
aacgggggtc aaggaattat ggttgccaat gaacaaggag tgttggagtc taaagtggag  16860
atgcaatttt tttctaacac tacaaccctt aatgcgcggg atggagctgg caatcccgaa  16920
ccaaaggtgg tgttgtacag tgaagatgtc cacttggaat ctcctgacac tcatttgtct  16980
tacaagccca aaaaggatga tgttaatgct aaaattatgt tgggtcagca agctatggct  17040
aacaggccca acctcattgc ttttagagat aatttcattg gactcatgta ctacaacagc  17100
actggtaaca tgggagtgct ggcgggtcag gcctctcagt tgaatgccgt ggtggacctg  17160
caggatagaa acacagaact gtcatatcag cttatgcttg attccattgg ggatagatcc  17220
agatacttct ccatgtggaa ccaggcagtg gatagctatg acccagatgt cagaatcatt  17280
```

gaaaaccatg gtgtcgagga cgagctaccc aactactgct tccctctggg cggcatagga 17340
attactgata cttatcaagg gatcaaaaat accaatggca atggtcagtg gaccaaagat 17400
gatcagttcg cggaccgtaa tgaaataggg gtgggaaaca acttcgccat ggagatcaac 17460
atccaggcca acctctggag gaacttcctc tatgcgaacg tggggctcta cctgccagac 17520
aagctcaagt acaaccccac caacgtggac atctctgaca accccaacac ctatgactac 17580
atgaacaagc gtgtggtggc tcccggcctg gtggactgct ttgtcaatgt gggagccagg 17640
tggtccctgg actacatgga caacgtcaac cccttcaacc accaccgcaa tgcgggtctg 17700
cgctaccgct ccatgatcct gggcaacggg cgctacgtgc ccttccacat tcaggtgccc 17760
cagaagttct ttgccatcaa gaacctcctc ctcctgccgg gctcctacac ttacgagtgg 17820
aacttcagga aggatgtcaa catggtcctg cagagctctc tgggcaatga ccttagggtg 17880
gacggggcca gcatcaagtt tgacagcgtc accctctatg ctaccttctt ccccatggct 17940
cacaacaccg cctccacgct cgaggccatg ctgaggaacg acaccaacga ccagtccttc 18000
aatgactacc tctctggggc caacatgctc taccccatcc ccgccaaggc caccaacgtg 18060
cccatctcca ttccctctcg caactgggcc gccttcagag gctgggcctt tacccgcctt 18120
aagaccaagg aaaccccctc cctgggctcg ggttttgacc cctactttgt ctactcggga 18180
tccatcccct acctggatgg caccttctac ctcaaccaca cttttaagaa gatatccatc 18240
atgtatgact cctccgtcag ctggccgggc aatgaccgcc tgctcacccc caatgagttc 18300
gaggtcaagc gcgccgtgga cggcgagggc tacaacgtgg cccagtgcaa catgaccaag 18360
gactggttcc tggtgcagat gctggccaac tacaacatag gctaccaggg cttctacatc 18420
ccagagagct acaaggacag gatgtactcc ttcttcagaa atttccaacc catgagcagg 18480
caggtggtgg acgagaccaa atacaaggac tatcaggcca ttggcatcac tcaccagcac 18540
aacaactcgg gattcgtggg ctacctggct cccaccatgc gcgaggggca ggcctacccc 18600
gccaacttcc cctacccgtt gataggcaag accgcggtcg acagcgtcac ccagaaaaag 18660
ttcctctgcg accgcaccct ctggcgcatc cccttctcta gcaacttcat gtccatgggt 18720
gcgctcacgg acctgggcca gaacctgctc tatgccaact ccgcccatgc gctggacatg 18780
acttttgagg tggaccccat ggacgagccc acccttctct atattgtgtt tgaagtgttc 18840
gacgtggtca gagtgcacca gccgcaccgc ggtgtcatcg agaccgtgta cctgcgcacg 18900
cccttctcgg ccggcaacgc caccacctaa ggagacagcg ccgccgcctg catgacgggt 18960
tccaccgagc aagagctcag ggccatcgcc agagacctgg gatgcggacc ctatttttg 19020
ggcacctatg acaaacgctt cccgggcttc atctcccgag acaagctcgc ctgcgccatc 19080
gtcaacacgg ccgcgcgcga gaccgggggc gtgcactggc tggcctttgg ctgggacccg 19140
cgctccaaaa cctgctacct cttcgacccc tttggcttct ccgatcagcg cctcagacag 19200
atctatgagt ttgagtacga ggggctgctg cgccgcagcg cgcttgcctc ctcgcccgac 19260
cgctgcatca cccttgagaa gtccaccgag accgtgcagg ggccccactc ggccgcctgc 19320
ggtctcttct gctgcatgtt tttgcacgcc tttgtgcgct ggccccagag tcccatggat 19380
cgcaacccca ccatgaactt gctcaaggga gtgcccaacg ccatgctcca gagcccccag 19440
gtccagccca ccctgcgcca caaccaggaa cagctctacc gcttcctgga gcgccactcc 19500
ccctacttcc gcagtcacag cgcgcacatc cggggggcca cctctttctg ccacttgcaa 19560
caaaacatgc aagacggaaa atgatgtaca gctcgctttt taataaatgt aaagactgtg 19620

```
cactttattt atacacgggc tctttctggt tatttattca acaccgccgt cgccatctag  19680
aaatcgaaag ggttctgccg cgcgtcgccg tgcgccacgg gcagagacac gttgcgatac  19740
tggaagcggc tcgcccactt gaactcgggc accaccatgc ggggcagtgg ctcctcgggg  19800
aagttctcgc cccacagggt gcgggtcagc tgcagcgcgc tcaggaggtc gggagccgag  19860
atcttgaagt cgcagttggg gccggaaccc tgcgcgcgcg agttgcggta cacggggttg  19920
cagcactgga acaccagcag ggccggatta cgcacgctgg ccagcaggct ctcgtcgctg  19980
atcatgtcgc tgtccagatc ctccgcgttg ctcagggcga atggggtcat cttgcagacc  20040
tgcctgccca ggaaaggcgg cagcccgggc ttgccgttgc agtcgcagcg caggggcatc  20100
agcaggtgcc cgtggcccgt ctgcgcctgc gggtacagcg cgcgcatgaa ggcttcgatc  20160
tgcctgaaag ccacctgcgt cttggctccc tccgaaaaga acatcccaca ggacttgctg  20220
gagaactggt tcgcgggaca gctggcatcg tgcaggcagc agcgcgcgtc ggtgttggcg  20280
atctgcacca cgttgcgacc ccaccggttc ttcactatct tggccttgga agcctgctcc  20340
ttcagcgcgc gctggccgtt ctcgctggtc acatccatct ctatcacctg ctccttgttg  20400
atcatgtttg tcccgtgcag acacttcagg tcgccctccg tctgggtgca gcggtgctcc  20460
cacagcgcgc aaccggtggg ctcccaattt ttgtgggtca cccccgcgta ggcctgcagg  20520
taggcctgca agaagcgccc catcatggcc acaaaggtct tctggctcgt aaaggtcagc  20580
tgcaggccgc gatgctcttc gttcagccag gtcttgcaga tggcggccag cgcctcggtc  20640
tgctcgggca gcatcctaaa atttgtcttc aggtcgttat ccacgtggta cttgtccatc  20700
atggcgcgcg ccgcctccat gcccttctcc caggcggaca ccatgggcag gcttaggggg  20760
tttatcactt ccaccggcga ggacaccgta ctttcgattt cttcttcctc cccctcttcc  20820
cggcgcgcgc ccacgctgct gcgcgctctc accgcctgca ccaaggggtc gtcttcaggc  20880
aagcgccgca ccgagcgctt gccgcccttg acctgcttaa tcagcaccgg cgggttgctg  20940
aagcccacca tggtcagctc cgcctgctct tcttcgtctt cgctgtctac cactatctct  21000
ggggaagggc ttctccgctc tgcggcggtg cgcttctttt ttttcttggg agcagccgtg  21060
acggagtccg ccacggcgac ggaggtcgag ggcgtggggc tgggggtgcg cggtaccagg  21120
gcctcgtcgc cctcggactc ttcctctgac tccaggcggc ggcggagacg cttctttggg  21180
ggcgcgcgcg tcagcggcgg cggagacggg gacggggacg gggacgggac gccctccaca  21240
gggggtggtc ttcgcgcaga cccgcggccg cgctcggggg tcttttcgag ctggtcttgg  21300
tcccgactgg ccattgtatc ctcctcctcc taggcagaga gacataagga gtctatcatg  21360
caagtcgaga aggaggagag cttaaccacc ccctctgaga ccgccgatgc gcccgccgtc  21420
gccgtcgccc ccgctgccgc cgacgcgccc gccacaccga gcgacacccc cgcggacccc  21480
ccagccgacg caccccctgtt cgaggaagcg gccgtggagc aggacccggg ctttgtctcg  21540
gcagaggagg atttgcgaga ggaggaggat aaggagaaga agccctcagt gccaaaagat  21600
gataaagagc aagacgagca cgacgcagat gcacaccagg gtgaagtcgg gcggggggac  21660
ggagggcatg acggcgccga ctacctagac gaagggaacg acgtgctctt gaagcacctg  21720
catcgtcagt gcgccatcgt ttgcgacgct ctgcaggagc gcagcgaagt gcccctcagc  21780
gtggcggagg tcagccacgc ctacgagctc agcctcttct ccccccgggt gccccccgc  21840
cgccgcgaaa acggcacatg cgagcccaac ccgcgcctca acttctaccc cgcctttgtg  21900
gtgcccgagg tcctggccac ctatcacatc ttctttcaaa attgcaagat ccccctctcg  21960
tgccgcgcca accgtagccg cgccgataag atgctggccc tgcgccaggg cgaccacata  22020
```

```
cctgatatcg ccgctttgga agatgtgcca aagatcttcg agggtctggg tcgcaacgag  22080
aagcgggcag caaactctct gcaacaggaa aacagcgaaa atgagagtca caccggggta  22140
ctggtggagc tcgagggcga caacgcccgc ctggcggtgg tcaagcgcag catcgaggtc  22200
acccactttg cctaccccgc gctcaacctg ccccccaaag tcatgaacgc ggccatggac  22260
gggctgatca tgcgccgcgg ccggcccctc gctccagatg caaacttgca tgaggagacc  22320
gaggacggcc agcccgtggt cagcgacgag cagctggcgc gctggctgga gaccgcggac  22380
cccgccgaac tggaggagcg gcgcaagatg atgatggccg cggtgctggt caccgtagag  22440
ctggagtgtc tgcagcgctt cttcggcgac cccgagatgc agagaaaggt cgaggagacc  22500
ctgcactaca ccttccgcca gggctacgtg cgccaggctt gcaagatctc caacgtggag  22560
ctcagcaacc tggtgtccta cctgggcatc ttgcatgaga accgcctcgg gcagagcgtg  22620
ctgcactcca ccctgcgcgg ggaggcgcgc cgcgactacg tgcgcgactg cgtttacctc  22680
ttcctctgct acacctggca gacggccatg ggggtctggc agcagtgcct ggaggagcgc  22740
aacctcaagg agctggagaa gctcctgcag cgcgcgctca aagacctctg gacgggctac  22800
aacgagcgct cggtggccgc cgcgctggcc gacctcatct tccccgagcg cctgctcaaa  22860
accctccagc aggggctgcc cgacttcacc agccaaagca tgttgcaaaa cttcaggaac  22920
tttatcctgg agcgttctgg catcctaccc gccacctgct gcgccctgcc cagcgacttt  22980
gtccccctcg tgtaccgcga gtgccccccg ccgctgtggg gtcactgcta cctgttccaa  23040
ctggccaact acctgtccta ccacgcggac ctcatggagg actccagcgg cgaggggctc  23100
atggagtgcc actgccgctg caacctctgc acgccccacc gctccctggt ctgcaacacc  23160
caactgctca gcgagagtca gattatcggt accttcgagc tacagggtcc gtcctcctca  23220
gacgagaagt ccgcggctcc ggggctaaaa ctcactccgg ggctgtggac ttccgcctac  23280
ctgcgcaaat ttgtacctga agactaccac gcccacgaga tcaggtttta cgaagaccaa  23340
tcccgcccgc ccaaggcgga gctgaccgcc tgcgtcatca cccagggcga gatcctaggc  23400
caattgcaag ccatccaaaa agcccgccaa gatttttttgc tgagaaaggg tcggggggtg  23460
tatctggacc cccagtcggg tgaggagctc aacccggttc cccgctgccc gccgccgcgg  23520
gaccttgctt cccaggataa gcatcgccat ggctcccaga aagaagcagc agcggccgcc  23580
actgccgcca ccccacatgc tggaggaaga ggaggaatac tgggacagtc aggcagagga  23640
ggtttcggac gaggaggagc cggagacgga gatggaagag tgggaggagg acagcttaga  23700
cgaggaggct tccgaagccg aagaggcaga cgcaacaccg tcaccctcgg ccgcagcccc  23760
ctcgcaggcg cccccgaagt ccgctcccag catcagcagc aacagcagcg ctataacctc  23820
cgctcctcca ccgccgcgac ccacggccga ccgcagaccc aaccgtagat gggacaccac  23880
cggaaccggg gccggtaagt cctccgggag aggcaagcaa gcgcagcgcc aaggctaccg  23940
ctcgtggcgc gctcacaaga acgccatagt cgcttgcttg caagactgcg gggggaacat  24000
ctccttcgcc cgccgcttcc tgctcttcca ccacggtgtg gccttccccc gtaacgtcct  24060
gcattactac cgtcatctct acagccccta ctgcggcggc agtgagccag agacggtcgg  24120
cggcggcggc ggcgcccgtt tcggcgccta ggaagaccca gggcaagact tcagccaaga  24180
aactcgcggc ggccgcggcg aacgcggtcg cgggggccct gcgcctgacg gtgaacgaac  24240
ccctgtcgac ccgcgaactg agaaaccgaa tcttccccac tctctatgcc atcttccagc  24300
agagcagagg gcaggatcag gaactgaaag taaaaaacag gtctctgcgc tccctcaccc  24360
```

-continued

```
gcagctgtct gtatcacaag agcgaagacc agcttcggcg cacgctggag gacgctgagg  24420
cactcttcag caaatactgc gcgctcactc ttaaggacta gctccgcgcc cttctcgaat  24480
ttaggcggga acgcctacgt catcgcagcg ccgccgtcat gagcaaggac attcccacgc  24540
catacatgtg gagctatcag ccgcagatgg gactcgcggc gggcgcctcc caagactact  24600
ccacccgcat gaactggctc agtgccggcc cacacatgat ctcacaggtt aatgatatcc  24660
gcacccatcg aaaccaaata ttggtggagc aggcggcaat taccaccacg ccccgcaata  24720
atcccaaccc cagggagtgg cccgcgtccc tggtgtatca ggaaattccc ggccccacca  24780
ccgtactact tccgcgtgat tcccaggccg aagtccaaat gactaactca ggggcgcagc  24840
tcgcgggcgg ctgtcgtcac agggtgcggc ctcctcgcca gggtataact cacctggaga  24900
tccgaggcag aggtattcag ctcaacgacg agtcggtgag ctcctcgctc ggtctaagac  24960
ctgacgggac cttccagata gccggagccg gccgatcttc cttcacgccc cgccaggcgt  25020
acctgactct gcagagctcg tcctcggcgc cgcgctcggg cggcatcggg actctccagt  25080
tcgtgcagga gtttgtgccc tcggtctact tcaacccctt ctcgggctct cccggtcgct  25140
acccggacca gttcatctcg aactttgacg ccgcgaggga ctcggtggac ggctacgact  25200
gaatgtcggg tggacccggt gcagagcaac ttcgcctgaa gcacctcgac cactgccgcc  25260
gccctcagtg ctttgcccgc tgtcagaccg gtgagttcca gtacttttcc ctgcccgact  25320
cgcacccgga cggcccggcg cacggggtgc gctttttcat cccgagtcag gtgcgctcta  25380
ccctaatcag ggagtttacc gcccgtcccc tactggcgga gttggaaaag gggccttcta  25440
tcctaaccat tgcctgcatc tgctctaacc ctggattgca ccaagatctt tgctgtcatt  25500
tgtgtgctga gtataataaa ggctgagatc agaatctact cgggctcctg tcgccatcct  25560
gtcaacgcca ccgtccaagc ccggcccgat cagcccgagg tgaacctcac ctgcggtctg  25620
caccggcgcc tgaggaaata cctagcttgg tactacaaca gcactccctt tgtggtttac  25680
aacagctttg accaggacgg ggtctcactg agggataacc tctcgaacct gagctactcc  25740
atcaggaaga acagcaccct cgagctactt cctccttacc tgcccgggac ttaccagtgt  25800
gtcaccggtc cctgcaccca cacccacctg ttgatcgtaa acgactctct tccgagaaca  25860
gacctcaata actcctcttc gcagttcccc agaacaggag gtgagctcag gaaaccccgg  25920
gtaaagaagg gtggacaaga gttaacactt gtggggtttc tggtgtatgt gacgctggtg  25980
gtggctcttt tgattaaggc ttttccttcc atgtctgaac tctccctctt ttatgaacaa  26040
ctcgactagt gctaacggga ccctacccaa cgaatcggga ttgaatatcg gtaaccaggt  26100
tgcagtttca cttttgatta ccttcatagt cctcttcctg ctagtgctgt cgcttctgtg  26160
cctgcggatc gggggctgct gcatccacgt ttatatctgg tgctggctgt ttagaaggtt  26220
cggagaccat cgcaggtaga ataaacatgc tgctgcttac cctctttgtc ctggcgctgg  26280
ccgccagctg ccaagccttt tccgaggctg actttataga gccccagtgt aacgtgactt  26340
ttaaagccca tgcacagcgt tgtcatacta taatcaaatg tgccaccgaa cacgatgaat  26400
accttatcca gtataaagat aaatcacaca aagtggcact tgttgacatc tggaaacccg  26460
aagacccttt ggaatacaat gtgaccgttt tccagggtga cctcttcaaa atttacaatt  26520
acactttccc atttgaccag atgtgtgact ttgtcatgta catggaaaag cagcacaagc  26580
tgtggcctcc gactccccag ggctgtgtgg aaaatccagg ctctttctgc atgatctctc  26640
tctgtgtaac tgtgctggca ctaatactca cgcttttgta tatcagattt aaatcaaggc  26700
aaagcttcat cgatgaaaag aaaatgcctt aaacgctttc acgcttgatt gctaacaccg  26760
```

```
ggtttttatc cgcagaatga ttggaatcac cctactaatc acctccctcc ttgcgattgc  26820
ccatgggttg gaacgaatcg aagcccctgt gggggccaat gttaccctgg tggggcctgt  26880
cggcaatgct acattaatgt gggaaaaata tactaaaaat caatgggtct cttactgcac  26940
taacaaaaac agccacaagc ccagagccat ctgcgatggg caaaatctaa ccttgattga  27000
tgttcaaatg ctggatgcgg gctactatta tgggcagctg ggtacaatga ttaattactg  27060
gagaccccac aaagattaca tgctccacgt agtaaagggt cccccttagca gcccacccac  27120
taccacctct actaccccca ctaccaccac tactcccacc accagcactg ccgcccagcc  27180
tcctcatagc agaacaacca cttttatcaa ttccaagtcc cactcccccc acattgccgg  27240
cgggccctcc gcctcagact ccgagaccac cgagatctgc ttctgcaaat gctctgacgc  27300
ctttgctgag gatttggaag accacgagga agatgagcat gacttcgcag atgcatgcca  27360
ggcatcagag gcagaagcgc tgccggtggc cctcaaacag tatgcagacc cccacaccac  27420
ccccaacctt cctccacctt cccagaagcc aagtttcctg ggggaaaatg aaactctgcc  27480
tctctccata ctcgctctga catctgttgc tatgttgacc gctctgctgg tgcttctatg  27540
ctctatatgc tacctgatct gctgcagaaa gaaaaaatct cacggccatg ctcaccagcc  27600
cctcatgcac ttcccttacc ctccagagct gggcgaccac aaactttaag tctgcagtaa  27660
ctatctgccc atcccttgtc agtcgacagc gatgagcccc actaatctaa cggcctctgg  27720
acttacaaca tcgtctctta atgagaccac cgctcctcaa gacctgtacg atggtgtctc  27780
cgcgctggtt aaccagtggg atcacctggg catatggtgg ctcctcatag gagcagtgac  27840
cctgtgccta atcctggtct ggatcatctg ctgcatcaaa agcagaagac ccaggcggcg  27900
gcccatctac aggccctttg tcatcacacc tgaagatgat gatgacacca cttccaggct  27960
gcagaggcta aagcagctac tcttctcttt tacagcatgg taaattgaat catgcctcgc  28020
attttcatct acttgtctct ccttccactt tttctgggct cttctacatt ggccgctgtg  28080
tcccacatcg aggtagactg cctcacgccc ttcacagtct acctgctttt cggctttgtc  28140
atctgcacct ttgtctgcag cgttatcact gtagtgatct gcttcataca gtgcatcgac  28200
tacgtctgcg tgcgggtggc ttactttaga caccaccccc agtatcgcaa cagggacata  28260
gcggctctcc taagacttgt ttaaaatcat ggccaaatta actgtgattg gtcttctgat  28320
catctgctgc gtcctagccg cgattgggac tcaagctcct accaccacca gcgctcccag  28380
aaagagacat gtatcctgca gcttcaagcg tccctggaat ataccccaat gctttactga  28440
tgaacctgaa atctctttgg cttggtactt cagcgtcacc gcccttctta tcttctgcag  28500
tacggttatt gcccttgcca tctacccttc ccttgacctg ggctggaatg ctgtcaactc  28560
tatggaatat cccaccttcc cagaaccaga cctgccagac ctggttgttc taaacgcgtt  28620
tcctcctcct gctcccgttc aaaatcagtt tcgccctccg tcccccacgc ccactgaggt  28680
cagctacttt aatctaacag gcggagatga ctgaaaacct agacctagaa atggacggtc  28740
tctgcagcga gcaacgcaca ctagagaggc gccggcaaaa agagctcgag cgtcttaaac  28800
aagagctcca agacgcggtg gccatacacc agtgcaaaaa aggtgtcttc tgtctggtaa  28860
aacaggccac gctcacctat gaaaaaacag gtgacaccca ccgcctagga tacaagctgc  28920
ccacacagcg ccagaagttc gccctcatga taggcgaaca acccatcacc gtgacccagc  28980
actccgtgga gacagaaggc tgcatacacg ctccctgtag ggcgctgac tgcctctaca  29040
ccttgatcaa aaccctctgc ggtctcagag acctcatccc ttttaattaa tcataactgt  29100
```

-continued

```
aatcaataaa aaatcactta cttgaaatct gatagcaagc ctctgtccaa ttttttcagc  29160
aacacttcct tcccctcctc ccaactctgg tactctaggc gcctcctagc tgcaaacttc  29220
ctccacagtc tgaagggaat gtcagattcc tcctcctgtc cctccgcacc cacgatcttc  29280
atgttgttgc agatgaaacg cgcgagatcg tctgacgaga ccttcaaccc cgtgtacccc  29340
tacgataccg agatcgctcc gacttctgtc cctttcctta cccctccctt tgtgtcatcc  29400
gcaggaatgc aagaaaatcc agctggggtg ctgtccctgc acttgtcaga gcccccttacc  29460
acccacaatg ggccctgac tctaaaaatg gggggcggcc tgaccctgga caaggaaggg  29520
aatctcactt cccaaaacat caccagtgtc gatccccctc tcaaaaaaag caagaacaac  29580
atcagccttc agaccgccgc acccctcgcc gtcagctccg gggccctaac actttttgcc  29640
actccccccc tagcggtcag tggtgacaac cttactgtgc agtctcaggc ccctctcact  29700
ttggaagact caaaactaac tctggccacc aaaggacccc taactgtgtc cgaaggcaaa  29760
cttgtcctag aaacagaggc tcccctgcat gcaagtgaca gcagcagcct gggccttagc  29820
gttacggccc cacttagcat taacaatgac agcctaggac tagacatgca agcgcccatt  29880
agctctcgag atggaaaact ggctctaaca gtggcggccc ccctaactgt ggtcgagggt  29940
atcaatgctt tggcagtagc cacaggtaag ggtattgggc taaatgaaac caacacacac  30000
ctgcaggcaa aactggtcgc acccctaggc tttgatacca acggcaacat taagctaagc  30060
gttgcaggag gcatgaggct aaacaataac acactgatac tagatgtaaa ctacccattt  30120
gaggctcaag gccaactgag cctaagagtg ggctcgggcc cactatatgt agattctagt  30180
agtcataacc taaccattag atgccttagg ggattgtata taacatcttc taacaaccaa  30240
aacggtctag aagccaacat taaactaaca agaggccttg tgtatgacgg aaatgccata  30300
gcagttaatg ttggcaaagg gctggaatac agccctactg acacaacaga aaaacctata  30360
cagactaaaa taggtctagg catggagtat gataccgagg gagccatgat gacaaaacta  30420
ggctctggac taagctttga caattcagga gccattgtag tgggaaacaa aaatgatgac  30480
aggcttactt tgtggaccac accggaccca tcgcccaact gtcagatcta ctctgaaaaa  30540
gatgctaaac taaccttggt actgactaaa tgtggcagtc aggttgtagg cacagtatct  30600
attgccgctc ttaaaggtag cctcgtgcca atcactagtg caatcagtgt ggttcaggta  30660
tacctaaggt ttgatgaaaa tggggtacta atgagtaact cttcacttaa tggcgaatac  30720
tggaatttta gaaacggaga ctcaactaat ggcacaccat atacaaacgc agtgggtttc  30780
atgcctaatc tactggccta tcctaaaggt caaactacaa ctgcaaaaag taacattgtc  30840
agccaggtct acatgaatgg ggacgatact aaacccatga catttacaat caacttcaat  30900
ggccttagtg aaacagggga taccccctgtt agtaaatatt ccatgacatt ctcatggagg  30960
tggccaaatg gaagctacat agggcacaat tttgtaacaa actcctttac cttctcctac  31020
atcgcccaag aataaagaaa gcacagagat gcttgttttt gatttcaaaa ttgtgtgctt  31080
ttatttattt tcagcttaca gtatttccag tagtcattca aataaagctt aatcaaactg  31140
catgagaacc cttccacata gcttaaatta gcaccagtgc aaatggagaa aacaattgac  31200
ggccgggatc ggtgatcacc gatccagaca tgataagata cattgatgag tttggacaaa  31260
ccacaactag aatgcagtga aaaaaatgct ttatttgtga aatttgtgat gctattgctt  31320
tatttgtaac cattataagc tgcaataaac aagttcccgg atcgcgatcc ggcccgaggc  31380
tgtagccgac gatggtgcgc caggagagtt gttgattcat tgtttgcctc cctgctgcgg  31440
tttttcaccg aagttcatgc cagtccagcg tttttgcagc agaaaagccg ccgacttcgg  31500
```

```
tttgcggtcg cgagtgaaga tccctttctt gttaccgcca acgcgcaata tgccttgcga  31560
ggtcgcaaaa tcggcgaaat tccatacctg ttcaccgacg acggcgctga cgcgatcaaa  31620
gacgcggtga tacatatcca gccatgcaca ctgatactct tcactccaca tgtcggtgta  31680
cattgagtgc agcccggcta acgtatccac gccgtattcg gtgatgataa tcggctgatg  31740
cagtttctcc tgccaggcca gaagttcttt ttccagtacc ttctctgccg tttccaaatc  31800
gccgctttgg acataccatc cgtaataacg gttcaggcac agcacatcaa agagatcgct  31860
gatggtatcg gtgtgagcgt cgcagaacat tacattgacg caggtgatcg gacgcgtcgg  31920
gtcgagttta cgcgttgctt ccgccagtgg cgcgaaatat tcccgtgcac cttgcggacg  31980
ggtatccggt tcgttggcaa tactccacat caccacgctt gggtggtttt tgtcacgcgc  32040
tatcagctct ttaatcgcct gtaagtgcgc ttgctgagtt tccccgttga ctgcctcttc  32100
gctgtacagt tctttcggct tgttgcccgc ttcgaaacca atgcctaaag agaggttaaa  32160
gccgacagca gcagtttcat caatcaccac gatgccatgt tcatctgccc agtcgagcat  32220
ctcttcagcg taagggtaat gcgaggtacg gtaggagttg gccccaatcc agtccattaa  32280
tgcgtggtcg tgcaccatca gcacgttatc gaatcctttg ccacgcaagt ccgcatcttc  32340
atgacgacca aagccagtaa agtagaacgg tttgtggtta atcaggaact gttcgccctt  32400
cactgccact gaccggatgc cgacgcgaag cgggtagata tcacactctg tctggctttt  32460
ggctgtgacg cacagttcat agagataacc ttcacccggt tgccagaggt gcggattcac  32520
cacttgcaaa gtcccgctag tgccttgtcc agttgcaacc acctgttgat ccgcatcacg  32580
cagttcaacg ctgacatcac cattggccac cacctgccag tcaacagacg cgtggttaca  32640
gtcttgcgcg acatgcgtca ccacggtgat atcgtccacc caggtgttcg gcgtggtgta  32700
gagcattacg ctgcgatgga ttccggcata gttaaagaaa tcatggaagt aagactgctt  32760
tttcttgccg ttttcgtcgg taatcaccat tcccggcggg atagtctgcc agttcagttc  32820
gttgttcaca caaacggtga tacgtacact tttcccggca ataacatacg gcgtgacatc  32880
ggcttcaaat ggcgtatagc cgccctgatg ctccatcact tcctgattat tgacccacac  32940
tttgccgtaa tgagtgaccg catcgaaacg cagcacgata cgctggcctg cccaaccttt  33000
cggtataaag acttcgcgct gataccagac gttgcccgca taattacgaa tatctgcatc  33060
ggcgaactga tcgttaaaac tgcctggcac agcaattgcc cggctttctt gtaacgcgct  33120
ttcccaccaa cgctgatcaa ttccacagtt ttcgcgatcc agactgaatg cccacaggcc  33180
gtcgagtttt ttgatttcac gggttggggt ttctacagga cggaccatgc gttcgacctt  33240
tctcttcttt tttgggccca tgatggcaga tccgtatagt gagtcgtatt agctggttct  33300
ttccgcctca gaagccatag agcccaccgc atccccagca tgcctgctat tgtcttccca  33360
atcctccccc ttgctgtcct gccccacccc acccccagaa atagaatgac acctactcag  33420
acaatgcgat gcaatttcct cattttatta ggaaaggaca gtgggagtgg caccttccag  33480
ggtcaaggaa ggcacggggg aggggcaaac aacagatggc tggcaactag aaggcacagt  33540
cgaggctgat cagcgagctc tagatgcatg ctcgagcggc cgccagtgtg atggatatct  33600
gcagaattcc agcacactgg cggccgttac tagtggatcc gagctcggta ccaacgcgtc  33660
gtaactataa cggtcctaag gtagcgaaaa gcactctcac agcaccagca ctaatcagag  33720
tgtgaagagg gccaagtgcc gaacgagtat atataggaat aaaaaatgac gtaaatgtgt  33780
aaaggtcaga aaacgcccag aaaaatacac agaccaacgc ccgaaacgaa aacccgcgaa  33840
```

aaaataccca gaacttcctc aacaaccgcc acttccgctt tctcacggta cgtcacttcc 33900
gcaagaaaag caaaactaca tttcccacat gtgtaaaaac gaaaccccgc cccttgtaac 33960
cgcccacaac ttacatcatc aaaacgtaaa ctcctacgtc acccgccccg cctctccccg 34020
cccacctcat tatcatattg gccacaatcc aaaataaggt atattattga tgatg 34075

<210> SEQ ID NO 26
<211> LENGTH: 34071
<212> TYPE: DNA
<213> ORGANISM: Gorilla beringei graueri

<400> SEQUENCE: 26
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagtgcgtaa tatttaccga gggccgaggg 360
actttgaccg attacgtgga ggactcgccc aggtgttttt tacgtgaatt tccgcgttcc 420
gggtcaaagt ctccgtttta ttgtcaccgt catttgacag gcctgaccat ctggtgctgg 480
cctgcaccag ggccgagttt gggtctagcg atgaggatac cgattgaggt gggtaaggtg 540
ggcgtggcta gaagggtggg gcgtgtataa attgggggtc taagggtctc tctgttttgt 600
cttgcaacag ccgccgccat gagcgacacc ggcaacagct ttgatggaag catctttagc 660
ccctatctga cagtgcgcat gcctcactgg gctggagtgc gtcagaatgt gatgggttcc 720
aacgtggatg gacgccccgt tctgccttca aattcgtcta caatggccta cgcgaccgtg 780
ggaggaactc cgctggacgc cgcgacctcc gccgccgcct ccgccgccgc cgcgaccgcg 840
cgcagcatgg ctacggacct ttacagctct ttggtggcga gcggcgcggc ctctcgcgcg 900
tctgctcggg atgagaaact gaccgctctg ctgcttaaac tggaagactt gacccgggag 960
ctggctcaac tgacccagca ggtctccagc ttgcgtgaga gcagccttgc ctccccctaa 1020
tggcccataa tataaataaa agccagtctg tttggattaa gcaagtgtat gttctttatt 1080
taactctccg cgcgcggtaa gcccgggacc agcggtctcg gtcgtttagg gtgcggtgga 1140
ttctttccaa cacgtggtac aggtggctct ggatgtttag atacatgggc atgagtccat 1200
ccctggggtg gaggtagcac cactgcagag cttcgtgctc gggggtggtg ttgtatatga 1260
tccagtcgta gcaggagcgc tgggcgtggt gctgaaaaat gtccttaagc aagaggctta 1320
tagctagggg gaggcccttg gtgtaagtgt ttacaaatct gctcagttgg gaggggtgca 1380
tccgggggga tataatgtgc atcttggact ggatttttag gttggctatg ttcccaccca 1440
gatcccttct gggattcatg ttgtgcagga ccaccagcac ggtatatcca gtacacttgg 1500
gaaatttatc gtggagctta gacgggaatg catggaagaa cttggagacg cccttgtggc 1560
ctcccagatt ttccatacat tcgtccatga tgatggcaat gggcccgtgg gaagctgcct 1620
gagcaaaaat gtttctggga tcgctcacat cgtagttatg ttccagggtg aggtcatcat 1680
aggacatctt tacaaatcgg gggcggaggg tcccggactg gggatgatg gtgccctcgg 1740 gccccggggc gtagttcccc tcacagatct gcatctccca ggctttcatt tcagagggag 1800
ggatcatatc cacctgcgga gcgatgaaaa acacagtttc tggcgcaggg gagattaact 1860
gggatgagag caggtttctg agcagctgtg actttccaca gccggtgggc ccatatatca 1920

```
cgcctatcac cggctgcagc tggtagttaa gagagctgca gctgccgtcc tcccggagca   1980
ggggggccac ctcgttcagc atatccctga cgtggatgtt ctccctgacc aattccgcca   2040
gaaggcgctc gccgcccagc gaaagcagct cttgcaagga agcaaaattt ttcagcggtt   2100
ttaggccgtc ggccgtgggc atgtttttca gcgtctgggt cagcagttcc agtctgtccc   2160
acagctcggt gatgtgctct acggcatctc gatccagcag atctcctcgt ttcgcgggtt   2220
ggggcggctt tcgctgtagg gcaccagccg atgggcgtcc agcggggcca gagtcatgtc   2280
cttccatggg cgcagggtcc tcgtcagggt ggtctgggtc acggtgaagg ggtgcgctcc   2340
gggttgggcg ctggccaggg tgcgcttgag gctggttctg ctggtgctga atcgctgccg   2400
ctcttcgccc tgcgcgtcgg ccaggtagca tttgaccatg gtctcgtagt cgagaccctc   2460
ggcggcgtgc cccttggcgc ggagctttcc cttggaggtg gcgccgcacg aggggcactg   2520
caggctcttc agggcgtaga gcttgggagc gagaaacacg gactctgggg agtaggcgtc   2580
cgcgccgcag gaagcgcaga ccgtctcgca ttccaccagc caagtgagct ccgggcggtc   2640
agggtcaaaa accaggttgc ccccatgctt tttgatgcgt ttcttacctc ggctctccat   2700
gaggcggtgt cccttctcgg tgacgaagag gctgtccgtg tctccgtaga ccgacttcag   2760
gggcctgtct tccagcggag tgcctctgtc ctcctcgtag agaaactctg accactctga   2820
gacgaaggcc cgcgtccagg ccaggacgaa ggaggccacg tgggaggggt agcggtcgtt   2880
gtccactagc gggtccacct tctccagggt gtgcaggcac atgtccccct cctccgcgtc   2940
cagaaaagtg attggcttgt aggtgtagga cacgtgaccg ggggttcccg acggggggt    3000
ataaaagggg gtgggcaccc tttcatcttc actctcttcc gcatcgctgt ctgcgagagc   3060
cagctgctgg ggtaagtatt ccctctcgaa ggcgggcatg acctcagcgc tcaggttgtc   3120
agtttctaaa aatgaggagg atttgatgtt cacctgtccg gaggtgatac ctttgagggt   3180
acctgggtcc atctggtcag aaaacactat ttttttgttg tcaagcttgg tggcgaacga   3240
cccgtagagg gcgttggaga gcagcttggc gatggagcgc agggtctggt tttgtcgcg    3300
gtcggctcgc tccttggccg cgatgttgag ttgcacgtac tcgcgggcca cgcacttcca   3360
ctcggggaag acggtggtgc gctcgtctgg gatcaggcgc accctccagc ctcggttgtg   3420
cagggtgacc atgtcgacgc tggtggcgac ctcgccgcgc aggcgctcgt tggtccagca   3480
gaggcggccg cccttgcgcg agcagaaggg gggtaggggg tccagctggt cctcgtttgg   3540
ggggtccgcg tcgatggtga agaccccggg gagcaagcgc gggtcaaagt agtcgatctt   3600
gcaagcttgc atgtccagag cccgctgcca ttcgcgggcg gcgagcgcgc gctcgtaggg   3660
gttgaggggc gggccccagg gcatggggtg ggtgagcgcg gaggcgtaca tgccgcagat   3720
gtcatacacg tacaggggtt ccctgaggat gccgaggtag gtggggtagc agcgcccccc   3780
gcggatgctg gcgcgcacgt agtcatagag ctcgtgggag ggggccagca tgttgggccc   3840
gaggttggtg cgctgggggc gctcggcgcg gaaggcgatc tgcctgaaga tggcatggga   3900
gttggaggag atggtgggcc gctggaagac gttgaagctt gcttcttgca agcccaccga   3960
gtccctgacg aagcaggcgt aggactcgcg cagcttgtgc accagctcgg cggtgacctg   4020
gacgtcgagc gcgcagtagt cgagggtctc gcggatgatg tcatacttat cctcccctt    4080
ctttttccac agctcgcggt tgaggacgaa ctcttcgcgg tctttccagt actcttggag   4140
gggaaacccg tccgtgtccg aacggtaaga gcctagcatg tagaactggt tgacggcctg   4200
gtaggggcaa cagcccttct ccacgggcag cgcgtaggcc tgcgccgcct tgcggaggga   4260
```

-continued

```
ggtgtgggtg agggcgaaag tgtccctgac catgactttg aggtattgat gtttgaagtc   4320
tgtgtcatcg cagccgccct gttcccacag ggtgtagtcc gtgcgctttt tggagcgcgg   4380
gttgggcagg gagaaggtga ggtcattgaa gaggatcttc cccgctcgag gcatgaagtt   4440
tctggtgatg cgaaagggcc ctgggaccga ggagcggttg ttgatgacct gggcggccag   4500
gacgatctcg tcaaagccgt ttatgttgtg gcccacgatg tagagctcca aaaagcgggg   4560
ctggcccttg atggagggga gctttttgag ttcctcgtag gtgagctcct cgggcgattc   4620
caggccgtgc tcctccaggg cccagtcttg caagtgaggg ttggccgcca ggaaggatcg   4680
ccagaggtcg cgggccatga gggtctgcag gcggtcgcgg aaggttctga actgtcgccc   4740
cacggccatc ttttcggggg tgatgcagta gaaggtgagg gggtctttct cccaggggtc   4800
ccatctgagc tctcgggcga ggtcgcgcgc ggcggcgacc agagcctcgt tgccccccag   4860
tttcatgacc agcatgaagg gcacgagctg cttgccaaag gctcccatcc aagtgtaggt   4920
ctctacatcg taggtgacaa agaggcgctc cgtgcgagga tgagagccga tcgggaagaa   4980
ctggatctcc cgccaccagt tggaggattg gctgttgatg tggtgaaagt agaagtcccg   5040
tctgcgggcc gagcactcgt gctggctttt gtaaaagcga ccgcagtact ggcagcgctg   5100
cacgggttgt atatcttgca cgaggtgaac ctggcgacct ctgacgagga agcgcagcgg   5160
gaatctaagt cccccgcctg gggtcccgtg tggctggtgg tcttctactt tggttgtctg   5220
gccgccagca tctgtctcct ggagggcgat ggtggagcag accaccacgc cgcgagagcc   5280
gcaggtccag atctcggcgc tcggcgggcg gagtttgatg acgacatcgc gcacattgga   5340
gctgtccatg gtctccagct cccgcggcgg caggtcagct gggagttcct ggaggttcac   5400
ctcgcagaga cgggtcaagg cgcgggcagt gttgagatgg tatctgattt caaggggcgt   5460
gttggcggcg gagtcgatgg cttgcaggag gccgcagccc cgggggggcca cgatggttcc   5520
ccgcggggcg cgaggggagg cggaagctgg gggtgtgttc agaagcggtg acgcgggcgg   5580
gcccccggag gtaggggggg ttccggcccc acaggcatgg gcggcagggg cacgtcttcg   5640
ccgcgcgcgg gcaggggctg gtgctggctc cgaagagcgc ttgcgtgcgc gacgacgcga   5700
cggttggtgt cctgtatctg acgcctctga gtgaagacca cgggtcccgt gaccttgaac   5760
ctgaaagaga gttcgacaga atcaatctcg gcatcgttga cagcggcctg gcgcaggatc   5820
tcctgcacgt cgcccgagtt gtcctggtag gcgatctctg ccatgaactg ctcgatctct   5880
tcttcctgga gatctcctcg tccggcgcgc tccacggtgg ccgccaggtc gttggagatg   5940
cgacccatga gctgcgagaa ggcgttgagc ccgccctcgt tccagacccg gctgtagacc   6000
acgcccccct cggcgttgcg ggcgcgcatg accacctggg ccaggttgag ctccacgtgt   6060
cgcgtgaaga cggcgtagtt gcgcaggcgc tggaaaaggt agttcagggt ggtggcggtg   6120
tgctcggcga cgaagaagta catgacccag cgccgcaacg tggattcatt gatgtccccc   6180
aaggcctcca ggcgctccat ggcctcgtag aagtccacgg cgaagttgaa aaactgggag   6240
ttgcgagcgg acacggtcaa ctcctcctcc agaagacgga tgagctcggc gacagtgtcg   6300
cgcacctcgc gctcgaaggc cacgggggggc gcttcttcct cttccacctc ttcttccatg   6360
atcgcttctt cttcttcctc agccgggacg ggaggggggcg gcggcggcgg gggaggggcg   6420
cggcggcggc ggcggcgcac cgggaggcgg tcgatgaagc gctcgatcat ctccccccgc   6480
atgcggcgca tggtctcggt gacggcgcgg ccgttctccc gggggcgcag ctcgaagacg   6540
ccgcctctca tctcgccgcg ggcgggcgg ccgtgaggta gcgagacggc gctgactatg   6600
catcttaaca attgctgtgt aggtacaccg ccgagggacc tgattgagtc cagatccacc   6660
```

```
ggatccgaaa acctttggag gaaagcgtct atccagtcgc agtcgcaagg taggctgagc   6720
accgtggcgg gcgggggcgg gtctggagag ttcctggcgg agatgctgct gatgatgtaa   6780
ttaaagtagg cggtcttgag aaggcggatg gtggacagga gcaccatgtc tttgggtccg   6840
gcctgttgga tgcggaggcg gtcggccatg ccccaggcct cgttctgaca ccggcgcagg   6900
tctttgtagt agtcttgcat gagtctttcc accggcacct cttctccttc ctcttctcca   6960
tctcgccggt ggtttctcgc gccgcccatg cgcgtgaccc caaagcccct gagcggctgc   7020
agcagggcca ggtcggcgac cacgcgctcg gccaagatgg cctgctgcac ctgagtgagg   7080
gtcctctcga agtcatccat gtccacgaag cggtggtagg cgcccgtgtt gatggtgtag   7140
gtgcagttgg ccatgacgga ccagttgacg gtctggtgtc ccggctgcga gagctccgtg   7200
taccgcaggc gcgagaaggc gcgggaatcg aacacgtagt cgttgcaagt ccgcaccaga   7260
tactggtagc ccaccaggaa gtgcggcgga ggttggcgat agaggggcca gcgctgggtg   7320
gcgggggcgc cgggcgccag gttttccagc atgaggcggt ggtatccgta gatgtacctg   7380
gacatccagg tgatgccggc ggcggtggtg gtggcgcgcg cgtagtcgcg gacccggttc   7440
cagatgtttc gcaggggcga gaagtgttcc atggtcggca cgctctggcc ggtgaggcgc   7500
gcgcagtcgt tgacgctcta tacacacaca aaaacgaaag cgtttacagg gctttcgttc   7560
tgtagcctgg aggaaagtaa atgggttggg ttgcggtgtg ccccggttcg agaccaagct   7620
gagctcggcc ggctgaagcc gcagctaacg tggtattggc agtcccgtct cgacccaggc   7680
cctgtatcct ccaggatacg gtcgagagcc cttttgcttt cttggccaag cgcccgtggc   7740
gcgatctggg atagatggtc gcgatgagag gacaaaagcg gctcgcttcc gtagtctgga   7800
gaaacaatcg ccagggttgc gttgcggcgt accccggttc gagcccctat ggcggcttga   7860
atcggccgga accgcggcta acgagggccg tggcagcccc gtcctcagga ccccgccagc   7920
cgacttctcc agttacggga gcgagcccct tttgtttttt attttttaga tgcatcccgt   7980
gctgcggcag atgcgcccct cgccccggcc cgatcagcag cagcaacagc aggcatgcag   8040
accccccctct ccccttccg ccccggtcac cacggccgcg gcggccgtgt cgggcgcggg   8100
gggcgcgctg gagtcagatg agccaccgcg gcggcgacct aggcagtatc tggacttgga   8160
agagggcgag ggactggcgc ggctgggggc gaactctcca gagcgccacc cgcgggtgca   8220
gttgaaaagg gacgcgcgcg aggcgtacct gccgcggcag aacctgtttc gcgaccgcgg   8280
gggcgaggag cccgaggaga tgcgagactg caggttccaa gcggggcgcg agctgcggcg   8340
cgggctggac agacagcgcc tgctgcgcga ggaggacttt gagcccgaca cgcagacggg   8400
catcagcccc gcgcgcgcgc acgtagccgc ggccgacctg gtgaccgcct acgagcagac   8460
ggtgaaccag gagcgcaact tccaaaagag cttcaacaac cacgtgcgca cgctggtggc   8520
gcgcgaggag gtgaccctgg gtctcatgca tctgtgggac ctggtggagg cgatcgtgca   8580
gaaccccagc agcaagcccc tgaccgcgca gctgttcctg gtggtgcagc acagcaggga   8640
caacgaggcc ttcagggagg cgctgctgaa catcaccgag ccggaggggc gctggctcct   8700
ggacctgata aacatcctgc agagcatagt ggtgcaggag cgcagcctga gcctggccga   8760
gaaggtggcg gccatcaact actctatgct gagcctgggc aagttctacg cccgcaagat   8820
ctacaagacc ccctacgtgc ccatagacaa ggaggtgaag atagacagct tctacatgcg   8880
catggcgctg aaggtgctga ccctgagcga cgacctggga gtgtaccgca acgagcgcat   8940
ccacaaggcc gtgagcgcca gccggcggcg cgagctgagc gaccgcgagc tgatgcacag   9000
```

-continued

```
tctgcagcgc gcgctgaccg gcgcgggcga gggcgacagg gaggtcgagt cctacttcga   9060
catgggggcc gacctgcact ggcagccgag ccgccgcgcc ctggaggcgg cgggggcgta   9120
cggcggcccc ctggcggccg atgaccagga agaggaggac tatgagctag aggagggcga   9180
gtacctggag gactgacctg gctggtggtg ttttggtata gatgcaagat ccgaacgtgg   9240
cggacccggc ggtccgggcg gcgctgcaaa gccagccgtc cggcattaac tcctctgacg   9300
actgggccgc ggccatgggt cgcatcatgg ccctgaccgc gcgcaacccc gaggctttca   9360
ggcagcagcc tcaggccaac cggctggcgg ccatcttgga agcggtagtg cccgcgcgct   9420
ccaaccccac ccacgagaag gtgctggcca tagtcaacgc gctggcggag agcagggcca   9480
tccgcgcgga cgaggccgga ctggtgtacg atgcgctgct gcagcgggtg gcgcggtaca   9540
acagcggcaa cgtgcagacc aacctggacc gcctggtgac ggacgtgcgc gaggccgtgg   9600
cgcagcgcga gcgcttgcat caggacggta acctgggctc gctggtggcg ctaaacgcct   9660
tcctcagcac ccagccggcc aacgtaccgc gggggcagga ggactacacc aactttttga   9720
gcgcgctgcg gctgatggtg accgaggtcc ctcagagcga ggtgtaccag tcggggcccg   9780
actacttctt ccagaccagc agacagggct tgcaaaccgt gaacctgagc caggctttca   9840
agaacctgcg gggctgtggg ggagtgaagg cgcccaccgg cgaccgggct acggtgtcca   9900
gcctgctaac ccccaactcg cgcctgctgc tgctgctgat cgcgcccttc acggacagcg   9960
ggagcgtctc gcgggagacc tatctgggcc acctgctgac gctgtaccgc gaggccatcg  10020
ggcaggcgca ggtggacgag cacaccttcc aagagatcac cagcgtgagc cacgcgctgg  10080
ggcaggagga cacgggcagc ctgcaggcga ccctgaacta cctgctgacc aacaggcggc  10140
agaagattcc cacgctgcac agcctgaccc aggaggagga gcgcatcttg cgctacgtgc  10200
agcagagcgt gagcctgaac ctgatgcgcg acggcgtgac gcccagcgtg gcgctggaca  10260
tgaccgcgcg caacatggaa ccgggcatgt acgcctccca ccggccgttc atcaaccgcc  10320
tgatggacta cttgcatcgg gcggcggccg tgaaccccga gtacttcact aatgccattc  10380
tgaatcccca ctggatgccc cctccgggtt tctacaacgg ggactttgag gtgcccgagg  10440
tcaacgacgg gttcctctgg gatgacatgg atgacagtgt gttctcaccc aacccgctgc  10500
gcgccgcgtc tctgcgattg aaggagggct ctgacaggga aggaccgaga agtctggcct  10560
cctccctggc tctgggagcg gtgggcgcca cgggcgcggc ggcgcggggc agtagcccct  10620
tccccagcct ggcagactct ctgaacagcg ggcgggtgag caggccccgc ttgctaggcg  10680
aggaggagta tctgaacaac tccctgctgc agcccgcgag ggacaagaac gctcagcggc  10740
agcagtttcc caacaatggg atagagagcc tggtggacaa gatgtccaga tggaagacgt  10800
atgcgcagga gtacaaggag tgggaggacc gccagccgcg gcccttgccg ccccctaggc  10860
agcgctggca gcggcgcgcg tccaaccgcc gctggaggca ggggcccgag gacgatgatg  10920
actctgcaga tgacagcagc gtgttggacc tgggcgggag cgggaacccc ttttcgcacc  10980
tgcgcccacg cctgggcaag atgttttaaa agaaaaaaaa aaaataaaac tcaccaaggc  11040
catggcgacg agcgttggtt ttttgttccc ttccttagta tgcggcgcgc ggcgatgttc  11100
gaggaggggc ctcccccctc ttacgagagc gcgatgggga tttctcctgc ggcgcccctg  11160
cagcctccct acgtgcctcc tcggtacctg caacctacag gggggagaaa tagcatctgt  11220
tactctgagc tgcagcccct gtacgatacc accagactgt acctggtgga caacaagtcc  11280
gcggacgtgg cctccctgaa ctaccagaac gaccacagcg atttttttgac cacggtgatc  11340
caaaacaacg acttcacccc aaccgaggcc agcactcaga ccataaacct ggataacagg  11400
```

```
tcgaactggg gcggcgacct gaagaccatc ttgcacacca acatgcccaa cgtgaacgag  11460
ttcatgttca ccaactcttt taaggcgcgg gtgatggtgg cgcgcgagca gggggaggcg  11520
aagtacgagt gggtggactt cacgctgccc gagggcaact actcagagac catgactctc  11580
gacctgatga acaatgcgat cgtggaacac tatctgaaag tgggcaggca gaacggggtg  11640
aaggaaagcg atatcggggt caagtttgac accagaaact tccgtctggg ctgggacccc  11700
gtgaccgggc tggtcatgcc gggggtctac accaacgagg cctttcatcc cgacatagtg  11760
cttctgcccg gctgtggggt ggacttcacc cagagccggc tgagcaacct gctgggcatt  11820
cgcaagcggc agcctttcca ggagggtttc aagatcacct atgaggatct gaaggggggc  11880
aacattcccg cgctccttga tctggacgcc tacgaggaga gcttgaaacc cgaggagagc  11940
gctggcgaca gcggcgagag tggcgaggag caagccggcg gcggtggcgg cgcgtcggta  12000
gaaaacgaaa gtacgcccgc agtggcggcg gacgctgcgg aggtcgagcc ggaggccatg  12060
cagcaggacg cagaggaggg cgcacaggag ggcgcgcaga aggacatgaa cgatggggag  12120
atcaggggag acacattcgc cacccggggc gaagaaaaag aggcagaggc ggcggcggcg  12180
gcgacggcgg aggccgaaac cgaggttgag gcagaggcag agcccgagac cgaagttatg  12240
gaagacatga atgatggaga acgtaggggc gacacgttcg ccacccgggg cgaagagaag  12300
gcggcggagg cagaagccgc ggctgaggag gcggctgcgg ctgcggccaa gactgaggct  12360
gcggctaagg ctgaggtcga agccaatgtt gcggttgagg ctcaggctga ggaggaggcg  12420
gcggctgaag cagttaagga aaaggcccag gcagagcagg aagagaaaaa acctgtcatt  12480
caacctctaa aagaagatag caaaaagcgc agttacaacg tcatcgaggg cagcaccttt  12540
acccagtacc gcagctggta cctggcgtac aactacggcg acccggtcaa gggggtgcgc  12600
tcgtggaccc tgctctgcac gccggacgtc acctgcggct ccgagcagat gtactggtcg  12660
ctgccgaaca tgatgcaaga cccggtgacc ttccgctcca cgcggcaggt tagcaacttc  12720
ccggtggtgg gcgccgaact gctgcccgtg cactccaaga gtttttacaa cgagcaggcc  12780
gtctactccc agctgatccg ccaggccacc tctctgaccc acgtgttcaa tcgctttccc  12840
gagaaccaga ttttggcgcg cccgccggcc cccaccatca ccaccgtgag tgaaaacgtt  12900
cctgccctca cagatcacgg gacgctaccg ctgcgcaaca gcatctcagg agtccagcga  12960
gtgaccatta ctgacgccag acgccggacc tgcccctacg tttacaaggc cttgggcata  13020
gtctcgccgc gcgtcctctc cagtcgcact ttttaaaaca catctaccca cacgttccaa  13080
aatcatgtcc gtactcatct cacccagcaa caacaccggc tgggggctgc gcgcgcccag  13140
caagatgttt ggaggggcga ggaagcgctc cgaccagcac cctgtgcgcg tgcgcggcca  13200
ctaccgcgcg ccctggggag cgcacaagcg cgggcgcaca gggcgcacca ctgtggacga  13260
cgtcattgac tccgtagtgg agcaagcgcg ccactacaca cccggcgcgc cgaccgcccc  13320
cgccgtgtcc accgtggacc aggcgatcga aagcgtggta cagggcgcgc ggcactatgc  13380
caaccttaaa agtcgccgcc gccgcgtggc ccgccgccat cgccggagac cccgggccac  13440
cgccgccgcg cgccttacta aggctctgct caggcgcgcc aggcgaactg gccaccgggc  13500
cgccatgagg gccgcacggc gggctgccgc tgccgcaagc gccgtggccc cgcgggcacg  13560
aaggcgcgcg gccgccgccg ccgccgccgc catttccagc ttggcctcga cgcggcgcgg  13620
taacatatac tgggtgcgcg actcggtaac cggcacgcgg gtacccgtgc gctttcgccc  13680
cccgcggaat tagcacaaga caacatacac actgagtctc ctgctgttgt gtatcccagc  13740
```

-continued

```
ggcgaccgtc agcagcggcg acatgtccaa gcgcaaaatt aaagaagaga tgctccaggt  13800
catcgcgccg gagatctatg ggcccccgaa gaaggaggag gatgattaca agccccgcaa  13860
gctaaagcgg gtcaaaaaga aaaagaaaga tgatgatgat gacgaggcgg tggagtttgt  13920
ccgccgcatg gcacccaggc gccccgtgca gtggaagggc cggcgcgtgc agcgcgtttt  13980
gcgccccggc accgcggtgg tcttcacgcc cggcgagcgc tccacgcgca ctttcaagcg  14040
ggtgtacgat gaggtgtacg gcgacgagga cctgttggag caggccaacc agcgctttgg  14100
ggagtttgca tatgggaaac ggccccgcga gagtctaaaa gaggacctgc tggcgctacc  14160
gctggacgag ggcaatccca ccccgagtct gaagccggta accctgcaac aggtgctgcc  14220
tttgagcgcg cccagcgagc ataagcgagg gttgaagcgc gaaggcgggg acctggcgcc  14280
caccgtgcag ttgatggtgc ccaagcggca gaagctggag gacgtgctgg agaaaatgaa  14340
agtagagccc gggatccagc ccgagatcaa ggtccgcccc atcaagcagg tggcgcccgg  14400
cgtgggagtc cagaccgtgg acgttaggat tcccacggag gagatggaaa cccaaaccgc  14460
cactccctct tcggcggcca gcgccaccac cggcaccgct tcggtagagg tgcagacgga  14520
cccctggcta cccgccaccg ctgttgccgc cgccgccccc cgttcgcgcg ggcgcaagag  14580
aaattatcca gcggccagcg cgctcatgcc ccagtacgca ctgcatccat ccatcgcgcc  14640
cacccccggc taccgcgggt actcgtaccg cccgcgcaga tcagccggca ctcgcggccg  14700
ccgccgccgt gcgaccacaa ccagccgccg ccgtcgccgc cgccgccagc cagtgctgac  14760
ccccgtgtct gtaaggaagg tggctcgctc ggggagcacg ctggtggtgc ccagagcgcg  14820
ctaccacccc agcatcgttt aaagccggtc tctgtatggt tcttgcagat atggccctca  14880
cttgtcgcct ccgcttcccg gtgccgggat accgaggaag aactcaccgc cgcagaggca  14940
tggcgggcag cggtctccgc ggcggccgtc gccatcgccg gcgcgcaaaa agcaggcgca  15000
tgcgcggcgg tgtgctgcct ctgctaatcc cgctaatcgc cgcggcgatc ggtgccgtac  15060
ccgggatcgc ctccgtggcc ctgcaggcgt cccagaaacg ttgactcttg caaccttgca  15120
agcttgcatt ttttggagga aaaataaaaa aagtctagac tctcacgctc gcttggtcct  15180
gtgactattt tgtagaaaaa agatggaaga catcaacttt gcgtcgctgg ccccgcgtca  15240
cggctcgcgc ccgttcatgg gagactggac agatatcggc accagcaata tgagcggtgg  15300
cgccttcagc tggggcagtc tgtggagcgg ccttaaaaat tttggttcca ccattaagaa  15360
ctatggcaac aaagcgtgga acagcagcac gggccagatg ctgagagaca agttgaaaga  15420
gcagaacttc caggagaagg tggcgcaggg cctggcctct ggcatcagcg gggtggtgga  15480
catagctaac caggccgtgc agaaaaagat aaacagtcat ctggaccccc gtcctcaggt  15540
ggaggaaatg cctccagcga tggagacggt gtctcccgag ggcaaaggcg aaaagcgccc  15600
gcggcccgac agagaagaga ccctggtgtc acacaccgag gagccgccct cttacgagga  15660
ggcagtcaag gccggcctgc ccaccactcg ccccatagcc cccatggcca ccggtgtggt  15720
gggccacagg caacacactc ccgcaacact agatctgccc ccgccgtccg agccgccgcg  15780
ccagccaaag gcggcgacgg tgcccgctcc ctccacttcc gccgccaaca gagtgcccct  15840
gcgccgcgcc gcgagcggcc cccgggcctc gcgagttagc ggcaactggc agagcacact  15900
gaacagcatc gtgggcctgg gagtgaggag tgtgaagcgc cgccgttgct actgaatgag  15960
caagctagct aacgtgttgt atgtgtgtat gcgtcctatg tcgccgccag aggagctgtt  16020
gagccgccgg cgccgtctgc actccagcga atttcaagat ggcgacccca tcgatgatgc  16080
ctcagtggtc gtacatgcac atctcgggcc aggacgcttc ggagtacctg agccccgggc  16140
```

```
tggtgcagtt cgcccgcgcc acagacacct acttcaacat gagtaacaag ttcaggaacc  16200
ccactgtggc gcccacccac gatgtgacca cggaccggtc gcagcgcctg acgctgcggt  16260
tcatccccgt ggatcgggag gacaccgcct actcttacaa ggcgcggttc acgctggccg  16320
tgggcgacaa ccgcgtgctg gacatggcct ccacttactt tgacatcagg ggggtgctgg  16380
acaggggccc caccttcaag ccctactcgg gtactgccta caactccctg gcccccaagg  16440
gcgctcccaa ttcttgcgag tgggaacaag aggaaaatca ggtggtcgct gcagatgatg  16500
aacttgaaga tgaagaagcg caagctcaag aggacgcccc agctaaaaaa attcatgtat  16560
atgcccaggc gcctcttgct ggcgaaaaga ttaccaagga tggtttgcaa ataggtactg  16620
aagttgtagg agatacatct aaggacactt ttgcagacaa aacattccaa cccgaacctc  16680
agataggcga gtctcagtgg aacgaggctg atgccacagt agcaggaggc agagtcttga  16740
aaaaaaccac ccctatgaga ccttgctatg gatcctatgc caggcctaca aatgccaacg  16800
ggggtcaagg aattatggtt gccaatgaac aaggagtgtt ggagtctaaa gtggagatgc  16860
aattttttc taacactaca acccttaatg cgcgggatgg agctggcaat cccgaaccaa  16920
aggtggtgtt gtacagtgaa gatgtccact tggaatctcc tgacactcat ttgtcttaca  16980
agcccaaaaa ggatgatgtt aatgctaaaa ttatgttggg tcagcaagct atggctaaca  17040
ggcccaacct cattgctttt agagataatt tcattggact catgtactac aacagcactg  17100
gtaacatggg agtgctggcg ggtcaggcct ctcagttgaa tgccgtggtg gacctgcagg  17160
atagaaacac agaactgtca tatcagctta tgcttgattc cattggggat agatccagat  17220
acttctccat gtggaaccag gcagtggata gctatgaccc agatgtcaga atcattgaaa  17280
accatggtgt cgaggacgag ctacccaact actgcttccc tctgggcggc ataggaatta  17340
ctgatactta tcaagggatc aaaaatacca atggcaatgg tcagtggacc aaagatgatc  17400
agttcgcgga ccgtaatgaa ataggggtgg gaaacaactt cgccatggag atcaacatcc  17460
aggccaacct ctggaggaac ttcctctatg cgaacgtggg gctctacctg ccagacaagc  17520
tcaagtacaa ccccaccaac gtggacatct ctgacaaccc caacacctat gactacatga  17580
acaagcgtgt ggtggctccc ggcctggtgg actgctttgt caatgtggga gccaggtggt  17640
ccctggacta catggacaac gtcaacccct tcaaccacca ccgcaatgcg ggtctgcgct  17700
accgctccat gatcctgggc aacgggcgct acgtgccctt ccacattcag gtgccccaga  17760
agttctttgc catcaagaac ctcctcctcc tgccgggctc ctacacttac gagtggaact  17820
tcaggaagga tgtcaacatg gtcctgcaga gctctctggg caatgacctt agggtggacg  17880
gggccagcat caagtttgac agcgtcaccc tctatgctac cttcttcccc atggctcaca  17940
acaccgcctc cacgctcgag gccatgctga ggaacgacac caacgaccag tccttcaatg  18000
actacctctc tggggccaac atgctctacc ccatccccgc caaggccacc aacgtgccca  18060
tctccattcc ctctcgcaac tggccgcct tcagaggctg ggcctttacc cgccttaaga  18120
ccaaggaaac cccctccctg ggctcgggtt ttgaccccta ctttgtctac tcgggatcca  18180
tcccctacct ggatggcacc ttctacctca accacacttt taagaagata tccatcatgt  18240
atgactcctc cgtcagctgg ccgggcaatg accgcctgct cacccccaat gagttcgagg  18300
tcaagcgcgc cgtggacggc gagggctaca acgtggccca gtgcaacatg accaaggact  18360
ggttcctggt gcagatgctg gccaactaca acataggcta ccagggcttc tacatcccag  18420
agagctacaa ggacaggatg tactccttct tcagaaattt ccaacccatg agcaggcagg  18480
```

```
tggtggacga gaccaaatac aaggactatc aggccattgg catcactcac cagcacaaca  18540
actcgggatt cgtgggctac ctggctccca ccatgcgcga ggggcaggcc taccccgcca  18600
acttccccta cccgttgata ggcaagaccg cggtcgacag cgtcacccag aaaaagttcc  18660
tctgcgaccg caccctctgg cgcatcccct tctctagcaa cttcatgtcc atgggtgcgc  18720
tcacggacct gggccagaac ctgctctatg ccaactccgc ccatgcgctg gacatgactt  18780
ttgaggtgga ccccatggac gagcccaccc ttctctatat tgtgtttgaa gtgttcgacg  18840
tggtcagagt gcaccagccg caccgcggtg tcatcgagac cgtgtacctg cgcacgccct  18900
tctcggccgg caacgccacc acctaaggag acagcgccgc cgcctgcatg acgggttcca  18960
ccgagcaaga gctcagggcc atcgccagag acctgggatg cggaccctat tttttgggca  19020
cctatgacaa acgcttcccg ggcttcatct cccgagacaa gctcgcctgc gccatcgtca  19080
acacggccgc gcgcgagacc gggggcgtgc actggctggc ctttggctgg gacccgcgct  19140
ccaaaacctg ctacctcttc gacccctttg gcttctccga tcagcgcctc agacagatct  19200
atgagtttga gtacgagggg ctgctgcgcc gcagcgcgct tgcctcctcg cccgaccgct  19260
gcatcaccct tgagaagtcc accgagaccg tgcaggggcc ccactcggcc gcctgcggtc  19320
tcttctgctg catgtttttg cacgcctttg tgcgctggcc ccagagtccc atggatcgca  19380
accccaccat gaacttgctc aagggagtgc ccaacgccat gctccagagc cccccaggtcc 19440
agcccaccct gcgccacaac caggaacagc tctaccgctt cctggagcgc cactccccct  19500
acttccgcag tcacagcgcg cacatccggg gggccacctc tttctgccac ttgcaacaaa  19560
acatgcaaga cggaaaatga tgtacagctc gctttttaat aaatgtaaag actgtgcact  19620
ttatttatac acgggctctt tctggttatt tattcaacac cgccgtcgcc atctagaaat  19680
cgaaagggtt ctgccgcgcg tcgccgtgcg ccacgggcag agacacgttg cgatactgga  19740
agcggctcgc ccacttgaac tcgggcacca ccatgcgggg cagtggctcc tcggggaagt  19800
tctcgcccca cagggtgcgg gtcagctgca gcgcgctcag gaggtcggga gccgagatct  19860
tgaagtcgca gttggggccg gaaccctgcg cgcgcgagtt gcggtacacg gggttgcagc  19920
actggaacac cagcagggcc ggattacgca cgctggccag caggctctcg tcgctgatca  19980
tgtcgctgtc cagatcctcc gcgttgctca gggcgaatgg ggtcatcttg cagacctgcc  20040
tgcccaggaa aggcggcagc ccgggcttgc cgttgcagtc gcagcgcagg ggcatcagca  20100
ggtgcccgtg gcccgtctgc gcctgcgggt acagcgcgcg catgaaggct tcgatctgcc  20160
tgaaagccac ctgcgtcttg gctccctccg aaaagaacat cccacaggac ttgctggaga  20220
actggttcgc gggacagctg gcatcgtgca ggcagcagcg cgcgtcggtg ttggcgatct  20280
gcaccacgtt gcgaccccac cggttcttca ctatcttggc cttggaagcc tgctccttca  20340
gcgcgcgctg gccgttctcg ctggtcacat ccatctctat cacctgctcc ttgttgatca  20400
tgtttgtccc gtgcagacac ttcaggtcgc cctccgtctg ggtgcagcgg tgctcccaca  20460
gcgcgcaacc ggtgggctcc caatttttgt gggtcacccc cgcgtaggcc tgcaggtagg  20520
cctgcaagaa gcgccccatc atggccacaa aggtcttctg gctcgtaaag gtcagctgca  20580
ggccgcgatg ctcttcgttc agccaggtct tgcagatggc ggccagcgcc tcggtctgct  20640
cgggcagcat cctaaaattt gtcttcaggt cgttatccac gtggtacttg tccatcatgg  20700
cgcgcgccgc ctccatgccc ttctcccagg cggacaccat gggcaggctt agggggttta  20760
tcacttccac cggcgaggac accgtacttt cgatttcttc ttcctccccc tcttcccggc  20820
gcgcgcccac gctgctgcgc gctctcaccg cctgcaccaa ggggtcgtct tcaggcaagc  20880
```

```
gccgcaccga gcgcttgccg cccttgacct gcttaatcag caccggcggg ttgctgaagc  20940
ccaccatggt cagctccgcc tgctcttctt cgtcttcgct gtctaccact atctctgggg  21000
aagggcttct ccgctctgcg gcggtgcgct tcttttttt cttgggagca gccgtgacgg   21060
agtccgccac ggcgacggag gtcgagggcg tggggctggg ggtgcgcggt accagggcct  21120
cgtcgccctc ggactcttcc tctgactcca ggcggcggcg gagacgcttc tttgggggcg  21180
cgcgcgtcag cggcggcgga gacggggacg gggacgggga cgggacgccc tccacagggg  21240
gtggtcttcg cgcagacccg cggccgcgct cgggggtctt ttcgagctgg tcttggtccc  21300
gactggccat tgtatcctcc tcctcctagg cagagagaca taaggagtct atcatgcaag  21360
tcgagaagga ggagagctta accacccct ctgagaccgc cgatgcgccc gccgtcgccg   21420
tcgcccccgc tgccgccgac gcgcccgcca caccgagcga cacccccgcg gaccccccag  21480
ccgacgcacc cctgttcgag gaagcggccg tggagcagga cccgggcttt gtctcggcag  21540
aggaggattt gcgagaggag gaggataagg agaagaagcc ctcagtgcca aaagatgata  21600
aagagcaaga cgagcacgac gcagatgcac accagggtga agtcgggcgg ggggacggag  21660
ggcatgacgg cgccgactac ctagacgaag ggaacgacgt gctcttgaag cacctgcatc  21720
gtcagtgcgc catcgtttgc gacgctctgc aggagcgcag cgaagtgccc ctcagcgtgg  21780
cggaggtcag ccacgcctac gagctcagcc tcttctcccc ccgggtgccc ccccgccgcc  21840
gcgaaaacgg cacatgcgag cccaacccgc gcctcaactt ctaccccgcc tttgtggtgc  21900
ccgaggtcct ggccacctat cacatcttct ttcaaaattg caagatcccc ctctcgtgcc  21960
gcgccaaccg tagccgcgcc gataagatgc tggccctgcg ccagggcgac cacatacctg  22020
atatcgccgc tttggaagat gtgccaaaga tcttcgaggg tctgggtcgc aacgagaagc  22080
gggcagcaaa ctctctgcaa caggaaaaca gcgaaaatga gagtcacacc ggggtactgg  22140
tggagctcga gggcgacaac gcccgcctgg cggtggtcaa gcgcagcatc gaggtcaccc  22200
actttgccta ccccgcgctc aacctgcccc ccaaagtcat gaacgcggcc atggacgggc  22260
tgatcatgcg ccgcggccgg cccctcgctc cagatgcaaa cttgcatgag gagaccgagg  22320
acggccagcc cgtggtcagc gacgagcagc tggcgcgctg gctggagacc gcggaccccg  22380
ccgaactgga ggagcggcgc aagatgatga tggccgcggt gctggtcacc gtagagctgg  22440
agtgtctgca gcgcttcttc ggcgaccccg agatgcagag aaaggtcgag gagaccctgc  22500
actacacctt ccgccagggc tacgtgcgcc aggcttgcaa gatctccaac gtggagctca  22560
gcaacctggt gtcctacctg ggcatcttgc atgagaaccg cctcgggcag agcgtgctgc  22620
actccaccct gcgcggggag gcgcgccgcg actacgtgcg cgactgcgtt tacctcttcc  22680
tctgctacac ctggcagacg gccatggggg tctggcagca gtgcctggag gagcgcaacc  22740
tcaaggagct ggagaagctc ctgcagcgcg cgctcaaaga cctctggacg ggctacaacg  22800
agcgctcggt ggccgccgcg ctggccgacc tcatcttccc cgagcgcctg ctcaaaaccc  22860
tccagcaggg gctgcccgac ttcaccagcc aaagcatgtt gcaaaacttc aggaacttta  22920
tcctggagcg ttctggcatc ctacccgcca cctgctgcgc cctgcccagc gactttgtcc  22980
ccctcgtgta ccgcgagtgc cccccgccgc tgtggggtca ctgctacctg ttccaactgg  23040
ccaactacct gtcctaccac gcggacctca tggaggactc cagcggcgag gggctcatgg  23100
agtgccactg ccgctgcaac ctctgcacgc ccaccgctc cctggtctgc aacacccaac   23160
tgctcagcga gagtcagatt atcggtacct tcgagctaca gggtccgtcc tcctcagacg  23220
```

```
agaagtccgc ggctccgggg ctaaaactca ctccggggct gtggacttcc gcctacctgc  23280
gcaaatttgt acctgaagac taccacgccc acgagatcag gttttacgaa gaccaatccc  23340
gcccgcccaa ggcggagctg accgcctgcg tcatcaccca gggcgagatc ctaggccaat  23400
tgcaagccat ccaaaaagcc cgccaagatt ttttgctgag aaagggtcgg ggggtgtatc  23460
tggaccccca gtcgggtgag gagctcaacc cggttccccc gctgccgccg ccgcgggacc  23520
ttgcttccca ggataagcat cgccatggct cccagaaaga agcagcagcg gccgccactg  23580
ccgccacccc acatgctgga ggaagaggag gaatactggg acagtcaggc agaggaggtt  23640
tcggacgagg aggagccgga gacggagatg gaagagtggg aggaggacag cttagacgag  23700
gaggcttccg aagccgaaga ggcagacgca acaccgtcac cctcggccgc agccccctcg  23760
caggcgcccc cgaagtccgc tcccagcatc agcagcaaca gcagcgctat aacctccgct  23820
cctccaccgc cgcgacccac ggccgaccgc agacccaacc gtagatggga caccaccgga  23880
accggggccg gtaagtcctc cgggagaggc aagcaagcgc agcgccaagg ctaccgctcg  23940
tggcgcgctc acaagaacgc catagtcgct tgcttgcaag actgcggggg gaacatctcc  24000
ttcgcccgcc gcttcctgct cttccaccac ggtgtggcct tcccccgtaa cgtcctgcat  24060
tactaccgtc atctctacag cccctactgc ggcggcagtg agccagagac ggtcggcggc  24120
ggcggcggcg cccgtttcgg cgcctaggaa gacccagggc aagacttcag ccaagaaact  24180
cgcggcggcc gcggcgaacg cggtcgcggg ggccctgcgc ctgacggtga acgaacccct  24240
gtcgacccgc gaactgagaa accgaatctt ccccactctc tatgccatct tccagcagag  24300
cagagggcag gatcaggaac tgaaagtaaa aaacaggtct ctgcgctccc tcacccgcag  24360
ctgtctgtat cacaagagcg aagaccagct tcggcgcacg ctggaggacg ctgaggcact  24420
cttcagcaaa tactgcgcgc tcactcttaa ggactagctc cgcgcccttc tcgaatttag  24480
gcgggaacgc ctacgtcatc gcagcgccgc cgtcatgagc aaggacattc ccacgccata  24540
catgtggagc tatcagccgc agatgggact cgcggcgggc gcctcccaag actactccac  24600
ccgcatgaac tggctcagtg ccggcccaca catgatctca caggttaatg atatccgcac  24660
ccatcgaaac caaatattgg tggagcaggc ggcaattacc accacgcccc gcaataatcc  24720
caaccccagg gagtggcccg cgtccctggt gtatcaggaa attcccggcc ccaccaccgt  24780
actacttccg cgtgattccc aggccgaagt ccaaatgact aactcagggg cgcagctcgc  24840
gggcggctgt cgtcacaggg tgcggcctcc tcgccagggt ataactcacc tggagatccg  24900
aggcagaggt attcagctca acgacgagtc ggtgagctcc tcgctcggtc taagacctga  24960
cgggaccttc cagatagccg gagccggccg atcttccttc acgccccgcc aggcgtacct  25020
gactctgcag agctcgtcct cggcgccgcg ctcgggcggc atcgggactc tccagttcgt  25080
gcaggagttt gtgccctcgg tctacttcaa ccccttctcg ggctctcccg gtcgctaccc  25140
ggaccagttc atctcgaact ttgacgccgc gagggactcg gtggacggct acgactgaat  25200
gtcgggtgga cccggtgcag agcaacttcg cctgaagcac ctcgaccact gccgccgccc  25260
tcagtgcttt gcccgctgtc agaccggtga gttccagtac ttttccctgc ccgactcgca  25320
cccggacggc ccggcgcacg gggtgcgctt tttcatcccg agtcaggtgc gctctaccct  25380
aatcagggag tttaccgccc gtcccctact ggcggagttg gaaaaggggc cttctatcct  25440
aaccattgcc tgcatctgct ctaaccctgg attgcaccaa gatctttgct gtcatttgtg  25500
tgctgagtat aataaaggct gagatcagaa tctactcggg ctcctgtcgc catcctgtca  25560
acgccaccgt ccaagcccgg cccgatcagc ccgaggtgaa cctcacctgc ggtctgcacc  25620
```

```
ggcgcctgag gaaataccta gcttggtact acaacagcac tccctttgtg gtttacaaca  25680
gctttgacca ggacggggtc tcactgaggg ataacctctc gaacctgagc tactccatca  25740
ggaagaacag caccctcgag ctacttcctc cttacctgcc cgggacttac cagtgtgtca  25800
ccggtccctg cacccacacc cacctgttga tcgtaaacga ctctcttccg agaacagacc  25860
tcaataactc ctcttcgcag ttccccagaa caggaggtga gctcaggaaa ccccgggtaa  25920
agaagggtgg acaagagtta acacttgtgg ggtttctggt gtatgtgacg ctggtggtgg  25980
ctcttttgat taaggctttt ccttccatgt ctgaactctc cctcttttat gaacaactcg  26040
actagtgcta acgggaccct acccaacgaa tcgggattga atatcggtaa ccaggttgca  26100
gtttcacttt tgattacctt catagtcctc ttcctgctag tgctgtcgct tctgtgcctg  26160
cggatcgggg gctgctgcat ccacgtttat atctggtgct ggctgtttag aaggttcgga  26220
gaccatcgca ggtagaataa acatgctgct gcttaccctc tttgtcctgg cgctggccgc  26280
cagctgccaa gccttttccg aggctgactt tatagagccc cagtgtaacg tgacttttaa  26340
agcccatgca cagcgttgtc atactataat caaatgtgcc accgaacacg atgaatacct  26400
tatccagtat aaagataaat cacacaaagt ggcacttgtt gacatctgga aacccgaaga  26460
ccctttggaa tacaatgtga ccgttttcca gggtgacctc ttcaaaattt acaattacac  26520
tttcccattt gaccagatgt gtgactttgt catgtacatg gaaaagcagc acaagctgtg  26580
gcctccgact ccccagggct gtgtggaaaa tccaggctct ttctgcatga tctctctctg  26640
tgtaactgtg ctggcactaa tactcacgct tttgtatatc agatttaaat caaggcaaag  26700
cttcatcgat gaaaagaaaa tgccttaaac gctttcacgc ttgattgcta acaccgggtt  26760
tttatccgca gaatgattgg aatcacccta ctaatcacct ccctccttgc gattgcccat  26820
gggttggaac gaatcgaagc ccctgtgggg gccaatgtta ccctggtggg gcctgtcggc  26880
aatgctacat taatgtggga aaaatatact aaaaatcaat gggtctctta ctgcactaac  26940
aaaaacagcc acaagcccag agccatctgc gatgggcaaa atctaacctt gattgatgtt  27000
caaatgctgg atgcgggcta ctattatggg cagctgggta caatgattaa ttactggaga  27060
ccccacaaag attacatgct ccacgtagta aagggtcccc ttagcagccc acccactacc  27120
acctctacta cccccactac caccactact cccaccacca gcactgccgc ccagcctcct  27180
catagcagaa caaccacttt tatcaattcc aagtcccact ccccccacat tgccggcggg  27240
ccctccgcct cagactccga gaccaccgag atctgcttct gcaaatgctc tgacgccttt  27300
gctgaggatt tggaagacca cgaggaagat gagcatgact tcgcagatgc atgccaggca  27360
tcagaggcag aagcgctgcc ggtggccctc aaacagtatg cagaccccca caccaccccc  27420
aaccttcctc caccttccca gaagccaagt ttcctggggg aaaatgaaac tctgcctctc  27480
tccatactcg ctctgacatc tgttgctatg ttgaccgctc tgctggtgct tctatgctct  27540
atatgctacc tgatctgctg cagaaagaaa aaatctcacg gccatgctca ccagcccctc  27600
atgcacttcc cttaccctcc agagctgggc gaccacaaac tttaagtctg cagtaactat  27660
ctgcccatcc cttgtcagtc gacagcgatg agccccacta atctaacggc ctctggactt  27720
acaacatcgt ctcttaatga gaccaccgct cctcaagacc tgtacgatgg tgtctccgcg  27780
ctggttaacc agtgggatca cctgggcata tggtggctcc tcataggagc agtgaccctg  27840
tgcctaatcc tggtctggat catctgctgc atcaaaagca gaagacccag gcggcggccc  27900
atctacaggc cctttgtcat cacacctgaa gatgatgatg acaccacttc caggctgcag  27960
```

```
aggctaaagc agctactctt ctcttttaca gcatggtaaa ttgaatcatg cctcgcattt  28020
tcatctactt gtctctcctt ccactttttc tgggctcttc tacattggcc gctgtgtccc  28080
acatcgaggt agactgcctc acgcccttca cagtctacct gcttttcggc tttgtcatct  28140
gcacctttgt ctgcagcgtt atcactgtag tgatctgctt catacagtgc atcgactacg  28200
tctgcgtgcg ggtggcttac tttagacacc acccccagta tcgcaacagg gacatagcgg  28260
ctctcctaag acttgtttaa aatcatggcc aaattaactg tgattggtct tctgatcatc  28320
tgctgcgtcc tagccgcgat tgggactcaa gctcctacca ccaccagcgc tcccagaaag  28380
agacatgtat cctgcagctt caagcgtccc tggaatatac cccaatgctt tactgatgaa  28440
cctgaaatct ctttggcttg gtacttcagc gtcaccgccc ttcttatctt ctgcagtacg  28500
gttattgccc ttgccatcta cccttccctt gacctgggct ggaatgctgt caactctatg  28560
gaatatccca ccttcccaga accagacctg ccagacctgg ttgttctaaa cgcgtttcct  28620
cctcctgctc ccgttcaaaa tcagtttcgc cctccgtccc ccacgcccac tgaggtcagc  28680
tactttaatc taacaggcgg agatgactga aaacctagac ctagaaatgg acggtctctg  28740
cagcgagcaa cgcacactag agaggcgccg gcaaaaagag ctcgagcgtc ttaaacaaga  28800
gctccaagac gcggtggcca tacaccagtg caaaaaaggt gtcttctgtc tggtaaaaca  28860
ggccacgctc acctatgaaa aaacaggtga cacccaccgc ctaggataca agctgcccac  28920
acagcgccag aagttcgccc tcatgatagg cgaacaaccc atcaccgtga cccagcactc  28980
cgtggagaca gaaggctgca tacacgctcc ctgtaggggc gctgactgcc tctacacctt  29040
gatcaaaacc ctctgcggtc tcagagacct catccctttt aattaatcat aactgtaatc  29100
aataaaaaat cacttacttg aaatctgata gcaagcctct gtccaatttt ttcagcaaca  29160
cttccttccc ctcctcccaa ctctggtact ctaggcgcct cctagctgca aacttcctcc  29220
acagtctgaa gggaatgtca gattcctcct cctgtccctc cgcacccacg atcttcatgt  29280
tgttgcagat gaaacgcgcg agatcgtctg acgagacctt caaccccgtg tacccctacg  29340
ataccgagat cgctccgact tctgtccctt tccttacccc tccctttgtg tcatccgcag  29400
gaatgcaaga aaatccagct ggggtgctgt ccctgcactt gtcagagccc cttaccaccc  29460
acaatggggc cctgactcta aaaatggggg gcggcctgac cctggacaag gaagggaatc  29520
tcacttccca aaacatcacc agtgtcgatc cccctctcaa aaaaagcaag aacaacatca  29580
gccttcagac cgccgcaccc ctcgccgtca gctccggggc cctaacactt tttgccactc  29640
ccccccctagc ggtcagtggt gacaacctta ctgtgcagtc tcaggcccct ctcactttgg  29700
aagactcaaa actaactctg gccaccaaag gacccctaac tgtgtccgaa ggcaaacttg  29760
tcctagaaac agaggctccc ctgcatgcaa gtgacagcag cagcctgggc cttagcgtta  29820
cggccccact tagcattaac aatgacagcc taggactaga catgcaagcg cccattagct  29880
ctcgagatgg aaaactggct ctaacagtgg cggccccct aactgtggtc gagggtatca  29940
atgctttggc agtagccaca ggtaagggta ttgggctaaa tgaaaccaac acacacctgc  30000
aggcaaaact ggtcgcaccc ctaggctttg ataccaacgg caacattaag ctaagcgttg  30060
caggaggcat gaggctaaac aataacacac tgatactaga tgtaaactac ccatttgagg  30120
ctcaaggcca actgagccta agagtgggct cgggcccact atatgtagat tctagtagtc  30180
ataacctaac cattagatgc cttaggggat tgtatataac atcttctaac aaccaaaacg  30240
gtctagaagc caacattaaa ctaacaagag gccttgtgta tgacggaaat gccatagcag  30300
ttaatgttgg caaagggctg gaatacagcc ctactgacac aacagaaaaa cctatacaga  30360
```

```
ctaaaatagg tctaggcatg gagtatgata ccgagggagc catgatgaca aaactaggct  30420
ctggactaag ctttgacaat tcaggagcca ttgtagtggg aaacaaaaat gatgacaggc  30480
ttactttgtg gaccacaccg gacccatcgc ccaactgtca gatctactct gaaaaagatg  30540
ctaaactaac cttggtactg actaaatgtg gcagtcaggt tgtaggcaca gtatctattg  30600
ccgctcttaa aggtagcctc gtgccaatca ctagtgcaat cagtgtggtt caggtatacc  30660
taaggtttga tgaaaatggg gtactaatga gtaactcttc acttaatggc gaatactgga  30720
attttagaaa cggagactca actaatggca caccatatac aaacgcagtg ggtttcatgc  30780
ctaatctact ggcctatcct aaaggtcaaa ctacaactgc aaaaagtaac attgtcagcc  30840
aggtctacat gaatggggac gatactaaac ccatgacatt tacaatcaac ttcaatggcc  30900
ttagtgaaac aggggatacc cctgttagta aatattccat gacattctca tggaggtggc  30960
caaatggaag ctacataggg cacaattttg taacaaactc ctttaccttc tcctacatcg  31020
cccaagaata aagaaagcac agagatgctt gtttttgatt tcaaaattgt gtgcttttat  31080
ttattttcag cttacagtat ttccagtagt cattcaaata aagcttaatc aaactgcatg  31140
agaacccttc cacatagctt aaattagcac cagtgcaaat ggagaaaaca attgacggcc  31200
gggatcggtg atcaccgatc cagacatgat aagatacatt gatgagtttg gacaaaccac  31260
aactagaatg cagtgaaaaa aatgctttat ttgtgaaatt tgtgatgcta ttgctttatt  31320
tgtaaccatt ataagctgca ataaacaagt tcccggatcg cgatccggcc cgaggctgta  31380
gccgacgatg gtgcgccagg agagttgttg attcattgtt tgcctccctg ctgcggtttt  31440
tcaccgaagt tcatgccagt ccagcgtttt tgcagcagaa aagccgccga cttcggtttg  31500
cggtcgcgag tgaagatccc tttcttgtta ccgccaacgc gcaatatgcc ttgcgaggtc  31560
gcaaaatcgg cgaaattcca tacctgttca ccgacgacgg cgctgacgcg atcaaagacg  31620
cggtgataca tatccagcca tgcacactga tactcttcac tccacatgtc ggtgtacatt  31680
gagtgcagcc cggctaacgt atccacgccg tattcggtga tgataatcgg ctgatgcagt  31740
ttctcctgcc aggccagaag ttcttttttcc agtaccttct ctgccgtttc caaatcgccg  31800
ctttggacat accatccgta ataacggttc aggcacagca catcaaagag atcgctgatg  31860
gtatcggtgt gagcgtcgca gaacattaca ttgacgcagg tgatcggacg cgtcgggtcg  31920
agtttacgcg ttgcttccgc cagtggcgcg aaatattccc gtgcaccttg cggacgggta  31980
tccggttcgt tggcaatact ccacatcacc acgcttgggt ggtttttgtc acgcgctatc  32040
agctctttaa tcgcctgtaa gtgcgcttgc tgagtttccc cgttgactgc ctcttcgctg  32100
tacagttctt tcggcttgtt gcccgcttcg aaaccaatgc ctaaagagag gttaaagccg  32160
acagcagcag tttcatcaat caccacgatg ccatgttcat ctgcccagtc gagcatctct  32220
tcagcgtaag ggtaatgcga ggtacggtag gagttggccc caatccagtc cattaatgcg  32280
tggtcgtgca ccatcagcac gttatcgaat cctttgccac gcaagtccgc atcttcatga  32340
cgaccaaagc cagtaaagta gaacggtttg tggttaatca ggaactgttc gcccttcact  32400
gccactgacc ggatgccgac gcgaagcggg tagatatcac actctgtctg gcttttggct  32460
gtgacgcaca gttcatagag ataaccttca cccggttgcc agaggtgcgg attcaccact  32520
tgcaaagtcc cgctagtgcc ttgtccagtt gcaaccacct gttgatccgc atcacgcagt  32580
tcaacgctga catcaccatt ggccaccacc tgccagtcaa cagacgcgtg gttacagtct  32640
tgcgcgacat gcgtcaccac ggtgatatcg tccacccagg tgttcggcgt ggtgtagagc  32700
```

```
attacgctgc gatggattcc ggcatagtta aagaaatcat ggaagtaaga ctgctttttc  32760
ttgccgtttt cgtcggtaat caccattccc ggcgggatag tctgccagtt cagttcgttg  32820
ttcacacaaa cggtgatacg tacacttttc ccggcaataa catacggcgt gacatcggct  32880
tcaaatggcg tatagccgcc ctgatgctcc atcacttcct gattattgac ccacactttg  32940
ccgtaatgag tgaccgcatc gaaacgcagc acgatacgct ggcctgccca acctttcggt  33000
ataaagactt cgcgctgata ccagacgttg cccgcataat tacgaatatc tgcatcggcg  33060
aactgatcgt taaaactgcc tggcacagca attgcccggc tttcttgtaa cgcgctttcc  33120
caccaacgct gatcaattcc acagttttcg cgatccagac tgaatgccca caggccgtcg  33180
agtttttga tttcacgggt tggggtttct acaggacgga ccatgcgttc gacctttctc  33240
ttcttttttg ggcccatgat ggcagatccg tatagtgagt cgtattagct ggttctttcc  33300
gcctcagaag ccatagagcc caccgcatcc ccagcatgcc tgctattgtc ttcccaatcc  33360
tcccccttgc tgtcctgccc caccccaccc cccagaatag aatgacacct actcagacaa  33420
tgcgatgcaa tttcctcatt ttattaggaa aggacagtgg gagtggcacc ttccagggtc  33480
aaggaaggca cgggggaggg gcaaacaaca gatggctggc aactagaagg cacagtcgag  33540
gctgatcagc gagctctaga tgcatgctcg agcggccgcc agtgtgatgg atatctgcag  33600
aattccagca cactggcggc cgttactagt ggatccgagc tcggtaccaa cgcgtcgtaa  33660
ctataacggt cctaaggtag cgaaaagcac tctcacagca ccagcactaa tcagagtgtg  33720
aagagggcca agtgccgaac gagtatatat aggaataaaa aatgacgtaa atgtgtaaag  33780
gtcagaaaac gcccagaaaa atacacagac caacgcccga aacgaaaacc cgcgaaaaaa  33840
tacccagaac ttcctcaaca accgccactt ccgctttctc acggtacgtc acttccgcaa  33900
gaaaagcaaa actacatttc ccacatgtgt aaaaacgaaa ccccgcccct tgtaaccgcc  33960
cacaacttac atcatcaaaa cgtaaactcc tacgtcaccc gccccgcctc tccccgccca  34020
cctcattatc atattggcca caatccaaaa taaggtatat tattgatgat g           34071
```

<210> SEQ ID NO 27
<211> LENGTH: 33489
<212> TYPE: DNA
<213> ORGANISM: Gorilla beringei graueri

<400> SEQUENCE: 27

```
catcatcaat aatatacctt attttggatt gtggccaata tgataatgag gtgggcgggg     60
agaggcgggg cgggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca attttcgcgc gcttttcacc ggatatcgta    240
gtaattttgg gcgggaccat gtaagatttg gccattttcg cgcgaaaagt gaaacgggga    300
agtgaaaact gaataatagg gcgttagtca tagtgcgtaa tatttaccga gggccgaggg    360
actttgaccg attacgtgga ggactcgccc aggtgttttt tacgtgaatt tccgcgttcc    420
gggtcaaagt ctccgtttta ttgtcaccgt catttgacgc ttaggcctga ccatctggtg    480
ctggcctgca ccagggccga gtttgggtct agcgatgagg ataccgattg aggtgggtaa    540
ggtgggcgtg gctagaaggg tggggcgtgt ataaattggg ggtctaaggg tctctctgtt    600
ttgtcttgca acagccgccg ccatgagcga caccggcaac agctttgatg gaagcatctt    660
tagcccctat ctgacagtgc gcatgcctca ctgggctgga gtgcgtcaga atgtgatggg    720
ttccaacgtg gatggacgcc ccgttctgcc ttcaaattcg tctacaatgg cctacgcgac    780
```

```
cgtgggagga actccgctgg acgccgcgac ctccgccgcc gcctccgccg ccgccgcgac    840
cgcgcgcagc atggctacgg acctttacag ctctttggtg gcgagcggcg cggcctctcg    900
cgcgtctgct cgggatgaga aactgaccgc tctgctgctt aaactggaag acttgacccg    960
ggagctggct caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcgggggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtacac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacaaa tcgggggcgg agggtcccgg actgggggat gatggtgccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagtctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aaggggtgcg   2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtctccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc accctttcat cttcactctc ttccgcatcg ctgtctgcga   3060
gagccagctg ctggggtaag tattccctct cgaaggcggg catgacctca gcgctcaggt   3120
```

```
tgtcagtttc taaaaatgag gaggatttga tgttcacctg tccggaggtg ataccttga    3180

gggtacctgg gtccatctgg tcagaaaaca ctattttttt gttgtcaagc ttggtggcga   3240

acgacccgta gagggcgttg gagagcagct tggcgatgga gcgcagggtc tggtttttgt   3300

cgcggtcggc tcgctccttg gccgcgatgt tgagttgcac gtactcgcgg gccacgcact   3360

tccactcggg gaagacggtg gtgcgctcgt ctgggatcag gcgcaccctc cagcctcggt   3420

tgtgcagggt gaccatgtcg acgctggtgg cgacctcgcc gcgcaggcgc tcgttggtcc   3480

agcagaggcg gccgcccttg cgcgagcaga aggggggtag ggggtccagc tggtcctcgt   3540

ttgggggggtc cgcgtcgatg gtgaagaccc cggggagcaa gcgcgggtca aagtagtcga  3600

tcttgcaagc ttgcatgtcc agagcccgct gccattcgcg ggcggcgagc gcgcgctcgt   3660

aggggttgag ggcgggcccc cagggcatgg ggtgggtgag cgcggaggcg tacatgccgc   3720

agatgtcata cacgtacagg ggttccctga ggatgccgag gtaggtgggg tagcagcgcc   3780

ccccgcggat gctggcgcgc acgtagtcat agagctcgtg ggagggggcc agcatgttgg   3840

gcccgaggtt ggtgcgctgg gggcgctcgg cgcggaaggc gatctgcctg aagatggcat   3900

gggagttgga ggagatggtg ggccgctgga agacgttgaa gcttgcttct tgcaagccca   3960

ccgagtccct gacgaagcag gcgtaggact cgcgcagctt gtgcaccagc tcggcggtga   4020

cctggacgtc gagcgcgcag tagtcgaggg tctcgcggat gatgtcatac ttatcctccc   4080

ccttcttttt ccacagctcg cggttgagga cgaactcttc gcggtctttc cagtactctt   4140

ggagggggaaa cccgtccgtg tccgaacggt aagagcctag catgtagaac tggttgacgg  4200

cctggtaggg gcaacagccc ttctccacgg gcagcgcgta ggcctgcgcc gccttgcgga   4260

gggaggtgtg ggtgagggcg aaagtgtccc tgaccatgac tttgaggtat tgatgtttga   4320

agtctgtgtc atcgcagccg ccctgttccc acagggtgta gtccgtgcgc tttttggagc   4380

gcgggttggg cagggagaag gtgaggtcat tgaagaggat cttccccgct cgaggcatga   4440

agtttctggt gatgcgaaag ggccctggga ccgaggagcg gttgttgatg acctgggcgg   4500

ccaggacgat ctcgtcaaag ccgtttatgt tgtggcccac gatgtagagc tccaaaaagc   4560

ggggctggcc cttgatggag ggagcttttt tgagttcctc gtaggtgagc tcctcgggcg   4620

attccaggcc gtgctcctcc agggcccagt cttgcaagtg agggttggcc gccaggaagg   4680

atcgccagag gtcgcgggcc atgagggtct gcaggcggtc gcggaaggtt ctgaactgtc   4740

gccccacggc catcttttcg gggtgatgc agtagaaggt gagggggtct ttctcccagg    4800

ggtcccatct gagctctcgg gcgaggtcgc gcgcggcggc gaccagagcc tcgttgcccc   4860

ccagtttcat gaccagcatg aagggcacga gctgcttgcc aaaggctccc atccaagtgt   4920

aggtctctac atcgtaggtg acaaagaggc gctccgtgcg aggatgagag ccgatcggga   4980

agaactggat ctcccgccac cagttggagg attggctgtt gatgtggtga aagtagaagt   5040

cccgtctgcg ggccgagcac tcgtgctggc ttttgtaaaa gcgaccgcag tactggcagc   5100

gctgcacggg ttgtatatct tgcacgaggt gaacctggcg acctctgacg aggaagcgca   5160

gcgggaatct aagtcccccg cctggggtcc cgtgtggctg gtggtcttct actttggttg   5220

tctggccgcc agcatctgtc tcctggaggg cgatggtgga gcagaccacc acgccgcgag   5280

agccgcaggt ccagatctcg gcgctcggcg ggcggagttt gatgacgaca tcgcgcacat   5340

tggagctgtc catggtctcc agctcccgcg gcggcaggtc agctgggagt tcctggaggt   5400

tcacctcgca gagacgggtc aaggcgcggg cagtgttgag atggtatctg atttcaaggg   5460

gcgtgttggc ggcggagtcg atggcttgca ggaggccgca gccccggggg gccacgatgg   5520
```

```
ttccccgcgg ggcgcgaggg gaggcggaag ctgggggtgt gttcagaagc ggtgacgcgg   5580
gcgggccccc ggaggtaggg ggggttccgg ccccacaggc atgggcggca ggggcacgtc   5640
ttcgccgcgc gcgggcaggg gctggtgctg gctccgaaga gcgcttgcgt gcgcgacgac   5700
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgcg agaaggcgtt gagcccgccc tcgttccaga cccggctgta   6000
gaccacgccc ccctcggcgt tgcgggcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
ggagttgcga gcggacacgg tcaactcctc ctccagaaga cggatgagct cggcgacagt   6300
gtcgcgcacc tcgcgctcga aggccacggg gggcgcttct tcctcttcca cctcttcttc   6360
catgatcgct tcttcttctt cctcagccgg gacgggaggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcgg gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggttttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacggtcgag agccctttg ctttcttggc caagcgcccg   7740
tggcgcgatc tgggatagat ggtcgcgatg agaggacaaa agcggctcgc ttccgtagtc   7800
tggagaaaca atcgccaggg ttgcgttgcg gcgtaccccg gttcgagccc ctatggcggc   7860
```

```
ttgaatcggc cggaaccgcg gctaacgagg gccgtggcag ccccgtcctc aggaccccgc   7920
cagccgactt ctccagttac gggagcgagc cccttttgtt ttttattttt tagatgcatc   7980
ccgtgctgcg gcagatgcgc ccctcgcccc ggcccgatca gcagcagcaa cagcaggcat   8040
gcagaccccc ctctcccctt tccgccccgg tcaccacggc cgcggcggcc gtgtcgggcg   8100
cggggggcgc gctggagtca gatgagccac cgcggcggcg acctaggcag tatctggact   8160
tggaagaggg cgagggactg gcgcggctgg gggcgaactc tccagagcgc cacccgcggg   8220
tgcagttgaa aagggacgcg cgcgaggcgt acctgccgcg gcagaacctg tttcgcgacc   8280
gcgggggcga ggagcccgag gagatgcgag actgcaggtt ccaagcgggg cgcgagctgc   8340
ggcgcgggct ggacagacag cgcctgctgc gcgaggagga ctttgagccc gacacgcaga   8400
cgggcatcag ccccgcgcgc gcgcacgtag ccgcggccga cctggtgacc gcctacgagc   8460
agacggtgaa ccaggagcgc aacttccaaa agagcttcaa caaccacgtg cgcacgctgg   8520
tggcgcgcga ggaggtgacc ctgggtctca tgcatctgtg ggacctggtg gaggcgatcg   8580
tgcagaaccc cagcagcaag cccctgaccg cgcagctgtt cctggtggtg cagcacagca   8640
gggacaacga ggccttcagg gaggcgctgc tgaacatcac cgagccggag gggcgctggc   8700
tcctggacct gataaacatc ctgcagagca tagtggtgca ggagcgcagc ctgagcctgg   8760
ccgagaaggt ggcggccatc aactactcta tgctgagcct gggcaagttc tacgcccgca   8820
agatctacaa gacccoctac gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg ccccoctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taacccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
```

```
gacatgaccg cgcgcaacat ggaaccgggc atgtacgcct cccaccggcc gttcatcaac  10320
cgcctgatgg actacttgca tcgggcggcg gccgtgaacc ccgagtactt cactaatgcc  10380
attctgaatc cccactggat gccccctccg ggtttctaca acggggactt tgaggtgccc  10440
gaggtcaacg acgggttcct ctgggatgac atggatgaca gtgtgttctc acccaacccg  10500
ctgcgcgccg cgtctctgcg attgaaggag ggctctgaca gggaaggacc gagaagtctg  10560
gcctcctccc tggctctggg agcggtgggc gccacgggcg cggcggcgcg gggcagtagc  10620
cccttcccca gcctggcaga ctctctgaac agcgggcggg tgagcaggcc ccgcttgcta  10680
ggcgaggagg agtatctgaa caactccctg ctgcagcccg cgagggacaa gaacgctcag  10740
cggcagcagt ttcccaacaa tgggatagag agcctggtgg acaagatgtc cagatggaag  10800
acgtatgcgc aggagtacaa ggagtgggag gaccgccagc cgcggccctt gccgcccccct  10860
aggcagcgct ggcagcggcg cgcgtccaac cgccgctgga ggcaggggcc cgaggacgat  10920
gatgactctg cagatgacag cagcgtgttg gacctgggcg ggagcgggaa cccctttttcg  10980
cacctgcgcc cacgcctggg caagatgttt taaaagaaaa aaaaaaaata aaactcacca  11040
aggccatggc gacgagcgtt ggtttttttgt tcccttcctt agtatgcggc gcgcggcgat  11100
gttcgaggag ggcctccccc cctcttacga gagcgcgatg ggatttctc ctgcggcgcc  11160
cctgcagcct ccctacgtgc ctcctcggta cctgcaacct acagggggga gaaatagcat  11220
ctgttactct gagctgcagc ccctgtacga taccaccaga ctgtacctgg tggacaacaa  11280
gtccgcggac gtggcctccc tgaactacca gaacgaccac agcgattttt tgaccacggt  11340
gatccaaaac aacgacttca ccccaaccga ggccagcact cagaccataa acctggataa  11400
caggtcgaac tggggcggcg acctgaagac catcttgcac accaacatgc ccaacgtgaa  11460
cgagttcatg ttcaccaact cttttaaggc gcgggtgatg gtggcgcgcg agcaggggga  11520
ggcgaagtac gagtgggtgg acttcacgct gcccgagggc aactactcag agaccatgac  11580
tctcgacctg atgaacaatg cgatcgtgga acactatctg aaagtgggca ggcagaacgg  11640
ggtgaaggaa agcgatatcg ggtcaagtt tgacaccaga aacttccgtc tgggctggga  11700
ccccgtgacc gggctggtca tgccggggt ctacaccaac gaggcctttc atcccgacat  11760
agtgcttctg cccggctgtg ggtggactt cacccagagc cggctgagca acctgctggg  11820
cattcgcaag cggcagcctt tccaggaggg tttcaagatc acctatgagg atctgaaggg  11880
gggcaacatt cccgcgctcc ttgatctgga cgcctacgag gagagcttga aacccgagga  11940
gagcgctggc gacagcggcg agagtggcga ggagcaagcc ggcggcggtg gcggcgcgtc  12000
ggtagaaaac gaaagtacgc ccgcagtggc ggcggacgct gcggaggtcg agccggaggc  12060
catgcagcag gacgcagagg agggcgcaca ggagggcgcg cagaaggaca tgaacgatgg  12120
ggagatcagg ggagacacat tcgccacccg gggcgaagaa aaagaggcag aggcggcggc  12180
ggcggcgacg gcggaggccg aaaccgaggt tgaggcagag gcagagcccg agaccgaagt  12240
tatggaagac atgaatgatg gagaacgtag gggcgacacg ttcgccaccc ggggcgaaga  12300
gaaggcggcg gaggcagaag ccgcggctga ggaggcggct gcggctgcgg ccaagactga  12360
ggctgcggct aaggctgagg tcgaagccaa tgttgcggtt gaggctcagg ctgaggagga  12420
ggcggcggct gaagcagtta aggaaaaggc ccaggcagag caggaagaga aaaaacctgt  12480
cattcaacct ctaaaagaag atagcaaaaa gcgcagttac aacgtcatcg agggcagcac  12540
ctttacccag taccgcagct ggtacctggc gtacaactac ggcgacccgg tcaagggggt  12600
```

```
gcgctcgtgg accctgctct gcacgccgga cgtcacctgc ggctccgagc agatgtactg  12660
gtcgctgccg aacatgatgc aagacccggt gaccttccgc tccacgcggc aggttagcaa  12720
cttcccggtg gtgggcgccg aactgctgcc cgtgcactcc aagagttttt acaacgagca  12780
ggccgtctac tcccagctga tccgccaggc cacctctctg acccacgtgt tcaatcgctt  12840
tcccgagaac cagattttgg cgcgcccgcc ggcccccacc atcaccaccg tgagtgaaaa  12900
cgttcctgcc ctcacagatc acgggacgct accgctgcgc aacagcatct caggagtcca  12960
gcgagtgacc attactgacg ccagacgccg gacctgcccc tacgtttaca aggccttggg  13020
catagtctcg ccgcgcgtcc tctccagtcg cactttttaa aacacatcta cccacacgtt  13080
ccaaaatcat gtccgtactc atctcaccca gcaacaacac cggctggggg ctgcgcgcgc  13140
ccagcaagat gtttggaggg gcgaggaagc gctccgacca gcaccctgtg cgcgtgcgcg  13200
gccactaccg cgcgccctgg ggagcgcaca agcgcgggcg cacagggcgc accactgtgg  13260
acgacgtcat tgactccgta gtggagcaag cgcgccacta cacacccggc gcgccgaccg  13320
cccccgccgt gtccaccgtg gaccaggcga tcgaaagcgt ggtacagggc gcgcggcact  13380
atgccaacct taaaagtcgc cgccgccgcg tggcccgccg ccatcgccgg agaccccggg  13440
ccaccgccgc cgcgcgcctt actaaggctc tgctcaggcg cgccaggcga actggccacc  13500
gggccgccat gagggccgca cggcgggctg ccgctgccgc aagcgccgtg gccccgcggg  13560
cacgaaggcg cgcggccgcc gccgccgccg ccgccatttc cagcttggcc tcgacgcggc  13620
gcggtaacat atactgggtg cgcgactcgg taaccggcac gcgggtaccc gtgcgctttc  13680
gcccccgcg gaattagcac aagacaacat acacactgag tctcctgctg ttgtgtatcc  13740
cagcggcgac cgtcagcagc ggcgacatgt ccaagcgcaa aattaaagaa gagatgctcc  13800
aggtcatcgc gccggagatc tatgggcccc cgaagaagga ggaggatgat tacaagcccc  13860
gcaagctaaa gcgggtcaaa aagaaaaaga aagatgatga tgatgacgag gcggtggagt  13920
ttgtccgccg catggcaccc aggcgccccg tgcagtggaa gggccggcgc gtgcagcgcg  13980
ttttgcgccc cggcaccgcg gtggtcttca cgcccggcga gcgctccacg cgcactttca  14040
agcgggtgta cgatgaggtg tacggcgacg aggacctgtt ggagcaggcc aaccagcgct  14100
ttggggagtt tgcatatggg aaacggcccc gcgagagtct aaaagaggac ctgctggcgc  14160
taccgctgga cgagggcaat cccacccga gtctgaagcc ggtaaccctg caacaggtgc  14220
tgcctttgag cgcgcccagc gagcataagc gagggttgaa gcgcgaaggc ggggacctgg  14280
cgcccaccgt gcagttgatg gtgcccaagc ggcagaagct ggaggacgtg ctggagaaaa  14340
tgaaagtaga gcccgggatc cagcccgaga tcaaggtccg ccccatcaag caggtggcgc  14400
ccggcgtggg agtccagacc gtggacgtta ggattcccac ggaggagatg gaaacccaaa  14460
ccgccactcc ctcttcggcg gccagcgcca ccaccggcac cgcttcggta gaggtgcaga  14520
cggacccctg gctacccgcc accgctgttg ccgccgccgc cccccgttcg cgcgggcgca  14580
agagaaatta tccagcggcc agcgcgctca tgccccagta cgcactgcat ccatccatcg  14640
cgcccacccc cggctaccgc gggtactcgt accgcccgcg cagatcagcc ggcactcgcg  14700
gccgccgccg ccgtgcgacc acaaccagcc gccgccgtcg ccgccgccgc cagccagtgc  14760
tgaccccgt gtctgtaagg aaggtggctc gctcggggag cacgctggtg gtgcccagag  14820
cgcgctacca ccccagcatc gtttaaagcc ggtctctgta tggttcttgc agatatggcc  14880
ctcacttgtc gcctccgctt cccggtgccg ggataccgag gaagaactca ccgccgcaga  14940
ggcatggcgg gcagcggtct ccgcggcggc cgtcgccatc gccggcgcgc aaaaagcagg  15000
```

```
cgcatgcgcg gcggtgtgct gcctctgcta atcccgctaa tcgccgcggc gatcggtgcc  15060
gtacccggga tcgcctccgt ggccctgcag gcgtcccaga aacgttgact cttgcaacct  15120
tgcaagcttg catttttttgg aggaaaaata aaaaaagtct agactctcac gctcgcttgg  15180
tcctgtgact attttgtaga aaaaagatgg aagacatcaa ctttgcgtcg ctggccccgc  15240
gtcacggctc gcgcccgttc atgggagact ggacagatat cggcaccagc aatatgagcg  15300
gtggcgcctt cagctggggc agtctgtgga gcggccttaa aaattttggt tccaccatta  15360
agaactatgg caacaaagcg tggaacagca gcacgggcca gatgctgaga gacaagttga  15420
aagagcagaa cttccaggag aaggtggcgc agggcctggc ctctggcatc agcggggtgg  15480
tggacatagc taaccaggcc gtgcagaaaa agataaacag tcatctggac ccccgtcctc  15540
aggtggagga aatgcctcca gcgatggaga cggtgtctcc cgagggcaaa ggcgaaaagc  15600
gcccgcggcc cgacagagaa gagaccctgg tgtcacacac cgaggagccg ccctcttacg  15660
aggaggcagt caaggccggc ctgcccacca ctcgccccat agcccccatg gccaccggtg  15720
tggtgggcca caggcaacac actcccgcaa cactagatct gcccccgccg tccgagccgc  15780
cgcgccagcc aaaggcggcg acggtgcccg ctccctccac ttccgccgcc aacagagtgc  15840
ccctgcgccg cgccgcgagc ggcccccggg cctcgcgagt tagcggcaac tggcagagca  15900
cactgaacag catcgtgggc ctgggagtga ggagtgtgaa gcgccgccgt tgctactgaa  15960
tgagcaagct agctaacgtg ttgtatgtgt gtatgcgtcc tatgtcgccg ccagaggagc  16020
tgttgagccg ccggcgccgt ctgcactcca gcgaatttca agatggcgac cccatcgatg  16080
atgcctcagt ggtcgtacat gcacatctcg ggccaggacg cttcggagta cctgagcccc  16140
gggctggtgc agttcgcccg cgccacagac acctacttca acatgagtaa caagttcagg  16200
aaccccactg tggcgcccac ccacgatgtg accacggacc ggtcgcagcg cctgacgctg  16260
cggttcatcc ccgtggatcg ggaggacacc gcctactctt acaaggcgcg gttcacgctg  16320
gccgtgggcg acaaccgcgt gctggacatg gcctccactt actttgacat caggggggtg  16380
ctggacaggg gccccacctt caagccctac tcgggtactg cctacaactc cctggccccc  16440
aagggcgctc ccaattcttg cgagtgggaa caagaggaaa atcaggtggt cgctgcagat  16500
gatgaacttg aagatgaaga agcgcaagct caagaggacg ccccagctaa aaaaattcat  16560
gtatatgccc aggcgcctct tgctggcgaa aagattacca aggatggttt gcaaataggt  16620
actgaagttg taggagatac atctaaggac acttttgcag acaaaaacatt ccaacccgaa  16680
cctcagatag gcgagtctca gtggaacgag gctgatgcca cagtagcagg aggcagagtc  16740
ttgaaaaaaa ccacccctat gagaccttgc tatggatcct atgccaggcc tacaaatgcc  16800
aacgggggtc aaggaattat ggttgccaat gaacaaggag tgttggagtc taaagtggag  16860
atgcaatttt tttctaacac tacaaccctt aatgcgcggg atggagctgg caatcccgaa  16920
ccaaaggtgg tgttgtacag tgaagatgtc cacttggaat ctcctgacac tcatttgtct  16980
tacaagccca aaaaggatga tgttaatgct aaaattatgt tgggtcagca agctatggct  17040
aacaggccca acctcattgc ttttagagat aatttcattg gactcatgta ctacaacagc  17100
actggtaaca tgggagtgct ggcgggtcag gcctctcagt tgaatgccgt ggtggacctg  17160
caggatagaa acacagaact gtcatatcag cttatgcttg attccattgg ggatagatcc  17220
agatacttct ccatgtggaa ccaggcagtg gatagctatg acccagatgt cagaatcatt  17280
gaaaaccatg gtgtcgagga cgagctaccc aactactgct tccctctggg cggcatagga  17340
```

```
attactgata cttatcaagg gatcaaaaat accaatggca atggtcagtg gaccaaagat  17400
gatcagttcg cggaccgtaa tgaaataggg gtgggaaaca acttcgccat ggagatcaac  17460
atccaggcca acctctggag gaacttcctc tatgcgaacg tggggctcta cctgccagac  17520
aagctcaagt acaaccccac caacgtggac atctctgaca accccaacac ctatgactac  17580
atgaacaagc gtgtggtggc tcccggcctg gtggactgct ttgtcaatgt gggagccagg  17640
tggtccctgg actacatgga caacgtcaac cccttcaacc accaccgcaa tgcgggtctg  17700
cgctaccgct ccatgatcct gggcaacggg cgctacgtgc ccttccacat tcaggtgccc  17760
cagaagttct ttgccatcaa gaacctcctc ctcctgccgg gctcctacac ttacgagtgg  17820
aacttcagga aggatgtcaa catggtcctg cagagctctc tgggcaatga ccttagggtg  17880
gacggggcca gcatcaagtt tgacagcgtc accctctatg ctaccttctt ccccatggct  17940
cacaacaccg cctccacgct cgaggccatg ctgaggaacg acaccaacga ccagtccttc  18000
aatgactacc tctctggggc caacatgctc taccccatcc ccgccaaggc caccaacgtg  18060
cccatctcca ttccctctcg caactgggcc gccttcagag gctgggcctt tacccgcctt  18120
aagaccaagg aaaccccctc cctgggctcg ggttttgacc cctactttgt ctactcggga  18180
tccatcccct acctggatgg caccttctac ctcaaccaca cttttaagaa gatatccatc  18240
atgtatgact cctccgtcag ctggccgggc aatgaccgcc tgctcacccc caatgagttc  18300
gaggtcaagc gcgccgtgga cggcgagggc tacaacgtgg cccagtgcaa catgaccaag  18360
gactggttcc tggtgcagat gctggccaac tacaacatag gctaccaggg cttctacatc  18420
ccagagagct acaaggacag gatgtactcc ttcttcagaa atttccaacc catgagcagg  18480
caggtggtgg acgagaccaa atacaaggac tatcaggcca ttggcatcac tcaccagcac  18540
aacaactcgg gattcgtggg ctacctggct cccaccatgc gcgaggggca ggcctacccc  18600
gccaacttcc cctacccgtt gataggcaag accgcggtcg acagcgtcac ccagaaaaag  18660
ttcctctgcg accgcaccct ctggcgcatc cccttctcta gcaacttcat gtccatgggt  18720
gcgctcacgg acctgggcca gaacctgctc tatgccaact ccgcccatgc gctggacatg  18780
acttttgagg tggaccccat ggacgagccc acccttctct atattgtgtt tgaagtgttc  18840
gacgtggtca gagtgcacca gccgcaccgc ggtgtcatcg agaccgtgta cctgcgcacg  18900
cccttctcgg ccggcaacgc caccacctaa ggagacagcg ccgccgcctg catgacgggt  18960
tccaccgagc aagagctcag ggccatcgcc agagacctgg gatgcggacc ctatttttg   19020
ggcacctatg acaaacgctt cccgggcttc atctcccgag acaagctcgc ctgcgccatc  19080
gtcaacacgg ccgcgcgcga gaccgggggc gtgcactggc tggcctttgg ctgggacccg  19140
cgctccaaaa cctgctacct cttcgacccc tttggcttct ccgatcagcg cctcagacag  19200
atctatgagt ttgagtacga ggggctgctg cgccgcagcg cgcttgcctc ctcgcccgac  19260
cgctgcatca cccttgagaa gtccaccgag accgtgcagg ggccccactc ggccgcctgc  19320
ggtctcttct gctgcatgtt tttgcacgcc tttgtgcgct ggccccagag tcccatggat  19380
cgcaacccca ccatgaactt gctcaaggga gtgcccaacg ccatgctcca gagcccccag  19440
gtccagccca ccctgcgcca caaccaggaa cagctctacc gcttcctgga gcgccactcc  19500
ccctacttcc gcagtcacag cgcgcacatc cggggggcca cctctttctg ccacttgcaa  19560
caaaacatgc aagacggaaa atgatgtaca gctcgctttt taataaatgt aaagactgtg  19620
cactttattt atacacgggc tctttctggt tatttattca acaccgccgt cgccatctag  19680
aaatcgaaag ggttctgccg cgcgtcgccg tgcgccacgg gcagagacac gttgcgatac  19740
```

```
tggaagcggc tcgcccactt gaactcgggc accaccatgc ggggcagtgg ctcctcgggg  19800
aagttctcgc cccacagggt gcgggtcagc tgcagcgcgc tcaggaggtc gggagccgag  19860
atcttgaagt cgcagttggg gccggaaccc tgcgcgcgcg agttgcggta cacggggttg  19920
cagcactgga acaccagcag ggccggatta cgcacgctgg ccagcaggct ctcgtcgctg  19980
atcatgtcgc tgtccagatc ctccgcgttg ctcagggcga atggggtcat cttgcagacc  20040
tgcctgccca ggaaaggcgg cagcccgggc ttgccgttgc agtcgcagcg caggggcatc  20100
agcaggtgcc cgtggcccgt ctgcgcctgc gggtacagcg cgcgcatgaa ggcttcgatc  20160
tgcctgaaag ccacctgcgt cttggctccc tccgaaaaga acatcccaca ggacttgctg  20220
gagaactggt tcgcgggaca gctggcatcg tgcaggcagc agcgcgcgtc ggtgttggcg  20280
atctgcacca cgttgcgacc ccaccggttc ttcactatct tggccttgga agcctgctcc  20340
ttcagcgcgc gctggccgtt ctcgctggtc acatccatct ctatcacctg ctccttgttg  20400
atcatgtttg tcccgtgcag acacttcagg tcgccctccg tctgggtgca gcggtgctcc  20460
cacagcgcgc aaccggtggg ctcccaattt ttgtgggtca cccccgcgta ggcctgcagg  20520
taggcctgca agaagcgccc catcatggcc acaaaggtct tctggctcgt aaaggtcagc  20580
tgcaggccgc gatgctcttc gttcagccag gtcttgcaga tggcggccag cgcctcggtc  20640
tgctcgggca gcatcctaaa atttgtcttc aggtcgttat ccacgtggta cttgtccatc  20700
atggcgcgcg ccgcctccat gcccttctcc caggcggaca ccatgggcag gcttaggggg  20760
tttatcactt ccaccggcga ggacaccgta ctttcgattt cttcttcctc cccctcttcc  20820
cggcgcgcgc ccacgctgct gcgcgctctc accgcctgca ccaaggggtc gtcttcaggc  20880
aagcgccgca ccgagcgctt gccgcccttg acctgcttaa tcagcaccgg cgggttgctg  20940
aagcccacca tggtcagctc cgcctgctct tcttcgtctt cgctgtctac cactatctct  21000
ggggaagggc ttctccgctc tgcggcggtg cgcttctttt ttttcttggg agcagccgtg  21060
acggagtccg ccacggcgac ggaggtcgag ggcgtggggc tgggggtgcg cggtaccagg  21120
gcctcgtcgc cctcggactc ttcctctgac tccaggcggc ggcggagacg cttctttggg  21180
ggcgcgcgcg tcagcggcgg cggagacggg gacggggacg gggacgggac gccctccaca  21240
gggggtggtc ttcgcgcaga cccgcggccg cgctcggggg tcttttcgag ctggtcttgg  21300
tcccgactgg ccattgtatc ctcctcctcc taggcagaga gacataagga gtctatcatg  21360
caagtcgaga aggaggagag cttaaccacc ccctctgaga ccgccgatgc gcccgccgtc  21420
gccgtcgccc ccgctgccgc cgacgcgccc gccacaccga gcgacacccc cgcggacccc  21480
ccagccgacg cacccctgtt cgaggaagcg gccgtggagc aggacccggg ctttgtctcg  21540
gcagaggagg atttgcgaga ggaggaggat aaggagaaga agccctcagt gccaaaagat  21600
gataaagagc aagacgagca cgacgcagat gcacaccagg gtgaagtcgg gcggggggac  21660
ggagggcatg acggcgccga ctacctagac gaagggaacg acgtgctctt gaagcacctg  21720
catcgtcagt gcgccatcgt ttgcgacgct ctgcaggagc gcagcgaagt gcccctcagc  21780
gtggcggagg tcagccacgc ctacgagctc agcctcttct ccccccgggt gccccccgc  21840
cgccgcgaaa acggcacatg cgagcccaac ccgcgcctca acttctaccc cgcctttgtg  21900
gtgcccgagg tcctggccac ctatcacatc ttctttcaaa attgcaagat ccccctctcg  21960
tgccgcgcca accgtagccg cgccgataag atgctggccc tgcgccaggg cgaccacata  22020
cctgatatcg ccgctttgga agatgtgcca aagatcttcg agggtctggg tcgcaacgag  22080
```

```
aagcgggcag caaactctct gcaacaggaa aacagcgaaa atgagagtca caccggggta  22140
ctggtggagc tcgagggcga caacgcccgc ctggcggtgg tcaagcgcag catcgaggtc  22200
acccactttg cctaccccgc gctcaacctg ccccccaaag tcatgaacgc ggccatggac  22260
gggctgatca tgcgccgcgg ccggcccctc gctccagatg caaacttgca tgaggagacc  22320
gaggacggcc agcccgtggt cagcgacgag cagctggcgc gctggctgga gaccgcggac  22380
cccgccgaac tggaggagcg gcgcaagatg atgatggccg cggtgctggt caccgtagag  22440
ctggagtgtc tgcagcgctt cttcggcgac cccgagatgc agagaaaggt cgaggagacc  22500
ctgcactaca ccttccgcca gggctacgtg cgccaggctt gcaagatctc caacgtggag  22560
ctcagcaacc tggtgtccta cctgggcatc ttgcatgaga accgcctcgg gcagagcgtg  22620
ctgcactcca ccctgcgcgg ggaggcgcgc cgcgactacg tgcgcgactg cgtttacctc  22680
ttcctctgct acacctggca gacggccatg gggtctggc agcagtgcct ggaggagcgc  22740
aacctcaagg agctggagaa gctcctgcag cgcgcgctca aagacctctg gacgggctac  22800
aacgagcgct cggtggccgc cgcgctggcc gacctcatct tccccgagcg cctgctcaaa  22860
accctccagc aggggctgcc cgacttcacc agccaaagca tgttgcaaaa cttcaggaac  22920
tttatcctgg agcgttctgg catcctaccc gccacctgct gcgccctgcc cagcgacttt  22980
gtcccccctcg tgtaccgcga gtgccccccg ccgctgtggg gtcactgcta cctgttccaa  23040
ctggccaact acctgtccta ccacgcggac ctcatggagg actccagcgg cgaggggctc  23100
atggagtgcc actgccgctg caacctctgc acgccccacc gctccctggt ctgcaacacc  23160
caactgctca gcgagagtca gattatcggt accttcgagc tacagggtcc gtcctcctca  23220
gacgagaagt ccgcggctcc ggggctaaaa ctcactccgg ggctgtggac ttccgcctac  23280
ctgcgcaaat ttgtacctga agactaccac gcccacgaga tcaggtttta cgaagaccaa  23340
tcccgcccgc ccaaggcgga gctgaccgcc tgcgtcatca cccagggcga gatcctaggc  23400
caattgcaag ccatccaaaa agcccgccaa gattttttgc tgagaaaggg tcggggggtg  23460
tatctggacc cccagtcggg tgaggagctc aacccggttc cccgctgcc gccgccgcgg  23520
gaccttgctt cccaggataa gcatcgccat ggctcccaga aagaagcagc agcggccgcc  23580
actgccgcca ccccacatgc tggaggaaga ggaggaatac tgggacagtc aggcagagga  23640
ggtttcggac gaggaggagc cggagacgga gatggaagag tgggaggagg acagcttaga  23700
cgaggaggct tccgaagccg aagaggcaga cgcaacaccg tcaccctcgg ccgcagcccc  23760
ctcgcaggcg cccccgaagt ccgctcccag catcagcagc aacagcagcg ctataacctc  23820
cgctcctcca ccgccgcgac ccacggccga ccgcagaccc aaccgtagat gggacaccac  23880
cggaaccggg gccggtaagt cctccgggag aggcaagcaa gcgcagcgcc aaggctaccg  23940
ctcgtggcgc gctcacaaga acgccatagt cgcttgcttg caagactgcg gggggaacat  24000
ctccttcgcc cgccgcttcc tgctcttcca ccacggtgtg gccttccccc gtaacgtcct  24060
gcattactac cgtcatctct acagccccta ctgcggcggc agtgagccag agacggtcgg  24120
cggcggcggc ggcgcccgtt tcggcgccta ggaagaccca gggcaagact tcagccaaga  24180
aactcgcggc ggccgcggcg aacgcggtcg cgggggccct gcgcctgacg gtgaacgaac  24240
ccctgtcgac ccgcgaactg agaaaccgaa tcttccccac tctctatgcc atcttccagc  24300
agagcagagg gcaggatcag gaactgaaag taaaaaacag gtctctgcgc tccctcaccc  24360
gcagctgtct gtatcacaag agcgaagacc agcttcggcg cacgctggag gacgctgagg  24420
cactcttcag caaatactgc gcgctcactc ttaaggacta gctccgcgcc cttctcgaat  24480
```

```
ttaggcggga acgcctacgt catcgcagcg ccgccgtcat gagcaaggac attcccacgc  24540

catacatgtg gagctatcag ccgcagatgg gactcgcggc gggcgcctcc caagactact  24600

ccacccgcat gaactggctc agtgccggcc cacacatgat ctcacaggtt aatgatatcc  24660

gcacccatcg aaaccaaata ttggtggagc aggcggcaat taccaccacg ccccgcaata  24720

atcccaaccc cagggagtgg cccgcgtccc tggtgtatca ggaaattccc ggccccacca  24780

ccgtactact tccgcgtgat tcccaggccg aagtccaaat gactaactca ggggcgcagc  24840

tcgcgggcgg ctgtcgtcac agggtgcggc ctcctcgcca gggtataact cacctggaga  24900

tccgaggcag aggtattcag ctcaacgacg agtcggtgag ctcctcgctc ggtctaagac  24960

ctgacgggac cttccagata gccggagccg gccgatcttc cttcacgccc cgccaggcgt  25020

acctgactct gcagagctcg tcctcggcgc cgcgctcggg cggcatcggg actctccagt  25080

tcgtgcagga gtttgtgccc tcggtctact tcaacccctt ctcgggctct cccggtcgct  25140

acccggacca gttcatctcg aactttgacg ccgcgaggga ctcggtggac ggctacgact  25200

gaatgtcggg tggacccggt gcagagcaac ttcgcctgaa gcacctcgac cactgccgcc  25260

gccctcagtg ctttgcccgc tgtcagaccg gtgagttcca gtacttttcc ctgcccgact  25320

cgcacccgga cggcccggcg cacggggtgc gctttttcat cccgagtcag gtgcgctcta  25380

ccctaatcag ggagtttacc gcccgtcccc tactggcgga gttggaaaag gggccttcta  25440

tcctaaccat tgcctgcatc tgctctaacc ctggattgca ccaagatctt tgctgtcatt  25500

tgtgtgctga gtataataaa ggctgagatc agaatctact cgggctcctg tcgccatcct  25560

gtcaacgcca ccgtccaagc ccggcccgat cagcccgagg tgaacctcac ctgcggtctg  25620

caccggcgcc tgaggaaata cctagcttgg tactacaaca gcactccctt tgtggtttac  25680

aacagctttg accaggacgg ggtctcactg agggataacc tctcgaacct gagctactcc  25740

atcaggaaga acagcaccct cgagctactt cctccttacc tgcccgggac ttaccagtgt  25800

gtcaccggtc cctgcaccca cacccacctg ttgatcgtaa acgactctct tccgagaaca  25860

gacctcaata actcctcttc gcagttcccc agaacaggag gtgagctcag gaaaccccgg  25920

gtaaagaagg gtggacaaga gttaacactt gtggggtttc tggtgtatgt gacgctggtg  25980

gtggctcttt tgattaaggc ttttccttcc atgtctgaac tctccctctt ttatgaacaa  26040

ctcgactagt gctaacggga ccctacccaa cgaatcggga ttgaatatcg gtaaccaggt  26100

tgcagtttca cttttgatta ccttcatagt cctcttcctg ctagtgctgt cgcttctgtg  26160

cctgcggatc gggggctgct gcatccacgt ttatatctgg tgctggctgt ttagaaggtt  26220

cggagaccat cgcaggtaga ataaacatgc tgctgcttac cctctttgtc ctggcgctgg  26280

ccgccagctg ccaagccttt tccgaggctg actttataga gccccagtgt aacgtgactt  26340

ttaaagccca tgcacagcgt tgtcatacta taatcaaatg tgccaccgaa cacgatgaat  26400

accttatcca gtataaagat aaatcacaca aagtggcact tgttgacatc tggaaacccg  26460

aagacccttt ggaatacaat gtgaccgttt tccagggtga cctcttcaaa atttacaatt  26520

acactttccc atttgaccag atgtgtgact ttgtcatgta catggaaaag cagcacaagc  26580

tgtggcctcc gactccccag ggctgtgtgg aaaatccagg ctctttctgc atgatctctc  26640

tctgtgtaac tgtgctggca ctaatactca cgcttttgta tatcagattt aaatcaaggc  26700

aaagcttcat cgatgaaaag aaaatgcctt aaacgctttc acgcttgatt gctaacaccg  26760

ggtttttatc cgcagaatga ttggaatcac cctactaatc acctccctcc ttgcgattgc  26820
```

-continued

```
ccatgggttg gaacgaatcg aagcccctgt gggggccaat gttaccctgg tggggcctgt  26880
cggcaatgct acattaatgt gggaaaaata tactaaaaat caatgggtct cttactgcac  26940
taacaaaaac agccacaagc ccagagccat ctgcgatggg caaaatctaa ccttgattga  27000
tgttcaaatg ctggatgcgg gctactatta tgggcagctg ggtacaatga ttaattactg  27060
gagaccccac aaagattaca tgctccacgt agtaaagggt cccccttagca gcccacccac  27120
taccacctct actaccccca ctaccaccac tactcccacc accagcactg ccgcccagcc  27180
tcctcatagc agaacaacca cttttatcaa ttccaagtcc cactcccccc acattgccgg  27240
cgggccctcc gcctcagact ccgagaccac cgagatctgc ttctgcaaat gctctgacgc  27300
ctttgctgag gatttggaag accacgagga agatgagcat gacttcgcag atgcatgcca  27360
ggcatcagag gcagaagcgc tgccggtggc cctcaaacag tatgcagacc cccacaccac  27420
ccccaacctt cctccacctt cccagaagcc aagtttcctg ggggaaaatg aaactctgcc  27480
tctctccata ctcgctctga catctgttgc tatgttgacc gctctgctgg tgcttctatg  27540
ctctatatgc tacctgatct gctgcagaaa gaaaaaatct cacggccatg ctcaccagcc  27600
cctcatgcac ttcccttacc ctccagagct gggcgaccac aaactttaag tctgcagtaa  27660
ctatctgccc atcccttgtc agtcgacagc gatgagcccc actaatctaa cggcctctgg  27720
acttacaaca tcgtctctta atgagaccac cgctcctcaa gacctgtacg atggtgtctc  27780
cgcgctggtt aaccagtggg atcacctggg catatggtgg ctcctcatag gagcagtgac  27840
cctgtgccta atcctggtct ggatcatctg ctgcatcaaa agcagaagac ccaggcggcg  27900
gcccatctac aggccctttg tcatcacacc tgaagatgat gatgacacca cttccaggct  27960
gcagaggcta aagcagctac tcttctcttt tacagcatgg taaattgaat catgcctcgc  28020
attttcatct acttgtctct ccttccactt tttctgggct cttctacatt ggccgctgtg  28080
tcccacatcg aggtagactg cctcacgccc ttcacagtct acctgctttt cggctttgtc  28140
atctgcacct ttgtctgcag cgttatcact gtagtgatct gcttcataca gtgcatcgac  28200
tacgtctgcg tgcgggtggc ttactttaga caccaccccc agtatcgcaa cagggacata  28260
gcggctctcc taagacttgt ttaaaatcat ggccaaatta actgtgattg gtcttctgat  28320
catctgctgc gtcctagccg cgattgggac tcaagctcct accaccacca gcgctcccag  28380
aaagagacat gtatcctgca gcttcaagcg tccctggaat ataccccaat gctttactga  28440
tgaacctgaa atctctttgg cttggtactt cagcgtcacc gcccttctta tcttctgcag  28500
tacggttatt gcccttgcca tctacccttc ccttgacctg ggctggaatg ctgtcaactc  28560
tatggaatat cccaccttcc cagaaccaga cctgccagac ctggttgttc taaacgcgtt  28620
tcctcctcct gctcccgttc aaaatcagtt tcgccctccg tcccccacgc ccactgaggt  28680
cagctacttt aatctaacag gcggagatga ctgaaaacct agacctagaa atggacggtc  28740
tctgcagcga gcaacgcaca ctagagaggc gccggcaaaa agagctcgag cgtcttaaac  28800
aagagctcca agacgcggtg gccatacacc agtgcaaaaa aggtgtcttc tgtctggtaa  28860
aacaggccac gctcacctat gaaaaaacag gtgacaccca ccgcctagga tacaagctgc  28920
ccacacagcg ccagaagttc gccctcatga taggcgaaca acccatcacc gtgacccagc  28980
actccgtgga gacagaaggc tgcatacacg ctccctgtag ggcgctgac tgcctctaca  29040
ccttgatcaa aaccctctgc ggtctcagag acctcatccc ttttaattaa tcataactgt  29100
aatcaataaa aaatcactta cttgaaatct gatagcaagc ctctgtccaa tttttcagc  29160
aacacttcct tcccctcctc ccaactctgg tactctaggc gcctcctagc tgcaaacttc  29220
```

```
ctccacagtc tgaagggaat gtcagattcc tcctcctgtc cctccgcacc cacgatcttc  29280
atgttgttgc agatgaaacg cgcgagatcg tctgacgaga ccttcaaccc cgtgtacccc  29340
tacgataccg agatcgctcc gacttctgtc cctttcctta cccctccctt tgtgtcatcc  29400
gcaggaatgc aagaaaatcc agctggggtg ctgtccctgc acttgtcaga gccccttacc  29460
acccacaatg gggccctgac tctaaaaatg gggggcggcc tgaccctgga caaggaaggg  29520
aatctcactt cccaaaacat caccagtgtc gatccccctc tcaaaaaaag caagaacaac  29580
atcagccttc agaccgccgc acccctcgcc gtcagctccg ggccctaac  actttttgcc  29640
actccccccc tagcggtcag tggtgacaac cttactgtgc agtctcaggc ccctctcact  29700
ttggaagact caaaactaac tctggccacc aaaggacccc taactgtgtc cgaaggcaaa  29760
cttgtcctag aaacagaggc tcccctgcat gcaagtgaca gcagcagcct gggccttagc  29820
gttacggccc cacttagcat taacaatgac agcctaggac tagacatgca agcgcccatt  29880
agctctcgag atggaaaact ggctctaaca gtggcggccc ccctaactgt ggtcgagggt  29940
atcaatgctt tggcagtagc cacaggtaag ggtattgggc taaatgaaac caacacacac  30000
ctgcaggcaa aactggtcgc acccctaggc tttgatacca acggcaacat taagctaagc  30060
gttgcaggag gcatgaggct aaacaataac acactgatac tagatgtaaa ctacccattt  30120
gaggctcaag gccaactgag cctaagagtg ggctcgggcc cactatatgt agattctagt  30180
agtcataacc taaccattag atgccttagg ggattgtata taacatcttc taacaaccaa  30240
aacggtctag aagccaacat taaactaaca agaggccttg tgtatgacgg aaatgccata  30300
gcagttaatg ttggcaaagg gctggaatac agccctactg acacaacaga aaaacctata  30360
cagactaaaa taggtctagg catggagtat gataccgagg gagccatgat gacaaaacta  30420
ggctctggac taagctttga caattcagga gccattgtag tgggaaacaa aaatgatgac  30480
aggcttactt tgtggaccac accggaccca tcgcccaact gtcagatcta ctctgaaaaa  30540
gatgctaaac taaccttggt actgactaaa tgtggcagtc aggttgtagg cacagtatct  30600
attgccgctc ttaaaggtag cctcgtgcca atcactagtg caatcagtgt ggttcaggta  30660
tacctaaggt ttgatgaaaa tggggtacta atgagtaact cttcacttaa tggcgaatac  30720
tggaatttta gaaacggaga ctcaactaat ggcacaccat atacaaacgc agtgggtttc  30780
atgcctaatc tactggccta tcctaaaggt caaactacaa ctgcaaaaag taacattgtc  30840
agccaggtct acatgaatgg ggacgatact aaacccatga catttacaat caacttcaat  30900
ggccttagtg aaacagggga taccccctgtt agtaaatatt ccatgacatt ctcatggagg  30960
tggccaaatg gaagctacat agggcacaat tttgtaacaa actcctttac cttctcctac  31020
atcgcccaag aataaagaaa gcacagagat gcttgttttt gatttcaaaa ttgtgtgctt  31080
ttatttattt tcagcttaca gtatttccag tagtcattca aataaagctt aatcaaactg  31140
catgagaacc cttccacata gcttaaatta gcaccagtgc aaatggagaa aaatcaacat  31200
accttttttt atccagatat cagagaactc tagtggtcag ttttccccca ccctcccagc  31260
tcacagaata cacagtcctt tccccccggc tggctttaaa caacactatc tcattggtaa  31320
cagacatatt cttaggtgta ataatccaca cggtctcttg gcgggccaaa cgctggtcgg  31380
tgatgttaat aaactcccca ggcagctctt tcaagttcac gtcgctgtcc aactgctgaa  31440
gcgctcgcgg ctccgactgc gcctctagcg gaggcaacgg caacacccga tccttgatca  31500
aagggaggta aacggtccct cgtgtaggga cagtggcggg ataatcgaga tcgtgttgaa  31560
```

```
cgtagagtca tgccaaaggg aacagcggac gtactcatat ttcctccagc agaaccaagt  31620
gcgcgcgtgg cagctatccc tgcgtcttct gtctcgccgc ctgccccgtt cggtgtagta  31680
gttgtaatac agccactccc tgagaccgtc aaggcgctcc ctggcgtccg gatctatgac  31740
aacaccgtcc tgcagcgccg ccctgatgac atccaccacc gtagagtatg ccaagcccag  31800
ccaggaaatg cattcacttt gacagcgaga gataggagga gcggggagag atggaagaac  31860
catgatagta aagagaactt ttattccaat cgatcttcta agatatcaaa gtggagatct  31920
ataagatgac actggtctta tcctccgctg agtcgatcaa aaataacagc taaaccacaa  31980
acaacacgat tggtcaaatg ctccacaagg gttacctgca gcagaaaatt gcctcggaac  32040
tccaccgcaa gcagaacagc aaagccaccg cctctatcgt gatcaagaat aaaaaacccca  32100
cagctatcca cttacagacc cagatagttt tcagctctcc atcgtgaaaa aagatttaca  32160
agctcctcct ttaaatcacc tccaaccaat tgaaaaagtt gaaccagacc gccctccacc  32220
ttcagtttca gcaagcgttt aattatgatt gcaaaaattc aggctcctca gacacctgta  32280
taagattgag aagcggaacg ttaacatcga tgtttcgctc gcgtaaatca cgcctcagtg  32340
caagcataat ataatcccac aggtcggagc ggatcagcga ggacacctcc ccgccaggaa  32400
ccaactcaac ggagcctatg ctgattataa tacgcatatt cggagctatg ctaaccagca  32460
cggcccccaa ataggcgtac tgcataggcg gcgacaaaaa gtgaacagtt tgggttaaaa  32520
aatcaggcaa acactcgcgc aaaaaagcaa gaacatcata accatgctca tgcaaataga  32580
tgcaagtaag ctcaggaaca accacagaaa aatgcacaat ttttctctca aacatgactg  32640
cgagccctgc aaaaaataaa aaagaaacat tacacaagag tagcctgtct tacgatggga  32700
tagactactc taaccaacat aagacgggcc acaacatcgc ccgcgtggcc ataaaaaaaa  32760
ttgtccgtgt gattaaaaag aagcacagat agctggccag tcatatccgg agtcatcacg  32820
tgtgaacccg tgtagacccc cgggttggac acatcggcca aagaaagaaa gcggccaatg  32880
tacccaggag gaattataac actaagacga agatacaaca gaataacccc atgaggggga  32940
ataacaaagt tagtaggtga ataaaaacga taaacacccg aaactccctc ctgcgtaggc  33000
aaaatagcac cctccccttc caaaacaaca tatagcgctt ccacagcagc catgacaaaa  33060
gactcaaaac actcaaaaga ctcagtctta ccaggaaaat aaaagcactc tcacagcacc  33120
agcactaatc agagtgtgaa gagggccaag tgccgaacga gtatatatag gaataaaaaa  33180
tgacgtaaat gtgtaaaggt cagaaaacgc ccagaaaaat acacagacca acgcccgaaa  33240
cgaaaacccg cgaaaaaata cccagaactt cctcaacaac cgccacttcc gctttctcac  33300
ggtacgtcac ttccgcaaga aaagcaaaac tacatttccc acatgtgtaa aaacgaaacc  33360
ccgccccttg taaccgccca caacttacat catcaaaacg taaactccta cgtcacccgc  33420
cccgcctctc cccgcccacc tcattatcat attggccaca atccaaaata aggtatatta  33480
ttgatgatg                                                          33489
```

<210> SEQ ID NO 28
<211> LENGTH: 33485
<212> TYPE: DNA
<213> ORGANISM: Gorilla beringei graueri

<400> SEQUENCE: 28

```
catcatcaat aatatacctt attttggatt gtggccaata tgataatgag gtgggcgggg     60
agaggcgggg cgggtgacgt aggacgcgcg agtagggttg ggaggtgtgg cggaagtgtg    120
gcatttgcaa gtgggaggag ctcacatgca agcttccgtc gcggaaaatg tgacgttttt    180
```

```
gatgagcgcc gcctacctcc ggaagtgcca attttcgcgc gcttttcacc ggatatcgta    240
gtaattttgg gcgggaccat gtaagatttg gccattttcg cgcgaaaagt gaaacgggga    300
agtgaaaact gaataatagg gcgttagtca tagtgcgtaa tatttaccga gggccgaggg    360
actttgaccg attacgtgga ggactcgccc aggtgttttt tacgtgaatt tccgcgttcc    420
gggtcaaagt ctccgtttta ttgtcaccgt catttgacag gcctgaccat ctggtgctgg    480
cctgcaccag ggccgagttt gggtctagcg atgaggatac cgattgaggt gggtaaggtg    540
ggcgtggcta gaagggtggg gcgtgtataa attgggggtc taagggtctc tctgttttgt    600
cttgcaacag ccgccgccat gagcgacacc ggcaacagct ttgatggaag catctttagc    660
ccctatctga cagtgcgcat gcctcactgg gctggagtgc gtcagaatgt gatgggttcc    720
aacgtggatg gacgccccgt tctgccttca aattcgtcta caatggccta cgcgaccgtg    780
ggaggaactc cgctggacgc cgcgacctcc gccgccgcct ccgccgccgc cgcgaccgcg    840
cgcagcatgg ctacggacct ttacagctct ttggtggcga gcggcgcggc ctctcgcgcg    900
tctgctcggg atgagaaact gaccgctctg ctgcttaaac tggaagactt gacccgggag    960
ctggctcaac tgacccagca ggtctccagc ttgcgtgaga gcagccttgc ctccccctaa   1020
tggcccataa tataaataaa agccagtctg tttggattaa gcaagtgtat gttctttatt   1080
taactctccg cgcgcggtaa gcccgggacc agcggtctcg gtcgtttagg gtgcggtgga   1140
ttctttccaa cacgtggtac aggtggctct ggatgtttag atacatgggc atgagtccat   1200
ccctggggtg gaggtagcac cactgcagag cttcgtgctc gggggtggtg ttgtatatga   1260
tccagtcgta gcaggagcgc tgggcgtggt gctgaaaaat gtccttaagc aagaggctta   1320
tagctagggg gaggcccttg gtgtaagtgt ttacaaatct gctcagttgg gaggggtgca   1380
tccgggggga tataatgtgc atcttggact ggatttttag gttggctatg ttcccaccca   1440
gatcccttct gggattcatg ttgtgcagga ccaccagcac ggtatatcca gtacacttgg   1500
gaaatttatc gtggagctta gacgggaatg catggaagaa cttggagacg cccttgtggc   1560
ctcccagatt ttccatacat tcgtccatga tgatggcaat gggcccgtgg gaagctgcct   1620
gagcaaaaat gtttctggga tcgctcacat cgtagttatg ttccagggtg aggtcatcat   1680
aggacatctt tacaaatcgg gggcggaggg tcccggactg gggatgatg gtgccctcgg    1740
gccccggggc gtagttcccc tcacagatct gcatctccca ggctttcatt tcagagggag   1800
ggatcatatc cacctgcgga gcgatgaaaa acacagtttc tggcgcaggg gagattaact   1860
gggatgagag caggtttctg agcagctgtg actttccaca gccggtgggc ccatatatca   1920
cgcctatcac cggctgcagc tggtagttaa gagagctgca gctgccgtcc tcccggagca   1980
ggggggccac ctcgttcagc atatccctga cgtggatgtt ctccctgacc aattccgcca   2040
gaaggcgctc gccgcccagc gaaagcagct cttgcaagga agcaaaattt ttcagcggtt   2100
ttaggccgtc ggccgtgggc atgtttttca gcgtctgggt cagcagttcc agtctgtccc   2160
acagctcggt gatgtgctct acggcatctc gatccagcag atctcctcgt ttcgcgggtt   2220
ggggcggctt tcgctgtagg gcaccagccg atgggcgtcc agcggggcca gagtcatgtc   2280
cttccatggg cgcagggtcc tcgtcagggt ggtctgggtc acggtgaagg ggtgcgctcc   2340
gggttgggcg ctggccaggg tgcgcttgag gctggttctg ctggtgctga atcgctgccg   2400
ctcttcgccc tgcgcgtcgg ccaggtagca tttgaccatg gtctcgtagt cgagaccctc   2460
ggcggcgtgc cccttggcgc ggagctttcc cttggaggtg gcgccgcacg aggggcactg   2520
```

```
caggctcttc agggcgtaga gcttgggagc gagaaacacg gactctgggg agtaggcgtc   2580
cgcgccgcag gaagcgcaga ccgtctcgca ttccaccagc caagtgagct ccgggcggtc   2640
agggtcaaaa accaggttgc cccatgcttt tttgatgcgt ttcttacctc ggctctccat   2700
gaggcggtgt cccttctcgg tgacgaagag gctgtccgtg tctccgtaga ccgacttcag   2760
gggcctgtct tccagcggag tgcctctgtc ctcctcgtag agaaactctg accactctga   2820
gacgaaggcc cgcgtccagg ccaggacgaa ggaggccacg tgggaggggt agcggtcgtt   2880
gtccactagc gggtccacct tctccagggt gtgcaggcac atgtcccccct cctccgcgtc   2940
cagaaaagtg attggcttgt aggtgtagga cacgtgaccg gggttcccg acggggggt   3000
ataaaagggg gtgggcaccc tttcatcttc actctcttcc gcatcgctgt ctgcgagagc   3060
cagctgctgg ggtaagtatt ccctctcgaa ggcgggcatg acctcagcgc tcaggttgtc   3120
agtttctaaa aatgaggagg atttgatgtt cacctgtccg gaggtgatac ctttgagggt   3180
acctgggtcc atctggtcag aaaacactat tttttgttg tcaagcttgg tggcgaacga   3240
cccgtagagg gcgttggaga gcagcttggc gatggagcgc agggtctggt ttttgtcgcg   3300
gtcggctcgc tccttggccg cgatgttgag ttgcacgtac tcgcgggcca cgcacttcca   3360
ctcggggaag acggtggtgc gctcgtctgg gatcaggcgc accctccagc ctcggttgtg   3420
cagggtgacc atgtcgacgc tggtggcgac ctcgccgcgc aggcgctcgt tggtccagca   3480
gaggcggccg cccttgcgcg agcagaaggg gggtaggggg tccagctggt cctcgtttgg   3540
ggggtccgcg tcgatggtga agaccccggg gagcaagcgc gggtcaaagt agtcgatctt   3600
gcaagcttgc atgtccagag cccgctgcca ttcgcgggcg gcgagcgcgc gctcgtaggg   3660
gttgaggggc gggccccagg gcatggggtg ggtgagcgcg gaggcgtaca tgccgcagat   3720
gtcatacacg tacaggggtt ccctgaggat gccgaggtag gtggggtagc agcgcccccc   3780
gcggatgctg gcgcgcacgt agtcatagag ctcgtgggag gggccagca tgttgggccc   3840
gaggttggtg cgctgggggc gctcggcgcg gaaggcgatc tgcctgaaga tggcatggga   3900
gttggaggag atggtgggcc gctggaagac gttgaagctt gcttcttgca agcccaccga   3960
gtccctgacg aagcaggcgt aggactcgcg cagcttgtgc accagctcgg cggtgacctg   4020
gacgtcgagc gcgcagtagt cgagggtctc gcggatgatg tcatacttat cctcccctt   4080
ctttttccac agctcgcggt tgaggacgaa ctcttcgcgg tctttccagt actcttggag   4140
gggaaacccg tccgtgtccg aacggtaaga gcctagcatg tagaactggt tgacggcctg   4200
gtaggggcaa cagcccttct ccacgggcag cgcgtaggcc tgcgccgcct tgcggaggga   4260
ggtgtgggtg agggcgaaag tgtccctgac catgactttg aggtattgat gtttgaagtc   4320
tgtgtcatcg cagccgccct gttcccacag ggtgtagtcc gtgcgctttt tggagcgcgg   4380
gttgggcagg gagaaggtga ggtcattgaa gaggatcttc cccgctcgag gcatgaagtt   4440
tctggtgatg cgaaagggcc ctgggaccga ggagcggttg ttgatgacct gggcggccag   4500
gacgatctcg tcaaagccgt ttatgttgtg gcccacgatg tagagctcca aaaagcgggg   4560
ctggcccttg atggagggga gctttttgag ttcctcgtag gtgagctcct cgggcgattc   4620
caggccgtgc tcctccaggg cccagtcttg caagtgaggg ttggccgcca ggaaggatcg   4680
ccagaggtcg cgggccatga gggtctgcag gcggtcgcgg aaggttctga actgtcgccc   4740
cacggccatc ttttcggggg tgatgcagta gaaggtgagg gggtctttct cccaggggtc   4800
ccatctgagc tctcgggcga ggtcgcgcgc ggcggcgacc agagcctcgt tgccccccag   4860
tttcatgacc agcatgaagg gcacgagctg cttgccaaag gctcccatcc aagtgtaggt   4920
```

```
ctctacatcg taggtgacaa agaggcgctc cgtgcgagga tgagagccga tcgggaagaa   4980
ctggatctcc cgccaccagt tggaggattg gctgttgatg tggtgaaagt agaagtcccg   5040
tctgcgggcc gagcactcgt gctggctttt gtaaaagcga ccgcagtact ggcagcgctg   5100
cacgggttgt atatcttgca cgaggtgaac ctggcgacct ctgacgagga agcgcagcgg   5160
gaatctaagt cccccgcctg gggtcccgtg tggctggtgg tcttctactt tggttgtctg   5220
gccgccagca tctgtctcct ggagggcgat ggtggagcag accaccacgc cgcgagagcc   5280
gcaggtccag atctcggcgc tcggcgggcg gagtttgatg acgacatcgc gcacattgga   5340
gctgtccatg gtctccagct cccgcggcgg caggtcagct gggagttcct ggaggttcac   5400
ctcgcagaga cgggtcaagg cgcgggcagt gttgagatgg tatctgattt caaggggcgt   5460
gttggcggcg gagtcgatgg cttgcaggag gccgcagccc cgggggggcca cgatggttcc   5520
ccgcggggcg cgaggggagg cggaagctgg gggtgtgttc agaagcggtg acgcgggcgg   5580
gcccccggag gtaggggggg ttccggcccc acaggcatgg gcggcagggg cacgtcttcg   5640
ccgcgcgcgg gcaggggctg gtgctggctc cgaagagcgc ttgcgtgcgc gacgacgcga   5700
cggttggtgt cctgtatctg acgcctctga gtgaagacca cgggtcccgt gaccttgaac   5760
ctgaaagaga gttcgacaga atcaatctcg gcatcgttga cagcggcctg gcgcaggatc   5820
tcctgcacgt cgcccgagtt gtcctggtag gcgatctctg ccatgaactg ctcgatctct   5880
tcttcctgga gatctcctcg tccggcgcgc tccacggtgg ccgccaggtc gttggagatg   5940
cgacccatga gctgcgagaa ggcgttgagc ccgccctcgt tccagacccg gctgtagacc   6000
acgccccccct cggcgttgcg ggcgcgcatg accacctggg ccaggttgag ctccacgtgt   6060
cgcgtgaaga cggcgtagtt gcgcaggcgc tggaaaaggt agttcagggt ggtggcggtg   6120
tgctcggcga cgaagaagta catgacccag cgccgcaacg tggattcatt gatgtccccc   6180
aaggcctcca ggcgctccat ggcctcgtag aagtccacgg cgaagttgaa aaactgggag   6240
ttgcgagcgg acacggtcaa ctcctcctcc agaagacgga tgagctcggc gacagtgtcg   6300
cgcacctcgc gctcgaaggc cacggggggc gcttcttcct cttccacctc ttcttccatg   6360
atcgcttctt cttcttcctc agccgggacg ggagggggcg gcggcggcgg gggagggggcg   6420
cggcggcggc ggcggcgcac cgggaggcgg tcgatgaagc gctcgatcat ctccccccgc   6480
atgcggcgca tggtctcggt gacggcgcgg ccgttctccc gggggcgcag ctcgaagacg   6540
ccgcctctca tctcgccgcg gggcgggcgg ccgtgaggta gcgagacggc gctgactatg   6600
catcttaaca attgctgtgt aggtacaccg ccgagggacc tgattgagtc cagatccacc   6660
ggatccgaaa acctttggag gaaagcgtct atccagtcgc agtcgcaagg taggctgagc   6720
accgtggcgg gcgggggcgg gtctggagag ttcctggcgg agatgctgct gatgatgtaa   6780
ttaaagtagg cggtcttgag aaggcggatg gtggacagga gcaccatgtc tttgggtccg   6840
gcctgttgga tgcggaggcg gtcggccatg ccccaggcct cgttctgaca ccggcgcagg   6900
tctttgtagt agtcttgcat gagtctttcc accggcacct cttctccttc ctcttctcca   6960
tctcgccggt ggtttctcgc gccgcccatg cgcgtgaccc caaagcccct gagcggctgc   7020
agcagggcca ggtcggcgac cacgcgctcg gccaagatgg cctgctgcac ctgagtgagg   7080
gtcctctcga agtcatccat gtccacgaag cggtggtagg cgcccgtgtt gatggtgtag   7140
gtgcagttgg ccatgacgga ccagttgacg gtctggtgtc ccggctgcga gagctccgtg   7200
taccgcaggc gcgagaaggc gcgggaatcg aacacgtagt cgttgcaagt ccgcaccaga   7260
```

-continued

```
tactggtagc ccaccaggaa gtgcggcgga ggttggcgat agaggggcca gcgctgggtg   7320
gcgggggcgc cgggcgccag gttttccagc atgaggcggt ggtatccgta gatgtacctg   7380
gacatccagg tgatgccggc ggcggtggtg gtggcgcgcg cgtagtcgcg gacccggttc   7440
cagatgtttc gcaggggcga gaagtgttcc atggtcggca cgctctggcc ggtgaggcgc   7500
gcgcagtcgt tgacgctcta tacacacaca aaaacgaaag cgtttacagg gctttcgttc   7560
tgtagcctgg aggaaagtaa atgggttggg ttgcggtgtg ccccggttcg agaccaagct   7620
gagctcggcc ggctgaagcc gcagctaacg tggtattggc agtcccgtct cgacccaggc   7680
cctgtatcct ccaggatacg gtcgagagcc cttttgcttt cttggccaag cgcccgtggc   7740
gcgatctggg atagatggtc gcgatgagag gacaaaagcg gctcgcttcc gtagtctgga   7800
gaaacaatcg ccagggttgc gttgcggcgt accccggttc gagcccctat ggcggcttga   7860
atcggccgga accgcggcta acgagggccg tggcagcccc gtcctcagga ccccgccagc   7920
cgacttctcc agttacggga gcgagcccct tttgtttttt attttttaga tgcatcccgt   7980
gctgcggcag atgcgcccct cgccccggcc cgatcagcag cagcaacagc aggcatgcag   8040
acccccctct cccctttccg ccccggtcac cacggccgcg gcggccgtgt cgggcgcggg   8100
gggcgcgctg gagtcagatg agccaccgcg gcggcgacct aggcagtatc tggacttgga   8160
agagggcgag ggactggcgc ggctgggggc gaactctcca gagcgccacc cgcgggtgca   8220
gttgaaaagg gacgcgcgcg aggcgtacct gccgcggcag aacctgtttc gcgaccgcgg   8280
gggcgaggag cccgaggaga tgcgagactg caggttccaa gcggggcgcg agctgcggcg   8340
cgggctggac agacagcgcc tgctgcgcga ggaggacttt gagcccgaca cgcagacggg   8400
catcagcccc gcgcgcgcgc acgtagccgc ggccgacctg gtgaccgcct acgagcagac   8460
ggtgaaccag gagcgcaact tccaaaagag cttcaacaac cacgtgcgca cgctggtggc   8520
gcgcgaggag gtgaccctgg gtctcatgca tctgtgggac ctggtggagg cgatcgtgca   8580
gaaccccagc agcaagcccc tgaccgcgca gctgttcctg gtggtgcagc acagcaggga   8640
caacgaggcc ttcagggagg cgctgctgaa catcaccgag ccggaggggc gctggctcct   8700
ggacctgata aacatcctgc agagcatagt ggtgcaggag cgcagcctga gcctggccga   8760
gaaggtggcg gccatcaact actctatgct gagcctgggc aagttctacg cccgcaagat   8820
ctacaagacc ccctacgtgc ccatagacaa ggaggtgaag atagacagct tctacatgcg   8880
catggcgctg aaggtgctga ccctgagcga cgacctggga gtgtaccgca acgagcgcat   8940
ccacaaggcc gtgagcgcca gccggcggcg cgagctgagc gaccgcgagc tgatgcacag   9000
tctgcagcgc gcgctgaccg gcgcgggcga gggcgacagg gaggtcgagt cctacttcga   9060
catgggggcc gacctgcact ggcagccgag ccgccgcgcc ctggaggcgg cgggggcgta   9120
cggcggcccc ctggcggccg atgaccagga agaggaggac tatgagctag aggagggcga   9180
gtacctggag gactgacctg gctggtggtg ttttggtata gatgcaagat ccgaacgtgg   9240
cggacccggc ggtccgggcg gcgctgcaaa gccagccgtc cggcattaac tcctctgacg   9300
actgggccgc ggccatgggt cgcatcatgg ccctgaccgc gcgcaacccc gaggctttca   9360
ggcagcagcc tcaggccaac cggctggcgg ccatcttgga agcggtagtg cccgcgcgct   9420
ccaaccccac ccacgagaag gtgctggcca tagtcaacgc gctggcggag agcagggcca   9480
tccgcgcgga cgaggccgga ctggtgtacg atgcgctgct gcagcgggtg gcgcggtaca   9540
acagcggcaa cgtgcagacc aacctggacc gcctggtgac ggacgtgcgc gaggccgtgg   9600
cgcagcgcga gcgcttgcat caggacggta acctgggctc gctggtggcg ctaaacgcct   9660
```

```
tcctcagcac ccagccggcc aacgtaccgc gggggcagga ggactacacc aactttttga    9720
gcgcgctgcg gctgatggtg accgaggtcc ctcagagcga ggtgtaccag tcggggcccg    9780
actacttctt ccagaccagc agacagggct tgcaaaccgt gaacctgagc caggctttca    9840
agaacctgcg gggctgtgg ggagtgaagg cgcccaccgg cgaccgggct acggtgtcca    9900
gcctgctaac ccccaactcg cgcctgctgc tgctgctgat cgcgcccttc acggacagcg    9960
ggagcgtctc gcgggagacc tatctgggcc acctgctgac gctgtaccgc gaggccatcg   10020
ggcaggcgca ggtggacgag cacaccttcc aagagatcac cagcgtgagc cacgcgctgg   10080
ggcaggagga cacgggcagc ctgcaggcga ccctgaacta cctgctgacc aacaggcggc   10140
agaagattcc cacgctgcac agcctgaccc aggaggagga gcgcatcttg cgctacgtgc   10200
agcagagcgt gagcctgaac ctgatgcgcg acggcgtgac gcccagcgtg gcgctggaca   10260
tgaccgcgcg caacatggaa ccgggcatgt acgcctccca ccggccgttc atcaaccgcc   10320
tgatggacta cttgcatcgg gcggcggccg tgaaccccga gtacttcact aatgccattc   10380
tgaatcccca ctggatgccc cctccgggtt tctacaacgg ggactttgag gtgcccgagg   10440
tcaacgacgg gttcctctgg gatgacatgg atgacagtgt gttctcaccc aacccgctgc   10500
gcgccgcgtc tctgcgattg aaggagggct ctgacaggga aggaccgaga agtctggcct   10560
cctccctggc tctgggagcg gtgggcgcca cgggcgcggc ggcgcggggc agtagcccct   10620
tccccagcct ggcagactct ctgaacagcg ggcgggtgag caggccccgc ttgctaggcg   10680
aggaggagta tctgaacaac tccctgctgc agcccgcgag ggacaagaac gctcagcggc   10740
agcagtttcc caacaatggg atagagagcc tggtggacaa gatgtccaga tggaagacgt   10800
atgcgcagga gtacaaggag tgggaggacc gccagccgcg gcccttgccg cccccctaggc   10860
agcgctggca gcggcgcgcg tccaaccgcc gctggaggca ggggcccgag gacgatgatg   10920
actctgcaga tgacagcagc gtgttggacc tgggcgggag cgggaacccc ttttcgcacc   10980
tgcgcccacg cctgggcaag atgttttaaa agaaaaaaaa aaaataaaac tcaccaaggc   11040
catggcgacg agcgttggtt ttttgttccc ttccttagta tgcggcgcgc ggcgatgttc   11100
gaggaggggc ctccccccctc ttacgagagc gcgatgggga tttctcctgc ggcgcccctg   11160
cagcctccct acgtgcctcc tcggtacctg caacctacag ggggggagaaa tagcatctgt   11220
tactctgagc tgcagcccct gtacgatacc accagactgt acctggtgga caacaagtcc   11280
gcggacgtgg cctccctgaa ctaccagaac gaccacagcg attttttgac cacggtgatc   11340
caaaacaacg acttcacccc aaccgaggcc agcactcaga ccataaacct ggataacagg   11400
tcgaactggg gcggcgacct gaagaccatc ttgcacacca acatgcccaa cgtgaacgag   11460
ttcatgttca ccaactcttt taaggcgcgg gtgatggtgg cgcgcgagca gggggaggcg   11520
aagtacgagt gggtggactt cacgctgccc gagggcaact actcagagac catgactctc   11580
gacctgatga acaatgcgat cgtggaacac tatctgaaag tgggcaggca gaacggggtg   11640
aaggaaagcg atatcggggt caagtttgac accagaaact tccgtctggg ctgggacccc   11700
gtgaccgggc tggtcatgcc gggggtctac accaacgagg cctttcatcc cgacatagtg   11760
cttctgcccg gctgtggggt ggacttcacc cagagccggc tgagcaacct gctgggcatt   11820
cgcaagcggc agcctttcca ggagggtttc aagatcacct atgaggatct gaagggggggc   11880
aacattcccg cgctccttga tctggacgcc tacgaggaga gcttgaaacc cgaggagagc   11940
gctggcgaca gcggcgagag tggcgaggag caagccggcg gcggtggcgg cgcgtcggta   12000
```

```
gaaaacgaaa gtacgcccgc agtggcggcg gacgctgcgg aggtcgagcc ggaggccatg  12060
cagcaggacg cagaggaggg cgcacaggag ggcgcgcaga aggacatgaa cgatggggag  12120
atcaggggag acacattcgc cacccggggc gaagaaaaag aggcagaggc ggcggcggcg  12180
gcgacggcgg aggccgaaac cgaggttgag gcagaggcag agcccgagac cgaagttatg  12240
gaagacatga atgatggaga acgtaggggc gacacgttcg ccacccgggg cgaagagaag  12300
gcggcggagg cagaagccgc ggctgaggag gcggctgcgg ctgcggccaa gactgaggct  12360
gcggctaagg ctgaggtcga agccaatgtt gcggttgagg ctcaggctga ggaggaggcg  12420
gcggctgaag cagttaagga aaaggcccag gcagagcagg aagagaaaaa acctgtcatt  12480
caacctctaa aagaagatag caaaaagcgc agttacaacg tcatcgaggg cagcaccttt  12540
acccagtacc gcagctggta cctggcgtac aactacggcg acccggtcaa gggggtgcgc  12600
tcgtggaccc tgctctgcac gccggacgtc acctgcggct ccgagcagat gtactggtcg  12660
ctgccgaaca tgatgcaaga cccggtgacc ttccgctcca cgcggcaggt tagcaacttc  12720
ccggtggtgg gcgccgaact gctgcccgtg cactccaaga gtttttacaa cgagcaggcc  12780
gtctactccc agctgatccg ccaggccacc tctctgaccc acgtgttcaa tcgctttccc  12840
gagaaccaga ttttggcgcg cccgccggcc cccaccatca ccaccgtgag tgaaaacgtt  12900
cctgccctca cagatcacgg gacgctaccg ctgcgcaaca gcatctcagg agtccagcga  12960
gtgaccatta ctgacgccag acgccggacc tgcccctacg tttacaaggc cttgggcata  13020
gtctcgccgc gcgtcctctc cagtcgcact ttttaaaaca catctaccca cacgttccaa  13080
aatcatgtcc gtactcatct cacccagcaa caacaccggc tgggggctgc gcgcgcccag  13140
caagatgttt ggaggggcga ggaagcgctc cgaccagcac cctgtgcgcg tgcgcggcca  13200
ctaccgcgcg ccctggggag cgcacaagcg cgggcgcaca gggcgcacca ctgtggacga  13260
cgtcattgac tccgtagtgg agcaagcgcg ccactacaca cccggcgcgc cgaccgcccc  13320
cgccgtgtcc accgtggacc aggcgatcga aagcgtggta cagggcgcgc ggcactatgc  13380
caaccttaaa agtcgccgcc gccgcgtggc ccgccgccat cgccggagac cccgggccac  13440
cgccgccgcg cgccttacta aggctctgct caggcgcgcc aggcgaactg gccaccgggc  13500
cgccatgagg gccgcacggc gggctgccgc tgccgcaagc gccgtggccc cgcgggcacg  13560
aaggcgcgcg gccgccgccg ccgccgccgc catttccagc ttggcctcga cgcggcgcgg  13620
taacatatac tgggtgcgcg actcggtaac cggcacgcgg gtacccgtgc gctttcgccc  13680
cccgcggaat tagcacaaga caacatacac actgagtctc ctgctgttgt gtatcccagc  13740
ggcgaccgtc agcagcggcg acatgtccaa gcgcaaaatt aaagaagaga tgctccaggt  13800
catcgcgccg gagatctatg ggccccccgaa gaaggaggag gatgattaca agccccgcaa  13860
gctaaagcgg gtcaaaaaga aaaagaaaga tgatgatgat gacgaggcgg tggagtttgt  13920
ccgccgcatg gcacccaggc gccccgtgca gtggaagggc cggcgcgtgc agcgcgtttt  13980
gcgccccggc accgcggtgg tcttcacgcc cggcgagcgc tccacgcgca ctttcaagcg  14040
ggtgtacgat gaggtgtacg gcgacgagga cctgttggag caggccaacc agcgctttgg  14100
ggagtttgca tatgggaaac ggccccgcga gagtctaaaa gaggacctgc tggcgctacc  14160
gctggacgag ggcaatccca ccccgagtct gaagccggta accctgcaac aggtgctgcc  14220
tttgagcgcg cccagcgagc ataagcgagg gttgaagcgc gaaggcgggg acctggcgcc  14280
caccgtgcag ttgatggtgc ccaagcggca gaagctggag gacgtgctgg agaaaatgaa  14340
agtagagccc gggatccagc ccgagatcaa ggtccgcccc atcaagcagg tggcgcccgg  14400
```

```
cgtgggagtc cagaccgtgg acgttaggat tcccacggag gagatggaaa cccaaaccgc  14460
cactccctct tcggcggcca gcgccaccac cggcaccgct tcggtagagg tgcagacgga  14520
cccctggcta cccgccaccg ctgttgccgc cgccgccccc cgttcgcgcg ggcgcaagag  14580
aaattatcca gcggccagcg cgctcatgcc ccagtacgca ctgcatccat ccatcgcgcc  14640
cacccccggc taccgcgggt actcgtaccg cccgcgcaga tcagccggca ctcgcggccg  14700
ccgccgccgt gcgaccacaa ccagccgccg ccgtcgccgc cgccgccagc cagtgctgac  14760
ccccgtgtct gtaaggaagg tggctcgctc ggggagcacg ctggtggtgc ccagagcgcg  14820
ctaccacccc agcatcgttt aaagccggtc tctgtatggt tcttgcagat atggccctca  14880
cttgtcgcct ccgcttcccg gtgccgggat accgaggaag aactcaccgc cgcagaggca  14940
tggcgggcag cggtctccgc ggcggccgtc gccatcgccg gcgcgcaaaa agcaggcgca  15000
tgcgcggcgg tgtgctgcct ctgctaatcc cgctaatcgc cgcggcgatc ggtgccgtac  15060
ccgggatcgc ctccgtggcc ctgcaggcgt cccagaaacg ttgactcttg caaccttgca  15120
agcttgcatt ttttggagga aaaataaaaa aagtctagac tctcacgctc gcttggtcct  15180
gtgactattt tgtagaaaaa agatggaaga catcaacttt gcgtcgctgg ccccgcgtca  15240
cggctcgcgc ccgttcatgg gagactggac agatatcggc accagcaata tgagcggtgg  15300
cgccttcagc tggggcagtc tgtggagcgg ccttaaaaat tttggttcca ccattaagaa  15360
ctatggcaac aaagcgtgga acagcagcac gggccagatg ctgagagaca agttgaaaga  15420
gcagaacttc caggagaagg tggcgcaggg cctggcctct ggcatcagcg gggtggtgga  15480
catagctaac caggccgtgc agaaaaagat aaacagtcat ctggaccccc gtcctcaggt  15540
ggaggaaatg cctccagcga tggagacggt gtctcccgag ggcaaaggcg aaaagcgccc  15600
gcggcccgac agagaagaga ccctggtgtc acacaccgag gagccgccct cttacgagga  15660
ggcagtcaag gccggcctgc ccaccactcg ccccatagcc cccatggcca ccggtgtggt  15720
gggccacagg caacacactc ccgcaacact agatctgccc ccgccgtccg agccgccgcg  15780
ccagccaaag gcggcgacgg tgcccgctcc ctccacttcc gccgccaaca gagtgcccct  15840
gcgccgcgcc gcgagcggcc cccgggcctc gcgagttagc ggcaactggc agagcacact  15900
gaacagcatc gtgggcctgg gagtgaggag tgtgaagcgc cgccgttgct actgaatgag  15960
caagctagct aacgtgttgt atgtgtgtat gcgtcctatg tcgccgccag aggagctgtt  16020
gagccgccgg cgccgtctgc actccagcga atttcaagat ggcgacccca tcgatgatgc  16080
ctcagtggtc gtacatgcac atctcgggcc aggacgcttc ggagtacctg agccccgggc  16140
tggtgcagtt cgcccgcgcc acagacacct acttcaacat gagtaacaag ttcaggaacc  16200
ccactgtggc gcccacccac gatgtgacca cggaccggtc gcagcgcctg acgctgcggt  16260
tcatccccgt ggatcgggag gacaccgcct actcttacaa ggcgcggttc acgctggccg  16320
tgggcgacaa ccgcgtgctg gacatggcct ccacttactt tgacatcagg ggggtgctgg  16380
acaggggccc caccttcaag ccctactcgg gtactgccta caactccctg gcccccaagg  16440
gcgctcccaa ttcttgcgag tgggaacaag aggaaaatca ggtggtcgct gcagatgatg  16500
aacttgaaga tgaagaagcg caagctcaag aggacgcccc agctaaaaaa attcatgtat  16560
atgcccaggc gcctcttgct ggcgaaaaga ttaccaagga tggtttgcaa ataggtactg  16620
aagttgtagg agatacatct aaggacactt ttgcagacaa aacattccaa cccgaacctc  16680
agataggcga gtctcagtgg aacgaggctg atgccacagt agcaggaggc agagtcttga  16740
```

```
aaaaaaccac ccctatgaga ccttgctatg gatcctatgc caggcctaca aatgccaacg  16800
ggggtcaagg aattatggtt gccaatgaac aaggagtgtt ggagtctaaa gtggagatgc  16860
aattttttc taacactaca acccttaatg cgcgggatgg agctggcaat cccgaaccaa  16920
aggtggtgtt gtacagtgaa gatgtccact tggaatctcc tgacactcat ttgtcttaca  16980
agcccaaaaa ggatgatgtt aatgctaaaa ttatgttggg tcagcaagct atggctaaca  17040
ggcccaacct cattgctttt agagataatt tcattggact catgtactac aacagcactg  17100
gtaacatggg agtgctggcg ggtcaggcct ctcagttgaa tgccgtggtg gacctgcagg  17160
atagaaacac agaactgtca tatcagctta tgcttgattc cattggggat agatccagat  17220
acttctccat gtggaaccag gcagtggata gctatgaccc agatgtcaga atcattgaaa  17280
accatggtgt cgaggacgag ctacccaact actgcttccc tctgggcggc ataggaatta  17340
ctgatactta tcaagggatc aaaaatacca atggcaatgg tcagtggacc aaagatgatc  17400
agttcgcgga ccgtaatgaa ataggggtgg gaaacaactt cgccatggag atcaacatcc  17460
aggccaacct ctggaggaac ttcctctatg cgaacgtggg gctctacctg ccagacaagc  17520
tcaagtacaa ccccaccaac gtggacatct ctgacaaccc caacacctat gactacatga  17580
acaagcgtgt ggtggctccc ggcctggtgg actgctttgt caatgtggga gccaggtggt  17640
ccctggacta catggacaac gtcaacccct tcaaccacca ccgcaatgcg ggtctgcgct  17700
accgctccat gatcctgggc aacgggcgct acgtgccctt ccacattcag gtgccccaga  17760
agttctttgc catcaagaac ctcctcctcc tgccgggctc ctacacttac gagtggaact  17820
tcaggaagga tgtcaacatg gtcctgcaga gctctctggg caatgacctt agggtggacg  17880
gggccagcat caagtttgac agcgtcaccc tctatgctac cttcttcccc atggctcaca  17940
acaccgcctc cacgctcgag gccatgctga ggaacgacac caacgaccag tccttcaatg  18000
actacctctc tggggccaac atgctctacc ccatccccgc caaggccacc aacgtgccca  18060
tctccattcc ctctcgcaac tgggccgcct tcagaggctg ggcctttacc cgccttaaga  18120
ccaaggaaac cccctccctg ggctcgggtt ttgaccccta ctttgtctac tcgggatcca  18180
tcccctacct ggatggcacc ttctacctca accacacttt taagaagata tccatcatgt  18240
atgactcctc cgtcagctgg ccgggcaatg accgcctgct cacccccaat gagttcgagg  18300
tcaagcgcgc cgtggacggc gagggctaca acgtggccca gtgcaacatg accaaggact  18360
ggttcctggt gcagatgctg gccaactaca acataggcta ccagggcttc tacatcccag  18420
agagctacaa ggacaggatg tactccttct tcagaaattt ccaacccatg agcaggcagg  18480
tggtggacga gaccaaatac aaggactatc aggccattgg catcactcac cagcacaaca  18540
actcgggatt cgtgggctac ctggctccca ccatgcgcga ggggcaggcc taccccgcca  18600
acttccccta cccgttgata ggcaagaccg cggtcgacag cgtcacccag aaaaagttcc  18660
tctgcgaccg caccctctgg cgcatcccct tctctagcaa cttcatgtcc atgggtgcgc  18720
tcacggacct gggccagaac ctgctctatg ccaactccgc ccatgcgctg gacatgactt  18780
ttgaggtgga ccccatggac gagcccaccc ttctctatat tgtgtttgaa gtgttcgacg  18840
tggtcagagt gcaccagccg caccgcggtg tcatcgagac cgtgtacctg cgcacgccct  18900
tctcggccgg caacgccacc acctaaggag acagcgccgc cgcctgcatg acgggttcca  18960
ccgagcaaga gctcagggcc atcgccagag acctgggatg cggaccctat tttttgggca  19020
cctatgacaa acgcttcccg ggcttcatct cccgagacaa gctcgcctgc gccatcgtca  19080
acacggccgc gcgcgagacc gggggcgtgc actggctggc ctttggctgg gacccgcgct  19140
```

```
ccaaaacctg ctacctcttc gacccctttg gcttctccga tcagcgcctc agacagatct  19200
atgagtttga gtacgagggg ctgctgcgcc gcagcgcgct tgcctcctcg cccgaccgct  19260
gcatcaccct tgagaagtcc accgagaccg tgcaggggcc ccactcggcc gcctgcggtc  19320
tcttctgctg catgtttttg cacgcctttg tgcgctggcc ccagagtccc atggatcgca  19380
accccaccat gaacttgctc aagggagtgc ccaacgccat gctccagagc cccccaggtcc  19440
agcccaccct gcgccacaac caggaacagc tctaccgctt cctggagcgc cactccccct  19500
acttccgcag tcacagcgcg cacatccggg gggccacctc tttctgccac ttgcaacaaa  19560
acatgcaaga cggaaaatga tgtacagctc gctttttaat aaatgtaaag actgtgcact  19620
ttatttatac acgggctctt tctggttatt tattcaacac cgccgtcgcc atctagaaat  19680
cgaaagggtt ctgccgcgcg tcgccgtgcg ccacgggcag agacacgttg cgatactgga  19740
agcggctcgc ccacttgaac tcgggcacca ccatgcgggg cagtggctcc tcggggaagt  19800
tctcgcccca cagggtgcgg gtcagctgca gcgcgctcag gaggtcggga gccgagatct  19860
tgaagtcgca gttggggccg gaaccctgcg cgcgcgagtt gcggtacacg gggttgcagc  19920
actggaacac cagcagggcc ggattacgca cgctggccag caggctctcg tcgctgatca  19980
tgtcgctgtc cagatcctcc gcgttgctca gggcgaatgg ggtcatcttg cagacctgcc  20040
tgcccaggaa aggcggcagc ccgggcttgc cgttgcagtc gcagcgcagg ggcatcagca  20100
ggtgcccgtg gcccgtctgc gcctgcgggt acagcgcgcg catgaaggct tcgatctgcc  20160
tgaaagccac ctgcgtcttg gctccctccg aaaagaacat cccacaggac ttgctggaga  20220
actggttcgc gggacagctg gcatcgtgca ggcagcagcg cgcgtcggtg ttggcgatct  20280
gcaccacgtt gcgaccccac cggttcttca ctatcttggc cttggaagcc tgctccttca  20340
gcgcgcgctg gccgttctcg ctggtcacat ccatctctat cacctgctcc ttgttgatca  20400
tgtttgtccc gtgcagacac ttcaggtcgc cctccgtctg ggtgcagcgg tgctcccaca  20460
gcgcgcaacc ggtgggctcc caatttttgt gggtcacccc cgcgtaggcc tgcaggtagg  20520
cctgcaagaa gcgccccatc atggccacaa aggtcttctg gctcgtaaag gtcagctgca  20580
ggccgcgatg ctcttcgttc agccaggtct tgcagatggc ggccagcgcc tcggtctgct  20640
cgggcagcat cctaaaattt gtcttcaggt cgttatccac gtggtacttg tccatcatgg  20700
cgcgcgccgc ctccatgccc ttctcccagg cggacaccat gggcaggctt agggggttta  20760
tcacttccac cggcgaggac accgtacttt cgatttcttc ttcctccccc tcttcccggc  20820
gcgcgcccac gctgctgcgc gctctcaccg cctgcaccaa ggggtcgtct tcaggcaagc  20880
gccgcaccga gcgcttgccg cccttgacct gcttaatcag caccggcggg ttgctgaagc  20940
ccaccatggt cagctccgcc tgctcttctt cgtcttcgct gtctaccact atctctgggg  21000
aagggcttct ccgctctgcg gcggtgcgct tctttttttt cttgggagca gccgtgacgg  21060
agtccgccac ggcgacggag gtcgagggcg tggggctggg ggtgcgcggt accagggcct  21120
cgtcgccctc ggactcttcc tctgactcca ggcggcggcg gagacgcttc tttgggggcg  21180
cgcgcgtcag cggcggcgga gacggggacg gggacgggga cgggacgccc tccacagggg  21240
gtggtcttcg cgcagacccg cggccgcgct cgggggtctt ttcgagctgg tcttggtccc  21300
gactggccat tgtatcctcc tcctcctagg cagagagaca taaggagtct atcatgcaag  21360
tcgagaagga ggagagctta accacccccct ctgagaccgc cgatgcgccc gccgtcgccg  21420
tcgcccccgc tgccgccgac gcgcccgcca caccgagcga cacccccgcg gaccccccag  21480
```

```
ccgacgcacc cctgttcgag gaagcggccg tggagcagga cccgggcttt gtctcggcag  21540
aggaggattt gcgagaggag gaggataagg agaagaagcc ctcagtgcca aaagatgata  21600
aagagcaaga cgagcacgac gcagatgcac accagggtga agtcgggcgg ggggacggag  21660
ggcatgacgg cgccgactac ctagacgaag ggaacgacgt gctcttgaag cacctgcatc  21720
gtcagtgcgc catcgtttgc gacgctctgc aggagcgcag cgaagtgccc ctcagcgtgg  21780
cggaggtcag ccacgcctac gagctcagcc tcttctcccc ccgggtgccc ccccgccgcc  21840
gcgaaaacgg cacatgcgag cccaacccgc gcctcaactt ctaccccgcc tttgtggtgc  21900
ccgaggtcct ggccacctat cacatcttct ttcaaaattg caagatcccc ctctcgtgcc  21960
gcgccaaccg tagccgcgcc gataagatgc tggccctgcg ccagggcgac cacatacctg  22020
atatcgccgc tttggaagat gtgccaaaga tcttcgaggg tctgggtcgc aacgagaagc  22080
gggcagcaaa ctctctgcaa caggaaaaca gcgaaaatga gagtcacacc ggggtactgg  22140
tggagctcga gggcgacaac gcccgcctgg cggtggtcaa gcgcagcatc gaggtcaccc  22200
actttgccta ccccgcgctc aacctgcccc ccaaagtcat gaacgcggcc atggacgggc  22260
tgatcatgcg ccgcggccgg cccctcgctc cagatgcaaa cttgcatgag gagaccgagg  22320
acggccagcc cgtggtcagc gacgagcagc tggcgcgctg gctggagacc gcggaccccg  22380
ccgaactgga ggagcggcgc aagatgatga tggccgcggt gctggtcacc gtagagctgg  22440
agtgtctgca gcgcttcttc ggcgaccccg agatgcagag aaaggtcgag gagaccctgc  22500
actacacctt ccgccagggc tacgtgcgcc aggcttgcaa gatctccaac gtggagctca  22560
gcaacctggt gtcctacctg ggcatcttgc atgagaaccg cctcgggcag agcgtgctgc  22620
actccaccct gcgcggggag gcgcgccgcg actacgtgcg cgactgcgtt tacctcttcc  22680
tctgctacac ctggcagacg gccatggggg tctggcagca gtgcctggag gagcgcaacc  22740
tcaaggagct ggagaagctc ctgcagcgcg cgctcaaaga cctctggacg ggctacaacg  22800
agcgctcggt ggccgccgcg ctggccgacc tcatcttccc cgagcgcctg ctcaaaaccc  22860
tccagcaggg gctgcccgac ttcaccagcc aaagcatgtt gcaaaacttc aggaacttta  22920
tcctggagcg ttctggcatc ctacccgcca cctgctgcgc cctgcccagc gactttgtcc  22980
ccctcgtgta ccgcgagtgc cccccgccgc tgtggggtca ctgctacctg ttccaactgg  23040
ccaactacct gtcctaccac gcggacctca tggaggactc cagcggcgag gggctcatgg  23100
agtgccactg ccgctgcaac ctctgcacgc cccaccgctc cctggtctgc aacacccaac  23160
tgctcagcga gagtcagatt atcggtacct tcgagctaca gggtccgtcc tcctcagacg  23220
agaagtccgc ggctccgggg ctaaaactca ctccggggct gtggacttcc gcctacctgc  23280
gcaaatttgt acctgaagac taccacgccc acgagatcag gttttacgaa gaccaatccc  23340
gcccgcccaa ggcggagctg accgcctgcg tcatcaccca gggcgagatc ctaggccaat  23400
tgcaagccat ccaaaaagcc cgccaagatt ttttgctgag aaagggtcgg ggggtgtatc  23460
tggaccccca gtcgggtgag gagctcaacc cggttccccc gctgccgccg ccgcgggacc  23520
ttgcttccca ggataagcat cgccatggct cccagaaaga agcagcagcg gccgccactg  23580
ccgccacccc acatgctgga ggaagaggag gaatactggg acagtcaggc agaggaggtt  23640
tcggacgagg aggagccgga gacggagatg gaagagtggg aggaggacag cttagacgag  23700
gaggcttccg aagccgaaga ggcagacgca acaccgtcac cctcggccgc agcccccctcg  23760
caggcgcccc cgaagtccgc tcccagcatc agcagcaaca gcagcgctat aacctccgct  23820
cctccaccgc cgcgacccac ggccgaccgc agacccaacc gtagatggga caccaccgga  23880
```

```
accggggccg gtaagtcctc cgggagaggc aagcaagcgc agcgccaagg ctaccgctcg  23940
tggcgcgctc acaagaacgc catagtcgct tgcttgcaag actgcggggg gaacatctcc  24000
ttcgcccgcc gcttcctgct cttccaccac ggtgtggcct tcccccgtaa cgtcctgcat  24060
tactaccgtc atctctacag cccctactgc ggcggcagtg agccagagac ggtcggcggc  24120
ggcggcggcg cccgtttcgg cgcctaggaa gacccagggc aagacttcag ccaagaaact  24180
cgcggcggcc gcggcgaacg cggtcgcggg ggccctgcgc ctgacggtga acgaacccct  24240
gtcgacccgc gaactgagaa accgaatctt ccccactctc tatgccatct tccagcagag  24300
cagagggcag gatcaggaac tgaaagtaaa aaacaggtct ctgcgctccc tcacccgcag  24360
ctgtctgtat cacaagagcg aagaccagct tcggcgcacg ctggaggacg ctgaggcact  24420
cttcagcaaa tactgcgcgc tcactcttaa ggactagctc cgcgcccttc tcgaatttag  24480
gcgggaacgc ctacgtcatc gcagcgccgc cgtcatgagc aaggacattc ccacgccata  24540
catgtggagc tatcagccgc agatgggact cgcggcgggc gcctcccaag actactccac  24600
ccgcatgaac tggctcagtg ccggcccaca catgatctca caggttaatg atatccgcac  24660
ccatcgaaac caaatattgg tggagcaggc ggcaattacc accacgcccc gcaataatcc  24720
caaccccagg gagtggcccg cgtccctggt gtatcaggaa attcccggcc ccaccaccgt  24780
actacttccg cgtgattccc aggccgaagt ccaaatgact aactcagggg cgcagctcgc  24840
gggcggctgt cgtcacaggg tgcggcctcc tcgccagggt ataactcacc tggagatccg  24900
aggcagaggt attcagctca acgacgagtc ggtgagctcc tcgctcggtc taagacctga  24960
cgggaccttc cagatagccg gagccggccg atcttccttc acgccccgcc aggcgtacct  25020
gactctgcag agctcgtcct cggcgccgcg ctcgggcggc atcgggactc tccagttcgt  25080
gcaggagttt gtgccctcgg tctacttcaa cccettctcg ggctctcccg gtcgctaccc  25140
ggaccagttc atctcgaact ttgacgccgc gagggactcg gtggacggct acgactgaat  25200
gtcgggtgga cccggtgcag agcaacttcg cctgaagcac ctcgaccact gccgccgccc  25260
tcagtgcttt gcccgctgtc agaccggtga gttccagtac ttttccctgc ccgactcgca  25320
cccggacggc ccggcgcacg ggtgcgcttt tttcatcccg agtcaggtgc gctctaccct  25380
aatcagggag tttaccgccc gtcccctact ggcggagttg gaaaaggggc cttctatcct  25440
aaccattgcc tgcatctgct ctaaccctgg attgcaccaa gatctttgct gtcatttgtg  25500
tgctgagtat aataaaggct gagatcagaa tctactcggg ctcctgtcgc catcctgtca  25560
acgccaccgt ccaagcccgg cccgatcagc ccgaggtgaa cctcacctgc ggtctgcacc  25620
ggcgcctgag gaaataccta gcttggtact acaacagcac tccctttgtg gtttacaaca  25680
gctttgacca ggacggggtc tcactgaggg ataacctctc gaacctgagc tactccatca  25740
ggaagaacag caccctcgag ctacttcctc cttacctgcc cgggacttac cagtgtgtca  25800
ccggtccctg cacccacacc cacctgttga tcgtaaacga ctctcttccg agaacagacc  25860
tcaataactc ctcttcgcag ttccccagaa caggaggtga gctcaggaaa ccccgggtaa  25920
agaagggtgg acaagagtta acacttgtgg ggtttctggt gtatgtgacg ctggtggtgg  25980
ctcttttgat taaggctttt ccttccatgt ctgaactctc cctcttttat gaacaactcg  26040
actagtgcta acgggaccct acccaacgaa tcgggattga atatcggtaa ccaggttgca  26100
gtttcacttt tgattacctt catagtcctc ttcctgctag tgctgtcgct tctgtgcctg  26160
cggatcgggg gctgctgcat ccacgtttat atctggtgct ggctgtttag aaggttcgga  26220
```

```
gaccatcgca ggtagaataa acatgctgct gcttaccctc tttgtcctgg cgctggccgc  26280
cagctgccaa gccttttccg aggctgactt tatagagccc cagtgtaacg tgacttttaa  26340
agcccatgca cagcgttgtc atactataat caaatgtgcc accgaacacg atgaatacct  26400
tatccagtat aaagataaat cacacaaagt ggcacttgtt gacatctgga aacccgaaga  26460
ccctttggaa tacaatgtga ccgttttcca gggtgacctc ttcaaaattt acaattacac  26520
tttcccattt gaccagatgt gtgactttgt catgtacatg gaaaagcagc acaagctgtg  26580
gcctccgact ccccagggct gtgtggaaaa tccaggctct ttctgcatga tctctctctg  26640
tgtaactgtg ctggcactaa tactcacgct tttgtatatc agatttaaat caaggcaaag  26700
cttcatcgat gaaaagaaaa tgccttaaac gctttcacgc ttgattgcta acaccgggtt  26760
tttatccgca gaatgattgg aatcacccta ctaatcacct ccctccttgc gattgcccat  26820
gggttggaac gaatcgaagc ccctgtgggg gccaatgtta ccctggtggg gcctgtcggc  26880
aatgctacat taatgtggga aaaatatact aaaaatcaat gggtctctta ctgcactaac  26940
aaaaacagcc acaagcccag agccatctgc gatgggcaaa atctaacctt gattgatgtt  27000
caaatgctgg atgcgggcta ctattatggg cagctgggta caatgattaa ttactggaga  27060
ccccacaaag attacatgct ccacgtagta aagggtcccc ttagcagccc acccactacc  27120
acctctacta cccccactac caccactact cccaccacca gcactgccgc ccagcctcct  27180
catagcagaa caaccacttt tatcaattcc aagtcccact ccccccacat tgccggcggg  27240
ccctccgcct cagactccga gaccaccgag atctgcttct gcaaatgctc tgacgccttt  27300
gctgaggatt tggaagacca cgaggaagat gagcatgact tcgcagatgc atgccaggca  27360
tcagaggcag aagcgctgcc ggtggccctc aaacagtatg cagaccccca caccaccccc  27420
aaccttcctc caccttccca gaagccaagt ttcctggggg aaaatgaaac tctgcctctc  27480
tccatactcg ctctgacatc tgttgctatg ttgaccgctc tgctggtgct tctatgctct  27540
atatgctacc tgatctgctg cagaaagaaa aaatctcacg gccatgctca ccagcccctc  27600
atgcacttcc cttaccctcc agagctgggc gaccacaaac tttaagtctg cagtaactat  27660
ctgcccatcc cttgtcagtc gacagcgatg agccccacta atctaacggc ctctggactt  27720
acaacatcgt ctcttaatga gaccaccgct cctcaagacc tgtacgatgg tgtctccgcg  27780
ctggttaacc agtgggatca cctgggcata tggtggctcc tcataggagc agtgaccctg  27840
tgcctaatcc tggtctggat catctgctgc atcaaaagca gaagacccag gcggcggccc  27900
atctacaggc cctttgtcat cacacctgaa gatgatgatg acaccacttc caggctgcag  27960
aggctaaagc agctactctt ctcttttaca gcatggtaaa ttgaatcatg cctcgcattt  28020
tcatctactt gtctctcctt ccactttttc tgggctcttc tacattggcc gctgtgtccc  28080
acatcgaggt agactgcctc acgcccttca cagtctacct gcttttcggc tttgtcatct  28140
gcacctttgt ctgcagcgtt atcactgtag tgatctgctt catacagtgc atcgactacg  28200
tctgcgtgcg ggtggcttac tttagacacc acccccagta tcgcaacagg gacatagcgg  28260
ctctcctaag acttgtttaa aatcatggcc aaattaactg tgattggtct tctgatcatc  28320
tgctgcgtcc tagccgcgat tgggactcaa gctcctacca ccaccagcgc tcccagaaag  28380
agacatgtat cctgcagctt caagcgtccc tggaatatac cccaatgctt tactgatgaa  28440
cctgaaatct ctttggcttg gtacttcagc gtcaccgccc ttcttatctt ctgcagtacg  28500
gttattgccc ttgccatcta cccttccctt gacctgggct ggaatgctgt caactctatg  28560
gaatatccca ccttcccaga accagacctg ccagacctgg ttgttctaaa cgcgtttcct  28620
```

```
cctcctgctc ccgttcaaaa tcagtttcgc cctccgtccc ccacgcccac tgaggtcagc  28680
tactttaatc taacaggcgg agatgactga aaacctagac ctagaaatgg acggtctctg  28740
cagcgagcaa cgcacactag agaggcgccg gcaaaaagag ctcgagcgtc ttaaacaaga  28800
gctccaagac gcggtggcca tacaccagtg caaaaaaggt gtcttctgtc tggtaaaaca  28860
ggccacgctc acctatgaaa aaacaggtga cacccaccgc ctaggataca agctgcccac  28920
acagcgccag aagttcgccc tcatgatagg cgaacaaccc atcaccgtga cccagcactc  28980
cgtggagaca gaaggctgca tacacgctcc ctgtaggggc gctgactgcc tctacacctt  29040
gatcaaaacc ctctgcggtc tcagagacct catccctttt aattaatcat aactgtaatc  29100
aataaaaaat cacttacttg aaatctgata gcaagcctct gtccaatttt ttcagcaaca  29160
cttccttccc ctcctcccaa ctctggtact ctaggcgcct cctagctgca aacttcctcc  29220
acagtctgaa gggaatgtca gattcctcct cctgtccctc cgcacccacg atcttcatgt  29280
tgttgcagat gaaacgcgcg agatcgtctg acgagacctt caaccccgtg taccccctacg  29340
ataccgagat cgctccgact tctgtccctt tccttacccc tccctttgtg tcatccgcag  29400
gaatgcaaga aaatccagct ggggtgctgt ccctgcactt gtcagagccc cttaccaccc  29460
acaatggggc cctgactcta aaaatggggg gcggcctgac cctggacaag gaagggaatc  29520
tcacttccca aaacatcacc agtgtcgatc cccctctcaa aaaaagcaag aacaacatca  29580
gccttcagac cgccgcaccc ctcgccgtca gctccggggc cctaacactt tttgccactc  29640
ccccccctagc ggtcagtggt gacaacctta ctgtgcagtc tcaggcccct ctcactttgg  29700
aagactcaaa actaactctg gccaccaaag gacccctaac tgtgtccgaa ggcaaacttg  29760
tcctagaaac agaggctccc ctgcatgcaa gtgacagcag cagcctgggc cttagcgtta  29820
cggccccact tagcattaac aatgacagcc taggactaga catgcaagcg cccattagct  29880
ctcgagatgg aaaactggct ctaacagtgg cggcccccct aactgtggtc gagggtatca  29940
atgctttggc agtagccaca ggtaagggta ttgggctaaa tgaaaccaac acacacctgc  30000
aggcaaaact ggtcgcaccc ctaggctttg ataccaacgg caacattaag ctaagcgttg  30060
caggaggcat gaggctaaac aataacacac tgatactaga tgtaaactac ccatttgagg  30120
ctcaaggcca actgagccta agagtgggct cgggcccact atatgtagat tctagtagtc  30180
ataacctaac cattagatgc cttaggggat tgtatataac atcttctaac aaccaaaacg  30240
gtctagaagc caacattaaa ctaacaagag gccttgtgta tgacggaaat gccatagcag  30300
ttaatgttgg caaagggctg gaatacagcc ctactgacac aacagaaaaa cctatacaga  30360
ctaaaatagg tctaggcatg gagtatgata ccgagggagc catgatgaca aaactaggct  30420
ctggactaag ctttgacaat tcaggagcca ttgtagtggg aaacaaaaat gatgacaggc  30480
ttactttgtg gaccacaccg gacccatcgc ccaactgtca gatctactct gaaaaagatg  30540
ctaaactaac cttggtactg actaaatgtg gcagtcaggt tgtaggcaca gtatctattg  30600
ccgctcttaa aggtagcctc gtgccaatca ctagtgcaat cagtgtggtt caggtatacc  30660
taaggtttga tgaaaatggg gtactaatga gtaactcttc acttaatggc gaatactgga  30720
attttagaaa cggagactca actaatggca caccatatac aaacgcagtg ggtttcatgc  30780
ctaatctact ggcctatcct aaaggtcaaa ctacaactgc aaaaagtaac attgtcagcc  30840
aggtctacat gaatggggac gatactaaac ccatgacatt tacaatcaac ttcaatggcc  30900
ttagtgaaac aggggatacc cctgttagta aatattccat gacattctca tggaggtggc  30960
```

```
caaatggaag ctacataggg cacaattttg taacaaactc ctttaccttc tcctacatcg  31020
cccaagaata aagaaagcac agagatgctt gtttttgatt tcaaaattgt gtgcttttat  31080
ttattttcag cttacagtat ttccagtagt cattcaaata aagcttaatc aaactgcatg  31140
agaacccttc cacatagctt aaattagcac cagtgcaaat ggagaaaaat caacatacct  31200
ttttttatcc agatatcaga gaactctagt ggtcagtttt cccccaccct cccagctcac  31260
agaatacaca gtcctttccc cccggctggc tttaaacaac actatctcat tggtaacaga  31320
catattctta ggtgtaataa tccacacggt ctcttggcgg gccaaacgct ggtcggtgat  31380
gttaataaac tccccaggca gctctttcaa gttcacgtcg ctgtccaact gctgaagcgc  31440
tcgcggctcc gactgcgcct ctagcggagg caacggcaac acccgatcct tgatcaaagg  31500
gaggtaaacg gtccctcgtg tagggacagt ggcgggataa tcgagatcgt gttgaacgta  31560
gagtcatgcc aaagggaaca gcggacgtac tcatatttcc tccagcagaa ccaagtgcgc  31620
gcgtggcagc tatccctgcg tcttctgtct cgccgcctgc cccgttcggt gtagtagttg  31680
taatacagcc actccctgag accgtcaagg cgctccctgg cgtccggatc tatgacaaca  31740
ccgtcctgca gcgccgccct gatgacatcc accaccgtag agtatgccaa gcccagccag  31800
gaaatgcatt cactttgaca gcgagagata ggaggagcgg ggagagatgg aagaaccatg  31860
atagtaaaga gaacttttat tccaatcgat cttctaagat atcaaagtgg agatctataa  31920
gatgacactg gtcttatcct ccgctgagtc gatcaaaaat aacagctaaa ccacaaacaa  31980
cacgattggt caaatgctcc acaagggtta cctgcagcag aaaattgcct cggaactcca  32040
ccgcaagcag aacagcaaag ccaccgcctc tatcgtgatc aagaataaaa accccacagc  32100
tatccactta cagacccaga tagttttcag ctctccatcg tgaaaaaaga tttacaagct  32160
cctcctttaa atcacctcca accaattgaa aaagttgaac cagaccgccc tccaccttca  32220
gtttcagcaa gcgtttaatt atgattgcaa aaattcaggc tcctcagaca cctgtataag  32280
attgagaagc ggaacgttaa catcgatgtt tcgctcgcgt aaatcacgcc tcagtgcaag  32340
cataatataa tcccacaggt cggagcggat cagcgaggac acctccccgc caggaaccaa  32400
ctcaacggag cctatgctga ttataatacg catattcgga gctatgctaa ccagcacggc  32460
ccccaaatag gcgtactgca taggcggcga caaaaagtga acagtttggg ttaaaaaatc  32520
aggcaaacac tcgcgcaaaa aagcaagaac atcataacca tgctcatgca aatagatgca  32580
agtaagctca ggaacaacca cagaaaaatg cacaattttt ctctcaaaca tgactgcgag  32640
ccctgcaaaa aataaaaaag aaacattaca caagagtagc ctgtcttacg atgggataga  32700
ctactctaac caacataaga cgggccacaa catcgcccgc gtggccataa aaaaaattgt  32760
ccgtgtgatt aaaaagaagc acagatagct ggccagtcat atccggagtc atcacgtgtg  32820
aacccgtgta gacccccggg ttggacacat cggccaaaga aagaaagcgg ccaatgtacc  32880
caggaggaat tataacacta agacgaagat acaacagaat aaccccatga gggggaataa  32940
caaagttagt aggtgaataa aaacgataaa cacccgaaac tccctcctgc gtaggcaaaa  33000
tagcaccctc cccttccaaa acaacatata gcgcttccac agcagccatg acaaaagact  33060
caaaacactc aaaagactca gtcttaccag gaaaataaaa gcactctcac agcaccagca  33120
ctaatcagag tgtgaagagg gccaagtgcc gaacgagtat atataggaat aaaaaatgac  33180
gtaaatgtgt aaaggtcaga aaacgcccag aaaaatacac agaccaacgc ccgaaacgaa  33240
aacccgcgaa aaaataccca gaacttcctc aacaaccgcc acttccgctt tctcacggta  33300
cgtcacttcc gcaagaaaag caaaactaca tttcccacat gtgtaaaaac gaaaccccgc  33360
```

-continued

```
cccttgtaac cgcccacaac ttacatcatc aaaacgtaaa ctcctacgtc acccgccccg  33420

cctctccccg cccacctcat tatcatattg gccacaatcc aaaataaggt atattattga  33480

tgatg                                                              33485
```

SIMIAN (GORILLA) ADENOVIRUS OR ADENOVIRAL VECTORS AND METHODS OF USE

CROSS-REFERENCE TO RELATED APPLICATIONS

This patent application is a continuation of U.S. patent application Ser. No. 15/482,991, filed on Apr. 10, 2017, now U.S. Pat. No. 10,059,962, which is a divisional of U.S. patent application Ser. No. 14/349,470, filed on Apr. 3, 2014, now U.S. Pat. No. 9,617,560, which was the U.S. national phase of International Patent Application No. PCT/US2012/059006, filed on Oct. 5, 2012, which claims the benefit of U.S. Provisional Patent Application No. 61/543,661, filed Oct. 5, 2011, which applications are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 415,921 Byte ASCII (Text) file named "740002_ST25.TXT," created on Jul. 23, 2018.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics,* 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine,* 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science,* 288 (5466): 669-672 (2000)), Lentivirus (see, e.g., Cartier et al., *Science,* 326: 818-823 (2009)), Adeno-associated virus (AAV) (see, e.g., Mease et al., *Journal of Rheumatology,* 27(4): 692-703 (2010)), Herpes Simplex Virus (HSV) (see, e.g., Goins et al., *Gene Ther.,* 16(4): 558-569 (2009)), Vaccinia Virus (see, e.g., Mayrhofer et al., *J. Virol.,* 83(10): 5192-5203 (2009)), and Adenovirus (see, e.g., Lasaro and Ertl, *Molecular Therapy,* 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology,* 165: 377-387 (1988), and Horvath et al., *J. Virology,* 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.,* 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) a nucleic acid sequence that is at least 97% identical to SEQ ID NO: 1, (b) a nucleic acid sequence that is at least 97.5% identical to SEQ ID NO: 2, (c) a nucleic acid sequence that is at least 80% identical to SEQ ID NO: 3, (d) a nucleic acid sequence that is at least 96% identical to SEQ ID NO: 4, and (e) a nucleic acid sequence that is at least 96% identical to SEQ ID NO: 5.

The invention provides an adenovirus or adenoviral vector comprising one or more of the nucleic acid sequences selected from the group consisting of (a) a nucleic acid sequence that is at least 98.4% identical to SEQ ID NO: 6, (b) a nucleic acid sequence that is at least 99.01% identical to SEQ ID NO: 7, (c) a nucleic acid sequence that is at least 97.08% identical to SEQ ID NO: 8, (d) a nucleic acid sequence that is at least 96.52% identical to SEQ ID NO: 9, and (e) a nucleic acid sequence that is at least 98.49% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) an amino acid sequence that is at least 93% identical to SEQ ID NO: 11, (b) an amino acid sequence that is at least 80% identical to SEQ ID NO: 13, (c) an amino acid sequence that is at least 92% identical to SEQ ID NO: 14, and (d) an amino acid sequence that is at least 88% identical to SEQ ID NO: 15.

The invention provides an adenovirus or adenoviral vector comprising one or more of the nucleic acid sequences selected from the group consisting of (a) a nucleic acid sequence encoding an amino acid sequence that is at least 93% identical to SEQ ID NO: 11, (b) a nucleic acid sequence encoding an amino acid sequence that is at least 95% identical to SEQ ID NO: 12, (c) a nucleic acid sequence encoding an amino acid sequence that is at least 80% identical to SEQ ID NO: 13, (d) a nucleic acid sequence encoding an amino acid sequence that is at least 92% identical to SEQ ID NO: 14, and (e) a nucleic acid sequence encoding an amino acid sequence that is at least 88% identical to SEQ ID NO: 15.

The invention provides an adenovirus or adenoviral vector comprising one or more of the amino acid sequences selected from the group consisting of (a) an amino acid sequence that is at least 99% identical to SEQ ID NO: 16, (b) an amino acid sequence that is at least 97.8% identical to SEQ ID NO: 18, (c) an amino acid sequence that is at least 99.1% identical to SEQ ID NO: 19, and (d) an amino acid sequence that is at least 99.2% identical to SEQ ID NO: 20.

The invention provides an adenovirus or adenoviral vector comprising one or more of the nucleic acid sequences selected from the group consisting of (a) a nucleic acid sequence encoding an amino acid sequence that is at least 99% identical to SEQ ID NO: 16, (b) a nucleic acid sequence encoding an amino acid sequence that is at least 99.5% identical to SEQ ID NO: 17, (c) a nucleic acid sequence encoding an amino acid sequence that is at least 97.8% identical to SEQ ID NO: 18, (d) a nucleic acid sequence encoding an amino acid sequence that is at least 99.1% identical to SEQ ID NO: 19, and (e) a nucleic acid sequence encoding an amino acid sequence that is at least 99.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 286 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 230 contiguous amino acid residues of SEQ ID NO: 19, and (e) a nucleic acid sequence encoding an amino acid sequence comprising at least 231 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World,* 3rd ed., Johns Hopkins University Press, Baltimore, Md. (2005)). The adenovirus of the invention was isolated from Eastern Lowland Gorilla (*Gorilla beringei graueri*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, $5^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gem Virol.,* 44: 783-800 (1979); Horwitz M. S., "Adenoviridae and their replication" in *Virology,* 2$^{nd}$ ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7. SEQ ID NO: 2 is a subset of SEQ ID NO: 7. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10. SEQ ID NO: 5 is a subset of SEQ ID NO: 10. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to αv integrins and adenoviruses that have point mutations in the RGD sequence of the penton base are restricted in their ability to infect cells (Bai et al., *J. Virol.,* 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids,* Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences,* Cambridge University Press, Cambridge UK (1997)).

In one embodiment, the adenovirus or adenoviral vector comprises one or more of the following nucleic acid sequences: (a) a nucleic acid sequence that is at least 97% identical (e.g., at least 98.20%, at least 99.41%, or 100% identical) to SEQ ID NO: 1, (b) a nucleic acid sequence that is at least 97.5% identical (e.g., at least 98.5%, at least 99.5%, or 100% identical) to SEQ ID NO: 2, (c) a nucleic acid sequence that is at least 80% identical (e.g., at least 82.22%, at least 84.44%, at least 86.67%, at least 88.89%, at least 91.11%, at least 93.33%, at least 95.56%, at least 97.78%, or 100% identical) to SEQ ID NO: 3, (d) a nucleic acid sequence that is at least 96% identical (e.g., at least 96.9%, at least 97.8%, at least 98.7%, at least 99.6%, or 100% identical) to SEQ ID NO: 4, and (e) a nucleic acid sequence that is at least 96% identical (e.g., at least 96.83% or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 97% identical to SEQ ID NO: 1. The adenovirus or adenoviral vector can comprise a nucleic acid sequence that is at least 97.5% identical to SEQ ID NO: 2 and a nucleic acid sequence that is at least 80% identical to SEQ ID NO: 3. The adenovirus or adenoviral vector can comprise a nucleic acid sequence that is at least 97% identical to SEQ ID NO: 1, a nucleic acid sequence that is at least 80% identical to SEQ ID NO: 3, and a nucleic acid sequence that is at least 96% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) a nucleic acid sequence that is at least 97% identical to SEQ ID NO: 1, (b) a nucleic acid sequence that is at least 97.5% identical to SEQ ID NO: 2, (c) a nucleic acid sequence that is at least 80% identical to SEQ ID NO: 3, (d) a nucleic acid sequence that is at least 96% identical to SEQ ID NO: 4, and (e) a nucleic acid sequence that is at least 96% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.4% identical (e.g., at least 98.65%, at least 98.9%, at least 99.15%, at least 99.4%, at least 99.65%, at least 99.9%, or 100% identical) to SEQ ID NO: 6, (b) a nucleic acid sequence that is at least 99.01% identical (e.g., at least 99.04%, at least 99.07%, at least 99.10%, at least 99.14%, at least 99.17%, at least 99.20%, at least 99.23%, at least 99.26%, at least 99.29%, at least 99.33%, at least 99.36%, at least 99.39%, at least 99.42%, at least 99.45%, at least 99.48%, at least 99.52%, at least 99.55%, at least 99.58%, at least 99.61%, at least 99.64%, at least 99.67%, at least 99.70%, at least 99.74%, at least 99.77%, at least 99.80%, at least 99.83%, at least 99.86%, at least 99.89%, at least 99.93%, at least 99.96%, at least 99.99%, or 100% identical) to SEQ ID NO: 7, (c) a nucleic acid sequence that is at least 97.08% identical (e.g., at least 97.13%, at least 97.18%, at least 97.23%, at least 97.28%, at least 97.33%, at least 97.38%, at least 97.43%, at least 97.49%, at least 97.54%, at least 97.59%, at least 97.64%, at least 97.69%, at least 97.74%, at least 97.79%, at least 97.84%, at least 97.89%, at least 97.94%, at least 97.99%, at least 98.04%, at least 98.09%, at least 98.14%, at least 98.19%, at least 98.25%, at least 98.30%, at least 98.35%, at least 98.40%, at least 98.45%, at least 98.50%, at least 98.55%, at least 98.60%, at least 98.65%, at least 98.70%, at least 98.75%, at least 98.80%, at least 98.85%, at least 98.90%, at least 98.95%, at least 99.01%, at least 99.06%, at least 99.11%, at least 99.16%, at least 99.21%, at least 99.26%, at least 99.31%, at least 99.36%, at least 99.41%, at least 99.46%, at least 99.5%1, at least 99.56%, at least 99.61%, at least 99.66%, at least 99.71%, at least 99.76%, at least 99.82%, at least 99.87%, at least 99.92%, at least 99.97%, or 100% identical) to SEQ ID NO: 8, (d) a nucleic acid sequence that is at least 96.52% identical (e.g., at least 96.55%, at least 96.59%, at least 96.62%, at least 96.66%, at least 96.69%, at least 96.73%, at least 96.76%, at least 96.80%, at least 96.83%, at least 96.87%, at least 96.90%, at least 96.94%, at least 96.97%, at least 97.01%, at least 97.04%, at least 97.08%, at least 97.11%, at least 97.15%, at least 97.18%, at least 97.22%, at least 97.25%, at least 97.29%, at least 97.32%, at least 97.36%, at least 97.39%, at least 97.43%, at least 97.46%, at least 97.50%, at least 97.53%, at least 97.57%, at least 97.60%, at least 97.64%, at least 97.67%, at least 97.71%, at least 97.74%, at least 97.78%, at least 97.81%, at least 97.85%, at least 97.88%, at least 97.92%, at least 97.95%, at least 97.99%, at least 98.02%, at least 98.06%, at least 98.09%, at least 98.13%, at least 98.16%, at least at least 98.20%, at least 98.23%, at least 98.27%, at least 98.30%, at least 98.34%, at least 98.37%, at least at least 98.40%, at least 98.44%, at least 98.47%, at least 98.51%, at least 98.54%, at least 98.58%, at least 98.61%, at least 98.65%, at least 98.68%, at least 98.72%, at least 98.75%, at least 98.79%, at least 98.82%, at least 98.86%, at least 98.89%, at least 98.93%, at least 98.96%, at least 99.00%, at least 99.03%, at least 99.07%, at least 99.10%, at least 99.14%, at least 99.17%, at least 99.21%, at least 99.24%, at least 99.28%, at least 99.31%, at least 99.35%, at least 99.38%, at least 99.42%, at least 99.45%, at least 99.49%, at least 99.52%, at least 99.56%, at least 99.59%, at least 99.63%, at least 99.66%, at least 99.70%, at least 99.73%, at least 99.77%, at least 99.80%, at least 99.84%, at least 99.87%, at least 99.91%, at least 99.94%, at least 99.98%, or 100% identical) to SEQ ID NO: 9, and (e) a nucleic acid sequence that is at least 98.49% identical (e.g., at least 98.55%, at least 98.60%, at least 98.66%, at least 98.72%, at least 98.78%, at least 98.83%, at least 98.89%, at least 98.95%, at least 99.01%, at least 99.06%, at least 99.12%, at least 99.18%, at least 99.24%, at least 99.29%, at least 99.35%, at least 99.41%, at least 99.47%, at least 99.52%, at least 99.58%, at least 99.64%, at least 99.70%, at least 99.75%, at least 99.81%, at least 99.87%, at least 99.93%, at least 99.98%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.4% identical to SEQ ID NO: 6. The adenovirus or adenoviral vector can comprise a nucleic acid sequence that is at least 99.01% identical to SEQ ID NO: 7 and a nucleic acid sequence that is at least 97.08% identical to SEQ ID NO: 8. The adenovirus or adenoviral vector can comprise a nucleic acid sequence that is at least 97.08% identical to SEQ ID NO: 8, a nucleic acid sequence that is at least 96.52% identical to SEQ ID NO: 9, and a nucleic acid sequence that is at least 98.49% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.4% identical to SEQ ID NO: 6, (b) a nucleic acid sequence that is at least 99.01% identical to SEQ ID NO: 7, (c) a nucleic acid sequence that is at least 97.08% identical to SEQ ID NO: 8, (d) a nucleic acid sequence that is at least 96.52% identical to SEQ ID NO: 9, and (e) a nucleic acid sequence that is at least 98.49% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2865 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,740 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) an amino acid sequence that is at least 93% identical (e.g., at least 96.57% or 100% identical) to SEQ ID NO: 11, (b) an amino acid sequence that is at least 80% identical (e.g., at least 86.67%, at least 93.33%, or 100% identical) to SEQ ID NO: 13, (c) an amino acid sequence that is at least 92% identical (e.g., at least 97.56% or 100% identical) to SEQ ID NO: 14, and (d) an amino acid sequence that is at least 88% identical (e.g., at least 94.67% or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence that is at least 93% identical to SEQ ID NO: 11. The adenovirus or adenoviral vector can comprise an amino acid sequence that is at least 93% identical to SEQ ID NO: 11, and an amino acid sequence that is at least 80% identical to SEQ ID NO: 13. The adenovirus or adenoviral vector can comprise an amino acid sequence that is at least 93% identical to SEQ ID NO: 11, an amino acid sequence that is at least 80% identical to SEQ ID NO: 13, and an amino acid sequence that is at least 88% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) an amino acid sequence that is at least 93% identical to SEQ ID NO: 11, (b) an amino acid sequence that is at least 80% identical to SEQ ID NO: 13, (c) an amino acid sequence that is at least 92% identical to SEQ ID NO: 14, and (d) an amino acid sequence that is at least 88% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) an amino acid sequence that is at least 99% identical (e.g., at least 99.75% or 100% identical) to SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, at least 99.93%, or 100% identical) to SEQ ID NO: 18, (c) an amino acid sequence that is at least 99.1% identical (e.g., at least 99.20%, at least 99.31%, at least 99.41%, at least 99.52%, at least 99.62%, at least 99.73%, at least 99.83%, at least 99.94%, or 100% identical) to SEQ ID NO: 19, and (d) an amino acid sequence that is at least 99.2% identical (e.g., at least 99.37%, at least 99.54%, at least 99.72%, at least 99.89%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence that is at least 99% identical to SEQ ID NO: 16. The adenovirus or adenoviral vector can comprise an amino acid sequence that is at least 99% identical to SEQ ID NO: 16, and an amino acid sequence that is at least 99.1% identical to SEQ ID NO: 19. The adenovirus or adenoviral vector can comprise an amino acid sequence that is at least 99% identical to SEQ ID NO: 16, an amino acid sequence that is at least 99.1% identical to SEQ ID NO: 19, and an amino acid sequence that is at least 99.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) an amino acid sequence that is at least 99% identical to SEQ ID NO: 16, (b) an amino acid sequence that is at least 97.8% identical to SEQ ID NO: 18, (c) an amino acid that is at least 99.1% identical to SEQ ID NO: 19, and (d) an amino acid sequence that is at least 99.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 230 (e.g., 250 or more, 300 or more, 350 or more, 400 or more, or 500 or more) contiguous amino acid residues of SEQ ID NO: 19, but no more than 955 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 230 to 800 contiguous amino acid residues (e.g., 240, 260, 270, 280, 290, 300, 350, 390, 400, 500, 600, or 750 contiguous amino acid residues) of SEQ ID NO: 19, 230 to 600 contiguous amino acid residues (e.g., 255, 265, 275, 285, 295, 305, 325, 335, 345, 355, 365, 375, 385, 395, 425, 445, 450, 465, 475, 525, 545, 550, 565 or 575 contiguous amino acid residues) of SEQ ID NO: 19, or 230 to 500 contiguous amino acid residues (e.g., 235, 245, 299, 320, 330, 340, 360, 370, 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 231 (e.g., 250 or more, 300 or more, or 350 or more) contiguous amino acid residues of SEQ ID NO: 20, but no more than 580 (e.g., 575 or less, 550 or less, 500 or less, 450 or less, or 400 or less) contiguous amino acid residues of SEQ ID NO: 20. Preferably, the adenovirus or adenoviral vector comprises an acid sequence comprising 231 to 500 contiguous amino acid residues (e.g., 245, 255, 275, 300, 350, 375, or 400 contiguous amino acid residues) of SEQ ID NO: 20, 231 to 400 contiguous amino acid residues (e.g., 235, 265, 280, 285, 295, 305, 315, 325, 335, 345, 355, 365, 375, 385, 395, or 399 contiguous amino acid residues) of SEQ ID NO: 20, or 231 to 300 contiguous amino acid residues (e.g., 240, 250, 260, 270, or 299 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 230 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 230 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 231 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.5% identical (e.g., at least 99.59%, at least 99.69%, at least 99.78%, at least 99.88%, at least 99.97%, or 100% identical) to SEQ ID NO: 17, or a nucleic acid sequence encoding an amino acid sequence that is at least 95% identical (e.g., at least 97.94% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA,* 95: 965-976 (1998); Chen et al., *Proc. Natl. Acad. Sci. USA,* 94: 1645-1650 (1997); and Kochanek et al., *Hum. Gene Ther.,* 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

EXAMPLE 1

This example demonstrates the immunogenicity of an adenoviral vector encoding a Respiratory Syncytial Virus (RSV) F protein in cotton rats.

A gorilla adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of the infected cells and a commercially available anti-RSV polyclonal antibody (Pab7133P, Maine Biotechnology, Portland, Me.).

Cotton rats (*Siginodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence that is at least 97% identical to SEQ ID NO: 1, (b) a nucleic acid sequence that is at least 97.5% identical to SEQ ID NO: 2, (c) a nucleic acid sequence that is at least 84.44% identical to SEQ ID NO: 3, (d) a nucleic acid sequence that is at least 96% identical to SEQ ID NO: 4, and (e) a nucleic acid sequence that is at least 96% identical to SEQ ID NO: 5.

2. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence that is at least 98.4% identical to SEQ ID NO: 6, (b) a nucleic acid sequence that is at least 99.01% identical to SEQ ID NO: 7, (c) a nucleic acid sequence that is at least 97.08% identical to SEQ ID NO: 8, (d) a nucleic acid sequence that is at least 96.52% identical to SEQ ID NO: 9, and (e) a nucleic acid sequence that is at least 98.49% identical to SEQ ID NO: 10.

3. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

4. A method of prophylactically or therapeutically treating a disease or infection in a mammal comprising administering to the mammal an adenovirus or adenoviral vector comprising a non-native nucleic acid sequence and one or more of the amino acid sequences selected from the group consisting of:

(a) an amino acid sequence that is at least 93% identical to SEQ ID NO: 11, (b) an amino acid sequence that is at least 95% identical to SEQ ID NO: 12, (c) an amino acid sequence that is at least 80% identical to SEQ ID NO: 13, (d) an amino acid sequence that is at least 97.56% identical to SEQ ID NO: 14, and (e) an amino acid sequence that is at least 88% identical to SEQ ID NO: 15.

5. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence encoding an amino acid sequence that is at least 93% identical to SEQ ID NO: 11, (b) a nucleic acid sequence encoding an amino acid sequence that is at least 95% identical to SEQ ID NO: 12, (c) a nucleic acid sequence encoding an amino acid sequence that is at least 80% identical to SEQ ID NO: 13, (d) a nucleic acid sequence encoding an amino acid sequence that is at least 97.56% identical to SEQ ID NO: 14, and (e) a nucleic acid sequence encoding an amino acid sequence that is at least 88% identical to SEQ ID NO: 15.

6. A method of prophylactically or therapeutically treating a disease or infection in a mammal comprising administering to the mammal an adenovirus or adenoviral vector comprising a non-native nucleic acid sequence and one or more of the amino acid sequences selected from the group consisting of:

(a) an amino acid sequence that is at least 99% identical to SEQ ID NO: 16, (b) an amino acid sequence that is at least 97.8% identical to SEQ ID NO: 18, (c) an amino acid sequence that is at least 99.41% identical to SEQ ID NO: 19, and (d) an amino acid sequence that is at least 99.2% identical to SEQ ID NO: 20.

7. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence encoding an amino acid sequence that is at least 99% identical to SEQ ID NO: 16, (b) a nucleic acid sequence encoding an amino acid sequence that is at least 99.5% identical to SEQ ID NO: 17, (c) a nucleic acid sequence encoding an amino acid sequence that is at least 97.8% identical to SEQ ID NO: 18, (d) a nucleic acid sequence encoding an amino acid sequence that is at least 99.41% identical to SEQ ID NO: 19, and (e) a nucleic acid sequence encoding an amino acid sequence that is at least 99.2% identical to SEQ ID NO: 20.

8. A method of prophylactically or therapeutically treating a disease or infection in a mammal comprising administering to the mammal an adenovirus or adenoviral vector comprising a non-native nucleic acid sequence and one or more of the amino acid sequences selected from the group consisting of:

(a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 230 contiguous amino acid residues of SEQ ID NO: 19, and (d) an amino acid sequence comprising at least 231 contiguous amino acid residues of SEQ ID NO: 20.

9. A method of prophylactically or therapeutically treating a disease or infection in a mammal comprising administering to the mammal an adenovirus or adenoviral vector comprising a non-native nucleic acid sequence and one or more of the nucleic acid sequences selected from the group consisting of:

(a) a nucleic acid sequence encoding an amino acid sequence comprising at least 89 contiguous amino acid residues of SEQ ID NO: 16, (b) a nucleic acid sequence encoding an amino acid sequence comprising at least 286 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 230 contiguous amino acid residues of SEQ ID NO: 19, and (e) a nucleic acid sequence encoding an amino acid sequence comprising at least 231 contiguous amino acid residues of SEQ ID NO: 20.

10. The method of claim 1, wherein the adenovirus or adenoviral vector requires complementation of a deficiency in one or more early regions of the adenoviral genome for propagation and does not require complementation of any other deficiency of the adenoviral genome for propagation.

11. The method of claim 1, wherein the adenovirus or adenoviral vector is formulated in a composition further comprising a pharmaceutically acceptable carrier.

12. The method of claim 1, wherein the non-native nucleic acid sequence encodes a cytokine, toxin, tumor suppressor protein, growth factor, hormone, receptor, mitogen, immunoglobulin, neuropeptide, neurotransmitter, enzyme, or antigen of a pathogen.

13. The method of claim 2, wherein the adenovirus or adenoviral vector requires complementation of a deficiency in one or more early regions of the adenoviral genome for propagation and does not require complementation of any other deficiency of the adenoviral genome for propagation.

14. The method of claim 2, wherein the adenovirus or adenoviral vector is formulated in a composition further comprising a pharmaceutically acceptable carrier.

15. The method of claim 2, wherein the non-native nucleic acid sequence encodes a cytokine, toxin, tumor suppressor protein, growth factor, hormone, receptor, mitogen, immunoglobulin, neuropeptide, neurotransmitter, enzyme, or antigen of a pathogen.

16. The method of claim 4, wherein the adenovirus or adenoviral vector requires complementation of a deficiency in one or more early regions of the adenoviral genome for propagation and does not require complementation of any other deficiency of the adenoviral genome for propagation.

17. The method of claim 4, wherein the adenovirus or adenoviral vector is formulated in a composition further comprising a pharmaceutically acceptable carrier.

18. The method of claim 4, wherein the non-native nucleic acid sequence encodes a cytokine, toxin, tumor suppressor protein, growth factor, hormone, receptor, mitogen, immunoglobulin, neuropeptide, neurotransmitter, enzyme, or antigen of a pathogen.

19. The method of claim 5, wherein the adenovirus or adenoviral vector requires complementation of a deficiency in one or more early regions of the adenoviral genome for propagation and does not require complementation of any other deficiency of the adenoviral genome for propagation.

20. The method of claim 5, wherein the adenovirus or adenoviral vector is formulated in a composition further comprising a pharmaceutically acceptable carrier.

21. The method of claim 5, wherein the non-native nucleic acid sequence encodes a cytokine, toxin, tumor suppressor protein, growth factor, hormone, receptor, mitogen, immunoglobulin, neuropeptide, neurotransmitter, enzyme, or antigen of a pathogen.

* * * * *